(12) United States Patent
Blake et al.

(10) Patent No.: US 11,884,664 B2
(45) Date of Patent: Jan. 30, 2024

(54) PROTEIN TYROSINE PHOSPHATASE INHIBITORS

(71) Applicant: Array BioPharma Inc., Boulder, CO (US)

(72) Inventors: James Francis Blake, Longmont, CO (US); Mark Laurence Boys, Lyons, CO (US); Mark Joseph Chicarelli, Longmont, CO (US); Adam Wade Cook, Broomfield, CO (US); Mohamed S. A. Elsayed, Boulder, CO (US); Jay Bradford Fell, Denver, CO (US); John P. Fischer, Longmont, CO (US); Ronald Jay Hinklin, Longmont, CO (US); Yutong Jiang, Longmont, CO (US); Oren Teague McNulty, Nederland, CO (US); Macedonio J. Mejia, Denver, CO (US); Martha E. Rodriguez, Lafayette, CO (US); Christina Elizabeth Wong, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 85 days.

(21) Appl. No.: 17/720,070

(22) Filed: Apr. 13, 2022

(65) Prior Publication Data
US 2022/0251083 A1    Aug. 11, 2022

Related U.S. Application Data

(63) Continuation of application No. 16/835,702, filed on Mar. 31, 2020, now Pat. No. 11,634,417.

(60) Provisional application No. 62/992,558, filed on Mar. 20, 2020, provisional application No. 62/828,356, filed on Apr. 2, 2019.

(51) Int. Cl.
| | |
|---|---|
| *C07D 401/04* | (2006.01) |
| *A61K 31/53* | (2006.01) |
| *C07D 471/04* | (2006.01) |
| *A61P 35/00* | (2006.01) |
| *C07D 401/14* | (2006.01) |
| *C07D 471/10* | (2006.01) |
| *C07D 513/10* | (2006.01) |
| *A61K 45/06* | (2006.01) |

(52) U.S. Cl.
CPC ............ *C07D 471/04* (2013.01); *A61P 35/00* (2018.01); *C07D 401/14* (2013.01); *C07D 471/10* (2013.01); *C07D 513/10* (2013.01); *A61K 45/06* (2013.01)

(58) Field of Classification Search
CPC .. C07D 401/04; C07D 401/14; C07D 253/07; A61K 31/53; A61P 35/00; C12Q 1/00

USPC .......................................... 544/182; 514/242
See application file for complete search history.

(56) References Cited

U.S. PATENT DOCUMENTS

2015/0259350 A1    9/2015    Jung et al.

FOREIGN PATENT DOCUMENTS

| WO | 2007/103694 | 9/2007 |
|---|---|---|
| WO | 2013056183 A1 | 4/2013 |
| WO | 2014036015 A1 | 3/2014 |
| WO | 2015/107493 | 7/2015 |
| WO | 2015/107494 | 7/2015 |
| WO | 2015/107495 | 7/2015 |
| WO | 2016/203404 | 2/2016 |
| WO | 2016/203405 | 12/2016 |
| WO | 2016/203406 | 12/2016 |
| WO | 2017/210134 | 12/2017 |
| WO | 2017/211303 | 12/2017 |
| WO | 2017/216706 | 12/2017 |
| WO | 2018/013597 | 1/2018 |
| WO | 2018/057884 | 3/2018 |
| WO | 2018/081091 | 5/2018 |
| WO | 2018/136264 | 7/2018 |
| WO | 2018/136265 | 7/2018 |
| WO | 2018/172984 | 9/2018 |
| WO | 2018/218133 | 11/2018 |
| WO | 2019/051084 | 3/2019 |
| WO | 2019/051469 | 3/2019 |
| WO | 2019/067843 | 4/2019 |
| WO | 2019/075265 | 4/2019 |
| WO | 2019/118909 | 6/2019 |
| WO | 2019/152454 | 8/2019 |

(Continued)

OTHER PUBLICATIONS

Official Action, Translation, Gorodissky, dated Dec. 15, 2022.

(Continued)

*Primary Examiner* — Charanjit Aulakh
(74) *Attorney, Agent, or Firm* — Corey M. Williams

(57) ABSTRACT

Compounds of Formula I or a stereoisomer, tautomer, prodrug or pharmaceutically acceptable salt thereof are provided, which are useful for the treatment of hyperproliferative diseases. Methods of using compounds of Formula I or a stereoisomer, tautomer, prodrug or pharmaceutically acceptable salt thereof, for in vitro, in situ, and in vivo diagnosis, prevention or treatment of such disorders in mammalian cells, or associated pathological conditions are disclosed.

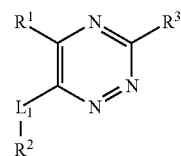

16 Claims, No Drawings

(56) References Cited

FOREIGN PATENT DOCUMENTS

| WO | 2019/182960 | 9/2019 |
| WO | 2019/183364 | 9/2019 |
| WO | 2019/183367 | 9/2019 |
| WO | 2020/033828 | 2/2020 |
| WO | 2020/063760 | 4/2020 |
| WO | 2020/081848 | 4/2020 |

OTHER PUBLICATIONS

Aceto N, et al. "Tyrosine phosphatase SHP2 promotes breast cancer progression and maintains tumor-initiating cells via activation of key transcription factors and a positive feedback signaling loop." Nat. Med. 2012;18:529-37.

Dardaei L, et al. "SHP2 inhibition restores sensitivity in ALK-rearranged non-small-cell lung cancer resistant to ALK Inhibitors." Nat. Med0 2018;24:512-7.

Frankson R, et al. "Therapeutic targeting of oncogenic tyrosine phosphatases." Cancer Res. Nov. 1, 2017; 77(21):5701-5705.

Gu S, et al. "SHP2 is required for BCR-ABL1-induced hematologic neoplasia." Leukemia 2018;32:203-13.

Jiang L, et al. "SHP2 inhibitor specifically suppresses the stemness of KRAS-mutant non-small cell lung cancer cells." Artif. Cells Nanomed Biotechnol. 2019;47:3231-8.

Liu Q, et al. "Targeting SHP2 as a promising strategy for cancer immunotherapy." Pharmacological Research 152 (2020) 104595.

Mainardi S, et al. "SHP2 is required for growth of KRAS-mutant non-small-cell lung cancer in vivo." Nat. Med. 2018;24:961-7.

Matalkah F, et al. "SHP2 acts both upstream and downstream of multiple receptor tyrosine kinases to promote basal-like and triple-negative breast cancer." Breast Cancer Res. 2016;18:2.

Mohi G, et al. "Critical Role of SHP2 in the Initiation and Maintenance of Myeloproliferative Neoplasms Evoked by JAK2V617F." Blood (2015) 126 (23):483.

Pandey R, et al. "SHP2 inhibition reduces leukemogenesis in models of combined genetic and epigenetic mutations." J. Clin. Invest. 2019;129:5468-73.

Richine BM, et al. "Syk kinase and Shp2 phosphatase inhibition cooperate to reduce FLT3-ITD-induced STAT5 activation and proliferation of acute myeloid leukemia." Leukemia 2016;30:2094-7.

Roccograndi L, et al. "SHP2 regulates proliferation and tumorigenicity of glioma stem cells." J. Neurooncol. (2017) 135:487-496.

Ruess DA, et al. "Mutant KRAS-driven cancers depend on PTPN11/SHP2 phosphatase." Nat. Med. 2018;24:954-60.

Song, Zhendong, et al. "Tyrosine phosphatase SHP2 inhibitors in tumor-targeted therapies." Acta Pharmaceutica Sinica B 2021;11(1):13-29.

Wong GS, et al. "Targeting wildtype KRAS-amplified gastroesophageal cancer through combined MEK and SHP2 inhibition." Nat. Med. 2018;24:968-77.

Zhao H, et al. "Conditional knockout of SHP2 in ErbB2 transgenic mice or inhibition in HER2-amplified breast cancer cell lines blocks oncogene expression and tumorigenesis." Oncogene 2019;38:2275-90.

Zhou X, et al. "SHP2 is up-regulated in breast cancer cells and in infiltrating ductal carcinoma of the breast, implying its involvement in breast oncogenesis." Histopathology 2008;53:389-402.

Jorge Garcia Fortanet, et al., 'Allosteric Inhibition of SHP2: Identification of a Potent, Selective, and Orally Efficacious Phosphatase Inhibitor', Journal of Medicinal Chemistry, vol. 59, No. 17, pp. 7773-7782, 2016.

Ciapetti and Giethlen, Edited by Wermuth, 'Chapter 15: Molecular Variations Based on Isosteric Replacements', The Practice of Medicinal Chemistry (Third Edition), Elsevier, NL, pp. 290-342, 2008.

Database Registry [Online] Chemical Abstracts Service, Columbus, Ohio, US; Aug. 10, 2017 (Aug. 10, 2017), XP055717177, retrieved from STN Database accession No. 2111623-79-9 compounds 2111623-79-9.

Database Registry [Online] Chemical Abstracts Service, Columbus, Ohio, US; Aug. 10, 2017 (Aug. 10, 2017), XP055717181, retrieved from STN Database accession No. 2111485-38-0 compounds 2111485-38-0.

Database Registry [Online] Chemical Abstracts Service, Columbus, Ohio, US; Aug. 9, 2017 (Aug. 9, 2017), XP055717192, retrieved from STN Database accession No. 2110890-17-8 compounds 2110890-17-8.

Database Registry [Online] Chemical Abstracts Service, Columbus, Ohio, US; Aug. 9, 2017 (Aug. 9, 2017), XP055 717193, retrieved from STN Database accession No. 2110200-53-6 compounds 2110200-53-6.

Database Registry [Online] Chemical Abstracts Service, Columbus, Ohio, US; Aug. 8, 2017 (Aug. 8, 2017), XP055717198, retrieved from STN Database accession No. 2109948-31-2 compounds 2109948-31-2.

Database Registry [Online] Chemical Abstracts Service, Columbus, Ohio, US; Aug. 2, 2017 (Aug. 2, 2017), XP055717200, retrieved from STN Database accession No. 2107245-21-4 compounds 2107245-21-4.

Database Registry [Online] Chemical Abstracts Service, Columbus, Ohio, US; Aug. 1, 2017 (Aug. 1, 2017), XP055717203, retrieved from STN Database accession No. 2106311-53-7 compounds 2106311-53-7.

Database Registry [Online] Chemical Abstracts Service, Columbus, Ohio, US; Jul. 30, 2017 (Jul. 30, 2017), XP055717204, retrieved from STN Database accession No. 2105086-20-0 compounds 2105086-20-0.

Database Registry [Online] Chemical Abstracts Service, Columbus, Ohio, US; Jul. 30, 2017 (Jul. 30, 2017), XP055717207, retrieved from STN Database accession No. 2104243-38-9 compounds 2104243-38-9.

PROTEIN TYROSINE PHOSPHATASE INHIBITORS

BACKGROUND OF THE INVENTION

Field of the Invention

The present invention relates to compounds that inhibit SHP2 and are useful for treating hyperproliferative and neoplastic diseases. The present invention further relates to methods for treating cancer or hyperproliferative diseases with compounds of the present invention.

Description of the State of the Art

SHP2 is a protein tryosine phosphatase (PTP) containing Src Homology 2 (SH2) domains encoded by the PTPN11 gene. SHP2 contributes to multiple cellular functions including proliferation, differentiation, cell cycle maintenance and migration. SHP2 is necessary for full activation of the Ras/ERK1/2 pathway, a key signaling cascade in cancer biology downstream of a wide array of receptor tyrosine kinases and other signal transducers. SHP2 has also been shown to promote PI3K/AKT, JAK/STAT, JNK, and NF-κB signaling, which are also associated with various human cancers. SHP2 is an oncoprotein. See Frankson, Rochelle, et al. "Therapeutic Targeting of Oncogenic Tyrosine Phosphatases." *Cancer Research*. Vol. 77, No. 21 (2017): pp. 5701-5705. Fedele, Carmine, et al. "SHP2 Inhibition Prevents Adaptive Resistance to MEK inhibitors in Multiple Cancer Models." *Cancer Discovery*. Vol. 8, No. 10 (2018): pp. 1237-49. Nichols, Robert J., et al. "Efficacy of SHP2 phosphatase inhibition in cancers with nucleotide-cycling oncogenic RAS, RAS-GTP dependent oncogenic BRAF and NF1 loss." bioRxiv 188730; doi: https://doi.org/10.1101/188730.

Therefore, small-molecular inhibitors of SHP2 would be useful for treating a broad spectrum of cancers, such as, for example, melanoma, juvenile myelomoncytic leukemias, neuroblastoma, Philadelphia chromosome positive chronic myeloid, Philadelphia chromosome positive acute lymphoblastic leukemias, acute myeloid leukemias, myeloproliferative neoplasms (such as Polycythemia Vera, Essential Thrombocythemia and Primary Myelofibrosis), breast cancer, lung cancer, liver cancer, colorectal cancer, esophageal cancer, gastric cancer, squamous-cell carcinoma of the head and neck, glioblastoma, anaplastic large-cell lymphoma, thyroid carcinoma, spitzoid neoplasms, as well as, Neurofibromatosis and Noonan Syndrome.

SHP2 inhibitors are known, see for example, WO 2015/107493; WO 2015/107494; WO 2015/107495; WO 2016/203404; WO 2016/203405; WO 2016/203406; WO 2017/210134; WO 2017/211303; WO 2017/216706; WO 2018/013597; WO 2018/057884; WO 2018/081091; WO 2018/136264; WO 2018/136265; WO 2018/172984; and WO 2019/051469. However, it is well known that there is difficulty in developing a compound into an approved medicine. DiMasi, Joseph A. "Success rates for new drugs entering clinical testing in the United States." *Clinical Pharmacology & Therapeutics*. Vol. 58, no. 1 (1995): pp. 1-14. Scannell, J W, Bosley J. "When Quality Beats Quantity: Decision Theory, Drug Discovery, and the Reproducibility Crisis." *PloS ONE* 11(2) (2016): e0147215. doi: 10.1371/journal.pone.0147215.

SUMMARY OF THE INVENTION

There is a continuing need for new and novel therapeutic agents that can be used for cancer and hyperproliferative conditions. Design and development of new pharmaceutical compounds is essential.

More specifically, one aspect provides compounds of Formula I:

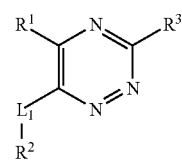

or a stereoisomer, tautomer, or pharmaceutically acceptable salt thereof, wherein $L_1$, $R^1$, $R^2$ and $R^3$ are as defined herein.

Another aspect provides a method for treating a hyperproliferative disorder by administering a therapeutically effective quantity of a compound according to Formula I, or a stereoisomer, tautomer or pharmaceutically acceptable salt thereof, to a patient in need thereof. The compound can be administered alone or co-administered with at least one other anti-hyperproliferative or chemotherapeutic compound.

Another aspect provides a method of inhibiting SHP2 protein tyrosine phosphatase activity in a cell comprising treating the cell with a compound according to Formula I, or a stereoisomer, tautomer or pharmaceutically acceptable salt thereof, in an amount effective to attenuate or eliminate SHP2 kinase activity.

Another aspect provides methods of treating or preventing a disease or disorder modulated by SHP2, comprising administering to a mammal in need of such treatment an effective amount of a compound of Formula I, or a stereoisomer, tautomer or pharmaceutically acceptable salt thereof. Examples of such diseases and disorders include, but are not limited to, hyperproliferative disorders, such as cancer.

Another aspect provides methods of treating or preventing cancer, comprising administering to a mammal in need of such treatment an effective amount of a compound of Formula I, or a stereoisomer, tautomer or pharmaceutically acceptable salt thereof, alone or in combination with one or more additional compounds having anti-cancer properties.

Another aspect provides a method of treating a hyperproliferative disease in a mammal comprising administering a therapeutically effective amount of a compound of Formula I, or a stereoisomer, tautomer or pharmaceutically acceptable salt thereof, to the mammal.

Another aspect provides the use of a compound of Formula I, or a stereoisomer, tautomer or pharmaceutically acceptable salt thereof, in the manufacture of a medicament for the treatment of a hyperproliferative disease.

Another aspect provides a compound of Formula I, or a stereoisomer, tautomer or pharmaceutically acceptable salt thereof, for use in the treatment of hyperproliferative diseases.

Another aspect provides a pharmaceutical composition comprising a compound of Formula I, or a stereoisomer, tautomer or pharmaceutically acceptable salt thereof, and a pharmaceutically acceptable carrier, diluent or excipient.

Another aspect provides intermediates for preparing compounds of Formula I. Certain compounds of the Formulas may be used as intermediates for other compounds of the Formulas.

Another aspect includes processes for preparing, methods of separation, and methods of purification of the compounds described herein.

DETAILED DESCRIPTION OF THE INVENTION

Reference will now be made in detail to certain embodiments, examples of which are illustrated in the accompanying structures and formulas. While enumerated embodiments will be described, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein" refers to the broadest definition for each group as provided in the Detailed Description of the Invention or the broadest claim. In all other embodiments provided below, substituents that can be present in each embodiment, and which are not explicitly defined, retain the broadest definition provided in the Detailed Description of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components. Additionally, the words "include," "including," and "includes" when used in this specification and in the following claims are intended to specify the presence of stated features, integers, components, or steps, but they do not preclude the presence or addition of one or more other features, integers, components, steps, or groups thereof.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X_1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable that is inherently continuous, the variable can be equal to any real value of the numerical range, including the end-points of the range. As an example, a variable that is described as having values between 0 and 2, can be 0, 1 or 2 for variables that are inherently discrete, and can be 0.0, 0.1, 0.01, 0.001, or any other real value for variables that are inherently continuous.

Compounds of Formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates; while in phenols, the enol form predominates. Common prototropic tautomers include keto/enol (—C(=O)—CH$_2$—↔—C(—OH)=CH—), amide/imidic acid (—C(=O)—NH—↔—C(—OH)=N—) and amidine (—C(=NR)—NH—↔—C(—NHR)=N—) tautomers. The lattertwo are particularly common in heteroaryl and heterocyclic rings, and the present invention encompasses all tautomeric forms of the compounds.

It will be appreciated by the skilled artisan that some of the compounds of Formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. The present invention includes all the individual stereoisomers (e.g., enantiomers), racemic mixtures or partially resolved mixtures of the compounds of Formula I and, where appropriate, the individual tautomeric forms thereof.

The compounds of Formula I may contain a basic center and suitable acid addition salts are formed from acids that form non-toxic salts. Examples of salts of inorganic acids include the hydrochloride, hydrobromide, hydroiodide, chloride, bromide, iodide, sulfate, bisulfate, nitrate, phosphate, and hydrogen phosphate. Examples of salts of organic acids include acetate, fumarate, pamoate, aspartate, besylate, carbonate, bicarbonate, camsylate, D and L-lactate, D and L-tartrate, esylate, mesylate, malonate, orotate, gluceptate, methylsulfate, stearate, glucuronate, 2-napsylate, tosylate, hibenzate, nicotinate, isethionate, malate, maleate, citrate, gluconate, succinate, saccharate, benzoate, esylate, and pamoate salts. For a review on suitable salts, see Berge, Stephen M., et al. "Pharmaceutical salts." *J. Pharm. Sci*. Vol. 66, No. 1 (1977): 1-19, and Paulekuhn, G. Steffen, et al. "Trends in Active Pharmaceutical Ingredient Salt Selection based on Analysis of the Orange Book Database." *J. Med. Chem*. Vol. 50, No. 26 (2007): 6665-6672.

Technical and scientific terms used herein have the meaning commonly understood by one of skill in the art to which the present invention pertains, unless otherwise defined. Reference is made herein to various methodologies and materials known to those of skill in the art. A standard reference work setting forth the general principles of pharmacology include Hardman, Joel Griffith, et al. *Goodman & Gilman's The Pharmacological Basis of Therapeutics*. New York: McGraw-Hill Professional, 2001. The starting materials and reagents used in preparing these compounds generally are either available from commercial suppliers, such as Sigma-Aldrich (St. Louis, MO), or are prepared by methods known to those skilled in the art following procedures set forth in references. Materials, reagents and the like to which reference are made in the following description and examples are obtainable from commercial sources, unless otherwise noted. General synthetic procedures have been described in treatises, such as Louis F. Fieser and Mary Fieser, *Reagents for Organic Synthesis*. v. 1-23, New York: Wiley 1967-2006 ed. (also available via the Wiley InterScience® website); LaRock, Richard C., *Comprehensive Organic Transformations: A Guide to Functional Group Preparations*. New York: Wiley-VCH, 1999; B. Trost and I. Fleming, eds. *Comprehensive Organic Synthesis*. v. 1-9, Oxford: Pergamon 1991; A. R. Katritzky and C. W. Rees, eds. *Comprehensive Heterocyclic Chemistry*. Oxford: Pergamon 1984; A. R. Katritzky and C. W. Rees, eds. *Comprehensive Heterocyclic Chemistry II*. Oxford: Pergamon 1996; and Paquette, Leo A., ed. *Organic Reactions*. v. 1-40, New York: Wiley & Sons 1991; and will be familiar to those skilled in the art.

The term "alkyl" includes linear or branched-chain radicals of carbon atoms. Some alkyl moieties have been abbreviated, for example, methyl ("Me"), ethyl ("Et"), propyl ("Pr") and butyl ("Bu"), and further abbreviations are used to designate specific isomers of compounds, for example, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu") and the like. The abbreviations are sometimes used in conjunction with elemental abbreviations and chemical structures, for example, methanol ("MeOH") or ethanol ("EtOH"). In certain embodiments, alkyl is $C_{1-10}$ alkyl. In certain embodiments, alkyl is $C_{1-6}$ alkyl.

Additional abbreviations used throughout the application may include, for example, benzyl ("Bn"), phenyl ("Ph"), acetate ("Ac") and mesylate ("Ms").

The term "BOC" or "boc" or "Boc" means a tert-butyloxycarbonyl protecting group.

The terms "alkenyl" and "alkynyl" also include linear or branched-chain radicals of carbon atoms.

The term "alkoxy", as used herein, means an alkyl substituent attached through an oxygen atom. Non-limiting examples include methoxy, ethoxy, propoxy, butoxy, pentoxy, and hexyloxy.

The term "bicyclic", as used herein, means a bicyclic, monovalent hydrocarbon group containing from six to ten carbon atoms in which the two rings are fused, spiro-fused or form a bridged structure. When used to modify heterocycle or heteroaryl, the bicyclic group may contain one to four heteroatoms selected from the group consisting of nitrogen, oxygen and sulfur.

The term "cycloalkyl", as used herein, means a cyclic, monovalent hydrocarbon group of formula —$C_nH(2_n-1)$ containing at least three carbon atoms. Non-limiting examples include cyclopropyl, cyclobutyl, cyclopentyl and cyclohexyl.

The term "aryl", as used herein, means phenyl or naphthalenyl.

The terms "heterocycle" and "heterocyclic" means a four to seven membered saturated or partially unsaturated rings containing one, two or three heteroatoms selected from the group consisting of O, N, S, S(=O) and S(=O)$_2$. In certain instances, these terms may be specifically further limited, such as, "five to six membered heterocyclic" only including five and six membered rings.

The term "heteroaryl" means a five to six membered aromatic rings containing one, two, three or four heteroatoms selected from the group consisting of O, N and S. In certain instances, these terms may be specifically further limited, such as, five to six membered heteroaryl, wherein the heteroaryl contains one or two nitrogen heteroatoms. As well known to those skilled in the art, heteroaryl rings have less aromatic characterthan their all-carbon counter parts. Thus, for the purposes of the invention, a heteroaryl group need only have some degree of aromatic character. Such a heteroaryl group may be attached through a ring carbon atom or, where valency permits, through a ring nitrogen atom.

The term "halogen", as used herein, refers to fluorine, chlorine, bromine, or iodine.

A bond drawn into ring system (as opposed to connected at a distinct vertex) indicates that the bond may be attached to any of the suitable ring atoms. A wavy  line (across a bond indicates the point of attachment.

The terms "treat" or "treatment" refer to therapeutic, prophylactic, palliative or preventative measures. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

The phrases "therapeutically effective amount" or "effective amount" mean an amount of a compound described herein that, when administered to a mammal in need of such treatment, sufficient to (i) treat or prevent the particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound that will correspond to such an amount will vary depending upon factors such as the particular compound, disease condition and its severity, the identity (e.g., weight) of the mammal in need of treatment, but can nevertheless be routinely determined by one skilled in the art.

The terms "cancer" and "cancerous" refer to or describe the physiological condition in mammals that is typically characterized by abnormal or unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, skin cancer, including melanoma, as well as head and neck cancer.

The phrase "pharmaceutically acceptable" indicates that the substance or composition is compatible chemically and/or toxicologically, with the other ingredients comprising a formulation, and/or the mammal being treated therewith.

The phrase "pharmaceutically acceptable salt," as used herein, refers to pharmaceutically acceptable organic or inorganic salts of a compound described herein.

The compounds described herein also include other salts of such compounds that are not necessarily pharmaceutically acceptable salts, and which may be useful as intermediates for preparing and/or purifying compounds described herein and/or for separating enantiomers of compounds described herein.

The term "mammal" means a warm-blooded animal that has or is at risk of developing a disease described herein and includes, but is not limited to, guinea pigs, dogs, cats, rats, mice, hamsters, and primates, including humans.

SHP2 Inhibitors

Provided herein are compounds, and pharmaceutical formulations thereof, that are potentially useful in the treatment of diseases, conditions and/or disorders modulated by SHP2.

This invention relates to a new class of triazine compounds. The invention also relates to the preparation of those compounds and intermediates used in the preparation, compositions containing the compounds, and uses of the compounds including treating hyperproliferative and neoplastic diseases, such as cancer.

One embodiment provides compounds of Formula I:

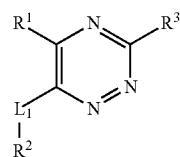

I or a stereoisomer, tautomer, or pharmaceutically acceptable salt thereof, wherein:
$L_1$ is selected from a direct bond, S, $CH_2$, O, NH and Se;
$R^1$ is selected from hydrogen and methyl;
$R^2$ is selected from (a) phenyl, (b) a 5 to 6 membered heteroaryl wherein the heteroaryl contains one to four heteroatoms selected from the group consisting of nitrogen, oxygen and sulfur, wherein one nitrogen heteroatom may be substituted with oxygen to form an oxide, (c) an 8-10 membered bicyclic cycloalkyl, (d) a 10 membered bicyclic aryl, (e) a 9-10 membered bicyclic heterocycle wherein the heterocycle contains one to three heteroatoms selected from the group consisting of nitrogen, oxygen and sulfur, and (f) a 9-10 membered bicyclic heteroaryl wherein the bicyclic heteroaryl contains one to three heteroatoms selected from the group consisting of nitrogen, oxygen and sulfur, wherein the phenyl, heteroaryl, bicyclic cycloalkyl, bicyclic aryl, bicyclic heterocycle and bicyclic heteroaryl are optionally substituted with one or more groups selected from the group consisting of halogen, cyano, oxo, $C_1$-$C_3$ alkyl optionally substituted with 1 to 3 groups selected from halogen, cyano and OH, $C_3$-$C_6$ cycloalkyl, $C_1$-$C_3$ alkoxy optionally substituted with 1 to 3 groups selected from halogen, cyano and OH, $NHR^a$, and a 3 to 6 membered heterocycle optionally substituted with 1 to 3 groups selected from halogen, cyano and OH, wherein the heterocycle contains one or two heteroatoms selected from nitrogen, oxygen and sulfur;

$R^3$ is selected from the group consisting of:

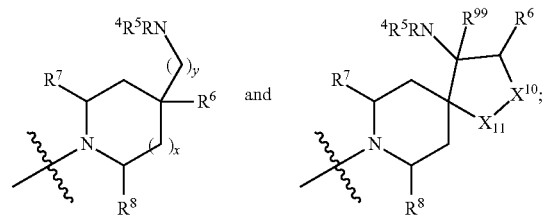

$X^{10}$ is $CR^9$ or O,
$X^{11}$ is $CH_2$ or O, wherein only one of $X^{10}$ and $X^{11}$ may be O;
$R^4$ and $R^5$ are independently selected from hydrogen and $C_1$-$C_3$ alkyl;
$R^6$ is selected from the group consisting of hydrogen, OH and $C_1$-$C_3$ alkyl optionally substituted with an OH group, or
$R^6$ and $R^9$ together with the atoms to which they are attached form a 6 membered aryl or a 5 to 6 membered heteroaryl, wherein the heteroaryl contains 1 or 2 heteroatoms selected from nitrogen, oxygen and sulfur, wherein the aryl and heteroaryl are optionally substituted with 1 or 2 groups selected from the group consisting of halogen, cyano, $C_1$-$C_3$ alkyl and $C_1$-$C_3$ alkoxy;
$R^7$ and $R^8$ are hydrogen, or
$R^7$ and $R^8$ together with the atoms to which they are attached form an ethyl bridge such that $R^3$ is an azabicyclic ring;
$R^{99}$ is hydrogen or deuterium;
x is 1 or 2;
y is 0 or 1; and
$R^a$ is hydrogen or $C_1$-$C_4$ alkyl optionally substituted with 1 to 3 groups selected from OH, methoxy, halogen and cyano.

In a certain embodiment is provided compounds of Formula I, or a stereoisomer, tautomer, or pharmaceutically acceptable salt thereof, wherein:
$L_1$ is selected from a direct bond, S, $CH_2$, O, NH and Se;
$R^1$ is selected from hydrogen and methyl;

$R^2$ is selected from (a) phenyl optionally substituted with one or two halogen groups; (b) a 5 to 6 membered heteroaryl wherein the heteroaryl contains one to four heteroatoms selected from the group consisting of nitrogen, oxygen and sulfur, wherein the heteroaryl is optionally substituted with one or two substituents selected from halogen, $C_1$-$C_3$ alkyl optionally substituted with 1 to 3 halogen groups, $C_3$-$C_6$ cycloalkyl, $C_1$-$C_3$ alkoxy, $NHR^a$, and a 3 to 6 membered heterocycle optionally substituted with an OH group, wherein the heterocycle contains one or two heteroatoms selected from nitrogen and oxygen; (c) an 8-10 membered bicyclic partially unsaturated cycloalkyl; (d) a 9-10 membered bicyclic partially unsaturated heterocycle, wherein the heterocycle contains one to three heteroatoms selected from nitrogen, oxygen and sulfur, wherein the heterocycle is optionally substituted with one to three groups selected from halogen and oxo; (e) a 9-10 membered bicyclic heteroaryl wherein the bicyclic heteroaryl contains one to three heteroatoms selected from the group consisting of nitrogen, oxygen and sulfur, wherein the bicyclic heteroaryl is optionally substituted with 1 to 3 groups selected from halogen and $C_1$-$C_3$ alkyl;

$R^3$ is selected from the group consisting of:

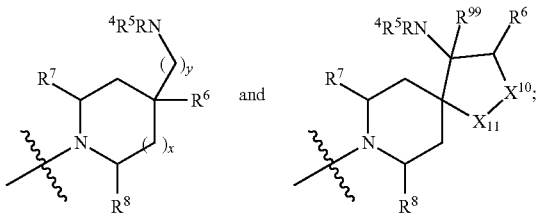

$X^{10}$ is $CR^9$ or O, $X^{11}$ is $CH_2$ or O, wherein only one of $X^{10}$ and $X^{11}$ may be O;

$R^4$ and $R^5$ are independently selected from hydrogen and $C_1$-$C_3$ alkyl;

$R^6$ is selected from the group consisting of hydrogen, OH and $C_1$-$C_3$ alkyl optionally substituted with an OH group, or $R^6$ and $R^9$ together with the atoms to which they are attached form a 6 membered aryl or a 5 to 6 membered heteroaryl, wherein the heteroaryl contains 1 or 2 heteroatoms selected from nitrogen, oxygen and sulfur, wherein the aryl and heteroaryl are optionally substituted with 1 or 2 groups selected from the group consisting of halogen, cyano, $C_1$-$C_3$ alkyl and $C_1$-$C_3$ alkoxy;

$R^7$ and $R^8$ are hydrogen, or $R^7$ and $R^8$ together with the atoms to which they are attached form an ethyl bridge such that $R^3$ is an azabicyclic ring;

$R^{99}$ is hydrogen or deuterium;

x is 1 or 2;

y is 0 or 1; and $R^a$ is hydrogen or $C_1$-$C_4$ alkyl optionally substituted with 1 to 3 groups selected from OH and cyano.

In a certain embodiment is provided compounds of Formula I, or a stereoisomer, tautomer, or pharmaceutically acceptable salt thereof, wherein:

$L_1$ is selected from a direct bond, S, $CH_2$, O, and NH;

$R^1$ is hydrogen;

$R^2$ is selected from (a) phenyl optionally substituted with one or two halogen groups; (b) a 5 to 6 membered heteroaryl wherein the heteroaryl contains one nitrogen heteroatom, wherein the heteroaryl is optionally substituted with one or two substituents selected from halogen, $C_1$-$C_3$ alkyl optionally substituted with 1 to 3 halogen groups, $C_3$ cycloalkyl, $C_1$-$C_3$ alkoxy, $NHR^a$, and a 6 membered heterocycle optionally substituted with an OH group, wherein the heterocycle contains one or two heteroatoms selected from nitrogen and oxygen; (c) an 8-10 membered bicyclic partially unsaturated cycloalkyl; (d) a 9 membered bicyclic partially unsaturated heterocycle, wherein the heterocycle contains two or three nitrogen heteroatoms, wherein the heterocycle is optionally substituted with one to three groups selected from halogen and oxo; and (e) a 9-10 membered bicyclic heteroaryl wherein the bicyclic heteroaryl contains one to three heteroatoms selected from the group consisting of nitrogen, oxygen and sulfur, wherein the bicyclic heteroaryl is optionally substituted with one group selected from halogen and $C_1$-$C_3$ alkyl;

$R^3$ is selected from the group consisting of:

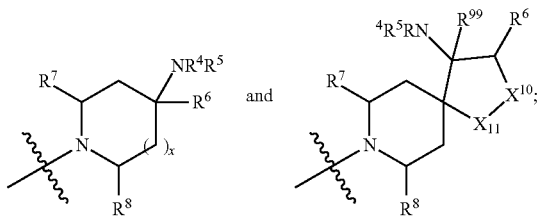

$X^{10}$ is $CR^9$ or O, $X^{11}$ is $CH_2$ or O, wherein only one of $X^{10}$ and $X^{11}$ may be O;

$R^4$ and $R^5$ are independently selected from hydrogen and methyl;

$R^6$ is methyl, or $R^6$ and $R^9$ together with the atoms to which they are attached form a 6 membered aryl or a 5 to 6 membered heteroaryl, wherein the heteroaryl contains 1 or 2 heteroatoms selected from nitrogen and sulfur, wherein the aryl and heteroaryl are optionally substituted with 1 or 2 groups selected from the group consisting of halogen, methyl, methoxy and cyano;

$R^7$ and $R^8$ are hydrogen, or $R^7$ and $R^8$ together with the atoms to which they are attached form an ethyl bridge such that $R^3$ is an azabicyclic ring;

$R^{99}$ is hydrogen or deuterium;

x is 1 or 2; and $R^a$ is hydrogen or $C_1$-$C_4$ alkyl optionally substituted with one group selected from OH and cyano.

In a certain embodiment is provided compounds of Formula I, or a stereoisomer, tautomer, or pharmaceutically acceptable salt thereof, wherein:

$L_1$ is selected from a direct bond, S, $CH_2$, O or NH;

$R^1$ is selected from hydrogen and methyl;

$R^2$ is selected from phenyl, a 5 to 6 membered heteroaryl wherein the heteroaryl contains one to four heteroatoms selected from the group consisting of nitrogen, oxygen and sulfur, a 10 membered bicyclic aryl, and a 9-10 membered bicyclic heteroaryl wherein the bicyclic heteroaryl contains one to three heteroatoms selected from the group consisting of nitrogen, oxygen and sulfur, wherein the phenyl, heteroaryl, bicyclic aryl and bicyclic heteroaryl are optionally substituted with one or more groups selected from the group consisting of halogen, cyano, $C_1$-$C_3$ alkyl optionally substituted with halogen, cyano or OH, —O($C_1$-$C_3$ alkyl) optionally substituted with halogen, cyano or OH, $NHR^a$, and 3 to 6 membered heterocycle optionally substituted with halogen, cyano or OH, wherein the heterocycle contains one or two heteroatoms selected from nitrogen, oxygen and sulfur;

$R^3$ is selected from the group consisting of:

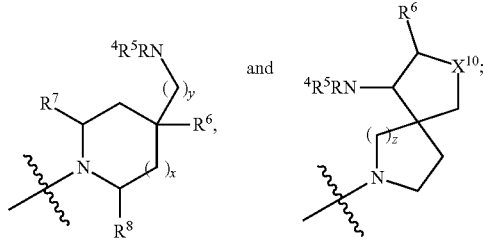

$X^{10}$ is $CR^9$ or O;
$R^4$ and $R^5$ are independently selected from hydrogen and methyl;
$R^6$ is selected from the group consisting of hydrogen, methyl, OH and $CH_2OH$;
$R^7$ and $R^8$ are hydrogen, or
$R^7$ and $R^8$ together with the atoms to which they are attached form an ethyl bridge such that $R^3$ is an azabicyclic ring;
$R^9$ is hydrogen, or
$R^6$ and $R^9$ together with the atoms to which they are attached form a 6 membered aryl;
$R^a$ is hydrogen or $C_1$-$C_3$ alkyl optionally substituted with OH, methoxy, halogen or cyano;
x is 1 or 2;
y is 0 or 1; and
z is 1 or 2.

In certain embodiments:
$L_1$ is selected from a direct bond or S;
$R^1$ is selected from hydrogen and methyl;
$R^2$ is selected from phenyl optionally substituted with halogen, a 5 to 6 membered heteroaryl wherein the heteroaryl contains one to four heteroatoms selected from the group consisting of nitrogen, oxygen and sulfur, wherein the heteroaryl is optionally substituted with one or two substituents selected from halogen, methyl and $NH_2$, and a 9-10 membered bicyclic heteroaryl wherein the bicyclic heteroaryl contains one to three heteroatoms selected from the group consisting of nitrogen, oxygen and sulfur, wherein the bicyclic heteroaryl is optionally substituted with halogen;
$R^3$ is selected from the group consisting of:

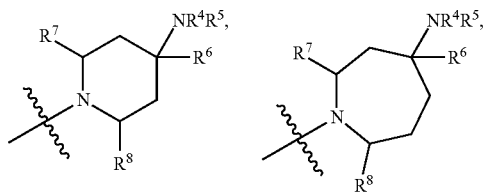

-continued

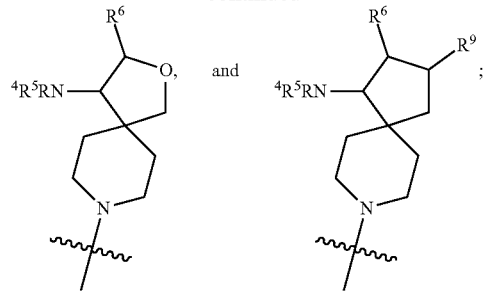

$R^4$ and $R^5$ are hydrogen;
$R^6$ is selected from hydrogen and methyl, or
$R^6$ and $R^9$ together with the atoms to which they are attached form a 6 membered aryl;
$R^7$ and $R^8$ are hydrogen, or
$R^7$ and $R^8$ together with the atoms to which they are attached form an ethyl bridge such that $R^3$ is an azabicyclic ring;
$R^a$ is hydrogen.

In another embodiment, compounds of Formula I or a stereoisomer or pharmaceutically acceptable salt thereof are provided.

In another embodiment, compounds of Formula I or a tautomer or pharmaceutically acceptable salt thereof are provided.

In another embodiment, compounds of Formula I or a stereoisomer or tautomer thereof are provided.

In another embodiment, compounds of Formula I or a stereoisomer thereof are provided.

In another embodiment, compounds of Formula I or a tautomer thereof are provided.

In another embodiment, compounds of Formula I or a pharmaceutically acceptable salt thereof are provided.

In certain embodiments, $L_1$ is selected from a direct bond, S, $CH_2$, O, NH or Se. In certain embodiments, $L_1$ is selected from a direct bond and S. In certain embodiments, $L_1$ is selected from S, $CH_2$, O or NH. In certain embodiments, $L_1$ is a direct bond. In certain embodiments, $L_1$ is S. In certain embodiments, $L_1$ is selenium (Se).

In certain embodiments, $L_1$ is selected from a direct bond, S, $CH_2$, O or NH. In certain embodiments, $L_1$ is selected from a direct bond and S. In certain embodiments, $L_1$ is selected from S, $CH_2$, O or NH. In certain embodiments, $L_1$ is a direct bond. In certain embodiments, $L_1$ is S.

In certain embodiments, $R^1$ is selected from hydrogen and methyl. In certain embodiments, $R^1$ is hydrogen. In certain embodiments, $R^1$ is methyl. In a preferred embodiment, $R^1$ is hydrogen.

In certain embodiments, $R^2$ is selected from (a) phenyl, (b) a 5 to 6 membered heteroaryl wherein the heteroaryl contains one to four heteroatoms selected from the group consisting of nitrogen, oxygen and sulfur, wherein one nitrogen heteroatom may be substituted with oxygen to form an oxide, (c) an 8-10 membered bicyclic cycloalkyl, (d) a 10 membered bicyclic aryl, (e) a 9-10 membered bicyclic heterocycle wherein the heterocycle contains one to three heteroatoms selected from the group consisting of nitrogen, oxygen and sulfur, and (f) a 9-10 membered bicyclic heteroaryl wherein the bicyclic heteroaryl contains one to three heteroatoms selected from the group consisting of nitrogen, oxygen and sulfur, wherein the phenyl, heteroaryl, bicyclic cycloalkyl, bicyclic aryl, bicyclic heterocycle and bicyclic heteroaryl are optionally substituted with one or more groups selected from the group consisting of halogen, cyano, oxo, $C_1$-$C_3$ alkyl optionally substituted with 1 to 3 groups selected from halogen, cyano and OH, $C_3$-$C_6$ cycloalkyl, $C_1$-$C_3$ alkoxy optionally substituted with 1 to 3 groups selected from halogen, cyano and OH, NHR$^a$, and a 3 to 6 membered heterocycle optionally substituted with 1 to 3 groups selected from halogen, cyano and OH, wherein the heterocycle contains one or two heteroatoms selected from nitrogen, oxygen and sulfur. The R$^2$ group may be substituted with one or more groups, meaning one to four substituents as valency allows. In certain embodiments, R$^2$ is selected from (a) phenyl optionally substituted with one or two halogen groups; (b) a 5 to 6 membered heteroaryl wherein the heteroaryl contains one to four heteroatoms selected from the group consisting of nitrogen, oxygen and sulfur, wherein the heteroaryl is optionally substituted with one or two substituents selected from halogen, $C_1$-$C_3$ alkyl optionally substituted with halogen, $C_3$-$C_6$ cycloalkyl, $C_1$-$C_3$ alkoxy, NHR$^a$, and a 3 to 6 membered heterocycle optionally substituted with an OH group, wherein the heterocycle contains one or two heteroatoms selected from nitrogen and oxygen; (c) an 8-10 membered bicyclic partially unsaturated cycloalkyl; (d) a 9-10 membered bicyclic partially unsaturated heterocycle, wherein the heterocycle contains one to three heteroatoms selected from nitrogen, oxygen and sulfur, wherein the heterocycle is optionally substituted with one to three groups selected from halogen and oxo; (e) a 9-10 membered bicyclic heteroaryl wherein the bicyclic heteroaryl contains one to three heteroatoms selected from the group consisting of nitrogen, oxygen and sulfur, wherein the bicyclic heteroaryl is optionally substituted with 1 to 3 groups selected from halogen and $C_1$-$C_3$ alkyl. In certain embodiments, R$^2$ is selected from (a) phenyl optionally substituted with one or two halogen groups; (b) a 5 to 6 membered heteroaryl wherein the heteroaryl contains one nitrogen heteroatom, wherein the heteroaryl is optionally substituted with one or two substituents selected from halogen, $C_1$-$C_3$ alkyl optionally substituted with 1 to 3 halogen groups, $C_3$ cycloalkyl, $C_1$-$C_3$ alkoxy, NHR$^a$, and a 6 membered heterocycle optionally substituted with an OH group, wherein the heterocycle contains one or two heteroatoms selected from nitrogen and oxygen; (c) an 8-10 membered bicyclic partially unsaturated cycloalkyl; (d) a 9 membered bicyclic partially unsaturated heterocycle, wherein the heterocycle contains two or three nitrogen heteroatoms, wherein the heterocycle is optionally substituted with one to three groups selected from halogen and oxo; and (e) a 9-10 membered bicyclic heteroaryl wherein the bicyclic heteroaryl contains one to three heteroatoms selected from the group consisting of nitrogen, oxygen and sulfur, wherein the bicyclic heteroaryl is optionally substituted with one group selected from halogen and $C_1$-$C_3$ alkyl. In certain embodiments, R$^2$ is selected from the group consisting of phenyl, 2-chlorophenyl, 3-chlorophenyl, 2,3-dichlorophenyl, 2-amino-3-chloropyridin-4-yl, 2,3-dichloropyridin-4-yl, 3-chloro-2-methylpyridin-4-yl, 3-chloro-2-(4-hydroxypiperidin-1-yl)pyridin-4-yl, 3-chloro-2-(methylamino)pyridin-4-yl, 2,3-dimethylpyridin-4-yl, 2-amino-3-cyclopropylpyridin-4-yl, 2-amino-5-chloropyridin-4-yl, 3-chloro-2-methoxypyridin-4-yl, 3-chloro-2-(trifluoromethyl)pyridin-4-yl, 6-amino-2-(trifluoromethyl)pyridin-3-yl, 2-amino-3-bromopyridin-4-yl, 6-aminopyridin-3-yl, 2-amino-3-fluoropyridin-4-yl, 3-chloro-2-((2-cyano-2-methylpropyl)amino)pyridin-4-yl, 2-amino-3-chloro-1-oxidopyridin-4-yl, 3-chloro-2-((2-hydroxyethyl)amino) pyridin-4-yl, bicyclo[4.2.0]octa-1(6),2,4-trien-2-yl, 2,3-dihydro-1H-pyrrolo[3,2-c]pyridin-1-yl, 3,3-difluoro-2-oxo-2,3-dihydro-1H-pyrrolo[2,3-b]pyridin-4-yl, 2,3-dihydro-1H-pyrrolo[2,3-b]pyridin-4-yl, 1H-pyrrolo[2,3-b]pyridin-4-yl, 5-chloro-1H-pyrrolo[2,3-b]pyridin-4-yl, 1-methyl-1H-pyrrolo[2,3-b]pyridin-4-yl, 1H-pyrrolo[2,3-b]pyridin-3-yl, imidazo[1,2-a]pyridin-3-yl, 1H-pyrazolo[3,4-b]pyridin-3-yl, 1H-indazol-3-yl, 1H-pyrrolo[2,3-b]pyridin-5-yl, imidazo[1,2-a]pyrimidin-3-yl, isoquinolin-5-yl and 1H-indol-3-yl.

In certain embodiments, R$^2$ is selected from phenyl, a 5 to 6 membered heteroaryl wherein the heteroaryl contains one to four heteroatoms selected from the group consisting of nitrogen, oxygen and sulfur, a 10 membered bicyclic aryl, and a 9-10 membered bicyclic heteroaryl wherein the bicyclic heteroaryl contains one to three heteroatoms selected from the group consisting of nitrogen, oxygen and sulfur, wherein the phenyl, heteroaryl, bicyclic aryl and bicyclic heteroaryl are optionally substituted with one or more groups selected from the group consisting of halogen, cyano, $C_1$-$C_3$ alkyl optionally substituted with halogen, cyano or OH, —O($C_1$-$C_3$ alkyl) optionally substituted with halogen, cyano or OH, NHR$^a$, and 3 to 6 membered heterocycle optionally substituted with halogen, cyano or OH, wherein the heterocycle contains one or two heteroatoms selected from nitrogen, oxygen and sulfur. In certain embodiments, R$^2$ is selected from phenyl optionally substituted with halogen, a 5 to 6 membered heteroaryl wherein the heteroaryl contains one to four heteroatoms selected from the group consisting of nitrogen, oxygen and sulfur, wherein the heteroaryl is optionally substituted with one or two substituents selected from halogen, methyl and NH$_2$, and a 9-10 membered bicyclic heteroaryl wherein the bicyclic heteroaryl contains one to three heteroatoms selected from the group consisting of nitrogen, oxygen and sulfur, wherein the bicyclic heteroaryl is optionally substituted with halogen. In certain embodiments, R$^2$ is selected from the group consisting of 2,3-dichlorophenyl, 2-amino-3-chloropyridin-4-yl, 2,3-dichloropyridin-4-yl, 3-chloro-2-methylpyridin-4-yl, 1H-pyrrolo[2,3-b]pyridin-4-yl and 5-chloro-1H-pyrrolo[2,3-b]pyridin-4-yl.

In certain embodiments, R$^2$ is phenyl optionally substituted with one or more groups selected from the group consisting of halogen, cyano, $C_1$-$C_3$ alkyl optionally substituted with 1 to 3 groups selected from halogen, cyano and OH, $C_1$-$C_3$ alkoxy optionally substituted with 1 to 3 groups selected from halogen, cyano and OH, NHR$^a$, and 3 to 6 membered heterocycle optionally substituted with 1 to 3 groups selected from halogen, cyano and OH, wherein the heterocycle contains one or two heteroatoms selected from nitrogen, oxygen and sulfur. In certain embodiments, R$^2$ is phenyl optionally substituted with halogen. In certain embodiments, R$^2$ is phenyl optionally substituted with one or two halogen groups. In certain embodiments, R$^2$ is selected from the group consisting of phenyl, 2-chlorophenyl, 3-chlorophenyl and 2,3-dichlorophenyl.

In certain embodiments, R$^2$ is phenyl optionally substituted with one or more groups selected from the group consisting of halogen, cyano, $C_1$-$C_3$ alkyl optionally substituted with halogen, cyano or OH, —O($C_1$-$C_3$ alkyl) optionally substituted with halogen, cyano or OH, NHR$^a$, and 3 to 6 membered heterocycle optionally substituted with halogen, cyano or OH, wherein the heterocycle contains one or two heteroatoms selected from nitrogen, oxygen and sulfur. In certain embodiments, R$^2$ is phenyl optionally substituted with halogen. In certain embodiments, R$^2$ is 2,3-dichlorophenyl.

In certain embodiments, R$^2$ is a 5 to 6 membered heteroaryl wherein the heteroaryl contains one to four heteroatoms selected from the group consisting of nitrogen, oxygen and sulfur, wherein one nitrogen heteroatom may be substituted with oxygen to form an oxide, wherein the heteroaryl may be optionally substituted with one or more groups selected from the group consisting of halogen, cyano, $C_1$-$C_3$ alkyl optionally substituted with 1 to 3 groups selected from halogen, cyano and OH, $C_3$-$C_6$ cycloalkyl, $C_1$-$C_3$ alkoxy optionally substituted with 1 to 3 groups selected from halogen, cyano and OH, NHR$^a$, and 3 to 6 membered heterocycle optionally substituted with 1 to 3 groups selected from halogen, cyano and OH, wherein the heterocycle contains one or two heteroatoms selected from nitrogen, oxygen and sulfur. In certain embodiments, R$^2$ is a 5 to 6 membered heteroaryl wherein the heteroaryl contains one to four heteroatoms selected from the group consisting of nitrogen, oxygen and sulfur, wherein one nitrogen heteroatom may be substituted with oxygen to form an oxide, wherein the heteroaryl is optionally substituted with one or two substituents selected from halogen, $C_1$-$C_3$ alkyl optionally substituted with 1 to 3 halogen groups, $C_3$-$C_6$ cycloalkyl, $C_1$-$C_3$ alkoxy, NHR$^a$, and a 3 to 6 membered heterocycle optionally substituted with an OH group, wherein the heterocycle contains one or two heteroatoms selected from nitrogen and oxygen. In certain embodiments, R$^2$ is a 5 to 6 membered heteroaryl wherein the heteroaryl contains one to four heteroatoms selected from the group consisting of nitrogen, oxygen and sulfur, wherein the heteroaryl is optionally substituted with one or two substituents selected from halogen, $C_1$-$C_3$ alkyl optionally substituted with 1 to 3 halogen groups, $C_3$-$C_6$ cycloalkyl, $C_1$-$C_3$ alkoxy, NHR$^a$, and a 3 to 6 membered heterocycle optionally substituted with an OH group, wherein the heterocycle contains one or two heteroatoms selected from nitrogen and oxygen. In certain embodiments, R$^2$ is a 5 to 6 membered heteroaryl wherein the heteroaryl contains one to four heteroatoms selected from the group consisting of nitrogen, oxygen and sulfur, wherein one nitrogen heteroatom may be substituted with oxygen to form an oxide, wherein the heteroaryl is optionally substituted with one or two substituents selected from halogen, methyl, trifluoromethyl, cyclopropyl, methoxy, NH$_2$, NHCH$_2$C(CH$_3$)$_2$CN, NHCH$_2$CH$_2$OH and 4-hydroxypiperdin-1-yl. In certain embodiments, R$^2$ is a 5 to 6 membered heteroaryl wherein the heteroaryl contains one nitrogen heteroatom, wherein the nitrogen heteroatom may be substituted with oxygen to form an oxide, wherein the heteroaryl is optionally substituted with one or two substituents selected from halogen, $C_1$-$C_3$ alkyl optionally substituted with 1 to 3 halogen groups, $C_3$-$C_6$ cycloalkyl, $C_1$-$C_3$ alkoxy, NHR$^a$, and a 3 to 6 membered heterocycle optionally substituted with an OH group, wherein the heterocycle contains one or two heteroatoms selected from nitrogen and oxygen. In certain embodiments, R$^2$ is a 5 to 6 membered heteroaryl wherein the heteroaryl contains one nitrogen heteroatom, wherein the heteroaryl is optionally substituted with one or two substituents selected from halogen, $C_1$-$C_3$ alkyl optionally substituted with 1 to 3 halogen groups, $C_3$-$C_6$ cycloalkyl, $C_1$-$C_3$ alkoxy, NHR$^a$, and a 3 to 6 membered heterocycle optionally substituted with an OH group, wherein the heterocycle contains one or two heteroatoms selected from nitrogen and oxygen. In certain embodiments, R$^2$ is a 5 to 6 membered heteroaryl wherein the heteroaryl contains one nitrogen heteroatom, wherein the nitrogen heteroatom may be substituted with oxygen to form an oxide, wherein the heteroaryl is optionally substituted with one or two substituents selected from halogen, methyl, trifluoromethyl, cyclopropyl, methoxy, NH$_2$, NHCH$_2$C(CH$_3$)$_2$CN, NHCH$_2$CH$_2$OH and 4-hydroxypiperdin-1-yl. In certain embodiments, R$^2$ is a 5 to 6 membered heteroaryl wherein the heteroaryl contains one nitrogen heteroatom, wherein the heteroaryl is optionally substituted with one or two substituents selected from halogen, methyl, trifluoromethyl, cyclopropyl, methoxy, NH$_2$, NHCH$_2$C(CH$_3$)$_2$CN, NHCH$_2$CH$_2$OH and 4-hydroxypiperdin-1-yl. In certain embodiments, R$^2$ is a pyridine, wherein the nitrogen heteroatom may be substituted with oxygen to form an oxide, wherein the pyridine is optionally substituted with one or two substituents selected from halogen, methyl, trifluoromethyl, cyclopropyl, methoxy, NH$_2$, NHCH$_2$C(CH$_3$)$_2$CN, NHCH$_2$CH$_2$OH and 4-hydroxypiperdin-1-yl. In certain embodiments, R$^2$ is selected from the group consisting of 2-amino-3-chloropyridin-4-yl, 2,3-dichloropyridin-4-yl, 3-chloro-2-methylpyridin-4-yl, 3-chloro-2-(4-hydroxypiperidin-1-yl)pyridin-4-yl, 3-chloro-2-(methylamino)pyridin-4-yl, 2,3-dimethylpyridin-4-yl, 2-amino-3-cyclopropylpyridin-4-yl, 2-amino-5-chloropyridin-4-yl, 3-chloro-2-methoxypyridin-4-yl, 3-chloro-2-(trifluoromethyl)pyridin-4-yl, 6-amino-2-(trifluoromethyl)pyridin-3-yl, 2-amino-3-bromopyridin-4-yl, 6-aminopyridin-3-yl, 2-amino-3-fluoropyridin-4-yl, 3-chloro-2-((2-cyano-2-methylpropyl)amino)pyridin-4-yl, 2-amino-3-chloro-1-oxidopyridin-4-yl and 3-chloro-2-((2-hydroxyethyl)amino)pyridin-4-yl.

In certain embodiments, R$^2$ is a 5 to 6 membered heteroaryl wherein the heteroaryl contains one to four heteroatoms selected from the group consisting of nitrogen, oxygen and sulfur, optionally substituted with one or more groups selected from the group consisting of halogen, cyano, $C_1$-$C_3$ alkyl optionally substituted with halogen, cyano or OH, —O($C_1$-$C_3$ alkyl) optionally substituted with halogen, cyano or OH, NHR$^a$, and 3 to 6 membered heterocycle optionally substituted with halogen, cyano or OH, wherein the heterocycle contains one or two heteroatoms selected from nitrogen, oxygen and sulfur. In certain embodiments, R$^2$ is a 5 to 6 membered heteroaryl wherein the heteroaryl contains one to four heteroatoms selected from the group consisting of nitrogen, oxygen and sulfur, wherein the heteroaryl is optionally substituted with one or two substituents selected from halogen, methyl and NH$_2$. In certain embodiments, R$^2$ is selected from the group consisting of 2-amino-3-chloropyridin-4-yl, 2,3-dichloropyridin-4-yl, and 3-chloro-2-methylpyridin-4-yl.

In certain embodiments, R$^2$ is an 8-10 membered bicyclic cycloalkyl. In certain embodiments, R$^2$ is an 8-10 membered bicyclic partially unsaturated cycloalkyl. In certain embodiments, R$^2$ is bicyclo[4.2.0]octa-1(6),2,4-trien-2-yl.

In certain embodiments, R$^2$ is a 9-10 membered bicyclic heterocycle, wherein the heterocycle contains one to three heteroatoms selected from nitrogen, oxygen and sulfur, wherein the heterocycle is optionally substituted with one or more groups selected from halogen and oxo. In certain embodiments, R$^2$ is a 9-10 membered bicyclic partially unsaturated heterocycle, wherein the heterocycle contains one to three heteroatoms selected from nitrogen, oxygen and sulfur, wherein the heterocycle is optionally substituted with one to three groups selected from halogen and oxo. In certain embodiments, R$^2$ is a 9 membered bicyclic partially unsaturated heterocycle, wherein the heterocycle contains two or three nitrogen heteroatoms, wherein the heterocycle is optionally substituted with one to three groups selected from halogen and oxo. In certain embodiments, R$^2$ is 2,3-dihydro-1H-pyrrolo[3,2-c]pyridin-1-yl, 3,3-difluoro-2-oxo-2,3-dihydro-1H-pyrrolo[2,3-b]pyridin-4-yl and 2,3-dihydro-1H-pyrrolo[2,3-b]pyridin-4-yl.

In certain embodiments, R$^2$ is a 9-10 membered bicyclic heteroaryl wherein the bicyclic heteroaryl contains one to three heteroatoms selected from the group consisting of nitrogen, oxygen and sulfur, wherein the bicyclic heteroaryl is optionally substituted with one or more groups selected from the group consisting of halogen, cyano, $C_1$-$C_3$ alkyl optionally substituted with 1 to 3 groups selected from halogen, cyano and OH, $C_1$-$C_3$ alkoxy optionally substituted with 1 to 3 groups selected from halogen, cyano and OH, NHR$^a$, and 3 to 6 membered heterocycle optionally substituted with 1 to 3 groups selected from halogen, cyano and OH, wherein the heterocycle contains one or two heteroatoms selected from nitrogen, oxygen and sulfur. In certain embodiments, $R^2$ is a 9-10 membered bicyclic heteroaryl wherein the bicyclic heteroaryl contains one to three heteroatoms selected from the group consisting of nitrogen, oxygen and sulfur, wherein the bicyclic heteroaryl is optionally substituted with 1 to 3 groups selected from halogen and $C_1$-$C_3$ alkyl. In certain embodiments, $R^2$ is a 9-10 membered bicyclic heteroaryl wherein the bicyclic heteroaryl contains one to three nitrogen heteroatoms, wherein the bicyclic heteroaryl is optionally substituted with one group selected from halogen and methyl. In certain embodiments, $R^2$ is selected from the group consisting of 1H-pyrrolo[2,3-b]pyridin-4-yl, 5-chloro-1H-pyrrolo[2,3-b]pyridin-4-yl, 1-methyl-1H-pyrrolo[2,3-b]pyridin-4-yl, 1H-pyrrolo[2,3-b]pyridin-3-yl, imidazo[1,2-a]pyridin-3-yl, 1H-pyrazolo[3,4-b]pyridin-3-yl, 1H-indazol-3-yl, 1H-pyrrolo[2,3-b]pyridin-5-yl, imidazo[1,2-a]pyrimidin-3-yl, isoquinolin-5-yl and 1H-indol-3-yl.

In certain embodiments, $R^2$ is a 9-10 membered bicyclic heteroaryl wherein the bicyclic heteroaryl contains one to three heteroatoms selected from the group consisting of nitrogen, oxygen and sulfur, optionally substituted with one or more groups selected from the group consisting of halogen, cyano, $C_1$-$C_3$ alkyl optionally substituted with halogen, cyano or OH, —O($C_1$-$C_3$ alkyl) optionally substituted with halogen, cyano or OH, NHR$^a$, and 3 to 6 membered heterocycle optionally substituted with halogen, cyano or OH, wherein the heterocycle contains one or two heteroatoms selected from nitrogen, oxygen and sulfur. In certain embodiments, $R^2$ is a 9-10 membered bicyclic heteroaryl wherein the bicyclic heteroaryl contains one to three heteroatoms selected from the group consisting of nitrogen, oxygen and sulfur, wherein the bicyclic heteroaryl is optionally substituted with halogen. In certain embodiments, $R^2$ is selected from the group consisting of 1H-pyrrolo[2,3-b]pyridin-4-yl and 5-chloro-1H-pyrrolo[2,3-b]pyridin-4-yl.

In certain embodiments, $R^a$ is hydrogen or $C_1$-$C_4$ alkyl optionally substituted with 1 to 3 groups selected from OH, methoxy, halogen and cyano. In certain embodiments, $R^a$ is hydrogen or $C_1$-$C_4$ alkyl optionally substituted with 1 to 3 groups selected from OH and cyano. In certain embodiments, $R^a$ is hydrogen, methyl, 2-cyano-2-methylpropyl or 2-hydroxyethyl. In certain embodiments, $R^a$ is hydrogen or methyl.

In certain embodiments, $R^a$ is hydrogen or $C_1$-$C_3$ alkyl optionally substituted with OH, methoxy, halogen or cyano. In certain embodiments, $R^a$ is hydrogen or $C_1$-$C_3$ alkyl optionally substituted with OH. In certain embodiments, $R^a$ is hydrogen.

In certain embodiments, $R^3$ is selected from the group consisting of:

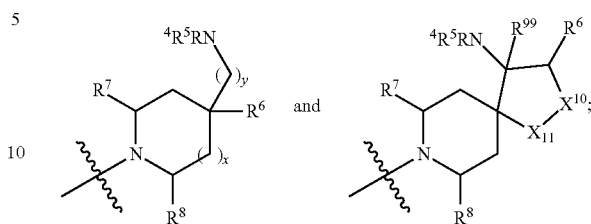

wherein $X^{10}$ is $CR^9$ or O, $X^{11}$ is $CH_2$ or O, wherein only one of $X^{10}$ and $X^{11}$ may be O; $R^4$ and $R^5$ are independently selected from hydrogen and $C_1$-$C_3$ alkyl; $R^6$ is selected from the group consisting of hydrogen, OH and $C_1$-$C_3$ alkyl optionally substituted with an OH group, or $R^6$ and $R^9$ together with the atoms to which they are attached form a 6 membered aryl or a 5 to 6 membered heteroaryl, wherein the heteroaryl contains 1 or 2 heteroatoms selected from nitrogen, oxygen and sulfur, wherein the aryl and heteroaryl are optionally substituted with 1 or 2 groups selected from the group consisting of halogen, cyano, $C_1$-$C_3$ alkyl and $C_1$-$C_3$ alkoxy; $R^7$ and $R^8$ are hydrogen, or $R^7$ and $R^8$ together with the atoms to which they are attached form an ethyl bridge such that $R^3$ is an azabicyclic ring; $R^{99}$ is hydrogen or deuterium; x is 1 or 2; and y is 0 or 1.

In certain embodiments, $R^3$ is selected from the group consisting of:

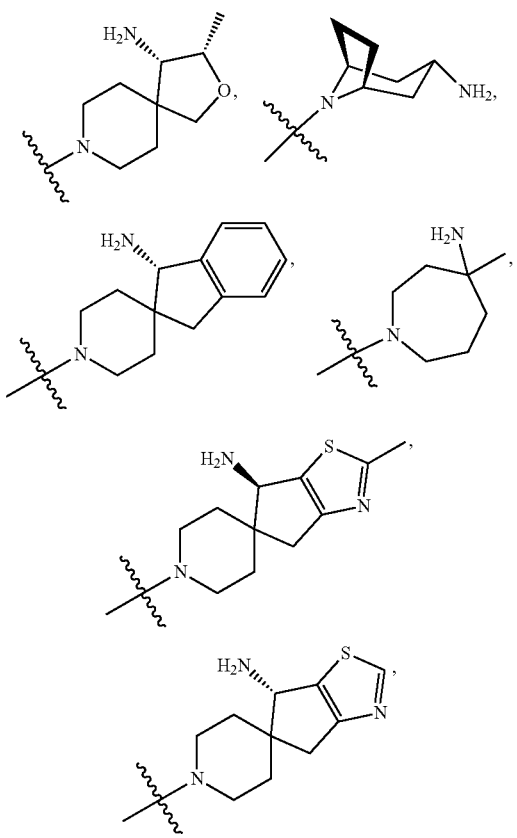

-continued
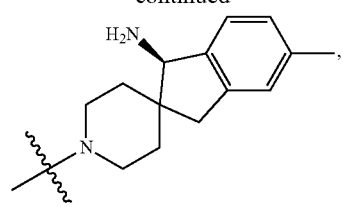
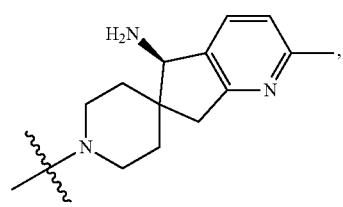
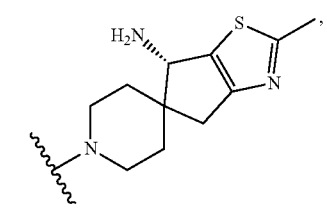
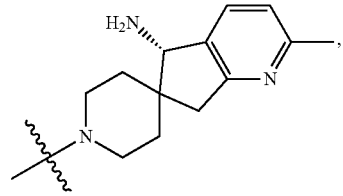
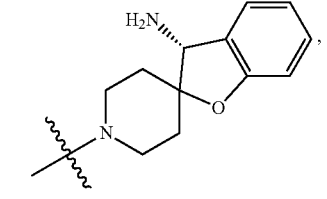
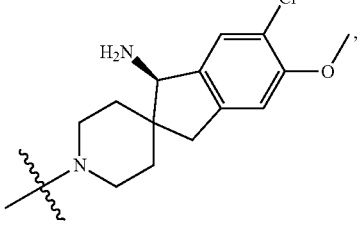
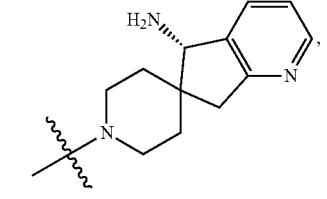
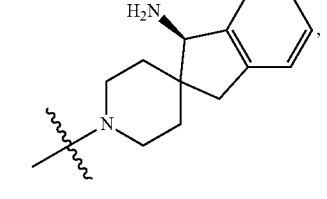
-continued
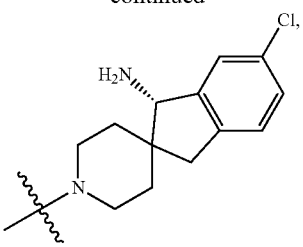
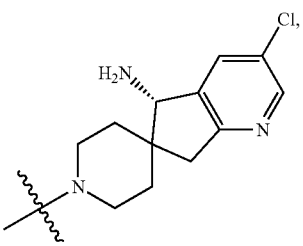
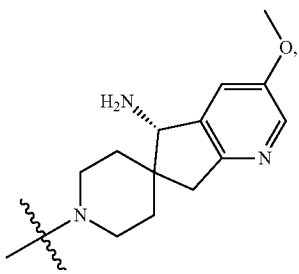
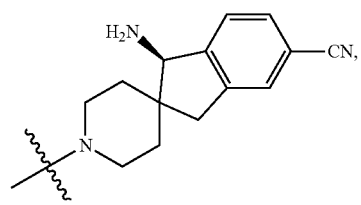
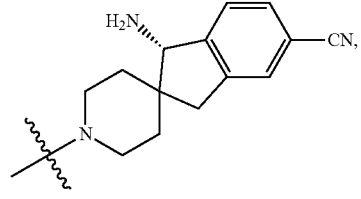
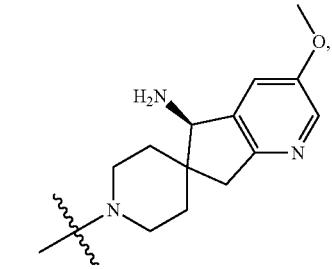
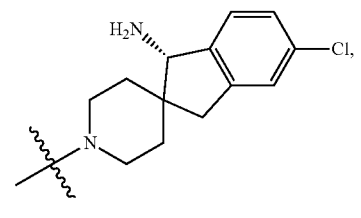

21
-continued

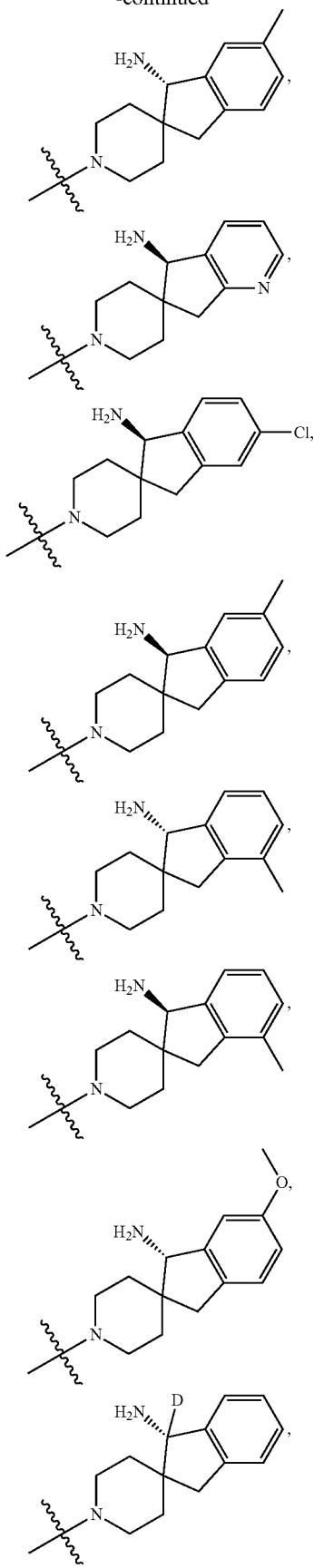

22
-continued

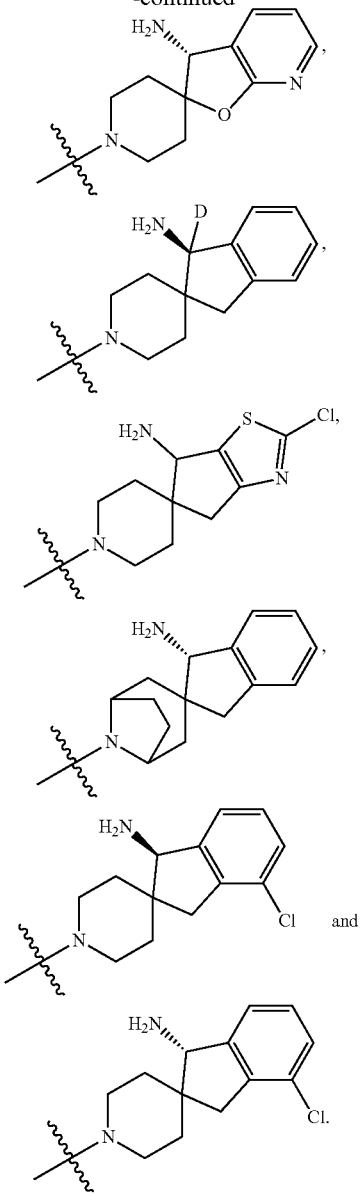

In certain embodiments, $R^3$ is selected from the group consisting of:

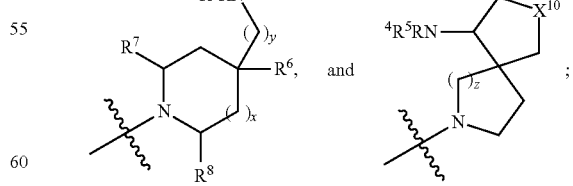

wherein $X^{10}$ is $CR^9$ or O; $R^4$ and $R^5$ are independently selected from hydrogen and methyl; $R^6$ is selected from the group consisting of hydrogen, methyl, OH and $CH_2OH$; $R^7$ is hydrogen, or $R^6$ and $R^7$ together with the atoms to which they are attached form a 6 membered aryl; $R^7$ and $R^8$ are hydrogen, or $R^7$ and $R^8$ together with the atoms to which they are attached form an ethyl bridge such that $R^3$ is an azabicyclic ring; x is 1 or 2; y is 0 or 1; and z is 1 or 2. In certain embodiments, $R^3$ is selected from the group consisting of (3S,4S)-4-amino-3-methyl-2-oxa-8-azaspiro[4.5]decan-8-yl, (1R,3s,5S)-3-amino-8-azabicyclo[3.2.1]octan-8-yl, 1-amino-1,3-dihydrospiro[indene-2,4'-piperidin]-1'-yl, and 4-amino-4-methylazepan-1-yl.

In certain embodiments, x is 1 or 2. In certain embodiments, x is 1. In certain embodiments, x is 2.

In certain embodiments, y is 0 or 1. In certain embodiments, y is 0. In certain embodiments, y is 1.

In certain embodiments, z is 1 or 2. In certain embodiments, z is 1. In certain embodiments, z is 2.

In certain embodiments, x is 1 and y is 0, such that $R^3$ has the structure:

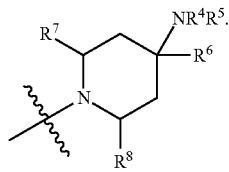

In certain embodiments, x is 1, y is 0, and $R^7$ and $R^8$ together with the atoms to which they are attached form an ethyl bridge such that $R^3$ is an azabicyclic ring, such that $R^3$ has the structure:

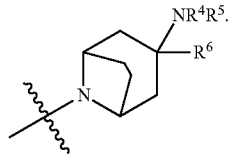

In certain embodiments, $R^3$ is (1R,3s,5S)-3-amino-8-azabicyclo[3.2.1]octan-8-yl.

In certain embodiments, x is 1, y is 0, and $R^7$ and $R^8$ together with the atoms to which they are attached form an ethyl bridge such that $R^3$ is an azabicyclic ring, such that $R^3$ has the structure:

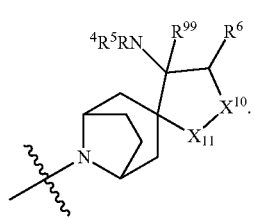

In certain embodiments, x is 2 and y is 0, such that $R^3$ has the structure:

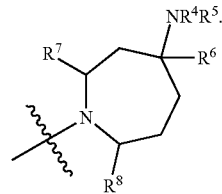

In certain embodiments, $R^3$ is 4-amino-4-methylazepan-1-yl.

In certain embodiments, $X^{10}$ is O, and $X^{11}$ is $CH_2$, such that $R^3$ has the structure:

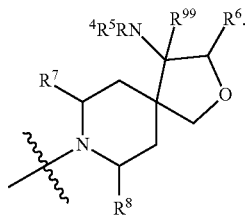

In certain embodiments, z is 2 and $X^{10}$ is O, such that $R^3$ has the structure:

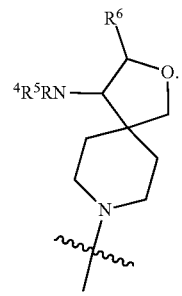

In certain embodiments, $R^3$ is (3S,4S)-4-amino-3-methyl-2-oxa-8-azaspiro[4.5]decan-8-yl.

In certain embodiments, $X^{10}$ is $CR^9$, and $X^{11}$ is O, such that $R^3$ has the structure:

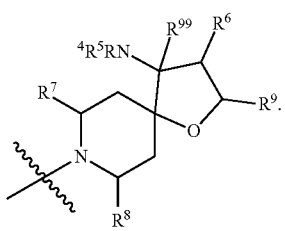

In these embodiments, $R^6$ and $R^9$ together with the atoms to which they are attached form a 6 membered aryl or a 5 to 6 membered heteroaryl, wherein the heteroaryl contains 1 or 2 heteroatoms selected from nitrogen, oxygen and sulfur, wherein the aryl and heteroaryl are optionally substituted with 1 or 2 groups selected from the group consisting of halogen, cyano, $C_1$-$C_3$ alkyl and $C_1$-$C_3$ alkoxy.

In certain embodiments, $X^{10}$ is $CR^9$, and $X^{11}$ is $CH_2$, such that $R^3$ has the structure:

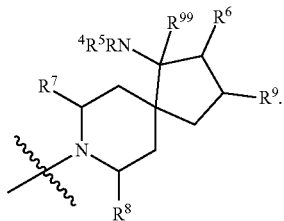

In these embodiments, $R^6$ and $R^9$ together with the atoms to which they are attached form a 6 membered aryl or a 5 to 6 membered heteroaryl, wherein the heteroaryl contains 1 or 2 heteroatoms selected from nitrogen, oxygen and sulfur, wherein the aryl and heteroaryl are optionally substituted with 1 or 2 groups selected from the group consisting of halogen, cyano, $C_1$-$C_3$ alkyl and $C_1$-$C_3$ alkoxy.

In certain embodiments, z is 2 and $X^{10}$ is $CR^9$, such that $R^3$ has the structure:

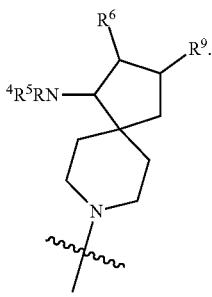

In certain embodiments, z is 2, $X^{10}$ is $CR^9$, and $R^6$ and $R^9$ together with the atoms to which they are attached form a 6 membered aryl, such that $R^3$ has the structure:

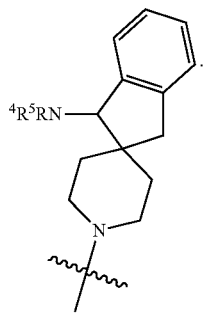

In certain embodiments, $R^3$ is 1-amino-1,3-dihydrospiro[indene-2,4'-piperidin]-1'-yl.

In certain embodiments, $R^3$ is selected from the group consisting of:

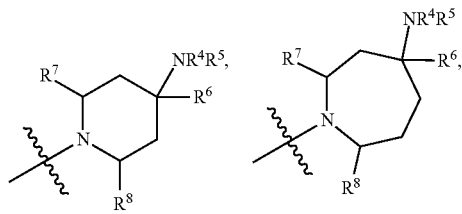

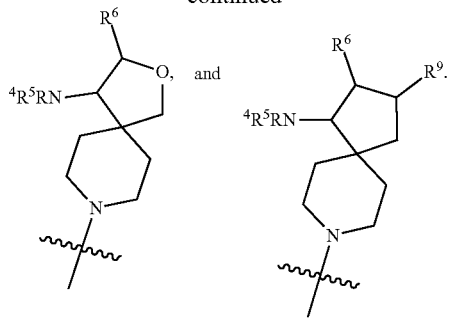

In certain embodiments, $R^4$ and $R^5$ are independently selected from hydrogen and methyl. In certain embodiments, $R^4$ and $R^5$ are hydrogen.

In certain embodiments, $R^6$ is selected from the group consisting of hydrogen, methyl, OH and $CH_2OH$. In certain embodiments, $R^6$ is selected from hydrogen and methyl. In certain embodiments, $R^6$ is methyl. In certain embodiments, $R^6$ is hydrogen.

In certain embodiments, $R^6$ is selected from the group consisting of hydrogen, methyl, OH and $CH_2OH$.

In certain embodiments, $X^{10}$ is $CR^9$ or O. In certain embodiments, $X^{10}$ is $CR^9$. In certain embodiments, $X^{10}$ is O.

In certain embodiments, $R^6$ is selected from the group consisting of hydrogen, methyl, OH and $CH_2OH$; and $R^9$ is hydrogen.

In certain embodiments, $X^{10}$ is $CR^9$, and $R^6$ and $R^9$ together with the atoms to which they are attached form a 6 membered aryl or a 5 to 6 membered heteroaryl, wherein the heteroaryl contains 1 or 2 heteroatoms selected from nitrogen, oxygen and sulfur, wherein the aryl and heteroaryl are optionally substituted with 1 or 2 groups selected from the group consisting of halogen, cyano, $C_1$-$C_3$ alkyl and $C_1$-$C_3$ alkoxy. In certain embodiments, $X^{10}$ is $CR^9$, and $R^6$ and $R^9$ together with the atoms to which they are attached form a 6 membered aryl or a 5 to 6 membered heteroaryl with 1 or 2 heteroatoms selected from nitrogen and sulfur, wherein the aryl and heteroaryl are optionally substituted with 1 or 2 groups selected from halogen, methyl, methoxy and cyano. In certain embodiments, $X^{10}$ is $CR^9$, and $R^6$ and $R^9$ together with the atoms to which they are attached form a 6 membered aryl or a 5 to 6 membered heteroaryl with 1 or 2 heteroatoms selected from nitrogen and sulfur, wherein the aryl is optionally substituted with 1 or 2 groups selected from halogen, methyl, methoxy and cyano, and the heteroaryl is optionally substituted with halogen, methyl or methoxy.

In certain embodiments, $X^{10}$ is $CR^9$, and $R^6$ and $R^9$ together with the atoms to which they are attached form a 6 membered aryl, such that $R^3$ has the structure:

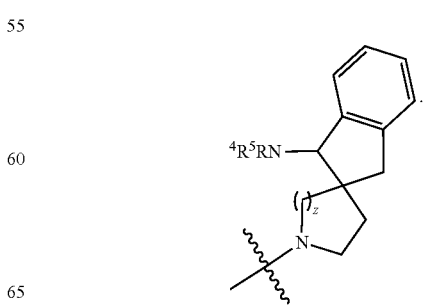

In certain embodiments, $R^7$ and $R^8$ together with the atoms to which they are attached form an ethyl bridge such that $R^3$ is an azabicyclic ring, such that $R^3$ has the structure:

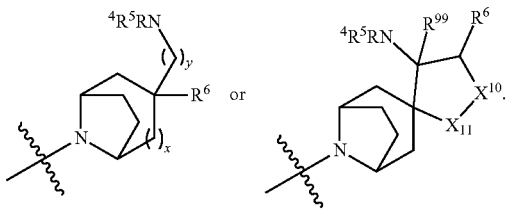

In certain embodiments, $R^7$ and $R^8$ are hydrogen, or $R^7$ and $R^8$ together with the atoms to which they are attached form an ethyl bridge such that $R^3$ is an azabicyclic ring. In certain embodiments, $R^7$ and $R^8$ are hydrogen. In certain embodiments, $R^7$ and $R^8$ together with the atoms to which they are attached form an ethyl bridge such that $R^3$ is an azabicyclic ring, such that $R^3$ has the structure:

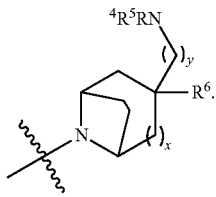

In certain embodiments, $R^{99}$ is hydrogen or deuterium. In a preferred embodiment, $R^{99}$ is hydrogen. In certain embodiments, $R^{99}$ is deuterium.

In certain embodiments a compound of Examples 1 to 84 is provided. In certain embodiments, a compound of Examples 1, 2, 4-9, 11-14, 16-20, 22-27, 29-55, 58-71, 73, 74, 76, 77, and 79-84 is provided. In certain embodiments, a compound of Examples 1, 2, 5-8, 14, 17-19, 22-27, 29-35, 37-41, 44-48, 50-54, 58, 61, 62, 64-71, 73, 76, 77, 79, 81, 83 and 84 is provided. In certain embodiments, a compound of Examples 7, 17, 18, 30, 31, 32, 37, 38, 40, 45, 67, 69, 81 and 84 is provided. In certain embodiments, a compound of Examples 1, 5-8, 14, 16-20, 22-27, 29-39, 41, 44-55, 57-59, 61, 62, 64-67, 69-71, 73-77, 81, 83 and 84 is provided. In certain embodiments, a compound of Examples 1, 6-8, 14, 16-18, 22-25, 27, 30, 32, 34-39, 41, 44, 45, 47, 48, 50-55, 58, 61, 62, 65-67, 70, 73, 74, 76, 77, 81, 83 and 84 is provided. In certain embodiments, a compound of Examples 6, 17, 18, 22-25, 27, 30, 32, 34-36, 39, 41, 44, 45, 48, 50, 52-54, 58, 61, 62, 66, 70, 73, 74, 76, 81, 83 and 84 is provided.

In certain embodiments a compound of Examples 1 to 14 is provided. In certain embodiments, a compound of Examples 1, 2, 4, 5, 6, 7, 8, 9, 11, 12, 13, and 14 is provided.

In certain embodiments, a compound of Formula I is provided. In certain embodiments, a compound of Formula I is provided, with the proviso that the compound is not Example 3, 10, 15, 21, 28, 56, 57, 72, 75 or 78. In certain embodiments, a compound of Formula I is provided, with the proviso that the compound is not Example 3, 4, 9-13, 15, 16, 20, 21, 28, 36, 42, 43, 49, 55-57, 60, 63, 72, 74, 75, 78, 80 or 82. In certain embodiments, a compound of Formula I is provided, with the proviso that the compound is not Example 1-6, 8-16, 19-29, 33-36, 39, 41-44, 46-66, 68, 70-80, 82 or 83. In certain embodiments, a compound of Formula I is provided, with the proviso that the compound is not Example 2-4, 9-13, 15, 21, 28, 40, 42, 43, 56, 60, 63, 68, 72, 78-80 or 82. In certain embodiments, a compound of Formula I is provided, with the proviso that the compound is not Example 2-5, 9-13, 15, 19-21, 26, 28, 29, 31, 33, 40, 42, 43, 46, 49, 56, 57, 59, 60, 63, 64, 68, 69, 71, 72, 75, 78-80 or 82. In certain embodiments, a compound of Formula I is provided, with the proviso that the compound is not Example 1-5, 7-16, 19-21, 26, 28, 29, 31, 33, 37, 38, 40, 42, 43, 46, 47, 49, 51, 55-57, 59, 60, 63-65, 67-69, 71, 72, 75, 77-80 or 82.

In certain embodiments, a compound of Formula I is provided. In certain embodiments, a compound of Formula I is provided, with the proviso that the compound is not Example 2, 3, 11, 12 or 13. In certain embodiments, a compound of Formula I is provided, with the proviso that the compound is not Example 2, 3, 4, 9, 10, 11, 12 or 13.

Every Example or pharmaceutically acceptable salt thereof may be claimed individually or grouped together in any combination with any number of each and every embodiment described herein.

It will be appreciated that certain compounds described herein may contain asymmetric or chiral centers, and therefore exist in different stereoisomeric forms. It is intended that all stereoisomeric forms of the compounds described herein, including but not limited to, diastereomers, enantiomers and atropisomers, as well as mixtures thereof such as racemic mixtures, form part of the present compounds.

In the structures shown herein, where the stereochemistry of any particular chiral atom is not specified, then all stereoisomers are contemplated and included as the compounds described herein. Where stereochemistry is specified by a solid wedge or dashed line representing a particular configuration, then that stereoisomer is so specified and defined.

The present invention includes all pharmaceutically acceptable isotopically-labeled compounds of Formula I wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $_{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of Formula I, for example those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements.

Isotopically-labeled compounds of Formula I can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g., $D_2O$, $d_6$-acetone (or $(CD_3)_2CO$), $d_6$-DMSO (or $(CD_3)_2SO$).

It will also be appreciated that certain compounds of Formula I may be used as intermediates for further compounds of Formula I.

It will be further appreciated that the compounds described herein may exist in unsolvated, as well as solvated forms with pharmaceutically acceptable solvents, such as water, ethanol, and the like, and it is intended that the compounds embrace both solvated and unsolvated forms.

Each of the embodiments of the compounds of the present invention described herein can be combined with one or more other embodiments of the compounds of the present invention described herein not inconsistent with the embodiment(s) with which it is combined.

Synthesis of Compounds

Compounds described herein may be synthesized by synthetic routes that include processes analogous to those well-known in the chemical arts, particularly in light of the description contained herein. The starting materials are generally available from commercial sources such as Sigma-Aldrich (St. Louis, MO), Alfa Aesar (Ward Hill, MA), or TCI (Portland, OR), or are readily prepared using methods well known to those skilled in the art (e.g., prepared by methods generally described in Louis F. Fieser and Mary Fieser, *Reagents for Organic Synthesis*. v. 1-23, New York: Wiley 1967-2006 ed. (also available via the Wiley InterScience® website), or *Beilsteins Handbuch der organischen Chemie*, 4, Aufl. ed. Springer-Verlag, Berlin, including supplements (also available via the Beilstein online database)).

For illustrative purposes, Schemes 1 and 2 show a general method for preparing the compounds described herein, as well as key intermediates. For a more detailed description of the individual reaction steps, see the Examples section below. Those skilled in the art will appreciate that other synthetic routes may be used to synthesize the compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

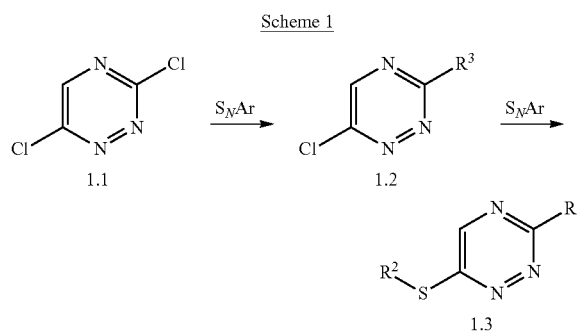

Scheme 1

Scheme 1 shows a general scheme for the synthesis of compound 1.3.3,6-Dichloro-1,2,4-triazine 1.1 may be subjected to a SNAr reaction to provide triazine 1.2, where $R^3$ is as defined herein. Triazine 1.2 may be subjected to a SNAr reaction to provide triazine 1.3, where $R^3$ is as defined herein.

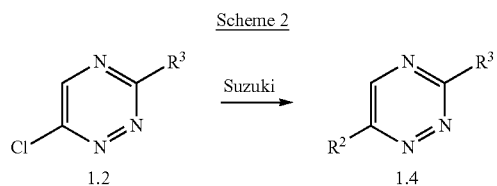

Scheme 2

Scheme 1 shows a general scheme for the synthesis of compound 1.4. Triazine 1.2 may be subjected to a Suzuki reaction to provide triazine 1.4, where $R^2$ and $R^3$ are as defined herein.

Methods of Separation

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. *Stereochemistry of Organic Compounds*. New York: John Wiley & Sons, Inc., 1994; Lochmuller, C. H., et al. "Chromatographic resolution of enantiomers: Selective review." *J. Chromatogr*. Vol. 113, No. 3 (1975): pp. 283-302). Racemic mixtures of chiral compounds described herein may be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., ed. *Drug Stereochemistry: Analytical Methods and Pharmacology*. New York: Marcel Dekker, Inc., 1993.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid, can result in formation of the diastereomeric salts.

Alternatively, by method (2), the substrate to be resolved is reacted with one enantiomer of a chiral compound to form a diastereomeric pair (Eliel, E. and Wilen, S. *Stereochemistry of Organic Compounds*. New York: John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, a-methoxy-α-(trifluoromethyl)phenyl acetate (Jacob III, Peyton. "Resolution of (±)-5-Bromonornicotine. Synthesis of (R)- and (S)-Nornicotine of High Enantiomeric Purity." *J. Org. Chem.* Vol. 47, No. 21 (1982): pp. 4165-4167), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111).

By method (3), a racemic mixture of two enantiomers can be separated by chromatography using a chiral stationary phase (Lough, W. J., ed. *Chiral Liquid Chromatography*. New York: Chapman and Hall, 1989; Okamoto, Yoshio, et al. "Optical resolution of dihydropyridine enantiomers by high-performance liquid chromatography using phenylcarbamates of polysaccharides as a chiral stationary phase." *J. of Chromatogr.* Vol. 513 (1990): pp. 375-378). Enriched or purified enantiomers can be distinguished by methods used to distinguish other chiral molecules with asymmetric carbon atoms, such as optical rotation and circular dichroism.

Biological Evaluation

The compounds of the invention are inhibitors of SHP2. In particular, they show an affinity for SHP2.

Determination of the activity of SHP2 activity of a compound of Formula I is possible by a number of direct and indirect detection methods. Certain exemplary compounds described herein were assayed for their SHP2 inhibition assay (Biological Example 1). A cell-based assay (Biological Example 2) was used to determine the effect of SHP2 inhibitors on downstream signaling by assaying ERK1/2 phosphorylation.

Administration and Pharmaceutical Formulations

The compounds described herein may be administered by any convenient route appropriate to the condition to be treated. The compounds of the invention are administered by any suitable route in the form of a pharmaceutical composition adapted to such a route, and in a dose effective for the treatment intended. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal.

The compounds may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents. If parenteral administration is desired, the compositions will be sterile and in a solution or suspension form suitable for injection or infusion. Suitable devices for parenteral administration include needle (including microneedle) injectors, needle-free injectors and infusion techniques.

Typically, a compound of the invention is administered in an amount effective to treat a condition as described herein. The compounds of the invention can be administered as compound per se, or alternatively, as a pharmaceutically acceptable salt. For administration and dosing purposes, the compound per se or pharmaceutically acceptable salt thereof will simply be referred to as the compounds of the invention.

A typical formulation is prepared by mixing a compound described herein and a carrier, diluent or excipient. Suitable carriers, diluents and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

One embodiment includes a pharmaceutical composition comprising a compound of Formula I, or a stereoisomer, tautomer or pharmaceutically acceptable salt thereof. A further embodiment provides a pharmaceutical composition comprising a compound of Formula I, or a stereoisomer, tautomer or pharmaceutically acceptable salt thereof, together with a pharmaceutically acceptable carrier, diluent or excipient.

In another embodiment, the invention provides a pharmaceutical composition comprising a compound of Formula I, or a pharmaceutically acceptable salt thereof, as defined in any of the embodiments described herein, in admixture with at least one pharmaceutically acceptable excipient.

In another embodiment, the invention comprises pharmaceutical compositions. Such pharmaceutical compositions comprise a compound of the invention presented with a pharmaceutically acceptable carrier. Other pharmacologically active substances can also be present. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof, and may include isotonic agents, for example, sugars, sodium chloride, or polyalcohols such as mannitol, or sorbitol in the composition. Pharmaceutically acceptable substances such as wetting agents or minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form depends on the intended mode of administration and therapeutic application.

Typical compositions are in the form of injectable or infusible solutions, such as compositions similar to those used for passive immunization of humans with antibodies in general. One mode of administration is parenteral (e.g., intravenous, subcutaneous, intraperitoneal, intramuscular). In another embodiment, the antibody is administered by intravenous infusion or injection. In yet another embodiment, the antibody is administered by intramuscular or subcutaneous injection.

Oral administration of a solid dose form may be, for example, presented in discrete units, such as hard or soft capsules, pills, cachets, lozenges, or tablets, each containing a predetermined amount of at least one compound of the invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the invention comprises a parenteral dose form. "Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated, see, for example, Finnin, Barrie C. and Timothy M. Morgan. "Transdermal penetration enhancers: Applications, limitations, and potential." *J. Pharm. Sci.* Vol. 88, No. 10 (1999): pp. 955-958.

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropyl methylcellulose, hydroxyethyl cellulose, or methylcellulose, or a heteropolysaccharide polymer, for example, gellan gum, may be incorporated together with a preservative, such as benzalkonium chloride. Such formulations may also be delivered by iontophoresis.

For intranasal administration or administration by inhalation, the compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks.

The dosage regimen for the compounds of the invention and/or compositions containing said compounds is based on a variety of factors, including the type, age, weight, sex and medical condition of the patient; the severity of the condition; the route of administration; and the activity of the particular compound employed. Thus, the dosage regimen may vary widely. In one embodiment, the total daily dose of a compound of the invention is typically from about 0.01 to about 100 mg/kg (i.e., mg compound of the invention per kg body weight) for the treatment of the indicated conditions discussed herein. In another embodiment, total daily dose of the compound of the invention is from about 0.1 to about 50 mg/kg, and in another embodiment, from about 0.5 to about 30 mg/kg. For an adult weighing 70 kg the total daily dose may be 0.1 mg-2 g; 1 mg-500 mg, etc. It is not uncommon that the administration of the compounds of the invention will be repeated a plurality of times in a day (typically no greaterthan 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Suitable subjects according to the invention include mammalian subjects. Mammals according to the invention include canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

Methods of Treatment with Compounds of the Invention

The compounds of the present invention may be useful in the treatment of a wide range of diseases, disorders, or conditions, including cancer. Other conditions that may be treated with the compounds of the present invention include hyperproliferative diseases, inflammatory disorders or pain.

Also provided are methods of treating or preventing a disease or condition by administering one or more compounds described herein, or a stereoisomer, tautomer or pharmaceutically acceptable salt thereof. In one embodiment, a method of treating a hyperproliferative disease in a mammal comprising administering a therapeutically effective amount of the compound of Formula I, or a stereoisomer, tautomer or pharmaceutically acceptable salt thereof, to the mammal is provided.

Another embodiment provides a method of treating or preventing cancer in a mammal in need of such treatment, wherein the method comprises administering to said mammal a therapeutically effective amount of a compound of Formula I, or a stereoisomer, tautomer or pharmaceutically acceptable salt thereof.

The invention also relates to a pharmaceutical composition comprising a compound of Formula I, or a pharmaceutically acceptable salt thereof, as defined in any of the embodiments described herein, for use in the treatment of cancer.

Another embodiment provides a method of treating or preventing pain in a mammal in need of such treatment, wherein the method comprises administering to said mammal a therapeutically effective amount of a compound of Formula I, or a stereoisomer, tautomer or pharmaceutically acceptable salt thereof.

Another embodiment provides a method of treating or preventing an inflammatory disorder in a mammal in need of such treatment, wherein the method comprises administering to said mammal a therapeutically effective amount of a compound of Formula I, or a stereoisomer, tautomer or pharmaceutically acceptable salt thereof.

Another embodiment provides a method of inhibiting SHP2 protein tyrosine phosphatase activity in a cell comprising treating the cell with a compound according to Formula I, or a stereoisomer, tautomer or pharmaceutically acceptable salt thereof.

Another embodiment provides a method of inhibiting SHP2 protein tyrosine phosphatase activity in a cell comprising treating the cell with a compound according to Formula I, or a stereoisomer, tautomer or pharmaceutically acceptable salt thereof, in an amount effective to attenuate or eliminate SHP2 kinase activity.

Another embodiment provides a method of inhibiting SHP2 protein tyrosine phosphatase activity in a patient in need thereof comprising the step of administering to said patient a compound according to Formula I, or a stereoisomer, tautomer or pharmaceutically acceptable salt thereof.

In another embodiment, the invention provides a method of inhibiting SHP2 protein tyrosine phosphatase activity for the treatment of cancer.

Another embodiment provides a method of treating or ameliorating the severity of a hyperproliferative disorder in a patient in need thereof comprising administering to said patient a compound according to Formula I, or a stereoisomer, tautomer or pharmaceutically acceptable salt thereof.

Another embodiment provides a method of treating or ameliorating the severity of a hyperproliferative disorder in a patient in need thereof comprising co-administering to said patient a compound according to Formula I, or a stereoisomer, tautomer or pharmaceutically acceptable salt thereof, with at least one other chemotherapeutic agent used to treat or ameliorate the hyperproliferative disorder.

Another embodiment provides a method of treating or ameliorating the severity of pain in a patient in need thereof comprising administering to said patient a compound according to Formula I, or a stereoisomer, tautomer or pharmaceutically acceptable salt thererof.

Another embodiment provides a method of treating or ameliorating the severity of an inflammatory disorder in a patient in need thereof comprising administering to said patient a compound according to Formula I, or a stereoisomer, tautomer or pharmaceutically acceptable salt thererof.

In another embodiment, a method of treating or preventing a disease or disorder modulated by SHP2, comprising administering to a mammal in need of such treatment an effective amount of a compound of Formula I, or a stereoisomer, tautomer or pharmaceutically acceptable salt thereof. Examples of such diseases and disorders include, but are not limited to, hyperproliferative diseases, such as cancer, and pain or inflammatory diseases.

Another embodiment provides the use of a compound of Formula I, or a stereoisomer, tautomer or pharmaceutically acceptable salt thereof, in the manufacture of a medicament for the treatment of a hyperproliferative disease. Another embodiment provides the use of a compound of Formula I, or a stereoisomer, tautomer or pharmaceutically acceptable salt thereof, in the manufacture of a medicament for the treatment of cancer.

Another embodiment provides the use of a compound of Formula I, or a stereoisomer, tautomer or pharmaceutically acceptable salt thereof, in the manufacture of a medicament for the treatment of pain.

Another embodiment provides the use of a compound of Formula I, or a stereoisomer, tautomer or pharmaceutically acceptable salt thereof, in the manufacture of a medicament for the treatment of an inflammatory disease.

Another embodiment provides the use of a compound of Formula I, or a stereoisomer, tautomer or pharmaceutically acceptable salt thereof, for use in the treatment of hyperproliferative diseases. Another embodiment provides the use of a compound of Formula I, or a stereoisomer, tautomer or pharmaceutically acceptable salt thereof, for use in the treatment of cancer.

Another embodiment provides the use of a compound of Formula I, or a stereoisomer, tautomer or pharmaceutically acceptable salt thereof, for use in the treatment of pain.

Another embodiment provides the use of a compound of Formula I, or a stereoisomer, tautomer or pharmaceutically acceptable salt thereof, for use in the treatment of inflammatory diseases.

The invention also includes the following embodiments:
a compound of Formula I, or a pharmaceutically acceptable salt thereof, as defined in any of the embodiments described herein, for use as a medicament;
a compound of Formula I, or a pharmaceutically acceptable salt thereof, as defined in any of the embodiments described herein, for use in the treatment of cancer;
a method of treating a disease for which an inhibitor of SHP2 is indicated, in a subject in need of such treatment, comprising administering to the subject a therapeutically effective amount of a compound of Formula I, or a pharmaceutically acceptable salt thereof, as defined in any of the embodiments described herein;
the use of a compound of Formula I, or a pharmaceutically acceptable salt thereof, as defined in any of the embodiments described herein, for the manufacture of a medicament for treating a disease or condition for which an inhibitor of SHP2 is indicated;
a compound of Formula I, or a pharmaceutically acceptable salt thereof, as defined in any of the embodiments described herein, for use in the treatment of a disease or condition for which an inhibitor of SHP2 is indicated; or
a pharmaceutical composition for the treatment of a disease or condition for which an inhibitor of SHP2 is indicated, comprising a compound of Formula I, or a pharmaceutically acceptable salt thereof, as defined in any of the embodiments described herein.

In certain embodiments, the hyperproliferative disease is cancer. In certain embodiments, the cancer may be selected from melanoma, juvenile myelomoncytic leukemias, neuroblastoma, Philadelphia chromosome positive chronic myeloid, Philadelphia chromosome positive acute lymphoblastic leukemias, acute myeloid leukemias, myeloproliferative neoplasms (such as Polycythemia Vera, Essential Thrombocythemia and Primary Myelofibrosis), breast cancer, lung cancer, liver cancer, colorectal cancer, esophageal cancer, gastric cancer, squamous-cell carcinoma of the head and neck, glioblastoma, anaplastic large-cell lymphoma, thyroid carcinoma, and spitzoid neoplasms. In certain embodiments, the cancer is melanoma. In certain embodiments, the cancer is juvenile myelomoncytic leukemias. In certain embodiments, the cancer is neuroblastoma. In certain embodiments, the cancer is Philadelphia chromosome positive chronic myeloid. In certain embodiments, the cancer is Philadelphia chromosome positive acute lymphoblastic leukemias. In certain embodiments, the cancer is acute myeloid leukemias. In certain embodiments, the cancer is myeloproliferative neoplasms, such as Polycythemia Vera, Essential Thrombocythemia and Primary Myelofibrosis. In certain embodiments, the cancer is selected from the group consisting of Polycythemia Vera, Essential Thrombocythemia and Primary Myelofibrosis. In certain embodiments, the cancer is Polycythemia Vera. In certain embodiments, the cancer is Essential Thrombocythemia. In certain embodiments, the cancer is Primary Myelofibrosis. In certain embodiments, the cancer is breast cancer. In certain embodiments, the cancer is lung cancer. In certain embodiments, the cancer is liver cancer. In certain embodiments, the cancer is colorectal cancer. In certain embodiments, the cancer is esophageal cancer. In certain embodiments, the cancer is gastric cancer. In certain embodiments, the cancer is squamous-cell carcinoma of the head and neck. In certain embodiments, the cancer is glioblastoma. In certain embodiments, the cancer is anaplastic large-cell lymphoma. In certain embodiments, the cancer is thyroid carcinoma. In certain embodiments, the cancer is spitzoid neoplasms. In certain embodiments, the cancer is selected from the group consisting of NSCLC, a colon cancer, an esophageal cancer, a rectal cancer, juvenile myelomonocytic leukemia ("JMML"), breast cancer, melanoma, and a pancreatic cancer.

In certain embodiments, the disease or disorder may be selected from Neurofibromatosis and Noonan Syndrome. In certain embodiments, the disease or disorder is Neurofibromatosis. In certain embodiments, the disease or disorder is Noonan Syndrome.

In certain embodiments, the disease or disorder is Schwannomatosis.

In certain embodiments, the disease or disorder comprising a cell containing a mutation encoding the $KRAS^{G12C}$ variant. See WO 2019/051084.

In certain embodiments, the hyperproliferative disease is a disease or disorder, comprising a cell with a mutation encoding an NF1 loss of function ("$NF1^{LOF}$") variant. In certain embodiments, the NF1 mutation is a loss of function mutation. In certain embodiments, the disease or disorder is a tumor comprising cells with an NF1 loss of function mutation. In certain embodiments, the tumor is an NSCLC or melanoma tumor. In certain embodiments, the disease is selected from neurofibromatosis type I, neurofibromatosis type II, schwannomatosis, and Watson syndrome.

In certain embodiments, the disease or disorder associated with a RAS pathway mutation in a cell of the subject that renders the cell at least partially dependent on signaling flux through SHP2. In certain embodiments, the RAS pathway mutation is a RAS mutation selected from a KRAS mutation, an NRAS mutation, a SOS mutation, a BRAF Class III mutation, a Class I MEK1 mutation, a Class II MEK1 mutation, and an F1 mutation. In certain embodiments, the KRAS mutation is selected from a $KRAS^{G12A}$ mutation, a $KRAS^{G12C}$ mutation, a $KRAS^{G12D}$ mutation, a $KRAS^{G12F}$ mutation, a $KRAS^{G12I}$ mutation, a $KRAS^{G12L}$ mutation, a $KRAS^{G12R}$ mutation, a $KRAS^{G12S}$ mutation, a $KRAS^{G12V}$ mutation, and a $KRAS^{G12Y}$ mutation. In certain embodiments, the KRAS mutation is a $KRAS^{G12A}$ mutation. In certain embodiments, the KRAS mutation is a $KRAS^{G12C}$ mutation. In certain embodiments, the KRAS mutation is a $KRAS^{G12D}$ mutation. In certain embodiments, the KRAS mutation is a $KRAS^{G12F}$ mutation. In certain embodiments, the KRAS mutation is a $KRAS^{G12I}$ mutation. In certain embodiments, the KRAS mutation is a $KRAS^{G12L}$ mutation. In certain embodiments, the KRAS mutation is a $KRAS^{G12R}$ mutation. In certain embodiments, the KRAS mutation is a $KRAS^{G12S}$ mutation. In certain embodiments, the KRAS mutation is a $KRAS^{G12V}$ mutation. In certain embodiments, the KRAS mutation is a $KRASG^{12Y}$ mutation. In certain embodiments, the BRAF Class III mutation is selected from one or more of the following amino acid substitutions in human BRAF: D287H; P367R; V459L; G466V; G466E; G466A; S467L; G469E; N581S; N581I; D594N; D594G; D594A; D594H; F595L; G596D; G596R and A762E. In certain embodiments, the Class I MEK1 mutation is selected from one or more of the following amino acid substitutions in human MEK1: D67N; P124L; P124S; and L177V. In certain embodiments, the Class II MEK1 mutation is selected from one or more of the following amino acid substitutions in human MEK1: AE51-Q58; AF53-Q58; E203K; L177M; C121S; F53L; K57E; Q56P; and K57N.

Combination Therapy

The compounds described herein and stereoisomers, tautomers and pharmaceutically acceptable salts thereof may be employed alone or in combination with other therapeutic agents for treatment. The compounds described herein may be used in combination with one or more additional drugs, for example an anti-hyperproliferative (or anti-cancer) agent that works through action on a different target protein. The second compound of the pharmaceutical combination formulation or dosing regimen preferably has complementary activities to the compound described herein, such that they do not adversely affect each other. Such molecules are suitably present in combination in amounts that are effective for the purpose intended. The compounds may be administered together in a unitary pharmaceutical composition or separately and, when administered separately this may occur simultaneously or sequentially in any order. Such sequential administration may be close in time or remote in time.

The phrases "concurrent administration," "co-administration," "simultaneous administration," and "administered simultaneously" mean that the compounds are administered in combination.

In another embodiment, the invention provides methods of treatment that include administering compounds of the present invention in combination with one or more other pharmaceutical agents, wherein the one or more other pharmaceutical agents may be selected from the agents discussed herein.

In certain embodiments, the compound of Formula I is administered in combination with an inhibitor of the RAS pathway. In certain embodiments, the inhibitor of the RAS pathway is a MEK inhibitor or ERK inhibitor. In certain embodiments, the inhibitor of the Ras pathway is selected from one or more of trametinib, binimetinib, selumetinib, cobimetinib, LErafAON (NeoPharm), ISIS 5132; vemurafenib, pimasertib, TAK733, R04987655; (CH4987655); CI-1040; PD-0325901; CH5126766; MAP855; AZD6244; Refametinib (RDEA 119/BAY 86-9766); GDC-0973/XL581; AZD8330 (ARRY-424704/ARRY-704); R05126766; ARS-853; LY3214996; BVD523; GSK1 120212; Ulixertinib, and Abemaciclib, including the pharmaceutically acceptable salts of the specifically named compounds and the pharmaceutically acceptable solvates of said specifically named compounds and salts. In certain embodiments, the inhibitor of the Ras pathway is selected from one or more of trametinib, binimetinib, selumetinib and cobimetinib, including the pharmaceutically acceptable salts of the specifically named compounds and the pharmaceutically acceptable solvates of said specifically named compounds and salts. In certain embodiments, the inhibitor of the Ras pathway is binimetinib including the pharmaceutically acceptable salts and the pharmaceutically acceptable solvates of binimetinib.

In certain embodiments, the inhibitor of the RAS pathway is a B-Raf inhibitor. In certain embodiments, the B-Raf inhibitor is selected from one or more of encorafenib, vemurafenib and dabrafenib, including the pharmaceutically acceptable salts of the specifically named compounds and the pharmaceutically acceptable solvates of said specifically named compounds and salts. In certain embodiments, the inhibitor of the RAS pathway is a B-Raf inhibitor. In certain embodiments, the B-Raf inhibitor is encorafenib, including the pharmaceutically acceptable salts and the pharmaceutically acceptable solvates of encorafenib.

In certain embodiments, the compound of Formula I is administered in combination with a MEK inhibitor and a B-Raf inhibitor. In certain embodiments, the MEK inhibitor is selected from trametinib, binimetinib, selumetinib and cobimetinib, and the B-Raf inhibitor is selected from encorafenib, vemurafenib and dabrafenib, including the pharmaceutically acceptable salts of the specifically named compounds and the pharmaceutically acceptable solvates of said specifically named compounds and salts. In certain embodiments, the MEK inhibitor is binimetinib, and the B-Raf inhibitor is encorafenib, including the pharmaceutically acceptable salts of the specifically named compounds and the pharmaceutically acceptable solvates of said specifically named compounds and salts.

In certain embodiments, the compound of Formula I is administered in combination with an inhibitor of the RAS pathway. In certain embodiments, the inhibitor of the RAS pathway is a KRAS inhibitor. In certain embodiments, the KRAS inhibitor is selected from the group consisting of BI 1701963 and BBP-454. In certain embodiments, the inhibitor of the RAS pathway is a KRAS G12C inhibitor. In certain embodiments, the KRAS G12C inhibitor is selected from the group consisting of MRTX849, AMG 510, and ARS1620.

In certain embodiments, the compound of Formula I is administered in combination with an ALK inhibitor. In certain embodiments, the ALK inhibitor is selected from the group consisting of lorlatinib, crizotinib, ceritinib, alectinib and brigatinib, including the pharmaceutically acceptable salts of the specifically named compounds and the pharmaceutically acceptable solvates of said specifically named compounds and salts. In certain embodiments, the ALK inhibitor is lorlatinib, including the pharmaceutically acceptable salts and the pharmaceutically acceptable solvates of lorlatinib.

These agents and compounds of the invention can be combined with pharmaceutically acceptable vehicles such as saline, Ringer's solution, dextrose solution, and the like. The particular dosage regimen, i.e., dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or Igs; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Liposomes containing these agents and/or compounds of the invention are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

These agents and/or the compounds of the invention may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington: The Science and Practice of Pharmacy, supra.

Sustained-release preparations may be used. Suitable examples of sustained-release preparations include semipermeable matrices of solid hydrophobic polymers containing the antibody/compound of the invention, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as those used in LUPRON DEPOT™ (injectable microspheres composed of lactic acid-glycolic acid copolymer and leuprolide acetate), sucrose acetate isobutyrate, and poly-D-(-)-3-hydroxybutyric acid.

The formulations to be used for intravenous administration must be sterile. This is readily accomplished by, for example, filtration through sterile filtration membranes. Compounds of the invention are generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing a compound of the invention with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

Another aspect of the invention provides kits comprising the compound of the invention or pharmaceutical compositions comprising the compound of the invention. A kit may include, in addition to the compound of the invention or pharmaceutical composition thereof, diagnostic or therapeutic agents. A kit may also include instructions for use in a diagnostic or therapeutic method. In some embodiments, the kit includes the compound or a pharmaceutical composition thereof and a diagnostic agent. In other embodiments, the kit includes the compound or a pharmaceutical composition thereof and one or more therapeutic agents, such as an inhibitor of the Ras pathway.

In yet another embodiment, the invention comprises kits that are suitable for use in performing the methods of treatment described herein. In one embodiment, the kit contains a first dosage form comprising one or more of the compounds of the invention in quantities sufficient to carry out the methods of the invention. In another embodiment, the kit comprises one or more compounds of the invention in quantities sufficient to carry out the methods of the invention and a container for the dosage and a container for the dosage.

EXAMPLES

For illustrative purposes, the following Examples are included. However, it is to be understood that these Examples do not limit the invention and are only meant to suggest a method of practicing the invention. Persons skilled in the art will recognize that the chemical reactions described may be readily adapted to prepare a number of other compounds described herein, and alternative methods for preparing the compounds are deemed to be within the scope of this invention. For example, the synthesis of non-exemplified compounds may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds described herein.

In the Examples described below, unless otherwise indicated all temperatures are set forth in degrees Celsius. Reagents were purchased from commercial suppliers such as Sigma-Aldrich, Alfa Aesar, or TCI, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters) (unless otherwise stated). $^1$H NMR spectra were recorded on a Varian instrument operating at 400 MHz. $^1$H-NMR spectra were obtained as $CDCl_3$, $CD_3OD$, $D_2O$, $(CD_3)_2SO$, $(CD_3)_2CO$, $C_6D_6$, $CD_3CN$ solutions (reported in ppm), using tetramethylsilane (0.00 ppm) or residual solvent ($CDCl_3$: 7.26 ppm; $CD_3OD$: 3.31 ppm; $D_2O$: 4.79 ppm; $(CD_3)_2SO$: 2.50 ppm; $(CD_3)_2CO$: 2.05 ppm; $C_6D_6$: 7.16 ppm; $CD_3CN$: 1.94 ppm) as the reference standard. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Biological Example 1

SHP2 Enzymatic Assay

A fluorescence intensity kinetic assay was configured for full-length SHP2 that monitors the amount of 6,8-difluoro-7-hydroxy-4-methylcoumarin ("DiFMU") formed upon hydrolysis of 6,8-difluoro-4-methylumbelliferyl phosphate ("DiFMUP") by SHP2. Assay mixtures consisted of 25 mM K$^+$HEPES, pH 7.4, 0.01% Triton X-100, 1 mM DTT, 50 mM KCl, 100 µg/mL bovine γ-globulin, 50 µM DiFMUP, 1 µM SHP2 activating peptide (LN(pY)IDLDLV(dPEG8)LST(pY)ASINFQK-amide), 1 nM full-length SHP2 (His6-tagged SHP2(2-527), recombinantly expressed in *E. coli* and purified in-house) and 2% dimethylsulfoxide ("DMSO") (from compound). Compounds were typically diluted in DMSO across a 10-point dosing range created using a 3-fold serial dilution protocol at a top dose of 20 µM. The assay was run in 384-well, polystyrene, low-volume, non-treated, black microtiter plates (Costar 4511) in a final volume of 20 µL. Low control wells lacked enzyme. The assays were initiated by the addition of a mixture of SHP2 and the activating peptide, and following a 15 second mix on an orbital shaker, were read in kinetic mode for 15 minutes (30 seconds/cycle) at ambient temperature on a PerkinElmer EnVision microplate reader (λEx=355 nm, 2\, λEm=460 nm). Initial velocities (slopes of the tangents at t=0) were estimated from exponential fits to the slightly nonlinear progress curves and then were converted to percent of control ("POC") using the following equation:

$$POC = \frac{\text{Sample} - \overline{X}_{min}}{\overline{X}_{max} - \overline{X}_{min}} \times 100$$

Where: $\overline{X}_{max}$ Average Uninhibited Controls $\overline{X}_{min}$ Average Background A 4-parameter logistic model was the fit to the POC data for each compound. From that fit, the IC$_{50}$ was estimated and is defined as the concentration of compound at which the curve crosses 50 POC.

Table 1 contains representative data for Examples disclosed herein. The reported IC$_{50}$ in Table 1 may be from a single assay or the mean of multiple assays. Examples 1-14 were tested in the above assay and were found to have an IC$_{50}$ of less than 10 µM. Examples 1, 2, 4, 5, 6, 7, 8, 9, 11, 12, 13, and 14 were tested in the above assay and were found to have an IC$_{50}$ of less than 500 µM. Examples 1-14 were tested in the above assay and were found to have an IC$_{50}$ of 1 µM or less.

Table 1 contains Examples tested in the above assay:

TABLE 1

| Example # | Biological Example 1 IC$_{50}$ (nM) |
|---|---|
| Example 1 | 59 |
| Example 2 | 76 |
| Example 3 | 626 |
| Example 4 | 114 |
| Example 5 | 28 |
| Example 6 | 28 |
| Example 7 | 17 |
| Example 8 | 69 |
| Example 9 | 358 |
| Example 10 | 551 |
| Example 11 | 210 |
| Example 12 | 174 |
| Example 13 | 141 |
| Example 14 | 53 |
| Example 15 | 7954 |
| Example 16 | 175 |
| Example 17 | 25 |
| Example 18 | 15 |
| Example 19 | 44 |
| Example 20 | 125 |
| Example 21 | 11127 |
| Example 22 | 32 |
| Example 23 | 35 |
| Example 24 | 47 |
| Example 25 | 26 |
| Example 26 | 49 |
| Example 27 | 17 |
| Example 28 | 879 |
| Example 29 | 96 |
| Example 30 | 22 |
| Example 31 | 23 |
| Example 32 | 5 |
| Example 33 | 98 |
| Example 34 | 79 |
| Example 35 | 26 |
| Example 36 | 110 |
| Example 37 | 11 |
| Example 38 | 13 |
| Example 39 | 78 |
| Example 40 | 8 |
| Example 41 | 79 |
| Example 42 | 209 |
| Example 43 | 142 |
| Example 44 | 37 |
| Example 45 | 14 |
| Example 46 | 91 |
| Example 47 | 38 |
| Example 48 | 30 |
| Example 49 | 157 |
| Example 50 | 44 |
| Example 51 | 93 |
| Example 52 | 27 |
| Example 53 | 46 |
| Example 54 | 62 |
| Example 55 | 116 |
| Example 56 | 1366 |
| Example 57 | 643 |
| Example 58 | 39 |
| Example 59 | 118 |
| Example 60 | 109 |
| Example 61 | 87 |
| Example 62 | 39 |
| Example 63 | 254 |
| Example 64 | 41 |
| Example 65 | 64 |
| Example 66 | 96 |
| Example 67 | 20 |
| Example 68 | 33 |
| Example 69 | 19 |
| Example 70 | 36 |
| Example 71 | 55 |
| Example 72 | 16399 |
| Example 73 | 32 |
| Example 74 | 110 |
| Example 75 | 1748 |
| Example 76 | 41 |
| Example 77 | 74 |
| Example 78 | 14978 |

TABLE 1-continued

| Example # | Biological Example 1 IC$_{50}$ (nM) |
|---|---|
| Example 79 | 84 |
| Example 80 | 429 |
| Example 81 | 4 |
| Example 82 | 205 |
| Example 83 | 46 |
| Example 84 | 24 |

Biological Example 2

Cellular Phospho-p44/42 MAPK (Erk1/2) (Thr202/Tyr204) Assay

Inhibition of ERK1/2 (Thr202/Tyr204) phosphorylation was determined by the following cellular assay, which comprises incubating cells with a compound for 1 hour and quantifying pERK signal by In-Cell Western on fixed cells and normalizing to GAPDH signal. KYSE520 cells were obtained from DSMZ and grown in RPMI supplemented with 10% fetal bovine serum, penicillin/streptomycin, 2 mM L-alanyl-L-glutamine dipeptide in 0.85% NaCl (Glutamax™), non-essential amino acids, and sodium pyruvate. Cells were plated in 96-well plates at 30,000 cells/well and allowed to attach overnight at 37° C./5% CO$_2$. Cells were treated with compounds prepared as a 10-point, 1:3 dilution series (range: 20 µM-1 nM), with a final DMSO concentration of 0.5%. After 1 hour incubation, cells were fixed in 3.7% formaldehyde in Dulbecco's phosphate-buffered saline ("dPBS") at room temperature for 20 minutes. Cells were then washed with dPBS and permeabilized in 100% MeOH at room temperature for 10 minutes. Following permeabilization, cells were washed in dPBS and incubated in LI-COR Blocking Buffer (LI-COR Biosciences, Cat#927-40000) for 1 hour or longer. Plates were then incubated with an antibody specific for the MEK-dependent ERK1/2 phosphorylation sites, threonine 202 and tyrosine 204 (Cell Signaling Technologies; Cat# 9101), downstream of SHP2 in the MAP kinase signal transduction pathway, as well as GAPDH (Millipore; Cat# MAB374). pErkl/2 (Thr202/Tyr204) antibody was diluted in LI-COR blocking buffer containing 0.05% polysorbate-20 (Tween-20) at 1:250; GAPDH was diluted at 1:2,500. The plates were incubated overnight at 4° C. After washing with PBS/0.05% Tween-20, the cells were incubated with fluorescently-labeled secondary antibodies (Anti-rabbit-Alexa Flour680, Invitrogen Cat#A21109; Anti-mouse-IRDye800CW, Li-cor Biosciecies Cat#926-32210, both at 1:1000 dilution) for 1 hour. Cells were then washed, as above, and analyzed for fluorescence at both 680 nm and 800 nm wavelengths using the Aerius Infrared Imaging System (LI-COR Biosciences, Model 9250). Phosphorylated Erk1/2 (Thr202/Tyr204) signal was normalized to GAPDH signal for each well. IC$_{50}$ values were calculated from the normalized values using a 4-parameter fit in BioAssay software. Table 2 contains representative data for Examples disclosed herein. The reported IC$_{50}$ in Table 2 may be from a single assay or the mean of multiple assays.

Table 2 contains selected Examples tested in the above assay:

TABLE 2

| Example # | Biological Example 2 IC$_{50}$ (nM) |
|---|---|
| Example 1 | 55 |
| Example 2 | 2776 |
| Example 3 | 1292 |
| Example 4 | 519 |
| Example 5 | 337 |
| Example 6 | 2 |
| Example 7 | 89 |
| Example 8 | 48 |
| Example 9 | 699 |
| Example 10 | 687 |
| Example 11 | 1971 |
| Example 12 | 1112 |
| Example 13 | 1032 |
| Example 14 | 61 |
| Example 15 | — |
| Example 16 | 49 |
| Example 17 | 9 |
| Example 18 | 8 |
| Example 19 | 208 |
| Example 20 | 206 |
| Example 21 | — |
| Example 22 | 17 |
| Example 23 | 12 |
| Example 24 | 5 |
| Example 25 | 2 |
| Example 26 | 120 |
| Example 27 | 11 |
| Example 28 | 1144 |
| Example 29 | 206 |
| Example 30 | 2 |
| Example 31 | 424 |
| Example 32 | 14 |
| Example 33 | 366 |
| Example 34 | 9 |
| Example 35 | 9 |
| Example 36 | 17 |
| Example 37 | 31 |
| Example 38 | 41 |
| Example 39 | 11 |
| Example 40 | — |
| Example 41 | 19 |
| Example 42 | 813 |
| Example 43 | 509 |
| Example 44 | 4 |
| Example 45 | 2 |
| Example 46 | 430 |
| Example 47 | 56 |
| Example 48 | 5 |
| Example 49 | 126 |
| Example 50 | 6 |
| Example 51 | 78 |
| Example 52 | 2 |
| Example 53 | 4 |
| Example 54 | 7 |
| Example 55 | 23 |
| Example 56 | — |
| Example 57 | 139 |
| Example 58 | 1 |
| Example 59 | 170 |
| Example 60 | 528 |
| Example 61 | 6 |
| Example 62 | 6 |
| Example 63 | 665 |
| Example 64 | 286 |
| Example 65 | 81 |
| Example 66 | 7 |
| Example 67 | 51 |
| Example 68 | — |
| Example 69 | 170 |
| Example 70 | 9 |
| Example 71 | 152 |
| Example 72 | — |

TABLE 2-continued

| Example # | Biological Example 2 IC$_{50}$ (nM) |
|---|---|
| Example 73 | 6 |
| Example 74 | 1 |
| Example 75 | 100 |
| Example 76 | 4 |
| Example 77 | 92 |
| Example 78 | — |
| Example 79 | 697 |
| Example 80 | 2992 |
| Example 81 | 8 |
| Example 82 | 541 |
| Example 83 | 3 |
| Example 84 | 2 |

Intermediate Example A

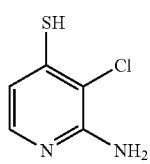

2-amino-3-chloropyridine-4-thiol

Step A: 3-Mercaptopropionic acid 2-ethylhexyl ester (2.3 mL, 22 mmol) and Hunig's base (6.9 mL, 39 mmol) were added to a mixture of 3-chloro-4-iodopyridin-2-amine (5.0 g, 20 mmol), Pd(OAc)$_2$ (0.22 g, 0.98 mmol) and xantphos (1.1 g, 2.0 mmol) in dioxane (65 mL, 20 mmol) under Ar gas. The reaction was heated to 100° C. under argon for 18 hours. The reaction was diluted in ethyl acetate ("EtOAc") and filtered through diatomaceous silica (Celite) The filtrate was concentrated to provide methyl 3-((2-amino-3-chloropyridin-4-yl)thio)propanoate (4.3 g, 17 mmol, 88% yield).

Step B: NaOEt (7.1 mL, 19 mmol) was added to methyl 3-((2-amino-3-chloropyridin-4-yl)thio)propanoate (4.3 g, 17 mmol) in tetrahydrofuran ("THF") (87 mL, 17 mmol) and was stirred under N$_2$ for 1 hour at room temperature. Dichloromethane ("DCM") (20 mL) was added, and this mixture was stirred for 5 minutes. The reaction was concentrated, and the solid was titrated with DCM, filtered, and dried. The solids were brought up in water (slurry), and 1N HCl was added to bring the pH to about 6. The solids were filtered and washed with water to provide 2-amino-3-chloropyridine-4-thiol (1.4 g, 9.0 mmol, 52% yield). $^1$H NMR (400 MHz, (CD$_3$)$_2$SO) δ 11.4 (br, 1H), 7.06 (d, 1H, J=6.8 Hz), 6.70 (br, 2H), 6.65 (d, 1H, J=7.0 Hz); m/z (esi/APCI) M+1=161.0.

Intermediate Example B

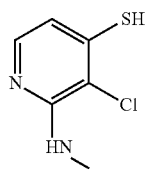

3-chloro-2-(methylamino)pyridine-4-thiol

Step A: 3-Chloro-2-fluoro-4-iodopyridine (8.0 g, 31.1 mmol) and methanamine (42.7 mL, 85.5 mmol) were placed in DMSO (20 mL) and heated to 70° C. for 30 minutes. Water was added, and the solids were filtered to provide crude product. Material was purified by silica gel (0-5% MeOH in DCM with 2% NH$_4$OH) to provide 3-chloro-4-iodo-N-methylpyridin-2-amine (6.34 g, 23.6 mmol, 76% yield).

Step B: 3-Chloro-4-iodo-N-methylpyridin-2-amine (1 g, 3.7 mmol) was diluted with dioxane (5 mL), followed by the addition of PdOA$_2$ (41.8 mg, 0.19 mmol), xantphos (215.5 mg, 0.37 mmol) and methyl 3-mercaptopropanoate (453.8 µL, 4.10 mmol). The reaction was placed under nitrogen, and DIEA (1301 µL, 7.50 mmol) was added. The reaction was heated to 100° C. and stirred for 2.3 hours. The reaction was allowed to cool, diluted with ethyl acetate and filtered through Celite® rinsing with ethyl acetate. The filtrate was concentrated to afford methyl 3-((3-chloro-2-(methylamino)pyridin-4-yl)thio)propanoate (905 mg, 3.471 mmol, 93% yield).

Methyl 3-((3-chloro-2-(methylamino)pyridin-4-yl)thio)propanoate (905 mg, 3.47 mmol) was diluted with THF (15 mL), followed by the addition of sodium ethoxide (1425 µL, 3.82 mmol). The reaction was placed under nitrogen and stirred at ambient temperature for 1 hour. The reaction was concentrated and triturated with DCM. The material was diluted with water, and the pH was adjusted to about 6. The mixture was filtered, rinsed with water and dried under vacuum to afford 3-chloro-2-(methylamino)pyridine-4-thiol (400 mg, 2.29 mmol, 66.0% yield). m/z (esi/APCI) M$^+$1=175.0.

Intermediate Example C

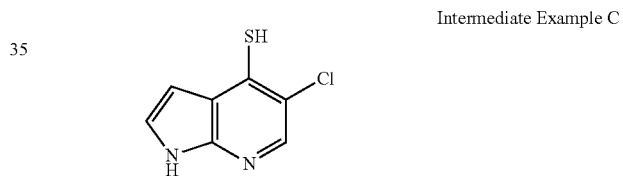

5-chloro-1H-pyrrolo[2,3-b]pyridine-4-thiol

Step A: 3-Mercaptopropionic acid 2-ethylhexyl ester (0.12 mL, 1.1 mmol) and Hunig's base (0.34 mL, 1.9 mmol) were added to a mixture of 5-chloro-4-iodo-1H-pyrrolo[2,3-b]pyridine (0.270 g, 0.97 mmol), Pd(OAc)$_2$ (0.011 g, 0.048 mmol) and xantphos (0.056 g, 0.097 mmol) in dioxane (3.2 mL, 0.97 mmol) under Ar gas. The reaction was heated to 100° C. under argon for 18 hours. The reaction was diluted in EtOAc and filtered through diatomaceous silica (Celite®). The filtrate was concentrated and then purified on silica gel eluting with 10-100% EtOAc/hexanes to provide methyl 3-((5-chloro-1H-pyrrolo[2,3-b]pyridin-4-yl)thio)propanoate (0.225 g, 0.83 mmol, 85% yield).

Step B: NaOEt (0.34 mL, 0.91 mmol) was added to methyl 3-((5-chloro-1H-pyrrolo[2,3-b]pyridin-4-yl)thio)propanoate (0.225 g, 0.83 mmol) in tetrahydrofuran ("THF") (4.146 mL, 0.83 mmol) and was stirred for 2 hours at room temperature. DCM (20 mL) was added, and this mixture was stirred for 5 minutes. The reaction was concentrated and then purified on silica gel eluting with 0-20% MeOH/DCM (2% NH$_4$OH) to afford 5-chloro-1H-pyrrolo[2,3-b]pyridine-4-thiol (0.080 g, 0.43 mmol, 52% yield). m/z (esi/APCI) M$^+$1=185.0.

Intermediate Example D

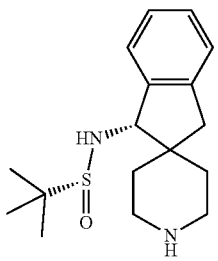

(R)-N-((S)-1,3-dihydrospiro[indene-2,4'-piperidin]-1-yl)-2-methylpropane-2-sulfinamide Step A: tert-Butyl 1-oxo-1,3-dihydrospiro[indene-2,4'-piperidine]-1'-carboxylate (25 g, 83 mmol) and (R)-2-methylpropane-2-sulfinamide (30 g, 249 mmol) and Ti(OEt)$_4$ (122 mL, 580 mmol) were heated to 90° C. for 18 hours. EtOAc was added, followed by water. The solids were filtered off, and the layers were separated. The organic layer was dried over MgSO$_4$, filtered and concentrated to the resulting residue that was purified by silica gel (0-40% EtOAc in hexanes) to provide tert-butyl (R,E)-1-((tert-butylsulfinyl)imino)-1,3-dihydrospiro[indene-2,4'-piperidine]-1'-carboxylate (16 g, 39 mmol, 47% yield).

Step B: tert-Butyl (R,E)-1-((tert-butylsulfinyl)imino)-1,3-dihydrospiro[indene-2,4'-piperidine]-1'-carboxylate (6.5 g, 16 mmol) was placed in THF (10 mL) and cooled to −78° C. Lithium borohydride (14 mL, 28 mmol) was added, and the reaction was allowed to slowly warm to room temperature and was stirred for 18 hours. Water was added, and the mixture was extracted with DCM (3×25 mL). The extracts were combined and concentrated, and the resulting residue was purified by silica gel (0-5% MeOH in DCM with 2% NH$_4$OH) to afford tert-butyl (S)-1-(((R)-tert-butylsulfinyl)amino)-1,3-dihydrospiro[indene-2,4'-piperidine]-1'-carboxylate (3.2 g, 8 mmol, 50% yield).

Step C: tert-Butyl (S)-1-(((R)-tert-butylsulfinyparnino)-1,3-dihydrospiro[indene-2,4'-piperidine]-1'-carboxylate (3.1 g, 7.6 mmol) was placed in DCM (50 mL) and cooled to 0° C. Trifluoroacetic acid ("TFA") (7 mL) was added, and the reaction was stirred for 2.5 hours. The reaction was concentrated, and the resulting residue was brought up in saturated bicarbonate. The mixture was extracted with DCM. The extracts were dried, filtered and concentrated to provide (R)-N-((S)-1,3-dihydrospiro[indene-2,4'-piperidin]-1-yl)-2-methylpropane-2-sulfinamide (1.8 g, 5.9 mmol, 78% yield).

Intermediate Example E

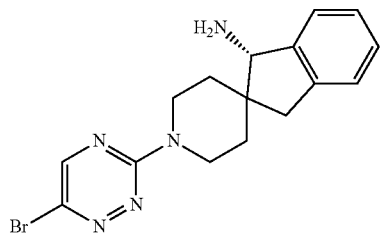

(S)-1'-(6-bromo-1,2,4-triazin-3-yl)-1,3-dihydrospiro[indene-2,4'-piperidin]-1-amine (S)-1,3-dihydrospiro[indene-2,4'-piperidin]-1-amine dihydrochloride (1.00 g, 3.63 mmol) was suspended in dioxane (15 mL), and triethylamine (1.84 g, 18.2 mmol) was added to the mixture. The mixture was stirred at room temperature for 20 minutes then 3,6-dibromo-1,2,4-triazine (0.868 g, 3.63 mmol) was added. The reaction was heated up to 50° C. and stirred for 2 hours. After 2 hours, the reaction was filtered, and the filtrate was evaporated to give a residue. The residue was purified using 40 g silica gel column chromatography (MeOH/DCM mixture 2-20%) to give (S)-1'-(6-bromo-1,2,4-triazin-3-yl)-1,3-dihydrospiro[indene-2,4'-piperidin]-1-amine (1.19 g, 3.30 mmol, 90.9% yield) as solid. m/z (esi/APCI) M$^+$1=400.2.

Intermediate Example F

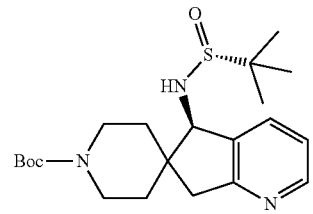

tert-butyl (R)-5-(((R)-tert-butylsulfinyl)amino)-5,7-dihydrospiro[cyclopenta[b]pyridine-6,4'-piperidine]-1'-carboxylate Step A: 2-Chloropyridine (458 mL, 4.84 mmol) was dissolved in dry THF (15 mL), and the solution was cooled down to −70° C. in IPA/dry ice bath. Lithium diisopropylamide ("LDA") (2.75 mL, 5.50 mmol) was added dropwise to the mixture, and the reaction was warmed to −60° C. and stirred at that temperature for 1.5 hours. tert-Butyl 4-formyl-4-methylpiperidine-1-carboxylate (1 g, 4.40 mmol) in THF (3 mL) was added to the mixture and stirred at −60° C. for 1 hour. The reaction was quenched with water and partitioned between EtOAc and water. The organic layer was separated, dried, and concentrated. The resulting residue was purified using 40 g silica gel column (EtOAc/hexanes 10-80%) yielded tert-butyl 4-((2-chloropyridin-3-yl)(hydroxy)methyl)-4-methylpiperidine-1-carboxylate (1.06 g, 3.11 mmol, 71% yield).

Step B: tert-Butyl 4-((2-chloropyridin-3-yl)(hydroxy)methyl)-4-methylpiperidine-1-carboxylate (1.06 g, 3.11 mmol) was dissolved in DCM (8 mL), and Dess-Martin periodinane ("DMP") (2.64 g, 6.22 mmol) was added to the solution. The mixture was stirred at room temperature for 1 hour, and it was quenched with 10% sodium bisulfate solution. The organic layer was separated, washed with saturated sodium bicarbonate solution and brine, dried and evaporated. The resulting residue was purified using silica gel flash chromatography (EtOAc/hexanes 10-100%) provided tert-butyl 4-(2-chloronicotinoyl)-4-methylpiperidine-1-carboxylate (0.31 g, 0.92 mmol, 29% yield) as an oil.

Step C: tert-Butyl 4-(2-chloronicotinoyl)-4-methylpiperidine-1-carboxylate (8.13 g, 24.0 mmol) was dissolved in mesitylene (70 mL) in a pressure tube. Tricyclohexyl phosphonium tetrafluoroborate (0.884 g, 2.40 mmol), diacetoxy palladium (0.269 g, 1.20 mmol), pivalic acid (0.735 g, 7.20 mmol) and cesium carbonate (15.6 g, 48.0 mmol) were added to the reaction mixture. Nitrogen gas was bubbled for 5 minutes in the reaction mixture, and the tube was sealed and heated at 140° C. for 72 hours. The reaction was cooled to room temperature and diluted with EtOAc (50 mL). The mixture was filtered using a pad of Celite® and was washed with EtOAc several times. The filtrate was evaporated under vacuum to give a residue. The residue was purified using 330 g silica column (EtOAc/hexane 20-80%) to give tert-butyl 5-oxo-5,7-dihydrospiro[cyclopenta[b]pyridine-6,4'-piperidine]-1'-carboxylate (2.23 g, 7.37 mmol, 31% yield) as a solid. m/z (esi/APCI) M+1=303.1.

Step D: tert-Butyl 5-oxo-5,7-dihydrospiro[cyclopenta[b]pyridine-6,4'-piperidine]-1'-carboxylate (2.23 g, 7.37 mmol) was suspended in tetraethoxytitanium (6.98 mL, 51.62 mmol), and (R)-2-methylpropane-2-sulfinamide (2.68 g, 22.12 mmol) was added to the mixture. The reaction was heated to 90° C. and stirred for 18 hours. The reaction was cooled to room temperature, and EtOAc (250 mL) was added followed by brine (200 mL). The mixture was stirred vigorously for 10 minutes and was filtered to remove the precipitate. EtOAc layer was separated and washed with brine twice, dried and evaporated. The resulting residue was purified using 120 g silica gel column (EtOAc/hexanes 10-100%). Collection of the second eluting peak provided tert-butyl (R,Z)-5-((tert-butylsulfinyl)imino)-5,7-dihydrospiro[cyclopenta[b]pyridine-6,4'-piperidine]-1'-carboxylate (2.8 g, 6.90 mmol, 94% yield) as a solid. m/z (esi/APCI) M+1=406.2.

Step E: tert-Butyl (R,Z)-5-((tert-butylsulfinyl)imino)-5,7-dihydrospiro[cyclopenta[b]pyridine-6,4'-piperidine]-1'-carboxylate (0.15 g, 0.37 mmol) was dissolved in THF (2 mL) in a vial. The solution was cooled to −78° C., and LiBH$_4$ (0.28 mL, 0.55 mmol) 2M in THF was added in one portion. The reaction was kept at −78° C. for 1 hour. The reaction was slowly warmed room temperature and was stirred for 18 hours. The reaction was quenched with saturated NH$_4$Cl followed by extraction with EtOAc (3×10 mL). The combined organic layers were washed with brine, dried and evaporated. The resulting residue was purified using column chromatography using 24 g silica column (EtOAc/hexanes 10-80%) to provide tert-butyl (R)-5-(((R)-tert-butylsulfinyl)amino)-5,7-dihydrospiro[cyclopenta[b]pyridine-6,4'-piperidine]-1'-carboxylate (30 mg, 0.27 mmol, 24% yield) as a solid as the minor product, and the other diastereomer as the major one tert-butyl (S)-5-(((R)-tert-butylsulfinyl)amino)-5,7-dihydrospiro[cyclopenta[b]pyridine-6,4'-piperidine]-1'-carboxylate (51 mg, 0.27 mmol, 35% yield). m/z (esi/APCI) M+1=408.2.

Intermediate Example G

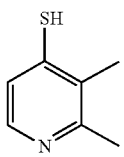

2,3-dimethylpyridine-4-thiol 2,3-Dimethylpyridine-4-thiol was prepared according to Intermediate Example A, substituting 3-chloro-4-iodopyridin-2-amine for 4-bromo-2,3-dimethylpyridine in Step A. m/z (esi/APCI) M+1=140.1.

Intermediate Example H

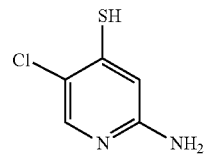

2-amino-5-chloropyridine-4-thiol

2-Amino-5-chloropyridine-4-thiol was prepared according to Intermediate Example A, substituting 3-chloro-4-iodopyridin-2-amine for 4-bromo-5-chloropyridin-2-amine in Step A. m/z (esi/APCI) M+1=161.1.

Intermediate Example I

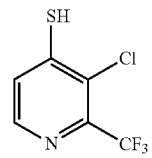

3-chloro-2-(trifluoromethyl)pyridine-4-thiol

3-Chloro-2-(trifluoromethyl)pyridine-4-thiol was prepared according to Intermediate Example A, substituting 3-chloro-4-iodopyridin-2-amine for 3-chloro-4-iodo-2-(trifluoromethyl)pyridine in Step A. m/z (esi/APCI) M+1=214.0.

Intermediate Example J

2-amino-3-bromopyridine-4-thiol

2-Amino-3-bromopyridine-4-thiol was prepared according to Intermediate Example A, substituting 3-chloro-4-iodopyridin-2-amine for 3-bromo-4-iodopyridin-2-amine in Step A. m/z (esi/APCI) M+1=205.0.

Intermediate Example K

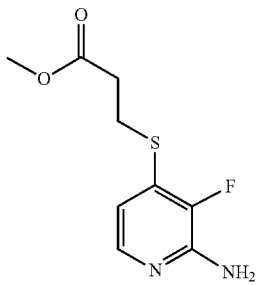

methyl 3-((2-amino-3-fluoropyridin-4-yl)thio)propanoate

2-Amino-3-fluoro-4-iodopyridine (1.1 g, 4.4 mmol) was dissolved in 1,4-dioxane (10 mL, 4.4 mmol). 4,5-Bis(diphenylphosphino)-9,9-dimethylxanthene (0.26 g, 0.45 mmol), and methyl 3-((2-amino-3-fluoropyridin-4-yl)thio)propanoate (0.95 g, 4.1 mmol) were added to the reaction solution. The reaction was placed under nitrogen. N,N-Diisopropylethylamine (1.5 mL, 8.9 mmol) was added, and the resulting solution was stirred at 100° C. overnight. The crude material was loaded onto an 80 g silica gel column and purified over a gradient of 0-100% EtOAc:hexane to provide methyl 3-((2-amino-3-fluoropyridin-4-yl)thio)propanoate (0.95 g, 92% yield). m/z (esi/APCI) M$^+$1=231.1.

Intermediate Example L

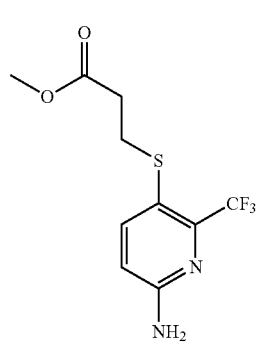

methyl 3-((6-amino-2-(trifluoromethyl)pyridin-3-yl)thio)propanoate

Methyl 3-((6-amino-2-(trifluoromethyl)pyridin-3-yl)thio)propanoate was prepared according to Intermediate Example K, substituting 2-amino-3-fluoro-4-iodopyridine for 5-bromo-6-trifluoromethylpyridin-2-ylamine in Step A. m/z (esi/APCI) M$^+$1=281.

Intermediate Example M

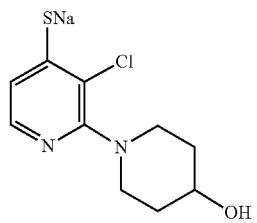

sodium 3-chloro-2-(4-hydroxypiperidin-1-yl)pyridine-4-thiolate

Step A: A solution of 3-chloro-2-fluoro-4-iodopyridine (2.0 g, 7.77 mmol) and 4-hydroxypiperidine (1.18 g, 11.7 mmol) in DMSO (5 mL) was heated to 75° C. for 1 hour. The solution was cooled to room temperature, diluted with water (10 mL) and partitioned with EtOAc/methyl tert-butyl ether ("MTBE") (2/1). The solid that formed between layers was filtered off and dried under vacuum to give 1-(3-chloro-4-iodopyridin-2-yl)piperidin-4-ol (1.08 g, 70%). m/z (esi) M$^+$1=339.0.

Step B: In a 20 mL vial, 1-(3-chloro-4-iodopyridin-2-yl)piperidin-4-ol (0.50 g, 1.48 mmol) was dissolved in dioxane (5 mL), and then the vial was sparged with nitrogen. 3-Mercaptopropionic acid methyl ester (0.195 g, 1.62 mmol) was added followed by Hunig's base (0.514 mL, 2.95 mmol). After 5 minutes, Pd(OAc)$_2$ (0.017 g, 0.074 mmol) was added followed by xantphos (0.086 g, 0.15 mmol). The vial was capped, sonicated and heated to 105° C. for 2.5 hours. The mixture was cooled to room temperature, diluted with EtOAc, and filtered through a Celite® pad. The pad was washed with EtOAc and solution was evaporated to dryness to give as a thick solid, which was carried on to the next step without further purification. m/z (esi) M$^+$1=331.0.

Step C: Methyl 3-((3-chloro-2-(4-hydroxypiperidin-1-yl)pyridin-4-yl)thio)propanoate (0.58 g, 1.75 mmol) was dissolved in dry dioxane (9 mL), and sodium ethanolate (21% weight in EtOH, 2.4 mL, 2.1 mmol) was added at room temperature under nitrogen. The mixture was stirred for 3 hours, and the solvent evaporated to dryness. The resulting solid was triturated twice with MTBE (5 mL). Crude material was dried under vacuum to give crude sodium 3-chloro-2-(4-hydroxypiperidin-1-yl)pyridine-4-thiolate (563 mg), which was used directly without further purification. m/z (esi) M$^+$1=245.0-247.0.

Intermediate Example N

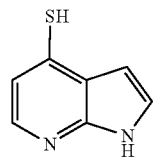

1H-pyrrolo[2,3-b]pyridine-4-thiol

Step A: 3-Mercaptopropionic acid 2-ethylhexyl ester (0.35 mL, 3.27 mmol) and Hunig's base (1.035 mL, 5.94 mmol) were added to a mixture of 4-iodo-1H-pyrrolo[2,3-b]pyridine (0.73 g, 2.971 mmol), Pd(OAc)$_2$ (0.033 g, 0.15 mmol) and xantphos (0.17 g, 0.30 mmol) in 1,4-dioxane (14.85 mL, 2.97 mmol) under argon gas. The reaction was heated to 100° C. under argon for 3 hours. The reaction was cooled, diluted in EtOAc (100 mL) and then filtered through diatomaceous silica (Celite®). The filtrate was concentrated, and the resulting crude product was purified using flash chromatography, eluting with a 10 to 100% EtOAc in hexanes gradient, to yield methyl 3-((1H-pyrrolo[2,3-b]pyridin-4-yl)thio)propanoate (0.69 g, 2.92 mmol, 98% yield) as a solid. m/z (esi/APCI) M$^+$1=237.1.

Step B: NaOEt (1.14 mL, 3.07 mmol) was added to methyl 3-((1H-pyrrolo[2,3-b]pyridin-4-yl)thio)propanoate (0.69 g, 2.92 mmol) in THF (14.6 mL, 2.92 mmol) and was stirred for 1 hour at room temperature. DCM (20 mL) was added, and this mixture was stirred for 5 minutes. The reaction was concentrated, and the solid was triturated with DCM (25 mL), filtered and air dried. The crude product was purified using flash chromatography, eluting with a 0 to 20% MeOH in DCM gradient with a 2% NH$_4$OH additive to yield 1H-pyrrolo[2,3-b]pyridine-4-thiol sodium salt (0.19 g, 1.07 mmol, 37% yield) as a solid. m/z (esi/APCI) M$^+$1=151.1.

Intermediate Example O

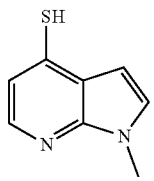

1-methyl-1H-pyrrolo[2,3-b]pyridine-4-thiol

1-Methyl-1H-pyrrolo[2,3-b]pyridine-4-thiol was prepared according to Intermediate Example N, substituting 4-bromo-1-methyl-1H-pyrrolo[2,3-b]pyridine for 4-iodo-1H-pyrrolo[2,3-b]pyridine in Step A. m/z (esi/APCI) M$^+$1=165.1.

Intermediate Example P

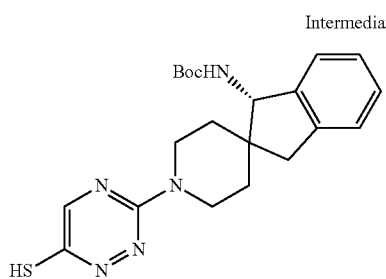

tert-butyl (S)-(1'-(6-mercapto-1,2,4-triazin-3-yl)-1,3-dihydrospiro[indene-2,4'-piperidin]-1-yl)carbamate Step A: A solution of (S)-1,3-dihydrospiro[indene-2,4'-piperidin]-1-amine dihydrochloride (11.3 g, 41.0 mmol) in dimethylacetamide ("DMA") (205 mL, 41.0 mmol) was purged with argon for 15 minutes before the addition of N,N-diisopropylethylamine ("DIEA") (28.7 mL, 164 mmol). This mixture was heated to 60° C. under nitrogen, and a solution of 3,6-dibromo-1,2,4-triazine (10.0 g, 41.9 mmol) in DMA (10 mL) was added slowly over 45 minutes by an addition funnel. The mixture was cooled, poured over water (1 L), and stirred for 30 minutes. The resulting solids were collected by filtration and washed with water (2×250 mL). This material was purified by flash chromatography, eluting with a 1 to 10% MeOH in DCM gradient with a 1% NH$_4$OH modifier, to afford (S)-1'-(6-bromo-1,2,4-triazin-3-yl)-1,3-dihydrospiro[indene-2,4'-piperidin]-1-amine (9.0 g, 25.0 mmol, 61% yield). m/z (esi/APCI) M$^+$1=361.2.

Step B: A mixture of (S)-1'-(6-bromo-1,2,4-triazin-3-yl)-1,3-dihydrospiro[indene-2,4'-piperidin]-1-amine (3.0 g, 8.33 mmol), di-tert-butyl dicarbonate (5.45 g, 25.0 mmol) and N,N-dimethylpyridin-4-amine (0.051 g, 0.42 mmol) in dichloroethane ("DCE") (41.6 mL, 8.33 mmol) was stirred at room temperature for two hours. The mixture was added to water (250 mL) and DCM (100 mL). The biphasic mixture was separated, and the water phase was extracted with DCM (2×150 mL). The organics were combined, washed with brine (150 mL), dried over Na$_2$SO$_4$, filtered and concentrated in vacuo. The material was purified via flash chromatography, eluting with 10-100% EtOAc in hexanes, to yield tert-butyl (S)-(1'-(6-bromo-1,2,4-triazin-3-yl)-1,3-dihydrospiro[indene-2,4'-piperidin]-1-yl)carbamate (0.75 g, 1.63 mmol, 20% yield) as a solid. m/z (esi/APCI) M, M$^+$2=460.1, 462.1.

Step C: 3-Mercaptopropionic acid 2-ethylhexyl ester (0.10 mL, 0.91 mmol) and Hunig's base (0.29 mL, 1.65 mmol) were added to a mixture of tert-butyl (S)-(1'-(6-bromo-1,2,4-triazin-3-yl)-1,3-dihydrospiro[indene-2,4'-piperidin]-1-yl)carbamate (0.38 g, 0.83 mmol), Pd(OAc)$_2$ (0.0093 g, 0.041 mmol) and xantphos (0.048 g, 0.083 mmol) in dioxane (8.25 mL, 0.83 mmol) under argon gas. This reaction mixture was heated to 100° C. for 1 hour. The mixture was cooled, diluted in EtOAc (25 mL) and then filtered through diatomaceous silica (Celite®). The filtrate was concentrated, and the resulting crude product was purified using flash chromatography, eluted with a 10 to 100% EtOAc in hexanes gradient, to yield methyl (S)-3-((3-(1-((tert-butoxycarbonyl)amino)-1,3-dihydrospiro[indene-2,4'-piperidin]-1'-yl)-1,2,4-triazin-6-yl)thio)propanoate (0.41 g, 0.83 mmol, 100% yield) as a solid. m/z (esi/APCI) M$^+$1=500.2.

Step D: NaOEt (0.62 mL, 1.65 mmol) was added to a solution of methyl (S)-3-((3-(1-((tert-butoxycarbonyl)amino)-1,3-dihydrospiro[indene-2,4'-piperidin]-1'-yl)-1,2,4-triazin-6-yl)thio)propanoate (0.41 g, 0.83 mmol) in THF (8.25 mL, 0.83 mmol). This mixture was stirred for 30 minutes at room temperature. The reaction mixture was concentrated in vacuo and purified using flash chromatography, eluting with a 0 to 20% MeOH in EtOAc gradient, to yield tert-butyl (S)-(1'-(6-mercapto-1,2,4-triazin-3-yl)-1,3-dihydrospiro[indene-2,4'-piperidin]-1-yl)carbamate (0.19 g, 0.45 mmol, 54% yield) as a solid. m/z (esi/APCI) M$^+$1=414.2.

Intermediate Example Q

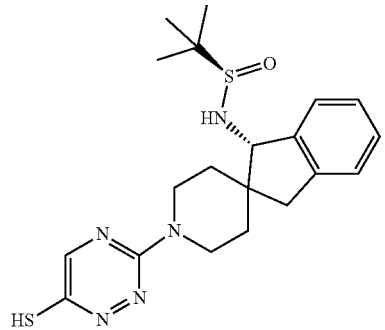

(R)-N-((S)-1'-(6-mercapto-1,2,4-triazin-3-yl)-1,3-dihydrospiro[indene-2,4'-piperidin]-1-yl)-2-methylpropane-2-sulfinamide Step A: A mixture of (R)-N-((S)-1,3-dihydrospiro[indene-2,4'-piperidin]-1-yl)-2-methylpropane-2-sulfinamide (6.41 g, 20.9 mmol) and 3,6-dibromo-1,2,4-triazine (5.00 g, 20.9 mmol) in 1,4-dioxane (52.3 mL, 20.9 mmol) was purged with argon for 15 minutes. DIEA (4.39 mL, 25.1 mmol) was added to the mixture, and then the mixture was heated to 60° C. for 1 hour. The mixture was cooled to room temperature, poured over water (1 L) and stirred for 30 minutes. The solids were collected by filtration and dried to yield (R)-N-((S)-1'-(6-bromo-1,2,4-triazin-3-yl)-1,3-dihydrospiro[indene-2,4'-piperidin]-1-yl)-2-methylpropane-2-sulfinamide (9.5 g, 20.5 mmol, 98% yield). m/z (esi/APCI) M, M$^+$2=464.1, 466.1.

Step B: 3-Mercaptopropionic acid 2-ethylhexyl ester (0.51 mL, 4.74 mmol) and Hunig's base (1.50 mL, 8.61 mmol) were added to a mixture of (R)-N-((S)-1'-(6-bromo-1,2,4-triazin-3-yl)-1,3-dihydrospiro[indene-2,4'-piperidin]-1-yl)-2-methyl propane-2-sulfinamide (2.0 g, 4.31 mmol), Pd(OAc)$_2$ (0.048 g, 0.22 mmol) and xantphos (0.25 g, 0.43 mmol) in 1,4-dioxane (43.06 mL, 4.30 mmol) under argon gas. This reaction mixture was heated to 100° C. for 1 hour. The mixture was cooled, diluted in EtOAc (25 mL) and then filtered through diatomaceous silica (Celite®). The filtrate was concentrated, and the resulting crude product was purified using flash chromatography, eluted with a 10 to 100% EtOAc in hexanes gradient, to yield methyl 3-((3-((S)-1-(((R)-tert-butylsulfinyl)amino)-1,3-dihydrospiro[indene-2,4'-piperidin]-1'-yl)-1,2,4-triazin-6-yl)thio)propanoate (0.88 g, 1.74 mmol, 40% yield) as a solid. m/z (esi/APCI) M$^+$1=504.2.

Step C: NaOEt (0.96 mL, 2.58 mmol) was added to a solution of methyl 3-((3-((S)-1-(((R)-tert-butylsulfinyl)amino)-1,3-dihydrospiro[indene-2,4'-piperidin]-1'-yl)-1,2,4-triazin-6-yl)thio)propanoate (0.65 g, 1.29 mmol) in THF (12.9 mL, 1.29 mmol). This mixture was stirred for 30 minutes at room temperature. The mixture was diluted in EtOAc (100 mL) and filtered through diatomaceous silica (Celite®). The filtrate was concentrated, and the resulting crude product was purified using flash chromatography, eluting with a 0 to 20% MeOH in EtOAc gradient, to yield (R)-N-((S)-1'-(6-mercapto-1,2,4-triazin-3-yl)-1,3-dihydrospiro[indene-2,4'-piperidin]-1-yl)-2-methylpropane-2-sulfinamide (0.34 g, 0.81 mmol, 63% yield) as a solid. m/z (esi/APCI) M$^+$1=418.2.

Intermediate Example R

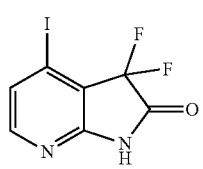

3,3-difluoro-4-iodo-1,3-dihydro-2H-pyrrolo[2,3-b]pyridin-2-one

A 35% aqueous solution of hydrogen peroxide (2.52 mL, 85.22 mmol) was added to a solution of 2-amino-4-iodopyridine (2.50 g, 11.36 mmol), ethyl bromodifluoroacetate (3.64 mL, 28.41 mmol), and bis(cyclopentadienyl)iron (0.22 g, 1.14 mmol) in DMSO (21.85 mL, 11.36 mmol) at −5° C. while stirring. The reaction was slowly warmed to room temperature and was stirred for 22 hours. The mixture was poured into water (100 mL), and the organics were extracted from the water phase with EtOAc (3×50 mL). Once pooled, the organic layers were washed with water (50 mL) and brine (3×50 mL). The organic layer was dried over Na$_2$SO$_4$, filtered and concentrated in vacuo. The residue was purified by flash chromatography using a 10 to 100% EtOAc in hexanes gradient to obtain 3,3-difluoro-4-iodo-1,3-dihydro-2H-pyrrolo[2,3-b]pyridin-2-one (0.93 g, 3.13 mmol, 27% yield). m/z (esi/APCI) M$^+$1=296.9.

Intermediate Example S

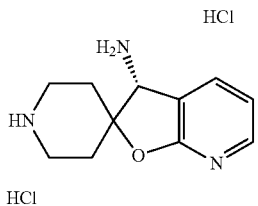

(R)-3H-spiro[furo[2,3-b]pyridine-2,4'-piperidin]-3-amine dihydrochloride

Step A: 3-(1,3-Dithian-2-yl)-2-fluoropyridine (1 g, 4.64 mmol) in THF (4.64 mL) was added to a stirred solution of LDA (4.06 mL, 8.13 mmol) in THF (4.64 mL) at −78° C. The reaction was warmed to 0° C. and stirred for 20 minutes. The reaction was cooled back to −78° C. followed by the dropwise addition of 1-boc-4-piperidone (0.97 g, 4.88 mmol) in THF (4.64 mL). The reaction was stirred for 1 hour, allowed to warm up to 0° C., and was stirred for 6 hours. The mixture was poured into saturated NH$_4$Cl. The product was extracted with ethyl acetate three times, combined organics, filtered through 1PS paper, evaporated in vacuo, concentrated, purified by silica gel chromatography (0-100% EA/hexane) to afford tert-butyl dispiro[piperidine-4,2'-furo[2,3-b]pyridine-3',2''-[1,3]dithiane]-1-carboxylate (993 mg, 2.52 mmol, 54% yield). LCMS (MM-ES+APCI, Pos): m/z 395.1 (M$^+$H).

Step B: Pyridinium perbromide (1.2 g, 3.78 mmol) and tetrabutylammonium bromide (81.1 mg, 0.25 mmol) were added to a stirred solution of tert-butyl dispiro[piperidine-4,2'-furo[2,3-b]pyridine-3',2''-[1,3]dithiane]-1-carboxylate (993 mg, 2.52 mmol) and pyridine (0.2 mL, 2.52 mmol) in a mixture of DCM-H$_2$O 5:1 (16.8 mL). After stirring at room temperature for 24 hours, the reaction was poured into water and DCM. The DCM layer was washed with water, brine, filtered through 1PS paper, concentrated and purified by silica gel chromatography (0-100% ethyl acetate/hexanes) to afford tert-butyl 3-oxo-3H-spiro[furo[2,3-b]pyridine-2,4'-piperidine]-1'-carboxylate (735 mg, 1.93 mmol, 77% yield). LCMS (MM-ES+APCI, Pos): m/z 205.1 (M$^+$H-Boc).

Step C: (R)-(+)-2-Methyl-2-propanesulfinamide (608.8 mg, 5.02 mmol) and tetraethoxytitanium (2.5 mL, 11.72 mmol) were added to a solution of tert-butyl 3-oxo-3H-spiro[furo[2,3-b]pyridine-2,4'-piperidine]-1'-carboxylate (637 mg, 1.67 mmol) in THF (8.4 mL), and the reaction was stirred overnight at 90° C. The reaction was diluted with ethyl acetate and washed with water. The layers were separated. The aqueous layer was extracted with ethyl acetate. The combined organics were washed with water, brine, filtered through 1PS paper and concentrated in vacuo. The material chromatographed using 0-50% EtOAc/hexanes as eluent to give tert-butyl (R,E)-3-((tert-butylsulfinyl)imino)-3H-spiro[furo[2,3-b]pyridine-2,4'-piperidine]-1'-carboxylate (426 mg, 1.04 mmol, 62% yield). LCMS (MM-ES+APCI, Pos): m/z 408.2 (M$^+$H).

Step D: tert-Butyl (R,E)-3-((tert-butylsulfinyl)imino)-3H-spiro[furo[2,3-b]pyridine-2,4'-piperidine]-1'-carboxylate (426 mg, 1.05 mmol) was dissolved in THF (2.6 mL), and the solution cooled down to −78° C. 1M BH$_3$·THF solution (2.2 mL, 2.20 mmol) was added to the solution via syringe over 30 minutes. The reaction was stirred at −78° C. for 1 hour and was warmed up to room temperature while stirring for 3 days. The reaction was quenched with saturated NH₄Cl and extracted with EtOAc. The combined organic layers were washed with water, brine, dried, evaporated in vacuo and purified by silica gel chromatography (0-20% MeOH/DCM) to give tert-butyl (R)-3-(((R)-tert-butylsulfinyl)amino)-3H-spiro[furo[2,3-b]pyridine-2,4'-piperidine]-1'-carboxylate (180 mg, 0.44 mmol, 42% yield). LCMS (MM-ES+APCI, Pos): m/z 410.2 (M⁺H).

Step E: A mixture of tert-butyl (R)-3-(((S)-tert-butylsulfinyl)amino)-3H-spiro[furo[2,3-b]pyridine-2,4'-piperidine]-1'-carboxylate (80 mg, 0.20 mmol) in DCM (1 mL) was purged with N₂ and treated with HCl in dioxane (0.25 mL, 0.98 mmol) via syringe at room temperature. The mixture was stirred at room temperature for 2 hours. The mixture was evaporated in vacuo to give (R)-3H-spiro[furo[2,3-b]pyridine-2,4'-piperidin]-3-amine dihydrochloride (44 mg, 0.13 mmol, 65% yield).

Intermediate Example T

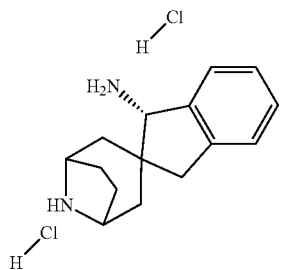

(1'S)-1',3'-dihydro-8-azaspiro[bicyclo[3.2.1]octane-3,2'-inden]-1'-amine dihydrochloride Step A: Lithium diisopropylamide, 2M solution in THF/n-heptane (2.78 mL, 5.57 mmol) was added dropwise to a −70° C. solution of 8-(tert-butyl) 3-methyl (1R,5S)-8-azabicyclo[3.2.1]octane-3,8-dicarboxylate (1 g, 3.71 mmol) in THF (9.28 mL). After stirring at −70° C. for 90 minutes, benzyl bromide (0.57 mL, 4.83 mmol) was added slowly. The reaction mixture was stirred at −70° C. for 3 hours. The mixture was carefully quenched with saturated aqueous NH₄Cl. The aqueous layer was separated, extracted with ethyl acetate, combined extracts filtered through 1PS paper, concentrated and purified by silica gel chromatography (0-50% ethyl acetate/hexanes) to give 8-(tert-butyl) 3-methyl (1R,3r,5S)-3-benzyl-8-azabicyclo[3.2.1]octane-3,8-dicarboxylate (1.1 g, 3.06 mmol, 82% yield). LCMS (MM-ES+APCI, Pos): m/z 260.1 (M⁺H-Boc).

Step B: A mixture of 8-(tert-butyl) 3-methyl (1R,3r,5S)-3-benzyl-8-azabicyclo[3.2.1]octane-3,8-dicarboxylate (1 g, 2.78 mmol) in polyphosphoric acid (5.54 mL, 139 mmol) was stirred at 120° C. for 5 days. The mixture was diluted with water, pH adjusted to 10 with NaOH. Boc-anhydride (0.97 mL, 4.17 mmol) was added, and the reaction was stirred at room temperature for 4 hours. The mixture was extracted with ethyl acetate, combined organics filtered through 1PS paper, and concentrated and purified by silica gel chromatography (0-50% ethyl acetate/hexanes) to give tert-butyl 1'-oxo-1',3'-dihydro-8-azaspiro[bicyclo[3.2.1]octane-3,2'-inden]-8-carboxylate (650 mg, 1.39 mmol, 50% yield). LCMS (MM-ES+APCI, Pos): m/z 228.1 (M⁺H-Boc).

Step C: (R)-(+)-2-Methyl-2-propanesulfinamide (721.8 mg, 5.95 mmol) and tetraethoxytitanium (2.9 mL, 13.90 mmol) was added to a solution of tert-butyl 1'-oxo-1',3'-dihydro-8-azaspiro[bicyclo[3.2.1]octane-3,2'-indene]-8-carboxylate (0.65 g 1.98 mmol) in THF (9.9 mL), and the reaction was stirred overnight at 90° C. The reaction was diluted with ethyl acetate and washed with water, and the layers were separated. The aqueous layer was extracted with ethyl acetate. The combined organics were washed with water, brine, filtered through 1PS paper and concentrated in vacuo. The material was chromatographed (0-50% EtOAc/hexanes) to give tert-butyl (Z)-1'-(((R)-tert-butylsulfinyl)imino)-1',3'-dihydro-8-azaspiro[bicyclo[3.2.1]octane-3,2'-indene]-8-carboxylate (307 mg, 0.71 mmol, 36% yield). LCMS (MM-ES+APCI, Pos): m/z 431.2 (M⁺H).

Step D: Sodium borohydride (108 mg, 2.85 mmol) was added to a solution of tert-butyl (Z)-1'-(((R)-tert-butylsulfinyl)imino)-1',3'-dihydro-8-azaspiro[bicyclo[3.2.1]octane-3,2'-indene]-8-carboxylate (307 mg, 0.71 mmol) in THF (0.79 mL) cooled to −70° C., and the reaction was stirred for 18 hours while warming to room temperature. The reaction was poured into water and extracted into ethyl acetate. The organics were washed with brine, filtered through 1PS paper and concentrated in vacuo to give tert-butyl (1'S)-1'-(((R)-tert-butylsulfinyl)amino)-1',3'-dihydro-8-azaspiro[bicyclo[3.2.1]octane-3,2'-indene]-8-carboxylate (274 mg, 0.63 mmol, 89% yield). LCMS (MM-ES+APCI, Pos): m/z 333.2 (M⁺H-Boc).

Step E: A mixture of tert-butyl (1'S)-1'-(((R)-tert-butylsulfinyl)amino)-1',3'-dihydro-8-azaspiro[bicyclo[3.2.1]octane-3,2'-indene]-8-carboxylate (274 mg, 0.63 mmol) in DCM (3.2 mL) was purged with N₂ and treated with 4N HCl in dioxane (0.79 mL, 3.17 mmol) via syringe at room temperature. The mixture was stirred at room temperature for 90 minutes. The mixture was evaporated in vacuo, residue shaken in MTBE, solids collected via filtration and dried to give (1'S)-1',3'-dihydro-8-azaspiro[bicyclo[3.2.1]octane-3,2'-inden]-1'-amine dihydrochloride (144 mg, 0.48 mmol, 76% yield). LCMS (MM-ES+APCI, Pos): m/z 229.2.

Intermediate Example U

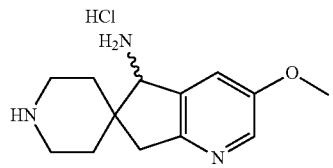

3-methoxy-5,7-dihydrospiro[cyclopenta[b]pyridine-6,4'-piperidin]-5-amine hydrochloride Step A: MeI (1.65 mL, 26.58 mmol) was added to a stirred solution of 5-bromo-6-chloropyridin-3-ol (5.0 g, 24.16 mmol) and K₂CO₃ (5.0 g, 36.25 mmol) in ACN (30 mL), and the mixture was stirred at room temperature for 16 hours. The reaction mixture was extracted with EtOAc. The organic phase was dried over Na₂SO₄, filtered and concentrated under reduced pressure. The residue was purified by silica gel column chromatography (0-10% EtOAc/hexane) to afford 3-bromo-2-chloro-5-methoxypyridine (3.48 g, 65% yield) as a solid. m/z (esi) M⁺1=223.9.

Step B: Isopropylmagnesium bromide (19.76 mL, 1.3 M in THF, 25.68 mmol) was added dropwise to a stirred solution of tert-butyl 4-formyl-4-methylpiperidine-1-carboxylate (3.89 g, 17.12 mmol) in THF (55 mL) at 0° C. and stirred at room temperature for 2 hours. 3-Bromo-2-chloro-5-methoxypyridine (5.68 g, 25.68 mmol) in THF (10 mL)

was added dropwise at 0° C. and stirred at room temperature for 30 minutes. The reaction mixture was quenched with saturated NH₄Cl solution and extracted with EtOAc. The organic part was dried over Na₂SO₄, filtered, concentrated and was purified by silica gel column chromatography (15-20% EtOAc/hexane) to afford tert-butyl 4-((2-chloro-5-methoxypyridin-3-yl)(hydroxy)methyl)-4-methylpiperidine-1-carboxylate (2.157 g, 83% yield) as a sticky solid. m/z (esi) M⁺1=371.4.

Step C: Dess-Martin periodinane (1.89 g, 4.45 mmol) was added to a stirred solution of tert-butyl 4-((2-chloro-5-methoxypyridin-3-yl)(hydroxy)methyl)-4-methylpiperidine-1-carboxylate (1.1 g, 2.97 mmol) in DCM (16 mL) at 0° C. and stirred at room temperature for 3 hours under nitrogen atmosphere. The reaction mixture was quenched with saturated sodium thiosulphate solution and extracted with DCM. The organic phase was washed with 1N NaOH solution, concentrated and was purified by silica gel column chromatography (15-20% EtOAc/hexane) to afford tert-butyl 4-(2-chloro-5-methoxynicotinoyl)-4-methylpiperidine-1-carboxylate (860 mg, 78% yield) as an oil. m/z (esi) M⁺1=369.1.

Step D: Tricyclohexylphosphonium tetrafluoroborate (145 mg, 0.39 mmol), palladium(II) acetate (44 mg, 0.19 mmol), pivalic acid (121 mg, 1.18 mmol), cesium carbonate (1.54 g, 4.72 mmol) and tert-butyl 4-(2-chloro-5-methoxynicotinoyl)-4-methylpiperidine-1-carboxylate (1.45 g, 3.94 mmol) in mesitylene (20 mL) were added to a flame-dried sealed tube under argon. The mixture was degassed with argon for 10 minutes and heated at 140° C. for 48 hours. The reaction mixture was cooled to room temperature, filtered through a Celite® bed and washed with EtOAc. The organic phase was washed with brine, dried over Na₂SO₄, filtered and concentrated. The residue was purified by silica gel column chromatography (0-10% EtOAc/hexane) to get tert-butyl 3-methoxy-5-oxo-5,7-dihydrospiro[cyclopenta[b]pyridine-6,4'-piperidine]-1'-carboxylate (0.84 g, 64% yield) as a solid. m/z (esi) M⁺1=333.2.

Step E: (R)-(+)-2-Methyl-2-propanesulfinamide (629 mg, 5.19 mmol) was added to a stirred solution of tert-butyl 3-methoxy-5-oxo-5,7-dihydrospiro[cyclopenta[b]pyridine-6,4'-piperidine]-1'-carboxylate (575 mg, 1.73 mmol) in titanium(IV) ethoxide (2.2 mL, 10.38 mmol), and the reaction was stirred at 110° C. for 4 hours. The reaction mixture was allowed to cool to room temperature, and the reaction mixture was diluted with EtOAc and water. The resulting mixture was vigorously stirred for 15 minutes at room temperature and then filtered through a pad of Celite®. The filtrate was extracted with EtOAc, washed with brine, dried over Na₂SO₄ and filtered. The organic phase was concentrated, and the resulting residue was purified by silica gel column chromatography (40-50% EtOAc/hexane) to provide tert-butyl (R,Z)-5-((tert-butylsulfinyl)imino)-3-methoxy-5,7-dihydrospiro[cyclopenta[b]pyridine-6,4'-piperidine]-1'-carboxylate as a semisolid (0.64 g, 84% yield). m/z (esi) M⁺1=437.2.

Step F: Sodium borohydride (256 mg, 6.77 mmol) was added to a stirred solution of tert-butyl (R,Z)-5-((tert-butylsulfinyl)imino)-3-methoxy-5,7-dihydrospiro[cyclopenta[b]pyridine-6,4'-piperidine]-1'-carboxylate (590 mg, 1.35 mmol) in MeOH (10 mL) at 0° C., and the reaction was stirred for 3 hours. The reaction mixture was allowed to increase to room temperature. Saturated aqueous NH₄Cl solution was slowly added to quench the reaction. MeOH was evaporated, and the reaction mixture was extracted with EtOAc. The organic phase was washed with brine, dried over Na₂SO₄, filtered and concentrated. The resulting residue was purified by silica gel column chromatography (0-4% MeOH/DCM) to get tert-butyl 5-(((R)-tert-butylsulfinyl)amino)-3-methoxy-5,7-dihydrospiro[cyclopenta[b]pyridine-6,4'-piperidine]-1'-carboxylate (0.58 g, 97% yield) as a solid. m/z (esi) M⁺1=437.9.

Step G: Dioxane-HCl (4M; 12 mL) was added to a stirred solution of tert-butyl 5-(((R)-tert-butylsulfinyl)amino)-3-methoxy-5,7-dihydrospiro[cyclopenta[b]pyridine-6,4'-piperidine]-1'-carboxylate (600 mg, 1.37 mmol) in MeOH (12 mL) at 0° C., and the reaction was stirred for 2 hours. The reaction mixture was concentrated, and the crude material was triturated with diethyl ether to afford 3-methoxy-5,7-dihydrospiro[cyclopenta[b]pyridine-6,4'-piperidin]-5-amine hydrochloride (418 mg, 99% yield) as a solid. The crude was used directly without further purification. m/z (esi) M⁺1=234.3.

Intermediate Example V

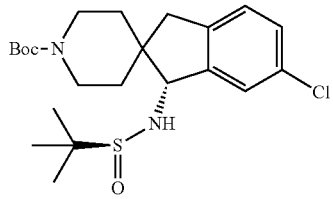

tert-butyl (R)-1-(((S)-tert-butylsulfinyl)amino)-6-chloro-1,3-dihydrospiro[indene-2,4'-piperidine]-1'-carboxylate Step A: NaH (60% in mineral oil) (1.45 g, 36.14 mmol) was added to a stirred solution of 6-chloro-2,3-dihydro-1H-inden-1-one (2.0 g, 12.05 mmol) in dimethylformamide ("DMF") (40 mL) at 0° C., and the mixture was stirred for 30 minutes at 0-5° C. N-Benzyl-2-chloro-N-(2-chloroethyl)ethan-1-amine hydrochloride (3.06 g, 13.25 mmol) was added portion wise, and the mixture was stirred at 60° C. for 16 hours. The reaction was quenched with brine solution and was extracted with EtOAc. The combined organic layers were washed with brine, dried over anhydrous Na₂SO₄, filtered, and concentrated under reduced pressure to get crude, which was purified by silica gel (EtOAc/hexane) solution to get 1'-benzyl-6-chlorospiro[indene-2,4'-piperidin]-1(3H)-one (1.55 g, 40% yield) as an oil. m/z (esi) M⁺1: 325.9.

Step B: 1-Chloroethyl chloroformate (1.55 mL, 14.34 mmol) was added to a stirred solution of 1'-benzyl-6-chlorospiro[indene-2,4'-piperidin]-1(3H)-one (1.55 g, 4.78 mmol) in DCE (24 mL), and the reaction was refluxed for 1 hour. The reaction was concentrated, and MeOH (24 mL) was added and refluxed for 1 hour. MeOH was evaporated to dryness to get 6-chlorospiro[indene-2,4'-piperidin]-1(3H)-one (1.13 g, crude) as a solid. m/z (esi) M⁺1: 236.2.

Step C: Triethylamine (2.66 mL, 19.16 mmol) was added to a stirred solution of 6-chlorospiro[indene-2,4'-piperidin]-1(3H)-one (1.13 g, 4.79 mmol) in DCM (20 mL), followed by boc-anhydride (1.65 mL, 7.19 mmol) at 0° C., and the reaction was stirred at room temperature for 1 hour. The reaction was evaporated to dryness and was purified by silica gel column chromatography (15-20% EtOAc/hexane) to afford tert-butyl 6-chloro-1-oxo-1,3-dihydrospiro[indene-2,4'-piperidine]-1'-carboxylate (1.3 g, 81%, 2 steps yield) as a solid. m/z (esi) M⁺1: 336.3.

Step D: A solution of tert-butyl 6-chloro-1-oxo-1,3-dihydrospiro[indene-2,4'-piperidine]-1'-carboxylate (800 mg, 2.38 mmol), titanium(IV) ethoxide (1.99 mL, 9.5 mmol), and (R)-(+)-2-methylpropane-2-sulfinamide (577.5 mg, 4.76 mmol) in THF (15 mL) was stirred at 90° C. for 12 hours. The reaction was cooled to room temperature and quenched with water. The compound was extracted with EtOAc. The combined organic phases were washed with brine, dried over anhydrous Na$_2$SO$_4$, filtered, and concentrated under reduced pressure to get crude, which was purified by silica gel column chromatography (20-25% EtOAc/hexane) to get tert-butyl (R,E)-1-((tert-butylsulfinyl)imino)-6-chloro-1,3-dihydrospiro[indene-2,4'-piperidine]-1'-carboxylate (861 mg, 94% yield) as a solid. m/z (esi) M$^+$1:438.8.

Intermediate Example W

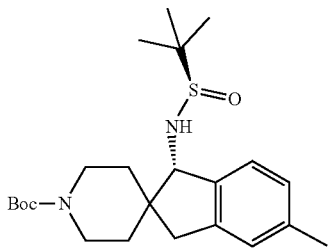

tert-butyl (S)-1-(((R)-tert-butylsulfinyl)amino)-5-methyl-1,3-dihydrospiro[indene-2,4'-piperidine]-1'-carboxylate Step A: NaH (60% dispersion in mineral oil, 1.97 g, 82.19 mmol) was added portion wise to a stirred solution of 5-methyl-2,3-dihydro-1H-inden-1-one (4.0 g, 27.39 mmol) in DMF (80 mL) at 0° C. The mixture was stirred at 0° C. for 30 minutes. N-Benzyl-2-chloro-N-(2-chloroethyl)ethan-1-amine hydrochloride (8.09 g, 30.13 mmol) was added portion wise to the reaction mixture, and the reaction was stirred at room temperature for 16 hours. The reaction was diluted with brine and extracted with EtOAc. The organic parts were combined and washed with brine, dried over anhydrous Na$_2$SO$_4$, filtered, and concentrated under reduced pressure. The residue was purified by silica gel column chromatography (25% EtOAc/hexane) to afford 1'-benzyl-5-methylspiro[indene-2,4'-piperidin]-1(3H-one (4.0 g, 48% yield) as a sticky solid. m/z (esi) M$^+$1=305.6.

Step B: Chloroethyl chloroformate (6.97 g, 49.11 mmol) was added to a stirred solution of 1'-benzyl-5-methylspiro[indene-2,4'-piperidin]-1(310-one (5.0 g, 16.37 mmol) in DCE (100 mL) at 0° C. and stirred for 10 minutes. The reaction mixture was stirred at 80° C. for 1 hour. The reaction mixture was concentrated to dryness, and MeOH (100 mL) was added and stirred at 75° C. for 1 hour. The reaction mixture was concentrated under reduced pressure to afford 5-methylspiro[indene-2,4'-piperidin]-1(3H)-one (3.5 g, crude) as a liquid, which was used for the next step without further purification. m/z (esi) M$^+$1=215.9.

Step C: Triethylamine (9.07 mL, 65.11 mmol) was added to a stirred solution of 5-methylspiro[indene-2,4'-piperidin]-1(3H)-one (3.5 g, 16.27 mmol) in DCM (35 mL) at 0° C. Boc anhydride (5.61 mL, 24.42 mmol) was added at 0° C., and the reaction mixture was stirred at room temperature for 16 hours. The reaction mixture was concentrated under reduced pressure and purified by silica gel column chromatography (10% EtOAc/hexane) to afford tert-butyl 5-methyl-1-oxo-1,3-dihydrospiro[indene-2,4'-piperidine]-1'-carboxylate (520 mg, 68% yield, 2 steps) as a solid. m/z (esi) M$^+$1=316.2.

Step D: tert-Butyl 5-methyl-1-oxo-1,3-dihydrospiro[indene-2,4'-piperidine]-1'-carboxylate (1.9 gm, 6.03 mmol) and (R)-(+)-2-methylpropane-2-sulfinamide (2.19 g, 18.09 mmol) were added into warm (100° C.) titanium (IV) ethoxide (4.12 g, 18.09 mmol) and stirred at 100° C. for 19 hours. The reaction mixture was poured into EtOAc and brine and was stirred for 15 minutes. Solids were filtered off, and the liquid part was separated. The organic layer was washed with brine, dried over anhydrous Na$_2$SO$_4$, and concentrated under reduced pressure. The resulting residue was purified by silica gel column chromatography (1% MeOH/DCM) to afford the tert-butyl (R,E)-1-((tert-butylsulfinyl)imino)-5-methyl-1,3-dihydrospiro[indene-2,4'-piperidine]-1'-carboxylate (1.25 g, 49% yield) as a solid. m/z (esi) M$^+$1=418.9.

Step E: Sodium borohydride (470 mg, 12.42 mmol) was added to a solution at 0° C. of tert-butyl (R,E)-1-((tert-butylsulfinyl)imino)-5-methyl-1,3-dihydro-spiro[indene-2,4'-piperidine]-1'-carboxylate (1.3 g, 3.10 mmol) in MeOH (30 mL), and the reaction was stirred at room temperature for 4 hours. The reaction mixture was quenched with the ice water and extracted with EtOAc. The combined organic layers were dried over anhydrous Na$_2$SO$_4$, filtered, and concentrated under reduced pressure. The resulting residue was purified by silica gel column chromatography (30% EtOAc/hexane) to afford tert-butyl (S)-1-(((R)-tert-butylsulfinyl)amino)-5-methyl-1,3-dihydrospiro[indene-2,4'-piperidine]-1'-carboxylate (310 mg, 24% yield) (m/z (esi) M$^-$1=419.3).

Intermediate Example X

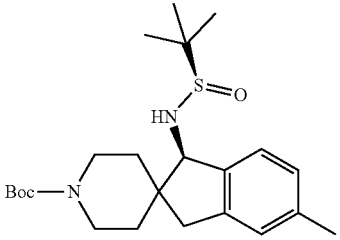

tert-butyl(R)-1-(((R)-tert-butylsulfinyl)amino)-5-methyl-1,3-dihydrospiro[indene-2,4'-piperidine]-1'-carboxylate tert-Butyl (R)-1-(((R)-tert-butylsulfinyl)amino)-5-methyl-1,3-dihydrospiro[indene-2,4'-piperidine]-1'-carboxylate was prepared according to Intermediate Example W, collecting the second peak in Step E. (m/z (esi) M$^-$1=419.3).

Intermediate Example Y

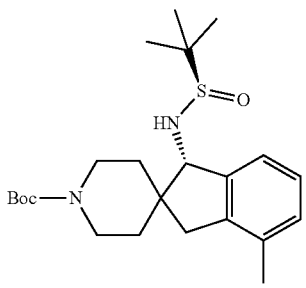

tert-butyl (S)-1-(((R)-tert-butylsulfinyl)amino)-4-methyl-1,3-dihydrospiro[indene-2,4'-piperidine]-1'-carboxylate Step A: NaH (60%, 0.98 g, 15.06 mmol) was added to a stirred solution of 4-methyl-2,3-dihydro-1H-inden-1-one (2 g, 13.69 mmol) in DMF (25 mL) at 0° C., and the reaction was stirred for 30 minutes at 0° C. N-Benzyl-2-chloro-N-(2-chloroethyl)ethan-1-amine hydrochloride salt was added and stirred for 18 hours at room temperature. The reaction was quenched with aqueous saturated NH₄Cl solution and extracted with ethyl acetate. The combined organic layer was washed with water, brine, dried over anhydrous sodium sulfate, filtered and concentrated. The resulting residue was purified by Combi-Flash column (eluted at 25% ethyl acetate in hexane) to afford 1'-benzyl-4-methylspiro[indene-2,4'-piperidin]-1(3H)-one (1.5 g, 39%) as a solid. m/z (esi) M⁺1=305.8.

Step B: 1-Chloroethyl chloroformate (1.59 mL, 14.73 mmol) was added to a stirred solution of 1'-benzyl-4-methylspiro[indene-2,4'-piperidin]-1(3H)-one (1.5 g, 4.91 mmol) in DCE (10 mL) and refluxed for 1 hour. The volatiles were concentrated under reduced pressure to get crude oil. Methanol was added and refluxed for 1 hour. The reaction was concentrated under reduced pressure to get 4-methylspiro[indene-2,4'-piperidin]-1(3H)-one as crude, which was used in next step without further purification. m/z (esi) M⁺1=215.7.

Step C: Triethylamine ("TEA") (3.23 mL, 23.22 mmol) was added to a stirred solution of 4-methylspiro[indene-2,4'-piperidin]-1(3H)-one (1 g, crude) in DCM (15 mL), followed by addition of boc-anhydride (2.13 mL, 9.28 mmol). The reaction was stirred for 18 hours at room temperature. The reaction was concentrated under reduced pressure to get crude, which was purified by Combi-Flash column (eluted at 10-15% ethyl acetate in hexane) to afford tert-butyl 4-methyl-1-oxo-1,3-dihydrospiro[indene-2,4'-piperidine]-1'-carboxylate (1.5 g, 66%, 2 steps) as a liquid.

Step D: Ti(OEt)4 (8.77 mL, 41.84 mmol) was added to tert-butyl 4-methyl-1-oxo-1,3-dihydrospiro[indene-2,4'-piperidine]-1'-carboxylate (1 g, 3.17 mmol) and heated to 90° C. (R)-2-Methyl propane-2-sulfinamide (1.1 g, 9.51 mmol) was added, and the heating was continued at 90° C. for 24 hours. The reaction was poured into ethyl acetate (50 mL), and aqueous saturated brine solution (50 mL) was added. The precipitated solid was filtered, and the filtrate was washed with water, brine, dried over anhydrous sodium sulfate, filtered and concentrated to get a crude, which was purified by Combi-Flash column (eluted at 20% ethyl acetate in hexane) to afford tert-butyl (R,Z)-1-((tert-butylsulfinyl)imino)-4-methyl-1,3-dihydrospiro[indene-2,4'-piperidine]-1'-carboxylate (800 mg, 60%) as a solid. m/z (esi) M⁺1=418.8.

Step E: Sodium borohydride (600 mg, 15.76 mmol) was added to a stirred solution of tert-butyl (R,Z)-1-((tert-butylsulfinyl)imino)-4-methyl-1,3-dihydrospiro[indene-2,4'-piperidine]-1'-carboxylate (1.1 g, 2.62 mmol) in methanol (60 mL) at room temperature and stirred for 4 hours. The reaction was quenched with saturated NH₄Cl solution and extracted with ethyl acetate. The combined organic part was washed with water, brine, dried over anhydrous sodium sulfate, filtered and concentrated. The resulting residue was purified by Combi-Flash column (eluted at 25% ethyl acetate in hexane) to afford tert-butyl (S)-1-(((R)-tert-butylsulfinyl)amino)-4-methyl-1,3-dihydrospiro[indene-2,4'-piperidine]-1'-carboxylate (440 mg, 40%) (m/z (esi) M⁺1=421.4) as a solid.

Intermediate Example Z

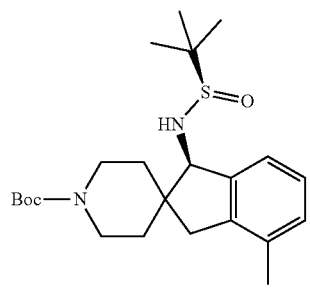

tert-butyl (R)-1-(((R)-tert-butylsulfinyl)amino)-4-methyl-1,3-dihydrospiro[indene-2,4'-piperidine]-1'-carboxylate tert-Butyl (R)-1-(((R)-tert-butylsulfinyl)amino)-4-methyl-1,3-dihydrospiro[indene-2,4'-piperidine]-1'-carboxylate, was prepared according to Intermediate Example Y, collecting the second peak. m/z (esi) M⁺1=421.4.

Intermediate Example AB

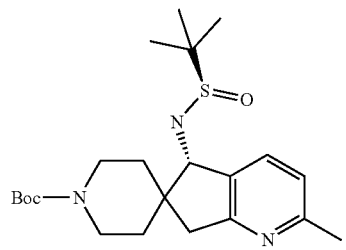

tert-butyl (S)-5-(((R)-tert-butylsulfinyl)amino)-2-methyl-5,7-dihydrospiro[cyclopenta[b]pyridine-6,4'-piperidine]-1'-carboxylate Step A: A mixture of cyclopentane-1,3-dione (20.0 g, 204.08 mmol), but-3-en-2-one (26.78 mL, 306.12 mmol), molecular sieves 4 Å (100 g) and NH₄OAc (31.42 g, 408.16 mmol) in toluene (800 mL) was stirred at reflux for 24 hours. The reaction mixture was filtered through a bed of Celite® and concentrated, and the resulting residue was purified by silica gel column chromatography (50% EtOAc/hexane) to afford 2-methyl-6,7-dihydro-5H-cyclopenta[b]pyridin-5-one (6.0 g, 20% yield) as a liquid. m/z (esi) M$^+$1=148.3.

Step B: NaH (60 weight % in paraffin) (4.0 g, 102.04 mmol) to a stirred solution of 2-methyl-6,7-dihydro-5H-cyclopenta[b]pyridin-5-one (5.0 g, 34.01 mmol) in DMF (60 mL) at 0° C. and stirred for 30 minutes at room temperature. N-Benzyl-2-chloro-N-(2-chloroethyl)ethan-1-amine hydrochloride (7.31 g, 27.21 mmol) was added portion wise at 0° C. and stirred for 16 hours at room temperature. The reaction mixture was quenched with ice water and extracted with ethyl acetate. The organic part was dried (Na$_2$SO$_4$), filtered and concentrated, and the crude material was purified by silica gel (0-15% MeOH in DCM) to afford 1'-benzyl-2-methylspiro[cyclopenta[b]pyridine-6,4'-piperidin]-5(7H)-one (1.2 g, 11% yield) as a liquid. m/z (esi) M$^+$1=306.9.

Step C: Ammonium formate (247.14 mg, 3.92 mmol) and Pd/C (200 mg) were added to a stirred solution of 1'-benzyl-2-methylspiro[cyclopenta[b]pyridine-6,4'-piperidin]-5(7H)-one (400.0 mg, 1.31 mmol) in ethanol (15 mL), and the reaction mixture was purged with argon for 10 minutes. The reaction mixture was refluxed at 80° C. for 16 hours and was concentrated to afford 2-methylspiro[cyclopenta[b]pyridine-6,4'-piperidin]-5(7H)-one, which was used for next step without further purification. m/z (esi) M$^+$1=217.2.

Step D: Triethylamine (0.72 mL, 5.18 mmol) was added to a stirred solution of 2-methylspiro[cyclopenta[b]pyridine-6,4'-piperidin]-5(7H)-one (280.0 mg, 1.29 mmol) in DCM (10 mL) at 0° C., followed by Boc anhydride (0.45 mL, 1.94 mmol), and the reaction mixture was stirred at room temperature for 1 hour. The reaction mixture was concentrated and purified by silica gel column chromatography (30% EtOAc/hexane) to afford tert-butyl 2-methyl-5-oxo-5,7-dihydrospiro[cyclopenta[b]pyridine-6,4'-piperidine]-1'-carboxylate (200 mg, 48% yield, 2 steps) as a solid. m/z (esi) M$^+$1=317.2.

Step E: tert-Butyl 2-methyl-5-oxo-5,7-dihydrospiro[cyclopenta[b]pyridine-6,4'-piperidine]-1'-carboxylate (400 mg, 1.26 mmol) and (R)-2-methylpropane-2-sulfinamide (460.21 mg, 3.80 mmol) were added to titanium (IV) ethoxide (866.20 mg, 3.79 mmol) at 90° C. and was stirred at 90° C. for 5 hours. The reaction mixture was poured onto ethyl acetate and brine. After stirring for 15 minutes, the precipitated solid was filtered off, and the liquid part was separated. The organic layer was washed with brine, dried (Na$_2$SO$_4$), filtered and concentrated under reduced pressure. The resulting residue was purified by silica gel column chromatography to afford the tert-butyl (R,E)-1-((tert-butylsulfinyl) imino)-5-methyl-1,3-dihydrospiro[indene-2,4'-piperidine]-1'-carboxylate (410 mg, 77% yield) as a gummy liquid. m/z (esi) M$^+$1=420.2.

Step F: NaBH$_4$ (185 mg, 4.89 mmol) was added to a solution of tert-butyl (R,E)-1-((tert-butylsulfinyl)imino)-5-methyl-1,3-dihydrospiro[indene-2,4'-piperidine]-1'-carboxylate (410 mg, 0.98 mmol) in MeOH (10 mL) at 0° C. and stirred at the room temperature for 4 hours. The reaction mixture was quenched with ice water and extracted with EtOAc. The combined organic layer was dried (Na$_2$SO$_4$), filtered and concentrated under reduced pressure. The resulting residue was purified by silica gel column chromatography (1% MeOH-DCM) and then with preparative HPLC (Chiralpak IG (21.0×250 mm), 5μ n-hexane/EtOH/Isopropylamine 80/20/0.1, 21.0 mL/minutes, 20 minutes, 276 nm, MeOH) to afford tert-butyl (S)-5-(((R)-tert-butylsulfinyl) amino)-2-methyl-5,7-dihydrospiro[cyclopenta[b]pyridine-6,4'-piperidine]-1'-carboxylate (40 mg, 10% yield). m/z (esi) M$^+$1=422.4.

Intermediate Example AC

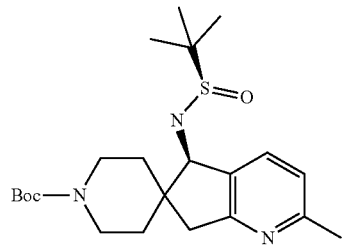

tert-butyl (R)-5-(((R)-tert-butylsulfinyl)amino)-2-methyl-5,7-dihydrospiro[cyclopenta[b]pyridine-6,4'-piperidine]-1'-carboxylate tert-Butyl (R)-5-(((R)-tert-butylsulfinyl)amino)-2-methyl-5,7-dihydrospiro[cyclopenta[b]pyridine-6,4'-piperidine]-1'-carboxylate was prepared according to Intermediate Example AB, collecting the second peak in Step F. m/z (esi) M$^+$1=422.5.

Intermediate Example AD

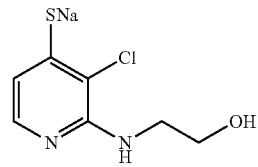

sodium 3-chloro-2-((2-hydroxyethyl)amino)pyridine-4-thiolate

Step A: 2-Aminoethan-1-ol (0.47 mL, 7.78 mmol) was added to a stirred solution of 3-chloro-2-fluoro-4-iodopyridine (1.0 g, 3.89 mmol) in DMSO (5 mL) and stirred at 70° C. for 16 hours. The reaction mixture was diluted with water and extracted with ethyl acetate. The organic part was dried (Na$_2$SO$_4$) and concentrated, and the resulting residue was purified by silica gel column chromatography (40% EtOAc-hexane) to afford 2-((3-chloro-4-iodopyridin-2-yl)amino) ethan-1-ol (820 mg, 70% yield) as a solid. m/z (esi) M$^+$1=298.8.

Step B: DIEA (0.6 mL, 3.35 mmol) was added to a stirred solution of 2-((3-chloro-4-iodopyridin-2-yl)amino)ethan-1-ol (500 mg, 1.67 mmol) and methyl 3-mercaptopropanoate (0.2 mL, 1.84 mmol) in dioxane (5 mL) and degassed with argon for 10 minutes. Xantphos (48 mg, 0.08 mmol) and Pd(OAc)$_2$ (23 mg, 0.10 mmol) were added and degassed for another 10 minutes. The reaction mixture was stirred in pre-heated oil bath in sealed tube at 100° C. for 4 hours. The reaction mixture was filtered through Celite® pad and washed with ethyl acetate. Solvent was evaporated, and the crude material was purified by silica gel column chromatography (60% EtOAc/hexane) to afford methyl 3-((3-chloro-2-((2-hydroxyethyl)amino)pyridin-4-yl)thio)propanoate (460 mg, 94% yield) as a solid. m/z (esi) M$^+$1=290.9.

Step C: NaOEt (21% weight in EtOH; 1.5 mL, 2.06 mmol) was added to a stirred solution of methyl 3-((3-chloro-2-((2-hydroxyethyl)amino)pyridin-4-yl)thio)propanoate (500 mg, 1.72 mmol) in THF (10 mL) at 0° C. and stirred for 30 minutes at 0° C. The reaction mixture was concentrated, and the crude was triturated with DCM. The solid precipitate was filtered to afford sodium 3-chloro-2-((2-hydroxyethyl)amino)pyridine-4-thiolate (350 mg, 90% yield) as a solid. m/z (esi) M+1=205.1.

Intermediate Example AE

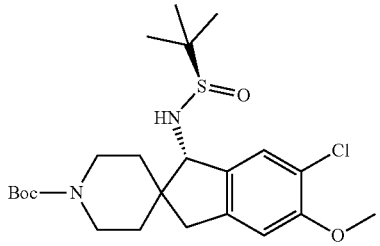

tert-butyl (S)-1-(((R)-tert-butylsulfinyl)amino)-6-chloro-5-methoxy-1,3-dihydrospiro[indene-2,4'-piperidine]-1'-carboxylate Step A: $AlCl_3$ (10.3 g, 77.14 mmol) was added portion wise to a solution of 1-chloro-2-methoxybenzene (10 g, 70.13 mmol) and 3-chloropropanoyl chloride (7.4 mL, 77.14 mmol) in DCM (80 mL) at 0° C. After 30 minutes, sulfuric acid (240 mL) was poured slowly into the reaction mixture. The DCM was removed by rotary evaporation under reduced pressure, and the viscous residue was stirred at 100° C. for 2 hours. After cooling to 20° C., the viscous reaction mixture was poured cautiously into ice (500 mL) and allowed to stand overnight. The mixture was filtered, and the cake of crude product was washed with water (100 mL). The crude product was dissolved in 5% methanol in DCM (200 mL), diluted with water (100 mL), extracted with 5% MeOH in DCM (100 mL), and washed thoroughly with brine (100 mL). The organic part was dried over $Na_2SO_4$, concentrated under vacuum and purified by chromatography on silica gel (100-200) flash chromatography (eluent: 20% ethyl acetate in hexane) to afford 6-chloro-5-methoxy-2,3-dihydro-1H-inden-1-one (4.5 g, 32%). m/z (esi) M+1=197.0.

Step B: NaH (2.7 g, 68.65 mmol) was added portion wise to a solution of 6-chloro-5-methoxy-2,3-dihydro-1H-inden-1-one (4.5 g, 22.88 mmol) in DMF (40 mL) at 0° C. to 5° C., and the reaction mixture was stirred for 30 minutes at the same temperature. Benzylbis(2-chloroethyl)amine (6.76 g, 25.17 mmol) was then added portion wise to the solution, and the mixture was stirred for 18 hours at room temperature. The reaction mixture was extracted with ethyl acetate (2×250 mL) and washed thoroughly with cold water (400 mL). The combined organic part was dried over anhydrous $Na_2SO_4$, concentrated and purified by silica gel flash chromatography (eluent: 40% ethyl acetate in hexane) to afford 1'-benzyl-6-chloro-5-methoxy-1,3-dihydrospiro[indene-2,4'-piperidine]-1-one (2.2 g, 27%). m/z (esi) M+1=356.0.

Step C: 1-Chloroethyl chloroformate (2.72 mL, 24.78 mmol) was added to a stirred solution of 1'-benzyl-6-chloro-5-methoxy-1,3-dihydrospiro[indene-2,4'-piperidine]-1-one (2.2 g, 6.19 mmol) in DCE (40 mL) and refluxed for 1 hour at 80° C. The DCE was then evaporated, and methanol (40 mL) was added to the reaction mixture. The reaction was refluxed for 1 hour at 65° C. The solvent was evaporated under reduced pressure to obtain 6-chloro-5-methoxy-1,3-dihydrospiro[indene-2,4'-piperidine]-1-one as crude, which was used directly in next step without further purification (crude amount: 1.7 g). m/z (esi) M+1=266.3.

Step D: TEA (1.78 mL, 12.83 mmol) was added to a stirred solution of 6-chloro-5-methoxy-1,3-dihydrospiro[indene-2,4'-piperidine]-1-one (1.7 g, 6.41 mmol) in DCM (20 mL) until the pH of the reaction mixture was basic. Boc anhydride (2.21 mL, 9.62 mmol) was added to the reaction mixture and stirred for 16 hours. The reaction mixture was diluted with water (30 mL) and extracted with DCM (2×30 mL). The organic part was dried over anhydrous $Na_2SO_4$, concentrated and purified by silica gel flash chromatography (eluent: 40% ethyl acetate in hexane) to afford tert-butyl 6-chloro-5-methoxy-1-oxo-1,3-dihydrospiro[indene-2,4'-piperidine]-1'-carboxylate (1.3 g, 55%). m/z (esi) M+1=366.0.

Step E: Titanium ethoxide (9.85 mL, 47.01 mmol) was added to tert-butyl 6-chloro-5-methoxy-1-oxo-1,3-dihydrospiro[indene-2,4'-piperidine]-1'-carboxylate (1.3 g, 3.56 mmol) and heated at 90° C. for 5 minutes, followed by the addition of (R)-2-methylpropane-2-sulfinamide (1.3 g, 10.68 mmol). The reaction mixture was heated at 90° C. for 18 hours. The reaction was quenched with water (30 mL) and diluted with ethyl acetate (90 mL). The solid residue was filtered, and the organic part was separated. The extracted combined organic part was washed with brine (50 mL), dried over anhydrous $Na_2SO_4$ and concentrated in vacuo to get crude mass, which was purified by silica gel flash chromatography (eluent: 40% ethyl acetate in hexane) to afford tert-butyl (1Z)-6-chloro-5-methoxy-1-{[(S)-2-methylpropane-2-sulfinyl]imino}-1,3-dihydrospiro[indene-2,4'-piperidine]-1'-carboxylate as a solid (800 mg, 48%). m/z (esi) M+1=469.3.

Step F: $NaBH_4$ (388 mg, 10.28 mmol) was added portion wise to a solution of tert-butyl (1Z)-6-chloro-5-methoxy-1-{[(S)-2-methylpropane-2-sulfinyl]imino}-1,3-dihydrospiro[indene-2,4'-piperidine]-1'-carboxylate (800 mg, 1.7 mmol) in MeOH (9 mL) and THF (18 mL) at 0° C. and stirred at room temperature for 4 hours. The reaction mixture was quenched with saturated solution of $NH_4Cl$ (20 mL) and extracted with ethyl acetate (2×20 mL). The organic part was dried over anhydrous $Na_2SO_4$, concentrated and submitted to preparative HPLC purification. Collection of the first eluting peak provided tert-butyl (1S)-6-chloro-5-methoxy-1-{[(R)-2-methylpropane-2-sulfinyl]amino}-1,3-dihydrospiro[indene-2,4'-piperidine]-1'-carboxylate. (60.3 mg, 7.51%) (m/z (esi) M+1=471.5).

Intermediate Example AF

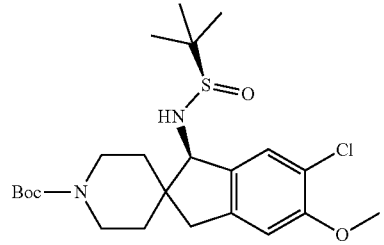

tert-butyl (R)-1-(((R)-tert-butylsulfinyl)amino)-6-chloro-5-methoxy-1,3-dihydrospiro[indene-2,4'-piperidine]-1'-carboxylate tert-Butyl (R)-1-(((R)-tert-butylsulfinyl)amino)-6-chloro-5-methoxy-1,3-dihydrospiro[indene-2,4'-piperidine]-1'-carboxylate (37.8 mg, 4.7%) was prepared according to Intermediate Example AE, collecting the second eluting peak in Step F. (m/z (esi) M+1=471.5).

Intermediate Example AG

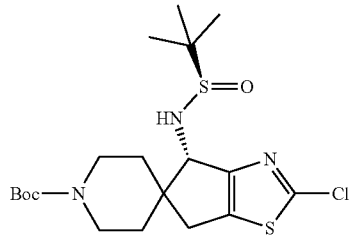

tert-butyl (S)-4-(((R)-tert-butylsulfinyl)amino)-2-chloro-4,6-dihydrospiro[cyclopenta[d]thiazole-5,4'-piperidine]-1'-carboxylate Step A: n-BuL$_1$ (2M in hexane) (7.5 mL, 14.37 mmol) was added dropwise to a stirred solution of diisopropylamine ("DIPA") (2.19 mL, 15.56 mmol) in THF (10 mL) at −78° C. and stirred at −78° C. for 1 hour. 1-(tert-Butyl) 4-ethyl piperidine-1,4-dicarboxylate (3.09 g, 11.97 mmol) in THF (15 mL) was added dropwise at −78° C. and stirred at that temperature for 1 hour. 2-Chloro-5-(chloromethyl)thiazole (2.0 g, 11.97 mmol) in THF (10 mL) was added dropwise at −78° C. and stirred for another 1 hour at −78° C. The reaction mixture was quenched with saturated NH$_4$Cl solution (30 mL) and extracted with EtOAc. The organic part was dried over anhydrous Na$_2$SO$_4$, filtered and concentrated, and the crude was purified by silica gel column chromatography (0-30% EtOAc/hexane) to afford 1-(tert-butyl) 4-ethyl 4-((2-chlorothiazol-5-yl)methyl)piperidine-1,4-dicarboxylate (1.0 g, 21% yield) as a liquid. m/z (esi) M+1=389.4.

Step B: n-BuL$_1$ (19.62 mL, 2M in hexane) was added dropwise to a stirring solution of DIPA (5.78 mL, 41.23 mmol) in THF (75 mL) at −78° C. and stirred for 1 hour. A solution of 1-(tert-butyl) 4-ethyl 4-((2-chlorothiazol-5-yl)methyl)piperidine-1,4-dicarboxylate (10 g, 25.77 mmol) in THF (75 mL) was added dropwise to the reaction mixture and stirred at −78° C. for 1 hour. The reaction mixture was quenched with brine (30 mL), and the organic layer was extracted with EtOAc. The organic layer was evaporated under reduced pressure to obtain crude which was purified by silica gel column chromatography (0-40% EtOAc/hexane) to obtain tert-butyl 2-chloro-4-oxo-4,6-dihydrospiro[cyclopenta[d]thiazole-5,4'-piperidine]-1'-carboxylate (3.3 g, 37% yield) as a solid. m/z (esi) M+1=343.3.

Step C: Titanium (IV) ethoxide (4.32 mL, 20.46 mmol) was added to a stirred solution of tert-butyl 2-chloro-4-oxo-4,6-dihydrospiro[cyclopenta[d]thiazole-5,4'-piperidine]-1'-carboxylate (1.4 g, 4.09 mmol) and (R)-(+)-2-methylpropane-2-sulfinamide (1.48 g, 12.28 mmol) and was stirred at 100° C. for 5 hours. The reaction mixture was diluted with water (30 mL) and extracted with EtOAc. The organic part was dried over anhydrous Na$_2$SO$_4$, concentrated to tert-butyl (R,Z)-4-((tert-butylsulfinyl)imino)-2-chloro-4,6-dihydrospiro[cyclopenta[d]thiazole-5,4'-piperidine]-1'-carboxylate (1.1 g, 60% yield) as a gummy liquid. m/z (esi) M+1=445.8.

Step D: Sodium borohydride (0.14 g, 3.70 mmol) was added to a stirred solution of tert-butyl (R,Z)-4-((tert-butylsulfinyl)imino)-2-chloro-4,6-dihydrospiro[cyclopenta[d]thiazole-5,4'-piperidine]-1'-carboxylate (1.1 g, 2.47 mmol) in THF (10 mL) at −50° C. and was stirred at room temperature for 16 hours. The reaction mixture was quenched with ice and concentrated to dryness. The crude was diluted with EtOAc and washed with water and brine. The organic part was dried over anhydrous Na$_2$SO$_4$ and concentrated under reduce pressure to get the crude, which was purified by silica gel column chromatography (0-1% MeOH/DCM). Collection of the first eluting peak provided tert-butyl (S)-4-(((R)-tert-butylsulfinyl)amino)-2-chloro-4,6-dihydrospiro[cyclopenta[d]thiazole-5,4'-piperidine]-1'-carboxylate (400 mg, 36% yield) (m/z (esi) M+1=448.4).

Intermediate Example AH

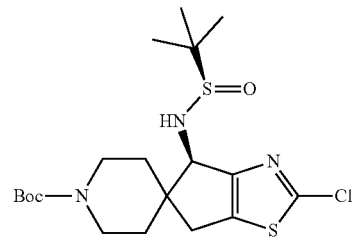

tert-butyl(R)-4-(((R)-tert-butylsulfinyl)amino)-2-chloro-4,6-dihydrospiro[cyclopenta[d]thiazole-5,4'-piperidine]-1'-carboxylate tert-Butyl(R)-4-(((R)-tert-butylsulfinyl)amino)-2-chloro-4,6-dihydrospiro[cyclopenta[d]thiazole-5,4'-piperidine]-1'-carboxylate (30 mg, 3% yield) was prepared according to Intermediate Example AG, collecting the second eluting peak in Step D (m/z (esi) M+1=448.3).

Intermediate Example AI

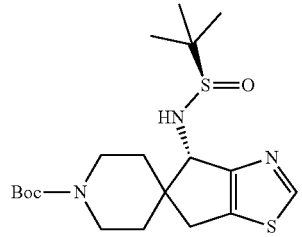

tert-butyl (S)-4-(((R)-tert-butylsulfinyl)amino)-4,6-dihydrospiro[cyclopenta[d]thiazole-5,4'-piperidine]-1'-carboxylate TEA (0.31 mL, 2.23 mmol) and Pd/C (500 mg) were added to a stirred solution of tert-butyl (S)-4-(((R)-tert-butylsulfinyl)amino)-2-chloro-4,6-dihydrospiro[cyclopenta[d]thiazole-5,4'-piperidine]-1'-carboxylate (500 mg, 1.11 mmol) in EtOH (20 mL) and stirred for 16 hours under H$_2$ atmosphere (100 psi). The reaction mixture was filtered through Celite® pad and washed with MeOH (50 mL). Solvent was evaporated under reduce pressure, and the crude material was purified by silica gel column chromatography (0-4% MeOH-DCM) to afford tert-butyl (S)-4-(((R)-tert-butylsulfinyl)amino)-4,6-dihydrospiro[cyclopenta[d]thiazole-5,4'-piperidine]-1'-carboxylate (220 mg, 47% yield) as a solid. m/z (esi) M+1=419.4.

Intermediate Example AJ

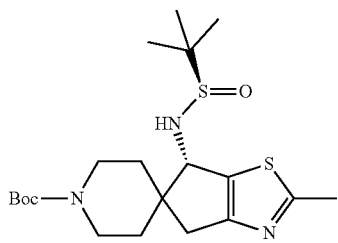

tert-butyl (S)-6-methyl-(((R)-tert butylsulfinyl)
amino)-2-methyl-4,6-dihydrospiro[cyclopenta[d]
thiazole-5,4'-piperidine]-1'-carboxylate Step A: Sodium borohydride (6.91 g, 182.63 mmol) was added in portions to a solution of ethyl 2-chlorothiazole-4-carboxylate (10 g, 52.18 mmol) in ethanol (150 mL) at room temperature. The reaction mixture was allowed to stir at 50° C. for 2 hours. The reaction mixture was quenched with aqueous NH$_4$Cl solution, and EtOH was removed under reduce pressure. The residue was diluted with water (200 mL) and extracted with EtOAc. The combined organic parts were washed with brine, dried over anhydrous Na$_2$SO$_4$, filtered, and concentrated under reduce pressure to get crude mass, which was purified by silica gel column chromatography (5-20% EtOAc/hexane) to get (2-chlorothiazol-4-yl) methanol (5.28 g, 68% yield) as a liquid. m/z (esi) M$^+$1=150.1.

Step B: Et$_3$N (36.5 mL, 267.38 mmol) was added to a solution of (2-chlorothiazol-4-yl)methanol (10 g, 66.85 mmol) in DCM (500 mL) and cooled to 0° C. under Ar. Methanesulphonyl chloride (7.8 mL, 100.27 mmol) was added slowly to the reaction over 10 minutes. The reaction was allowed to stir at the same temperature for 30 minutes. The reaction was quenched with NaHCO$_3$ solution, and the organic part was separated. The organic part was washed with brine, dried over anhydrous Na$_2$SO$_4$, filtered, and concentrated under reduced pressure to get (2-chlorothiazol-4-yl)methyl methanesulfonate (13.7 g, 90%, crude), which was used directly in the next step without further purification. m/z (esi) M$^+$1=228.0.

Step C: A solution of DIPA (4 mL, 28.55 mmol) in THF (12 mL) was cooled to −78° C. under Ar. n-BuL$_1$ (2M in hexane) (13.2 mL) was added slowly to it. The reaction mixture was allowed to stir for 30 minutes at −78° C. and then at room temperature for 30 minutes. The LDA solution was again cooled to −78° C., and 1-tert-butyl 4-ethyl piperidine-1,4-dicarboxylate (6.215 g, 24.16 mmol) in THF (6 mL) was added to it slowly. The reaction was stirred for 1 hour at −78° C. A solution of (2-chlorothiazol-4-yl)methyl methanesulfonate (5 g, 21.96 mmol) in THF (12 mL) was then added, and the reaction mixture was stirred at room temperature for 30 minutes. This was quenched with brine (100 mL) and was extracted with EtOAc. The combined organic parts were dried over anhydrous Na$_2$SO$_4$, filtered, and concentrated under reduced pressure, and the resulting residue was purified by silica-gel column chromatography (5-15% EtOAc/hexane) to get 1-(tert-butyl) 4-ethyl 4-((2-chlorothiazol-4-yl)methyl)piperidine-1,4-dicarboxylate (2.56 g, 30% yield) as a liquid. m/z (esi) M$^+$1=388.9.

Step D: A solution of DIPA (4.7 mL, 33.43 mmol) in THF (30 mL) was cooled to −78° C. under Ar, followed by the addition of n-BuL$_1$ (2M in hexane) (16.1 mL) over 25 minutes. The mixture was allowed to stir for 30 minutes at −78° C. and then at room temperature for 10 minutes. The LDA solution was added slowly to 1-(tert-butyl) 4-ethyl 4-((2-chlorothiazol-4-yl)methyl)piperidine-1,4-dicarboxylate (5.0 g, 12.86 mmol) in THF (40 mL) at −78° C. over 30 minutes. This was quenched with aqueous NH$_4$Cl solution and was extracted with EtOAc. The combined organic parts were dried over anhydrous Na$_2$SO$_4$, filtered, and concentrated under reduced pressure. The resulting residue was purified by silica gel column chromatography (5-10% EtOAc/hexane) to get tert-butyl 2-chloro-6-oxo-4,6-dihydrospiro[cyclopenta[d]thiazole-5,4'-piperidine]-1'-carboxylate (1.95 g, 44% yield) as solid. m/z (esi) M$^+$1=343.4.

Step E: to a solution of tert-butyl 2-chloro-6-oxo-4,6-dihydrospiro[cyclopenta[d]thiazole-5,4'-piperidine]-1'-carboxylate (500 mg, 1.46 mmol) in dioxane (10 mL) was added K$_2$CO$_3$ (403 mg, 2.92 mmol) and degassed with Ar for 5 minutes, followed by the addition of Pd(dppf)Cl$_2$·DCM (357 mg, 0.44 mmol) and trimethylboroxine (0.8 mL, 5.83 mmol). The reaction mixture was sealed and was heated at 100° C. for 2 hours. The reaction was filtered through sintered funnel and concentrated under reduced pressure. The resulting residue was purified by silica gel column chromatography (10-30% EtOAc/hexane) to get tert-butyl 2-methyl-6-oxo-4,6-dihydrospiro[cyclopenta[d]thiazole-5,4'-piperidine]-1'-carboxylate (330 mg, 70% yield) as a solid. m/z (esi) M$^+$1=323.1.

Step F: Titanium (IV) ethoxide (2.1 mL, 10.24 mmol) was added to tert-butyl 2-methyl-6-oxo-4,6-dihydrospiro[cyclopenta[d]thiazole-5,4'-piperidine]-1'-carboxylate (250 mg, 0.78 mmol) and was heated at 100° C. for 5 minutes, followed by the addition of (R)-2-methylpropane-2-sulfinamide (282 mg, 2.33 mmol). The mixture was heated at 100° C. for 16 hours. The reaction was quenched with brine (50 mL) and extracted with EtOAc. The combined organic parts were washed with brine, dried over anhydrous Na$_2$SO$_4$, filtered, and concentrated under reduce pressure. The resulting residue was purified by silica gel column chromatography (10-40% EtOAc/hexane) to get tert-butyl (R,Z)-6-((tert-butylsulfinyl)imino)-2-methyl-4,6-dihydrospiro[cyclopenta[d]thiazole-5,4'-piperidine]-1'-carboxylate (255 mg, 77% yield) as a solid. m/z (esi) M$^+$1=425.9.

Step G: Sodium borohydrate (251 mg, 6.63 mmol) was added in portions to a solution of tert-butyl (R,Z)-6-((tert-butylsulfinyl)imino)-2-methyl-4,6-dihydrospiro[cyclopenta[d]thiazole-5,4'-piperidine]-F-carboxylate (470 mg, 1.10 mmol) in THF (10 mL) and methanol (5 mL) at 0° C. The reaction mixture was stirred for 30 minutes at the same temperature. The reaction mixture was quenched with aqueous NH$_4$Cl solution and extracted with EtOAc. The combined organic parts were dried over anhydrous Na$_2$SO$_4$, filtered, and concentrated under reduce pressure. The resulting residue was purified by reverse phase prep HPLC (5-95% ACN:water) to get tert-butyl (S)-6-methyl-(((R)-tert-butylsulfinyl]amino)-2-methyl-4,6-dihydrospiro[cyclopenta[d]thiazole-5,4'-piperidine]-1'-carboxylate (120 mg, 25% yield). m/z (esi) M$^+$1=428.2.

Intermediate Example AK

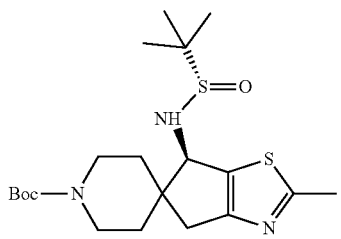

tert-butyl (R)-6-(((S)-tert-butylsulfinyl)amino)-2-methyl-4,6-dihydrospiro[cyclopenta[d]thiazole-5,4'-piperidine]-1'-carboxylate Step A: K₂CO₃ (403 mg, 2.92 mmol) was added to a solution of tert-butyl 2-chloro-6-oxo-4,6-dihydrospiro[cyclopentakathiazole-5,4'-piperidine]-1'-carboxylate (500 mg, 1.46 mmol) in dioxane (10 mL) and degassed with Ar for 5 minutes, followed by the addition of Pd(dppf)Cl₂·CH₂Cl₂ (357 mg, 0.44 mmol) and trimethylboroxine (0.8 mL, 5.83 mmol). The reaction mixture was sealed and heated at 100° C. for 2 hours. The reaction was filtered through sintered funnel and concentrated under reduced pressure. The resulting residue was purified by column chromatography (10-30% EtOAc/hexane) to get tert-butyl 2-methyl-6-oxo-4,6-dihydrospiro[cyclopenta[d]thiazole-5,4'-piperidine]-1'-carboxylate (330 mg, 70% yield) as a solid. m/z (esi) M⁺1=323.1.

Step B: Titanium (IV) ethoxide (5.84 mL, 25.8 mmol) was added to tert-butyl 2-methyl-6-oxo-4,6-dihydrospiro[cyclopenta[d]thiazole-5,4'-piperidine]-1'-carboxylate (630 mg, 1.95 mmol) and was heated at 100° C. for 5 minutes, followed by addition of (S)-2-methylpropane-2-sulfinamide (711 mg, 5.86 mmol). The mixture was heated at 100° C. for 6 hours. The reaction was quenched with brine. The solid was filtered through sintered funnel and was extracted with EtOAc. The combined organic parts were washed with brine, dried over anhydrous Na₂SO₄, filtered, and concentrated under reduced pressure. The resulting residue was purified by silica gel column chromatography (10-40% EtOAc/hexane) to get tert-butyl (S,Z)-6-((tert-butylsulfinyl)imino)-2-methyl-4,6-dihydrospiro[cyclopenta[d]thiazole-5,4'-piperidine]-1'-carboxylate (450 mg, 54% yield) as a solid. m/z (esi) M⁺1=425.9.

Step C: Sodium borohydrate (240 mg, 6.35 mmol) was added to a solution of tert-butyl (S,Z)-6-((tert-butyl sulfinymino)-2-methyl-4,6-dihydrospiro[cyclopenta[d]thiazole-5,4'-piperidine]-1'-carboxylate (450 mg, 1.05 mmol) in THF (9 mL) and methanol (4.5 mL) at 0° C. in portions. The reaction mixture was stirred for 1 hour at 0° C., was quenched with aqueous NH₄Cl solution and extracted with EtOAc. The combined organic parts were dried over anhydrous Na₂SO₄, filtered, and concentrated under reduced pressure. The resulting residue was purified by reverse phase preparative HPLC (5-95% ACN:water, 20 mM ammonium bicarbonate, 16 mL/min) to provide tert-butyl (R)-6-(((S)-tert-butylsulfinyl)amino)-2-methyl-4,6-dihydrospiro[cyclopenta[d]thiazole-5,4'-piperidine]-1'-carboxylate (46 mg, 10% yield). m/z (esi) M⁺1=428.2.

Intermediate Example AL

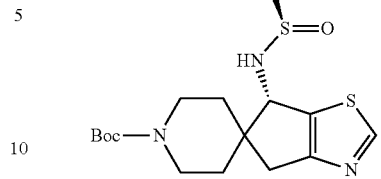

tert-butyl (S)-6-(((R)-tert-butylsulfinyl)amino)-4,6-dihydrospiro[cyclopenta[d]thiazole-5,4'-piperidine]-1'-carboxylate Step A: Titanium (IV) ethoxide (13.1 mL, 57.76 mmol) was added to tert-butyl 2-chloro-6-oxo-4,6-dihydrospiro[cyclopenta[d]thiazole-5,4'-piperidine]-1'-carboxylate (1.5 g, 4.38 mmol) and was heated at 100° C. for 5 minutes, followed by the addition of (R)-2-methylpropane-2-sulfinamide (1.59 g, 13.13 mmol). The mixture was heated at 100° C. for 16 hours. The reaction was quenched with brine (500 mL). The solid was filtered through sintered funnel and was washed with EtOAc. The organic part was separated, and the aqueous part was extracted with EtOAc. The combined organic parts were washed with brine, dried over anhydrous Na₂SO₄, filtered, and concentrated under reduce pressure. The resulting residue was purified by column chromatography (5-15% EtOAc/hexane) to get tert-butyl (R,Z)-6-((tert-butylsulfinyl)imino)-2-chloro-4,6-dihydrospiro[cyclopentakathiazole-5,4'-piperidine]-1'-carboxylate (1050 mg, 54% yield) as a solid. m/z (esi) M⁺1=446.1.

Step B: Sodium borohydride (267 mg, 7.05 mmol) was added in portions to a solution of tert-butyl (R,Z)-6-((tert-butylsulfinyl)imino)-2-chloro-4,6-dihydrospiro[cyclopenta[d]thiazole-5,4'-piperidine]-1'-carboxylate (500 mg, 1.18 mmol) in THF (10 mL) and methanol (5 mL) over 1 hour at 0° C. and was stirred for another 1 hour at 0° C. The reaction mixture was quenched with aqueous NH₄Cl solution and extracted with EtOAc. The combined organic part was dried over anhydrous Na₂SO₄, filtered and concentrated under reduced pressure. The resulting residue was purified by reverse phase preparative HPLC (5-95% ACN:water, 10 mM ammonium bicarbonate, 16 mL/min) to get tert-butyl (S)-6-(((R)-tert-butylsulfinyl)amino)-2-chloro-4,6-dihydrospiro[cyclopenta[d]thiazole-5,4'-piperidine]-1'-carboxylate (115 mg, 22% yield) as a solid. m/z (esi) M⁻1=446.2.

Step C: Triethylamine (0.2 mL, 1.43 mmol) was added to a solution of tert-butyl (S)-6-(((R)-tert-butylsulfinyl)amino)-2-chloro-4,6-dihydrospiro[cyclopenta[d]thiazole-5,4'-piperidine]-1'-carboxylate (320 mg, 0.71 mmol) in methanol (40 mL) and degassed with Ar for 10 minutes followed by the addition of Pd—C (10% load, 50% weight) (640 mg), while degassing with Ar. After 5 minutes, the reaction mixture was put under hydrogen atmosphere of balloon pressure. After 18 hours, the reaction was filtered through Celite® bed and concentrated under reduced pressure. The resulting residue was purified by column chromatography using amine silica (10-30% EtOAc/hexane) to get tert-butyl (S)-6-(((R)-tert-butylsulfinyl)amino)-4,6-dihydrospiro[cyclopenta[d]thiazole-5,4'-piperidine]-1'-carboxylate (185 mg, 63% yield) as a solid. m/z (esi) M⁺1=414.4.

Intermediate Example AM

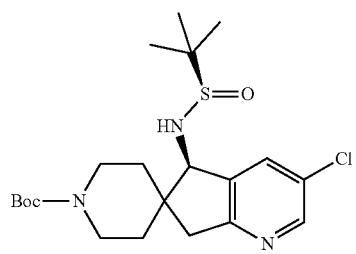

tert-butyl (R)-5-(((R)-tert-butylsulfinyl)amino)-3-chloro-5,7-dihydrospiro[cyclopenta[b]pyridine-6,4'-piperidine]-1'-carboxylate Step A: H$_2$SO$_4$ (5.76 mL, 105.7 mmol) was added to a stirred solution of 3-bromo-5-chloropicolinic acid (5 g, 21.1 mmol) in MeOH (50 mL) at 0° C., and it was stirred at 90° C. for 4 hours. The reaction was cooled to 25° C., and MeOH was evaporated to dryness. The residue was neutralized by 2N NaHCO$_3$ solution and was extracted with EtOAc. The combined layers were washed with brine and concentrated under reduced pressure to get methyl 3-bromo-5-chloropicolinate (4.8 g, 91% yield) as a solid. m/z (esi) M$^+$1=252.0.

Step B: Sodium borohydride (4.37 g, 115.7 mmol) was added in small portions to a cooled (0° C.) solution of methyl 3-bromo-5-chloropicolinate (4.8 g, 19.3 mmol) in methanol (70 mL) over approximately 30 minutes. The reaction mixture was stirred at room temperature for 16 hours. The reaction mixture was then diluted with brine, and MeOH was evaporated under reduced pressure. The residue was extracted with EtOAc. The combined organic layers were dried over anhydrous Na$_2$SO$_4$, filtered, and evaporated to get (3-bromo-5-chloropyridin-2-yl)methanol (3.72 g, 88% yield) as a semisolid. m/z (esi) M$^+$1=224.0.

Step C: MsCl (1.42 mL, 18.4 mmol) was added dropwise to a −15° C. solution of (3-bromo-5-chloropyridin-2-yl)methanol (3.72 g, 16.7 mmol) and triethylamine (4.66 mL, 33.4 mmol) in DCM (50 mL). The resulting mixture was allowed to stir at same temperature for 2 hours. The reaction mixture was quenched with water and diluted with EtOAc, and the aqueous layer was separated. The organic layer was washed with brine, dried over anhydrous Na$_2$SO$_4$, filtered, and concentrated under reduced pressure to get crude. The crude was purified by silica gel column chromatography (15-20% EtOAc/hexane) to get (3-bromo-5-chloropyridin-2-yl)methyl methanesulfonate (3.8 g, 76% yield) as a semisolid. m/z (esi) M$^+$1=302.0.

Step D: n-BuL$_1$ (1.72 M solution in THF/Hexane, 6.1 mL, 10.5 mmol) was added dropwise to a −70° C. solution of DIPA (1.69 mL, 11.8 mmol) in THF (10 mL). The resulting mixture was allowed to warm to −40° C. over 1 hour. A solution of 1-(tert-butyl) 4-ethyl piperidine-1,4-dicarboxylate (1.8 g, 6.9 mmol) in THF (20 mL) was added to the LDA at −70° C. and was stirred at −70° C. for 1 hour. Then a solution of (3-bromo-5-chloropyridin-2-yl)methyl methanesulfonate (2.52 g, 8.4 mmol) in THF (10 mL) was added dropwise, and the mixture was stirred at −70° C. for 1 hour. The reaction was quenched with water. The aqueous layer was separated and extracted with EtOAc. The combined organic layers were washed with brine, dried over anhydrous Na$_2$SO$_4$, filtered, and concentrated under reduced pressure. The resulting residue was purified by silica gel column chromatography (30-40% EtOAc/hexane) to get 1-(tert-butyl) 4-ethyl 4-((3-bromo-5-chloropyridin-2-yl)methyl)piperidine-1,4-dicarboxylate (2.35 g, 73% yield) as a gum. m/z (esi) M$^+$1=462.9.

Step E: NaOH (1.95 mg, 48.8 mmol) was added to a stirred solution of 1-(tert-butyl) 4-ethyl 4-((3-bromo-5-chloropyridin-2-yl)methyl)piperidine-1,4-dicarboxylate (4.5 g, 9.7 mmol) in MeOH (50 mL) and water (10 mL) at 25° C. and stirred at 65° C. for 16 hours. The mixture was concentrated to dryness, and the crude was dissolved with water and washed with Et$_2$O. The aqueous layer was separated and was maintained at pH 7-6 by 2N HCl. The compound was extracted with EtOAc. Organic layer was separated, washed with brine, dried over anhydrous Na$_2$SO$_4$, filtered, and concentrated under reduced pressure to get 4-((3-bromo-5-chloropyridin-2-yl)methyl)-1-(tert-butoxycarbonyl)piperidine-4-carboxylic acid (4.1 g, 97% yield) as a solid. m/z (esi) M$^+$1=435.3.

Step F: NaH (60% dispersion in mineral oil, 456 mg, 11.4 mmol) was added in portions to a −15° C. solution of 4-((3-bromo-5-chloropyridin-2-yl)methyl)-1-(tert-butoxycarbonyl)piperidine-4-carboxylic acid (4.1 g, 9.5 mmol) in THF (23 mL) under N$_2$ atmosphere. After stirring for 15 minutes at this temperature, the mixture was cooled to −60° C. n-BuL$_1$ (1.72 M solution in hexane, 7.66 mL, 13.2 mmol) was added dropwise to the mixture, stirred for 30 minutes, and then the temperature was raised to −20° C. over 30 minutes. The reaction mixture was quenched with water and extracted with EtOAc. The organic layer was washed with brine, dried over anhydrous Na$_2$SO$_4$, filtered, and concentrated under reduced pressure to get crude. The crude was purified by silica gel column chromatography (30% EtOAc/hexane) to get tert-butyl 3-chloro-5-oxo-5,7-dihydrospiro[cyclopenta[b]pyridine-6,4'-piperidine]-1'-carboxylate (1.1 g, 34% yield) as a semisolid. m/z (esi) M$^+$1=337.3.

Step G: Titanium(IV) ethoxide (4.11 mL, 19.6 mmol) was added to a stirred solution of tert-butyl 3-chloro-5-oxo-5,7-dihydrospiro[cyclopenta[b]pyridine-6,4'-piperidine]-1'-carboxylate (1.1 g, 3.3 mmol) and was stirred for 5 minutes at 95° C. (R)-(+)-2-Methylpropanes-2-sulfinamide (1.18 g, 9.8 mmol) was added and stirred at 95° C. for 5 hours. The mixture was allowed to cool at room temperature and was diluted with EtOAc and water. The resulting mixture was vigorously stirred for 15 minutes at room temperature and then filtered with a pad of Celite®. The filtrate was extracted with EtOAc and washed with brine. The organic phase was dried over anhydrous Na$_2$SO$_4$ and concentrated under reduced pressure to get the crude. The crude was purified by silica gel column chromatography (30% EtOAc/hexane) to get tert-butyl (R,Z)-5-((tert-butylsulfinyl)imino)-3-chloro-5,7-dihydrospiro[cyclopenta[b]pyridine-6,4'-piperidine]-1'-carboxylate (911 mg, 63% yield) as a semisolid. m/z (esi) M$^+$1=440.2.

Step H: Sodium borohydride (391 mg, 10.3 mmol) was added to a stirred solution of tert-butyl (R,Z)-5-((tert-butylsulfinyl)imino)-3-chloro-5,7-dihydrospiro[cyclopenta[b]pyridine-6,4'-piperidine]-1'-carboxylate (910 mg, 2.1 mmol) in MeOH (28.0 mL) at 0° C. and was stirred for 3 hours. The reaction mixture was allowed to warm to room temperature, saturated aqueous NH$_4$Cl solution was slowly added to quench the excess of sodium borohydride and MeOH was evaporated. The residue was diluted with EtOAc and water. The organic layers were separated. The combined organic layers were washed with brine, dried over anhydrous Na$_2$SO$_4$, filtered, and were concentrated under reduced pressure to get the crude. The crude was purified by normal phase preparative HPLC purification (Chiralpak IG (21.0×

250 mm), 5μ, hexane/ethanol: 85/15) to get tert-butyl (R)-5-(((R)-t ert-butylsulfinyl)amino)-3-chloro-5,7-dihydrospiro[cyclopenta[b]pyridine-6,4'-piperidine]-1'-carboxylate (580 mg, 50% yield) (m/z (esi) M+1=442.1) as a solid.

Intermediate Example AN

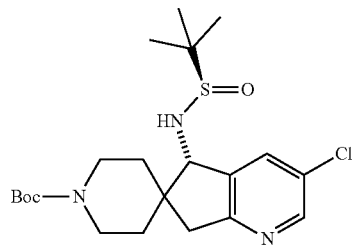

tert-butyl (S)-5-(((R)-t ert-butylsulfinyl)amino)-3-chloro-5,7-dihydrospiro[cyclopenta[b]pyridine-6,4'-piperidine]-1'-carboxylate tert-Butyl (S)-5-(((R)-tert-butylsulfinyl)amino)-3-chloro-5,7-dihydrospiro[cyclopenta[b]pyridine-6,4'-piperidine]-1'-carboxylate was prepared according to Intermediate Example AM, isolating material in Step G and was purified by normal phase preparative HPLC purification (Chiralpak IG (21.0×250 mm), 5μ, hexane/ethanol: 85/15) to get pure material as a sticky solid (117 mg, 11% yield, m/z (esi) M+1=442.2).

Intermediate Example AO

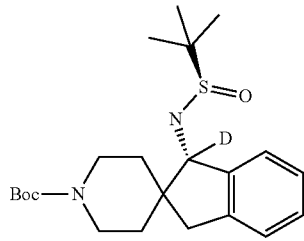

tert-butyl(S)-1-(((R)-tert-butylsulfinyl)amino)-1,3-dihydrospiro[indene-2,4'-piperidine]-1'-carboxylate-1-d Step A: NaH (60% in mineral oil) (2.72 g, 68.08 mmol) was added to a stirred solution of 2,3-dihydro-1H-inden-1-one (3.0 g, 22.69 mmol) in DMF (60 mL) at 0° C. The reaction mixture was stirred for 30 minutes at 5° C. N-Benzyl-2-chloro-N-(2-chloroethyl)ethan-1-amine hydrochloride (5.76 g, 24.96 mmol) was added portion wise, and the mixture was stirred at 60° C. for 16 hours. The reaction was quenched with brine, extracted with EtOAc. The organic layers were combined and washed with excess water, followed by brine, dried over anhydrous Na2SO4, and concentrated under reduced pressure. The residue was purified by silica gel column chromatography (35-40% EtOAc/hexane) to afford 1'-benzylspiro[indene-2,4'-piperidin]-1(3H)-one (2.7 g, 41% yield) as an oil. m/z (esi) M+1=292.5.

Step B: 1-Chloroethyl chloroformate (3.07 mL, 28.44 mmol) was added to a stirred solution of 1'-benzylspiro[indene-2,4'-piperidin]-1(3H)-one (2.76 g, 9.48 mmol) in DCE (45 mL), and it was refluxed for 1 hour. DCE was evaporated to dryness, and methanol was added (45 mL). The reaction mixture was refluxed for another 1 hour. The reaction was evaporated to dryness to get spiro[indene-2,4'-piperidin]-1(3H)-one (1.91 g, crude) as a semisolid. m/z (esi) M+1=202.3.

Step C: Triethylamine (5.28 mL, 37.95 mmol) was added to a stirred solution of spiro[indene-2,4'-piperidin]-1(3H)-one (1.91 g, 9.49 mmol) in DCM (45 mL), followed by boc-anhydride (3.27 mL, 14.23 mmol). The reaction was stirred at room temperature for 1 hour. The reaction was concentrated, and the resulting residue was purified by silica gel column chromatography (15-17% EtOAC/hexane) to get tert-butyl 1-oxo-1,3-dihydrospiro[indene-2,4'-piperidine]-1'-carboxylate (1.47 g, 52% 2 step yield) as a solid. m/z (esi) M+1=LCMS: 302.1.

Step D: Titanium(IV) ethoxide (2.29 mL, 10.93 mmol) and (R)-(+)-2-methyl-2-propanesulfinamide (662.40 mg, 5.46 mmol) were added to a stirred solution of tert-butyl 1-oxo-1,3-dihydrospiro[indene-2,4'-piperidine]-1'-carboxylate (823 mg, 2.73 mmol) in THF (5 mL), and the reaction was heated at 90° C. for 12 hours. The reaction mixture was cooled to room temperature and was diluted with water and extracted with EtOAc. The combined organic phases were washed with brine, dried over Na2SO4, and concentrated to get the crude. The crude was mixed with another batch or tert-butyl 1-oxo-1,3-dihydrospiro[indene-2,4'-piperidine]-1'-carboxylate (200 mg) and was purified by silica gel column chromatography (20-25% EtOAC/hexane) to get tert-butyl (R,E)-1-((tert-butylsulfinyl)imino)-6-chloro-1,3-dihydrospiro[indene-2,4'-piperidine]-1'-carboxylate (545 mg, 42%, yield). m/z (esi) M+1=405.0.

Step E: NaBD4 (46.62 mg, 1.11 mmol) was added to a stirred solution of tert-butyl (R,E)-1-((tert-butylsulfinyl)imino)-6-chloro-1,3-dihydrospiro[indene-2,4'-piperidine]-1'-carboxylate (300 mg, 0.74 mmol) in THF (12 mL) at −50° C., and the temperature was allowed to raise to room temperature over 16 hours. The reaction was quenched with saturated NH4Cl solution and was extracted with EtOAc. The organic layer was washed with brine, dried over Na2SO4, and concentrated. The crude was purified by SFC [Chiralpak IG (250×21 mm) 5μ, of 25 g/min. Mobile Phase: 60% CO2+40% methanol. ABPR: 100 bar. Collection of the first eluting peak provided tert-butyl (S)-1-(((R)-tert-butylsulfinyl)amino)-1,3-dihydrospiro[indene-2,4'-piperidine]-1'-carboxylate-1-d (152 mg, 51% yield). m/z (esi) M+1=408.4.

Intermediate Example AP

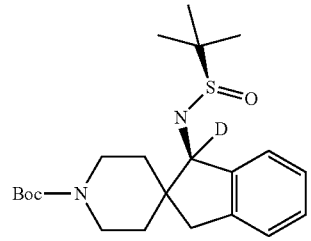

tert-butyl (R)-1-(((R)-tert-butylsulfinyl)amino)-1,3-dihydrospiro[indene-2,4'-pipendine]-1'-carboxylate-1-d tert-Butyl (R)-1-(((R)-t ert-butylsulfinyl)amino)-1,3-dihydrospiro[indene-2,4'-piperidine]-1'-carboxylate-1-d was prepared according to Intermediate Example AO, collecting second eluting peak in Step D (34 mg, 11% yield) m/z (esi) M⁺1=408.4.

Intermediate Example AQ

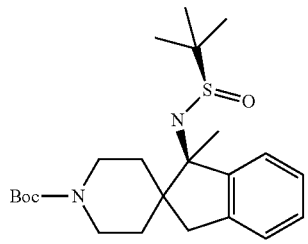

tert-butyl (R)-1-(((R)-tert-butylsulfinyl)amino)-1-methyl-1,3-dihydrospiro[indene-2,4'-piperidine]-1'-carboxylate MeMgBr (3M in ether) (0.4 mL, 1.23 mmol) was added to a stirred solution of tert-butyl (R,Z)-1-((tert-butylsulfinyl)imino)-1,3-dihydrospiro[indene-2,4'-piperidine]-1'-carboxylate (100 mg, 0.247 mmol) in THF (0.5 mL) at 0° C. and was stirred at that temperature for 3 hours. The reaction was quenched with saturated NH₄Cl solution and was extracted with EtOAc. The organic layers were combined, washed with brine, dried over anhydrous Na₂SO₄, filtered, and concentrated under reduced pressure. The crude was mixed with another batch of tert-butyl (R,Z)-1-((tert-butylsulfinyl)imino)-1,3-dihydrospiro[indene-2,4'-piperidine]-1'-carboxylate (120 mg) and was purified by normal phase prep HPLC purification (Chiralpak IG (21.0×250 mm), 5µ, hexane/EtOH/iPrNH₂ 80/20/0.1, 1.0 mL/min)). Collecting the second eluting peak provided a sticky solid (76 mg, 33% yield). m/z (esi) M⁺1=421.4.

Intermediate Example AR

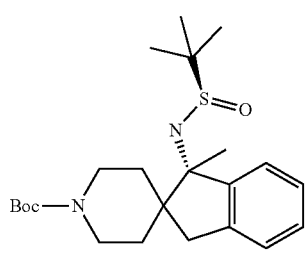

tert-butyl (S)-1-(((R)-tert-butylsulfinyl)amino)-1-methyl-1,3-dihydrospiro[indene-2,4'-piperidine]-1'-carboxylate tert-Butyl (S)-1-(((R)-tert-butylsulfinyl)amino)-1-methyl-1,3-dihydrospiro[indene-2,4'-piperidine]-1'-carboxylate was prepared according to Intermediate Example AQ, collecting the first eluting peak. m/z (esi) M⁺1=421.4.

Intermediate Example AS

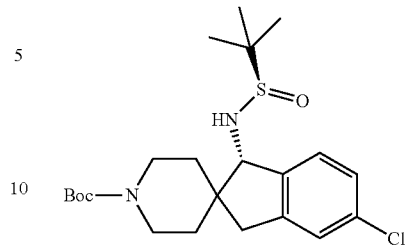

tert-butyl (S)-1-(((R)-tert-butylsulfinyl)amino)-5-chloro-1,3-dihydrospiro[indene-2,4'-piperidine]-1'-carboxylate Step A: NaH (60% dispersion in mineral oil, 500 mg, 12.05 mmol) was added to a stirred solution of 5-chloro-2,3-dihydro-1H-inden-1-one (1 g, 6.02 mmol) in DMF (10 mL) at 0° C. and stirred for 30 minutes. N-Benzyl-2-chloro-N-(2-chloroethyl)ethan-1-amine hydrochloride (1.5 g, 6.63 mmol) was added to reaction mixture at 0° C. The reaction mixture was stirred at room temperature for 16 hours. The reaction mixture was quenched with water and extracted with EtOAc. The organic layer was concentrated to dryness, and the crude was purified by silica gel column chromatography (30% EtOAc/hexane) to afford 1'-benzyl-5-chlorospiro[indene-2,4'-piperidin]-1(3H)-one (300 mg, 15%, yield) as a solid. m/z (esi) M⁺1=325.8.

Step B: Chloroethyl chloroformate (270 mg, 1.84 mmol) was added to a stirred solution of 1'-benzyl-5-chlorospiro[indene-2,4'-piperidin]-1(3H)-one (300 mg, 0.92 mmol) in DCE (10 mL) at 0° C. and stirred for 10 minutes. The reaction mixture was stirred at 80° C. for 1 hour. The reaction mixture was concentrated to dryness. The crude was dissolved in MeOH (10 mL) and again stirred for 75° C. for another 1 hour. The reaction mixture was concentrated under reduced pressure to afford 5-chlorospiro[indene-2,4'-piperidin]-1(3H)-one as a sticky solid (250 mg), which was directly used for the next step without further purification. m/z (esi) M⁺1=236.1.

Step C: Triethylamine (0.3 mL, 2.13 mmol) was added to a stirred solution of 5-chlorospiro[indene-2,4'-piperidin]-1(3H)-one (250 mg, 1.06 mmol) in DCM (10 mL) at 0° C. Boc anhydride (0.5 mL, 2.13 mmol) was added to the solution at 0° C., and the reaction mixture was stirred at room temperature for 16 hours. The reaction mixture was concentrated under reduced pressure and purified by silica gel column chromatography (10% EtOAc/hexane) to afford tert-butyl 5-chloro-1-oxo-1,3-dihydrospiro[indene-2,4'-piperidine]-1'-carboxylate (130 mg, 30% yield, 2 steps) as a solid. m/z (esi) M⁺1=335.3.

Step D: tert-Butyl 5-chloro-1-oxo-1,3-dihydrospiro[indene-2,4'-piperidine]-1'-carboxylate (700 mg, 2.09 mmol) and (R)-(+)-2-methylpropane-2-sulfinamide (760.0 mg, 6.26 mmol) were added into warm (100° C.) titanium (IV) ethoxide (1.43 g, 6.26 mmol) and was stirred at 100° C. for 16 hours. The reaction mixture was poured into EtOAc and brine. The mixture was stirred for 15 minutes, and the precipitated solid was filtered off. The liquid part was separated. The organic layer was washed with brine, dried over anhydrous Na₂SO₄ and concentrated under reduced pressure. The resulting residue was purified by silica gel column chromatography (1% MeOH/DCM) to afford the tert-butyl (R,E)-1-((tert-butylsulfinyl)imino)-5-chloro-1,3-dihydrospiro[indene-2,4'-piperidine]-1'-carboxylate (600 mg, 41% yield) as a solid. m/z (esi) M+1=439.2.

Step E: Sodium borohydride (217 mg, 5.70 mmol) was added to ice cold solution of tert-butyl (R,E)-1-((tert-butylsulfinyl)imino)-5-chloro-1,3-dihydro-spiro[indene-2,4'-piperidine]-1'-carboxylate (500 mg, 1.14 mmol) in MeOH (15 mL) and was stirred at room temperature for 4 hours. The reaction mixture was quenched with the ice water and was extracted with EtOAc. The combined organic layers were dried over anhydrous Na$_2$SO$_4$, filtered, and concentrated under reduced pressure. The resulting residue was purified by silica gel column chromatography (30% EtOAc/hexane) to afford tert-butyl (S)-1-(((R)-tert-butylsulfinyl)amino)-5-chloro-1,3-dihydrospiro[indene-2,4'-piperidine]-1'-carboxylate (195 mg, 39% yield) (m/z (esi) M−1=439.2) as a solid.

Intermediate Example AT

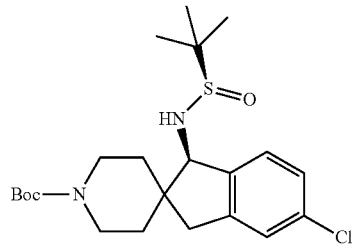

tert-butyl (R)-1-(((R)-tert-butylsulfinyl)amino)-5-chloro-1,3-dihydrospiro[indene-2,4'-piperidine]-1'-carboxylate tert-Butyl (R)-1-(((R)-tert-butylsulfinyl)amino)-5-chloro-1,3-dihydrospiro[indene-2,4' piperidine]-1'-carboxylate was prepared according to Intermediate Example AS, collecting the second eluting peak in Step E as a solid (255 mg, 23% yield) (m/z (esi) M+1=441.4).

Intermediate Example AU

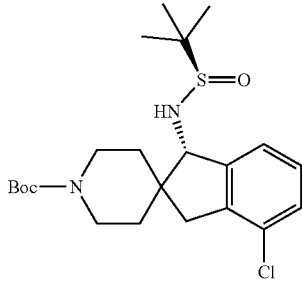

tert-butyl-(S)-1-(((R)-tert-butylsulfinyl)amino)-4-chloro-1,3-dihydrospiro[indene-2,4'-piperidine]-1'-carboxylate Step A: NaH (60% dispersion in mineral oil, 2.16 g, 90.0 mmol) was added portion wise to a stirred solution of 4-chloro-2,3-dihydro-1H-inden-1-one (5.0 g, 30.0 mmol) in DMF (10 mL) in ice cold condition and stirred for 30 minutes. N-Benzyl-2-chloro-N-(2-chloroethyl)ethan-1-amine hydrochloride was added slowly into the reaction mixture and was stirred at room temperature for 16 hours. The reaction was quenched with water, and the organic layer was extracted with EtOAc. The combined organic layers were washed with cold water and brine, dried over anhydrous Na$_2$SO$_4$, and filtered. The organic layer was evaporated to dryness. The resulting residue was purified by silica-gel column chromatography (10% EtOAc/hexane) to obtain 1'-benzyl-4-chlorospiro[indene-2,4'-piperidin]-1(3H)-one (2.9 g, 30% yield) as a gummy. m/z (esi) M+1=326.0.

Step B: Chloroethyl chloroformate (2.78 mL, 25.84 mmol) was added to a stirred solution of 1'-benzyl-4-chlorospiro[indene-2,4'-piperidin]-1(3H)-one (2.8 g, 8.61 mmol) in DCE (10 mL), and the reaction mixture was refluxed for 2 hours. Solvent was evaporated to dryness, and reaction mixture was dissolved in MeOH (5 mL) and further heated at 80° C. for 1 hour. The reaction was evaporated to dryness to obtain crude reaction mixture 4-chlorospiro[indene-2,4'-piperidin]-1(3H)-one hydrochloride (3.2 g, crude), which was used for the next step without further purification. m/z (esi) M+1=235.7.

Step C: The crude 4-chlorospiro[indene-2,4'-piperidin]-1(3H)-one hydrochloride (3.2 g, 11.76 mmol) was dissolved in DCM (5 mL) at ice cold condition, and triethylamine (6.68 mL, 47.83 mmol) was added dropwise. Boc anhydride (2.63 mL, 11.47 mmol) was added to the reaction mixture and continued stirring for 16 hours at room temperature. Water was added to the reaction mixture, and it was extracted with DCM. The combined organic layers were washed with brine, dried over anhydrous Na$_2$SO$_4$, filtered, and evaporated under reduce pressure to obtain crude, which was purified by silica gel column chromatography (5% EtOAc/hexane) to obtain tert-butyl 4-chloro-1-oxo-1,3-dihydrospiro[indene-2,4'-piperidine]-1'-carboxylate (1.6 g, 50% yield, 2 steps) as a solid. m/z (esi) M+1=336.2.

Step D: R-(+)-2-Methylpropane-2-sulfnamide (705 mg, 5.82 mmol) was added to a solution of tert-butyl 4-chloro-1-oxo-1,3-dihydrospiro[indene-2,4'-piperidine]-1'-carboxylate (1.5 g, 4.47 mmol) into warm (100° C.) titanium(IV) ethoxide (4.0 mL, 19.08 mmol), and the resulting mixture was heated at 100° C. for 16 hours. The reaction mixture was stirred with EtOAc (15 mL) and H$_2$O (15 mL) for 20 minutes and filtered through pad of Celite®. The organic layer was separated, and water part was extracted with EtOAc. The combined organic layers were evaporated under reduced pressure, and the crude reaction mixture was purified by silica gel column chromatography (20% EtOAc/hexane) to afford tert-butyl (S,E)-1-((tert-butylsulfinyl)imino)-4-chloro-1,3-dihydrospiro[indene-2,4'-piperidine]-1'-carboxylate (870 mg, 44% yield) as a solid. m/z (esi) M+1=438.8.

Step E: Sodium borohydride (368 mg, 9.7 mmol) was added portion wise to a stirred solution of tert-butyl (S,E)-1-((tert-butylsulfinyl)imino)-4-chloro-1,3-dihydrospiro[indene-2,4'-piperidine]-1'-carboxylate (850 mg, 1.94 mmol) in MeOH (5 mL) at 0° C. and stirred at room temperature for 4 hours. The reaction was evaporated to dryness, and water was added to the reaction mixture. The mixture was extracted with EtOAc. The combined organic layers were washed with brine, dried over anhydrous Na$_2$SO$_4$, filtered, and concentrated under reduced pressure. The resulting residue was purified by chiral preparative HPLC (Chiralpak IC 4.6×250 mm, 5μ, DCM/EtOH/iPrNH2 50/50/0.1, 1.0 mL/min) to obtain tert-butyl (S)-1-(((R)-tert-butylsulfinyl)

amino)-4-chloro-1,3-dihydrospiro[indene-2,4'-piperidine]-1'-carboxylate, (231 mg, 27% yield; m/z (esi) M⁺1=441.2) as a sticky solid.

Intermediate Example AV

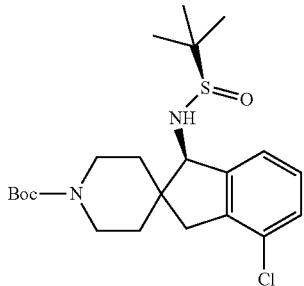

tert-butyl-(R)-1-(((R)-tert-butylsulfinyl)amino)-4-chloro-1,3-dihydrospiro[indene-2,4'-piperidin]-1'-carboxylate tert-Butyl-(R)-1-(((R)-tert-butylsulfinyl)amino)-4-chloro-1,3-dihydrospiro[indene-2,4'-piperidine]-1'-carboxylate was prepared according to Intermediate Example AU, collecting the second eluting peak in Step E as a sticky solid (295 mg, 34% yield) (m/z (esi) M⁺1=441.2).

Intermediate Example AW

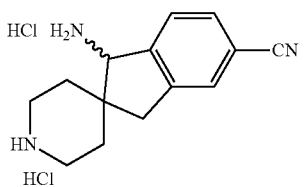

1-amino-1,3-dihydrospiro[indene-2,4'-piperidine]-5-carbonitrile dihydrochloride

Step A: NaH (60% weight in paraffin) (3.61 g, 90.36 mmol) was added to a stirred solution of 5-chloro-2,3-dihydro-1H-inden-1-one (5.0 g, 30.12 mmol) in DMF (50 mL) at 0° C. and stirred at room temperature for 30 minutes. N-Benzyl-2-chloro-N-(2-chloroethyl)ethan-1-amine (8.89 g, 33.13 mmol) was added portion wise at 0° C. and stirred at room temperature for another 5 hours. The reaction mixture was quenched with ice water and extracted with ethyl acetate. The organic part was dried (Na₂SO₄), filtered, concentrated and crude was purified by silica gel column chromatography (25% EtOAc-hexane) to afford 1'-benzyl-5-chlorospiro[indene-2,4'-piperidin]-1(3H)-one (2 g, 20% yield) as a liquid. m/z (esi) M⁺1=325.9.

Step B: 1-Chloroethyl chloroformate (3.49 g, 24.61 mmol) was added to a stirred solution of 1'-benzyl-5-chlorospiro[indene-2,4'-piperidin]-1(3H)-one (2.0 g, 6.15 mmol) in DCE (20 mL) at 0° C. and stirred for 10 minutes. The reaction mixture was stirred at 80° C. for 16 hours. The reaction mixture was concentrated, and the crude material was dissolved in MeOH (20 mL) and stirred at 80° C. for 1 hour. The reaction mixture was concentrated to afford 5-chlorospiro[indene-2,4'-piperidin]-1(3H)-one hydrochloride (1.45 g, crude) as a gummy liquid, which was used for the next step without further purification. m/z (esi) M⁺1=236.1.

Step C: Triethylamine (3.43 mL, 24.68 mmol) and boc anhydride (2.12 mL, 9.25 mmol) were added to a stirred solution of 5-chlorospiro[indene-2,4'-piperidin]-1(3H)-one hydrochloride (1.45 g, 6.17 mmol) in DCM (15 mL) at 0° C., and the reaction mixture was stirred at room temperature for 16 hours. The reaction mixture was concentrated and purified by silica gel column chromatography (30% EtOAc-hexane) to afford tert-butyl 5-chloro-1-oxo-1,3-dihydrospiro[indene-2,4'-piperidine]-1'-carboxylate (400 mg, 19% yield, 2 steps) as a solid. m/z (esi) M⁺1=336.3.

Step D: Zn(CN)₂ (982.0 mg, 8.35 mmol) and zinc powder (55.0 mg, 0.83 mmol) were added to a stirred solution of tert-butyl 5-chloro-1-oxo-1,3-dihydrospiro[indene-2,4'-piperidine]-1'-carboxylate (1.4 g, 4.14 mmol) in DMF (10 mL) and stirred for 10 minutes. The reaction mixture was degassed with argon, then trixiephos (383.0 mg, 0.41 mmol), followed by Pd(OAc)₂ (232.0 mg, 0.41 mmol) were added, and the reaction mixture was stirred at 120° C. for 16 hours. The reaction mixture was diluted with water and extracted with ethyl acetate. The organic part was dried (Na₂SO₄), filtered and concentrated, and crude material was purified by silica gel column chromatography (30% EtOAc-hexane) to afford tert-butyl 5-cyano-1-oxo-1,3-dihydrospiro[indene-2,4'-piperidine]-1'-carboxylate (250 mg, 18% yield) as a sticky solid. m/z (esi) M⁺1=326.3.

Step E: (R)-2-Methylpropane-2-sulfinamide (204.5 mg, 1.68 mmol) was added to a stirred solution of tert-butyl 5-cyano-1-oxo-1,3-dihydrospiro[indene-2,4'-piperidine]-1'-carboxylate (500 mg, 1.53 mmol) in titanium (IV) ethoxide (1.62 mL, 7.66 mmol) and stirred at 90° C. for 1 hour. The reaction mixture was poured onto EtOAc and brine and stirred for 15 minutes. Solid precipitated was filtered off. The organic layer was washed with brine, dried (Na₂SO₄) and concentrated to afford tert-butyl 1-(((R)-tert-butylsulfinyl)amino)-5-cyano-1,3-dihydrospiro[indene-2,4'-piperidine]-1'-carboxylate (600 mg, crude) as a gummy liquid, which was used for the next step without further purification. m/z (esi) M⁺1=430.3.

Step F: NaBH₄ (105.8 mg, 2.79 mmol) was added to a stirred solution of tert-butyl 1-(((R)-tert-butylsulfinyl)amino)-5-cyano-1,3-dihydrospiro[indene-2,4'-piperidine]-1'-carboxylate (600.0 mg, 1.39 mmol) in MeOH (10 mL) at −10° C. and stirred at room temperature for 2 hours. The reaction mixture was concentrated, diluted with ethyl acetate and washed with water. The organic layer was dried (Na₂SO₄), filtered, concentrated and purified by silica gel column chromatography (40% EtOAc-hexane) to afford tert-butyl 1-(((R)-tert-butylsulfinyl)amino)-5-cyano-1,3-dihydrospiro[indene-2,4'-piperidine]-1'-carboxylate (430 mg, 71% yield) as a solid. m/z (esi) M⁺1=432.1.

Step G: 4M HCl in dioxane (3 mL) was added to a stirred solution of tert-butyl 1-(((R)-tert-butylsulfinyl)amino)-5-cyano-1,3-dihydrospiro[indene-2,4'-piperidine]-1'-carboxylate (430.0 mg, 0.99 mmol) in MeOH (3 mL) at 0° C. and stirred at 0° C. for 2 hours. The reaction mixture was concentrated, and crude was triturated with diethyl ether to afford 3-amino-1,3-dihydrospiro[indene-2,4'-piperidine]-6-carbonitrile dihydrochloride (250 mg, 84% yield) as a solid. m/z (esi) M⁺1=228.4.

Intermediate Example AX

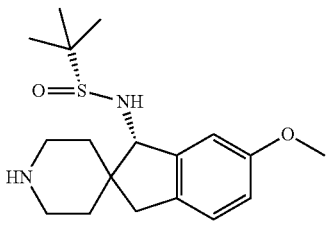

(R)-N-((S)-5-methoxy-1,3-dihydrospiro[indene-2,4'-piperidin]-3-yl)-2-methylpropane-2-sulfinamide 2,2,2-trifluoroacetate Step A: Sodium hydride, 60% dispersion in mineral oil (0.74 g, 18 mmol) was added in portions to a solution of 6-methoxy-1-indanone (1 g, 6.2 mmol) in DMF (6.9 mL, 6.2 mmol) under argon. The mixture was stirred at room temperature for 10 minutes. N-Benzyl-2-chloro-N-(2-chloroethyl)ethan-1-amine (1.6 g, 6.8 mmol) was added, and the mixture continued to stir overnight. The reaction was poured into water and partitioned with EtOAc. The combined organics were washed with brine, dried over $Na_2SO_4$, and concentrated in vacuo. The resulting residue was purified by silica gel chromatography (0%-10% DCM:MeOH (2% $NH_4OH$)) to give 1'-benzyl-6-methoxyspiro[indene-2,4'-piperidin]-1(3H)-one (1.6 g, 5 mmol, 81% yield). m/z (esi) $M^+1=322.2$.

Step B: A solution of 1'-benzyl-6-methoxyspiro[indene-2,4'-piperidin]-1(3H)-one (1.6 g, 5 mmol) and di-tert-butyl dicarbonate (1.2 g, 5.5 mmol) in EtOH (25 mL, 5 mmol) and THF (25 mL, 5 mmol) was purged with $N_2$ for 5 minutes. Palladium (Degussa Type, 10 weight %, 50% $H_2O$) (1.3 g, 1.2 mmol) was added to this solution, and was immediately capped and purged with $N_2$ for an additional 5 minutes. The solution then stirred under 1 atm $H_2$ pressure. The mixture was stirred at ambient temperature for 1 hour. The mixture was diluted with MeOH and filtered through packed Celite®. The filtrate was concentrated in vacuo to provide crude tert-butyl 6-methoxy-1-oxo-1,3-dihydrospiro[indene-2,4'-piperidine]-1'-carboxylate (1.12 g, 3.38 mmol, 68% yield). m/z (esi) $M^+1=232.2$.

Step C: (R)-(+)-2-Methyl-2-propanesulfinamide (1.2 g, 10.14 mmol) and tetraethoxytitanium (5.4 g, 23.66 mmol) were added to a solution of tert-butyl 6-methoxy-1-oxo-1,3-dihydrospiro[indene-2,4'-piperidine]-1'-carboxylate (1.12 g, 3.34 mmol) in THF (16.9 mL, 3.34 mmol), and the reaction stirred overnight at 90° C. EtOAc was added followed by water. The solids were filtered off, and the layers were separated. The organic layer was dried, filtered and concentrated. The resulting residue was purified by normal phase chromatography (0%-100% hexanes:EtOAc) to give tert-butyl (R,Z)-1-((tert-butylsulfinyl)imino)-6-methoxy-1,3-dihydrospiro[indene-2,4'-piperidine]-1'-carboxylate (0.79 g, 1.83 mmol, 54% yield). m/z (esi) $M^+1=435.2$.

Step D: tert-Butyl (R,Z)-1-((tert-butylsulfinyl)imino)-6-methoxy-1,3-dihydrospiro[indene-2,4'-piperidine]-1'-carboxylate (0.79 g, 1.83 mmol) was placed in THF (15 mL) and cooled to 0° C. $NaBH_4$ (0.1 g, 2.74 mmol) was added, and the reaction was allowed to slowly warm to room temperature and stir for 18 hours. Water was added, and the mixture was extracted with DCM (3×25 mL). The extracts were combined and concentrated. The resulting residue was purified by silica gel (0-5% MeOH in DCM with 2% $NH_4OH$). The first eluting peak was collected to provide tert-butyl (S)-1-(((R)-tert-butylsulfinyl)amino)-6-methoxy-1,3-dihydrospiro[indene-2,4'-piperidine]-1'-carboxylate (0.343 g, 0.79 mmol, 43% yield). m/z (esi) $M^+1=437.3$.

Step E: TFA (303 μL, 3.93) was added to a solution of tert-butyl (S)-1-(((R)-tert-butylsulfinyl)amino)-6-methoxy-1,3-dihydrospiro[indene-2,4'-piperidine]-1'-carboxylate (343 mg, 0.79 mmol) in DCM (1.57 mL, 0.79 mmol), and the reaction was stirred at room temperature for 1 hour. The reaction was concentrated in vacuo and taken forward as crude (R)-N-((S)-5-methoxy-1,3-dihydrospiro[indene-2,4'-piperidin]-3-yl)-2-methylpropane-2-sulfinamide 2,2,2-trifluoroacetate (354 mg, 0.79 mmol, 100% yield). m/z (esi) $M^+1=337.2$.

Example 1

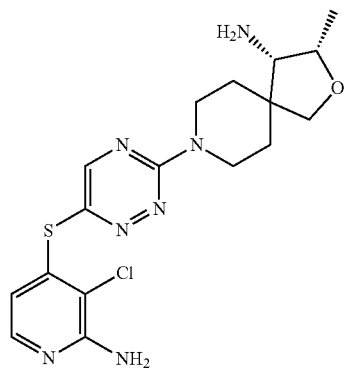 [SMILES: C[C@@H]1OCC2(CCN(c3ncc(Sc4ccnc(N)c4Cl)nn3)CC2)[C@@H]1N]

(3S,4S)-8-(6-((2-amino-3-chloropyridin-4-yl)thio)-1,2,4-triazin-3-yl)-3-methyl-2-oxa-8-azaspiro[4.5]decan-4-amine Step A: (3S,4S)-3-Methyl-2-oxa-8-azaspiro[4.5]decan-4-amine dihydrochloride (320 mg, 1.3 mmol) was diluted with dioxane (6 mL), followed by the addition of DIEA (815 μL, 4.67 mmol) and 3,6-dichloro-1,2,4-triazine (200 mg, 1.33 mmol). The reaction was heated to 50° C. and stirred for 3 hours. The reaction was allowed to cool and diluted with DCM/IPA and 10% sodium carbonate. The layers were separated, and the aqueous was extracted twice with DCM/IPA. The organics were combined, dried over $MgSO_4$, filtered and concentrated. The material was purified on silica gel eluting with 1-10% methanol/DCM (1% $NH_4OH$) to afford (3S,4S)-8-(6-chloro-1,2,4-triazin-3-yl)-3-methyl-2-oxa-8-azaspiro[4.5]decan-4-amine (290 mg, 1.02 mmol, 76.6% yield).

(3S,4S)-8-(6-Chloro-1,2,4-triazin-3-yl)-3-methyl-2-oxa-8-azaspiro[4.5]decan-4-amine (30 mg, 0.11 mmol) and 2-amino-3-chloropyridine-4-thiol (20 mg, 0.13 mmol) were diluted with dioxane, followed by the addition of DIEA (55 μL, 0.32 mmol). The reaction was placed under nitrogen and heated to 100° C. After stirring for 4 hours, the reaction was diluted with DCM/IPA and 10% sodium carbonate. The material was extracted two more times with DCM/IPA. The organics were combined, dried over $MgSO_4$, filtered and concentrated. The material was purified on silica gel eluting with 10% methanol/DCM (1% $NH_4OH$). The material was purified again on C-18 silica gel eluting with 5-95% ACN/water (0.1% TFA). The pure fractions were diluted with

89

DCM/IPA and saturated sodium bicarbonate. The layers were separated, and the organics were dried over MgSO₄, filtered and concentrated to afford (3S,4S)-8-(6-((2-amino-3-chloropyridin-4-yl)thio)-1,2,4-triazin-3-yl)-3-methyl-2-oxa-8-azaspiro[4.5]decan-4-amine (6 mg, 0.015 mmol, 14% yield). ¹H NMR (400 MHz, CDCl₃) δ 8.2 (s, 1H), 7.75 (d, 1H, J=5.5 Hz), 6.12 (d, 1H, 5.5 Hz) 4.9 (br, 2H), 4.18-4.40 (m, 3H), 3.84 (d, 1H, J=8.6 Hz), 3.6-3.8 (m, 3H), 3.02 (d, 1H, J=4.7 Hz), 1.4-1.95 (m, 6H); m/z (esi/APCI) M⁺1=408.2.

Example 2

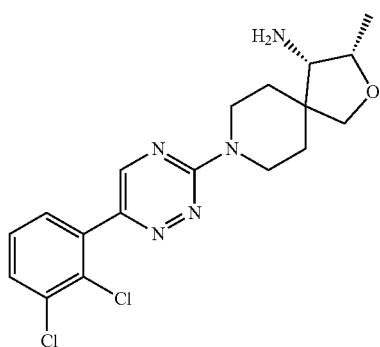 [SMILES: C[C@@H]1OCC2(CCN(c3ncc(-c4cccc(Cl)c4Cl)nn3)CC2)[C@@H]1N]

(3S,4S)-8-(6-(2,3-dichlorophenyl)-1,2,4-triazin-3-yl)-3-methyl-2-oxa-8-azaspiro[4.5]decan-4-amine Step A: (3S,4S)-3-Methyl-2-oxa-8-azaspiro[4.5]decan-4-amine dihydrochloride (320 mg, 1.3 mmol) was diluted with dioxane (6 mL), followed by the addition of DIEA (815 µL, 4.67 mmol) and 3,6-dichloro-1,2,4-triazine (200 mg, 1.3 mmol). The reaction was heated to 50° C. and stirred for 3 hours. The reaction was allowed to cool and diluted with DCM/IPA and 10% sodium carbonate. The layers were separated, and the aqueous was extracted twice with DCM/IPA. The organics were combined, dried over MgSO₄, filtered and concentrated. The material was purified on silica gel eluting with 1-10% methanol/DCM (1% NH₄OH) to afford (3S,4S)-8-(6-chloro-1,2,4-triazin-3-yl)-3-methyl-2-oxa-8-azaspiro[4.5]decan-4-amine (290 mg, 1.0 mmol, 76.6% yield).

Step B: (3S,4S)-8-(6-Chloro-1,2,4-triazin-3-yl)-3-methyl-2-oxa-8-azaspiro[4.5]decan-4-amine (30 mg, 0.11 mmol), (2,3-dichlorophenyl)boronic acid (30 mg, 0.16 mmol) and Tetrakis (3.7 mg, 0.0032 mmol) were diluted with dioxane (1.0 mL), followed by the addition of Na₂CO₃ (132 µL, 0.26 mmol). The reaction was purged with argon, sealed and heated to 95° C. for 4 hours. The reaction was allowed to cool, diluted with ethyl acetate and water. The layers were separated, and the ethyl acetate was dried over MgSO₄, filtered and concentrated. The material was purified on silica gel eluting with 10% methanol/DCM (1% NH₄OH) to afford (3S,4S)-8-(6-(2,3-dichlorophenyl)-1,2,4-triazin-3-yl)-3-methyl-2-oxa-8-azaspiro[4.5]decan-4-amine (10 mg, 0.025 mmol, 24% yield). ¹H NMR (400 MHz, CDCl₃) δ 8.51 (s, 1H), 7.61 (dd, 1H, J=7.83, 1.57 Hz), 7.54 (dd, 1H, J=7.83, 1.57 Hz), 7.33 (t, 1H), 4.18-4.40 (m, 3H), 3.84 (d, 1H, J=9.0 Hz), 3.55-3.75 (m, 3H), 3.05 (d, 1H, J=4.7 Hz), 1.4-1.95 (m, 6H); m/z (esi/APCI) M⁺1=394.1.

Example 3

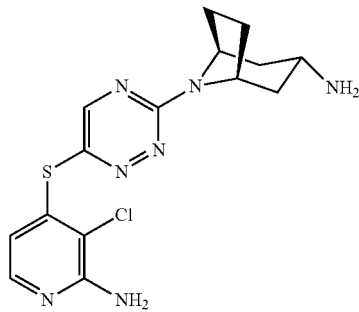 [SMILES: Nc1nccc(Sc2cnc(N3[C@H]4CC[C@H]3CC(N)C4)nn2)c1Cl]

(1R,3s,5S)-8-(6-((2-amino-3-chloropyridin-4-yl)thio)-1,2,4-triazin-3-yl)-8-azabicyclo[3.2.1]octan-3-amine Step A: tert-Butyl 41R,3s,5S)-8-azabicyclo[3.2.1]octan-3-yl)carbamate (226 mg, 1.00 mmol) was diluted with dioxane (5 mL), followed by the addition of DIEA (611 µL, 3.50 mmol) and 3,6-dichloro-1,2,4-triazine (150 mg, 1.00 mmol). The reaction was heated to 50° C. and stirred for 3 hours. The reaction was allowed to cool, diluted with DCM/IPA and 10% sodium carbonate. The layers were separated, and the aqueous was extracted twice with DCM/IPA. The organics were combined, dried over MgSO₄, filtered and concentrated. The material was purified on silica gel eluting with 10-50% ethyl acetate/hexanes to afford tert-butyl ((1R,3s,5S)-8-(6-chloro-1,2,4-triazin-3-yl)-8-azabicyclo[3.2.1]octan-3-yl)carbamate (235 mg, 0.692 mmol, 69.1% yield).

Step B: tert-Butyl ((1R,3s,5S)-8-(6-chloro-1,2,4-triazin-3-yl)-8-azabicyclo[3.2.1]octan-3-yl)carbamate (30 mg, 0.088 mmol) and 2-amino-3-chloropyridine-4-thiol (14 mg, 0.088 mmol) were diluted with dioxane, followed by the addition of DIEA (46 µL, 0.26 mmol). The reaction was placed under nitrogen and heated to 90° C. After stirring for 4 hours, the reaction was diluted with DCM/IPA and 10% sodium carbonate. The material was extracted two more times with DCM/IPA. The organics were combined, dried over MgSO₄, filtered and concentrated. The material was purified on silica gel eluting with 1-10% methanol/DCM (1% NH₄OH) to afford tert-butyl 41R,3s,5S)-8-(6-((2-amino-3-chloropyridin-4-yl)thio)-1,2,4-triazin-3-yl)-8-azabicyclo[3.2.1]octan-3-yl)carbamate (25 mg, 0.054 mmol, 61% yield).

Step C: tert-Butyl ((1R,3s,5S)-8-(6-((2-amino-3-chloropyridin-4-yl)thio)-1,2,4-triazin-3-yl)-8-azabicyclo[3.2.1]octan-3-yl)carbamate (25 mg, 0.054 mmol) was diluted with DCM (1 mL), followed by the addition of TFA (1 mL). After stirring for 2 hours, the reaction was concentrated. The material was purified on C-18 silica gel eluting with 5-95% ACN/water (0.1% TFA). The pure fractions were diluted with DCM/IPA and saturated sodium bicarbonate. The layers were separated, and the organics were dried over MgSO₄, filtered and concentrated. The material was purified again on silica gel eluting with 10% methanol/DCM (1% NH₄OH) to afford (1R,3s,5S)-8-(6-((2-amino-3-chloropyridin-4-yl)thio)-1,2,4-triazin-3-yl)-8-azabiyclo[3.2.1]octan-3-amine (3 mg, 0.0082 mmol, 15% yield). ¹H NMR (400 MHz, CDCl₃) δ 8.2 (s, 1H), 7.76 (d, 1H, J=5.48 Hz), 6.17

(d, 1H, J=5.48 Hz), 5.10 (br, 1H), 4.92 (br, 2H), 4.74 (br, 1H), 3.37 (m, 1H), 1.2-2.2 (m, 10H); m/z (esi/APCI) M+1=364.1.

Example 4

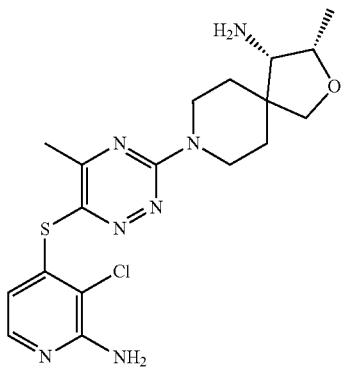 [SMILES: Cc1nc(N2CCC3(CC2)CO[C@@H](C)[C@H]3N)nnc1Sc1ccnc(N)c1Cl]

(3S,4S)-8-(6-((2-amino-3-chloropyridin-4-yl)thio)-5-methyl-1,2,4-triazin-3-yl)-3-methyl-2-oxa-8-azaspiro[4.5]decan-4-amine Step A: (3S,4S)-3-Methyl-2-oxa-8-azaspiro[4.5]decan-4-amine dihydrochloride (175 mg, 0.720 mmol) was diluted with dioxane (4 mL), followed by the addition of DIEA (377 μL, 2.16 mmol) and 3,6-dichloro-5-methyl-1,2,4-triazine (118 mg, 0.720 mmol). The reaction was purged with nitrogen, sealed and heated to 120° C. After stirring for 12 hours, the reaction was allowed to cool, diluted with DCM (25% IPA) and 10% sodium carbonate. The layers were separated, and the aqueous was extracted two more times with DCM/IPA. The organics were combined, dried over MgSO$_4$, filtered and concentrated. The material was purified on silica gel eluting with 1-10% methanol/DCM to afford (3S,4S)-8-(6-chloro-5-methyl-1,2,4-triazin-3-yl)-3-methyl-2-oxa-8-azaspiro[4.5]decan-4-amine (125 mg, 0.420 mmol, 58.3% yield).

Step B: (3S,4S)-8-(6-Chloro-5-methyl-1,2,4-triazin-3-yl)-3-methyl-2-oxa-8-azaspiro[4.5]decan-4-amine (23 mg, 0.077 mmol) and 2-amino-3-chloropyridine-4-thiol (15 mg, 0.093 mmol) were diluted with dioxane, followed by the addition of DIEA (40 μL, 0.23 mmol). The reaction was placed under nitrogen and heated to 100° C. After stirring for 4 hours, the reaction was diluted with DCM/IPA and 10% sodium carbonate. The layers were separated, and the organics were dried over MgSO$_4$, filtered and concentrated. The material was purified on silica gel eluting with 10% methanol/DCM (1% NH$_4$OH) to afford (3S,4S)-8-(6-((2-amino-3-chloropyridin-4-yl)thio)-5-methyl-1,2,4-triazin-3-yl)-3-methyl-2-oxa-8-azaspiro[4.5]decan-4-amine (2.5 mg, 0.0059 mmol, 7.7% yield). $^1$H NMR (400 MHz, CDCl$_3$) δ 7.34 (dd, 1H, J=7.8, 1.6 Hz), 7.09 (t, 1H, J=7.8 Hz), 7.02 (dd, 1H, J=7.8, 1.6 Hz), 4.1-4.3 (m, 3H), 3.82 (d, 1H, J=8.6 Hz), 3.70 (d, 1H, J=8.6 Hz), 3.6 (m, 2H), 3.04 (d, 1H, J=4.7 Hz), 2.22 (s, 3H), 1.55-1.91 (m, 6H), 1.2 (d, 3H, J=6.3 Hz); m/z (esi/APCI) M+1=422.2.

Example 5

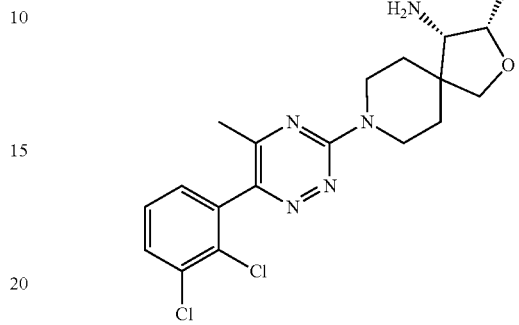

(3S,4S)-8-(6-(2,3-dichlorophenyl-5-methyl-1,2,4-triazin-3-yl)-3-methyl-2-oxa-8-azaspiro[4.5]decan-4-amine Step A: (3S,4S)-3-Methyl-2-oxa-8-azaspiro[4.5]decan-4-amine dihydrochloride (175 mg, 0.720 mmol) was diluted with dioxane (4 mL), followed by the addition of DIEA (377 μL, 2.16 mmol) and 3,6-dichloro-5-methyl-1,2,4-triazine (118 mg, 0.720 mmol). The reaction was purged with nitrogen, sealed and heated to 120° C. After stirring for 12 hours, the reaction was allowed to cool and diluted with DCM (25% IPA) and 10% sodium carbonate. The layers were separated, and the aqueous was extracted two more times with DCM/IPA. The organics were combined, dried over MgSO$_4$, filtered and concentrated. The material was purified on silica gel eluting with 1-10% methanol/DCM to afford (3S,4S)-8-(6-chloro-5-methyl-1,2,4-triazin-3-yl)-3-methyl-2-oxa-8-azaspiro[4.5]decan-4-amine (125 mg, 0.420 mmol, 58.3% yield).

Step B: (3S,4S)-8-(6-Chloro-5-methyl-1,2,4-triazin-3-yl)-3-methyl-2-oxa-8-azaspiro[4.5]decan-4-amine (100 mg, 0.336 mmol), (2,3-dichlorophenyl)boronic acid (96.1 mg, 0.504 mmol) and Tetrakis (11.6 mg, 0.0101 mmol) were diluted with dioxane (1.5 mL), followed by the addition of Na$_2$CO$_3$ (420 μL, 0.840 mmol). The reaction was purged with argon, sealed and heated to 130° C. for 4 hours. The reaction was allowed to cool and diluted with ethyl acetate and water. The layers were separated, and the ethyl acetate was dried over MgSO$_4$, filtered and concentrated. The material was purified on silica gel eluting with 10% methanol/DCM (1% NH$_4$OH) to afford (3S,4S)-8-(6-(2,3-dichlorophenyl)-5-methyl-1,2,4-triazin-3-yl)-3-methyl-2-oxa-8-azaspiro[4.5]decan-4-amine (32 mg, 0.0784 mmol, 23.3% yield). $^1$H NMR (400 MHz, CDCl$_3$) δ 7.56 (m, 1H), 7.31 (m, 2H), 4.33 (m, 2H), 4.21 (m, 1H), 3.86 (d, 1H, J=8.9 Hz), 3.73 (d, 1H, J=8.9 Hz), 3.5-3.7 (m, 2H), 3.04 (d, 1H, J=4.7 Hz), 2.22 (s, 3H), 1.55-1.91 (m, 6H), 1.25 (d, 3H, J=6.65 Hz); m/z (esi/APCI) M+1=408.1.

Example 6

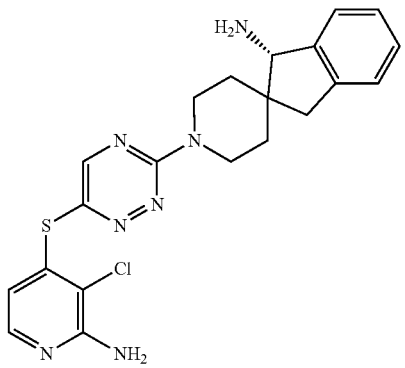

(S)-1'-(6-((2-amino-3-chloropyridin-4-yl)thio)-1,2,4-triazin-3-yl)-1,3-dihydrospiro[indene-2,4'-piperidin]-1-amine Step A: (R)-N-((S)-1,3-Dihydrospiro[indene-2,4'-piperidin]-1-yl)-2-methylpropane-2-sulfinamide (163 mg, 0.53 mmol) was diluted with dioxane (2 mL), followed by the addition of DIEA (326 µL, 1.9 mmol). After stirring for 5 minutes, 3,6-dichloro-1,2,4-triazine (80 mg, 0.53 mmol) was added. The reaction was heated to 50° C. and stirred for 3 hours. The reaction was allowed to cool and diluted with DCM/IPA and 10% sodium carbonate. The layers were separated, and the aqueous was extracted twice with DCM/IPA. The organics were combined, dried over MgSO₄, filtered and concentrated. The material was purified on silica gel eluting with 1-10% methanol/DCM (1% NH₄OH) to afford (R)-N-((S)-1'-(6-chloro-1,2,4-triazin-3-yl)-1,3-dihydrospiro[indene-2,4'-piperidin]-1-yl)-2-methylpropane-2-sulfinamide (25 mg, 0.060 mmol, 11% yield).

Step B: (R)-N-((S)-1'-(6-Chloro-1,2,4-triazin-3-yl)-1,3-dihydrospiro[indene-2,4'-piperidin]-1-yl)-2-methylpropane-2-sulfinamide (55 mg, 0.13 mmol) and sodium 2-amino-3-chloropyridine-4-thiolate (48 mg, 0.26 mmol) were diluted with NMP (437 µL, 0.13 mmol), followed by the addition of DIEA (46 µL, 0.26 mmol). The reaction was purged with argon, sealed and heated to 110° C. After stirring for 12 hours, the reaction was allowed to cool and diluted with ethyl acetate and washed with water and brine. The ethyl acetate was dried over MgSO₄, filtered and concentrated. The material was purified on silica gel eluting with 100% ethyl acetate to afford (R)-N-((S)-1'-(6-((2-amino-3-chloropyridin-4-yl)thio)-1,2,4-triazin-3-yl)-1,3-dihydrospiro[indene-2,4'-piperidin]-1-yl)-2-methylpropane-2-sulfinamide (55 mg, 0.10 mmol, 77% yield).

Step C: (R)-N-((S)-1'-(6-((2-amino-3-chloropyridin-4-yl)thio)-1,2,4-triazin-3-yl)-1,3-dihydrospiro[indene-2,4'-piperidin]-1-yl)-2-methylpropane-2-sulfinamide (20 mg, 0.037 mmol) was diluted with dioxane (1 mL), followed by the addition of HCl (92 µL, 0.37 mmol). After stirring for 30 minutes, the reaction was diluted with DCM and saturated aqueous sodium bicarbonate. After stirring the mixture for 10 minutes, the layers were separated, and the DCM was dried over MgSO₄, filtered and concentrated. The material was purified on silica gel eluting with 20% methanol/ethyl acetate to afford (S)-1'-(6-((2-amino-3-chloropyridin-4-yl)thio)-1,2,4-triazin-3-yl)-1,3-dihydrospiro[indene-2,4'-piperidin]-1-amine (15 mg, 0.034 mmol, 93% yield). $^1$H NMR (400 MHz, CDCl₃) δ 8.2 (s, 1H), 7.76 (d, 1H, J=5.2 Hz), 7.2-7.35 (m, 4H), 6.15 (d, 1H, J=5.2 Hz), 4.92 (br, 2H), 4.78 (br, 1H), 4.01 (s, 1H), 3.37 (m, 2H), 3.14 (d, 1H, J=15.6 Hz), 2.78 (d, 1H, J=15.6), 1.3-1.91 (m, 7H); m/z (esi/APCI) M$^+$1=440.1.

The following compounds in Table 3 were prepared according to the above procedures using appropriate starting materials and intermediates.

TABLE 3

| Ex. # | Structure | Name | Prep | MS |
|---|---|---|---|---|
| 7 | 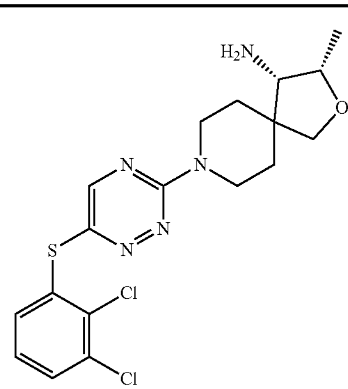 | (3S,4S)-8-(6-((2,3-dichlorophenyl)thio)-1,2,4-triazin-3-yl)-3-methyl-2-oxa-8-azaspiro[4.5]decan-4-amine | Ex. 1 | 426.1 |

TABLE 3-continued
| Ex. # | Structure | Name | Prep | MS |
|---|---|---|---|---|
| 8 | 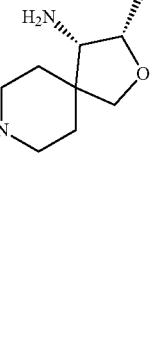 | (3S,4S)-8-(6-((1H-pyrrolo[2,3-b]pyridin-4-yl)thio)-1,2,4-triazin-3-yl)-3-methyl-2-oxa-8-azaspiro[4.5]decan-4-amine | Ex. 1 | 398.2 |
| 9 | 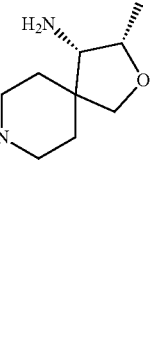 | (3S,4S)-8-(6-((5-chloro-1H-pyrrolo[2,3-b]pyridin-4-yl)thio)-1,2,4-triazin-3-yl)-3-methyl-2-oxa-8-azaspiro[4.5]decan-4-amine | Ex. 1 | 432.1 |
| 10 | 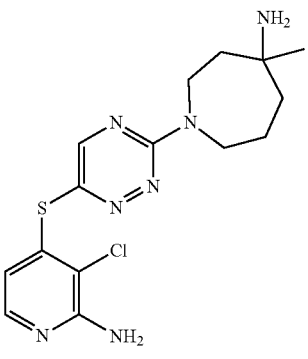 [SMILES: CC1(N)CCCN(c2ncc(Sc3ccnc(N)c3Cl)nn2)CC1] | 1-(6-((2-amino-3-chloropyridin-4-yl)thio)-1,2,4-triazin-3-yl)-4-methylazepan-4-amine | Ex. 1 | 366.1 |
| 11 | 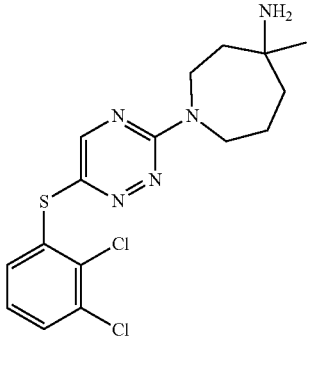 [SMILES: CC1(N)CCCN(c2ncc(Sc3cccc(Cl)c3Cl)nn2)CC1] | 1-(6-((2,3-dichlorophenyl)thio)-1,2,4-triazin-3-yl)-4-methylazepan-4-amine | Ex. 1 | 384.1 |

TABLE 3-continued

| Ex. # | Structure | Name | Prep | MS |
|---|---|---|---|---|
| 12 | 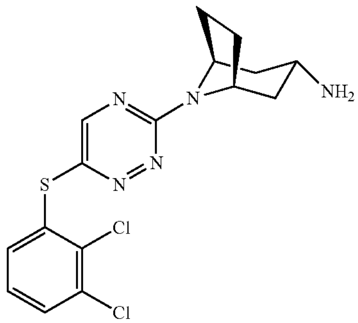 [SMILES: NC1C[C@@H]2CC[C@@H](C1)N2c1ncc(Sc2cccc(Cl)c2Cl)nn1] | (1R,3s,5S)-8-(6-((2,3-dichlorophenyl)thio)-1,2,4-triazin-3-yl)-8-azabicyclo[3.2.1]octan-3-amine | Ex. 3 | 382.1 |
| 13 | 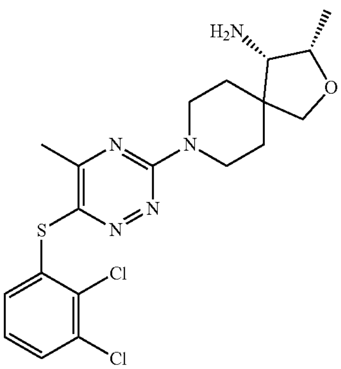 [SMILES: Cc1nc(N2CCC3(CC2)CO[C@@H](C)[C@H]3N)nnc1Sc1cccc(Cl)c1Cl] | (3S,4S)-8-(6-((2,3-dichlorophenyl)thio)-5-methyl-1,2,4-triazin-3-yl)-3-methyl-2-oxa-8-azaspiro[4.5]decan-4-amine | Ex. 4 | 440.1 |
| 14 | 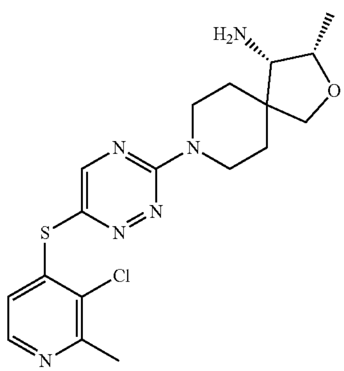 [SMILES: Cc1nccc(Sc2cnc(N3CCC4(CC3)CO[C@@H](C)[C@H]4N)nn2)c1Cl] | (3S,4S)-8-(6-((3-chloro-6-methylpyridin-4-yl)thio)-1,2,4-triazin-3-yl)-3-methyl-2-oxa-8-azaspiro[4.5]decan-4-amine | Ex. 1 | 402.1 |

Example 15

(S)-1'-(6-(2,3-dihydro-1H-pyrrolo[3,2-c]pyridin-1-yl)-1,2,4-triazin-3-yl)-1,3-dihydrospiro[indene-2,4'-piperidin]-1-amine

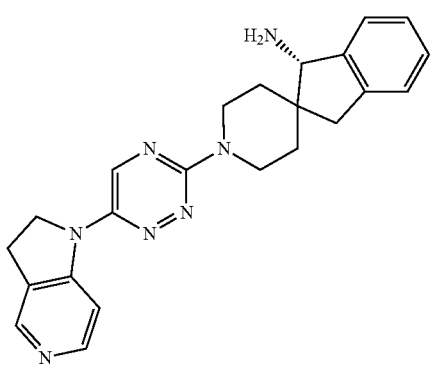 [SMILES: N[C@@H]1c2ccccc2CC12CCN(c1ncc(N3CCc4cnccc43)nn1)CC2]

In a small vial with Teflon cap, Pd$_2$(dba)$_3$ (13 mg, 0.014 mmol), xantphos (16 mg, 0.028 mmol), cesium carbonate (113 mg, 0.35 mmol), 2,3-dihydro-1H-pyrrolo[3,2-c]pyridine (22 mg, 0.18 mmol) and (S)-1'-(6-bromo-1,2,4-triazin-3-yl)-1,3-dihydrospiro[indene-2,4'-piperidin]-1-amine (50 mg, 0.14 mmol) were mixed together with dioxane (3 mL). The vial was evacuated and backfilled with Ar three times. The vial was then heated up to 90° C. for 18 hours. The reaction was diluted with DCM (5 mL), and the mixture was filtered through a Celite® pad. The filtrate was evaporated, and the residue was purified using 12 g silica gel column (MeOH/DCM mixture 2-20%) to provide (S)-1'-(6-(2,3-dihydro-1H-pyrrolo[3,2-c]pyridin-1-yl)-1,2,4-triazin-3-yl)-1,3-dihydrospiro[indene-2,4'-piperidin]-1-amine (9 mg, 0.023 mmol, 16% yield) as a solid. m/z (esi/APCI) M$^+$1=360.0; $^1$H NMR (400 MHz, CDCl$_3$) δ 8.32 (s, 2H), 8.17 (s, 1H), 7.64 (s, 1H), 7.33 (d, J=5.5 Hz, 1H), 7.23 (s, 3H), 4.62 4.49 (m, 2H), 4.18 (t, J=8.7 Hz, 2H), 4.00 (s, 1H), 3.39 3.24 (m, 4H), 3.13 (d, J=15.6 Hz, 1H), 2.76 (d, J=15.6 Hz, 1H), 1.87 (td, J=12.5, 4.3 Hz, 1H), 1.81 1.71 (m, 1H), 1.48 1.33 (m, 3H).

Example 16

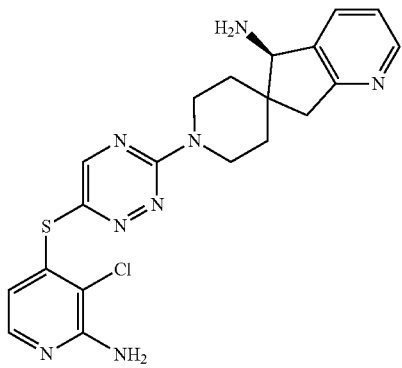 [SMILES: Nc1nccc(Sc2cnc(N3CCC4(CC3)Cc3ncccc3[C@@H]4N)nn2)c1Cl]

(R)-1'-(6-((2-amino-3-chloropyridin-4-yl)thio)-1,2,4-triazin-3-yl)-5,7-dihydrospiro[cyclopenta[b]pyridine-6,4'-piperidin]-5-amine trihydrochloride Step A: tert-Butyl (R)-5-(((R)-tert-butylsulfinyl)amino)-5,7-dihydrospiro[cyclopenta[b]pyridine-6,4'-piperidine]-1'-carboxylate (0.193 g, 0.474 mmol) was dissolved in DCM (3 mL), and then 2,2,2-trifluoroacetic acid (0.270 g, 2.37 mmol) was added. After stirring for 1 hour, reaction was evaporated, and the remaining TFA salt was used in the next step without further purification.

Step B: (R)-N-((R)-5,7-Dihydrospiro[cyclopenta[b]pyridine-6,4'-piperidin]-5-yl)-2-methylpropane-2-sulfinamide (0.07 g, 0.23 mmol) as TFA salt was dissolved in dioxane (4 mL), and TEA (0.16 mL, 1.1 mmol) was added to the solution. 3,6-Dichloro-1,2,4-triazine (0.032 g, 0.22 mmol) was added, and the mixture was heated up to 50° C. for 3 hours. Sodium 2-amino-3-chloropyridine-4-thiolate (0.050 g, 0.27 mmol) was added to the reaction mixture, and the mixture was heated up to 90° C. for 18 hours. The reaction was cooled down to room temperature, quenched with water (10 mL) and extracted with EtOAc (3×15 mL). The combined organic layers were washed with brine, dried and evaporated to give a residue. The residue was purified using 24 g silica gel column (MeOH/DCM mixture 2-20%) provided (R)-N-((R)-1'-(6-((2-amino-3-chloropyridin-4-yl)thio)-1,2,4-triazin-3-yl)-5,7-dihydrospiro[cyclopenta[b]pyridine-6,4'-piperidin]-5-yl)-2-methylpropane-2-sulfinamide (0.081 g, 0.15 mmol, 65% yield) as a solid. m/z (esi/APCI) M+1=545.2.

Step C: (R)-N-((R)-1'-(6-((2-Amino-3-chloropyridin-4-yl)thio)-1,2,4-triazin-3-yl)-5,7-dihydrospiro[cyclopenta[b]pyridine-6,4'-piperidin]-5-yl-2-methylpropane-2-sulfinamide (0.081 g, 0.15 mmol) was dissolved in DCM (2 mL), and HCl in dioxane (4M) (0.5 mL) was added to the mixture. The reaction was stirred at room temperature for 30 minutes, then ether (5 mL) was added to the mixture. The product was filtered and washed with ether three times to provide (R)-1'-(6-((2-amino-3-chloropyridin-4-yl)thio)-1,2,4-triazin-3-yl)-5,7-dihydrospiro[cyclopenta[b]pyridine-6,4'-piperidin]-5-amine trihydrochloride (0.057 g, 0.13 mmol, 87% yield). m/z (esi/APCI) M+1=441.1; $^1$H NMR (400 MHz, (CD$_3$)$_2$SO)) δ 8.73 (s, 1H), 8.57-8.52 (m, 2H), 8.08 (d, J=7.4 Hz, 1H), 7.75 (d, J=6.3 Hz, 1H), 7.44-7.38 (m, 1H), 6.20 (d, J=6.2 Hz, 1H), 4.50 (s, 1H), 3.15 (d, J=17.1 Hz, 2H), 1.86 (d, J=11.8 Hz, 2H), 1.62 (d, J=12.5 Hz, 2H), 1.07 (t, J=7.0 Hz, 1H).

Example 17

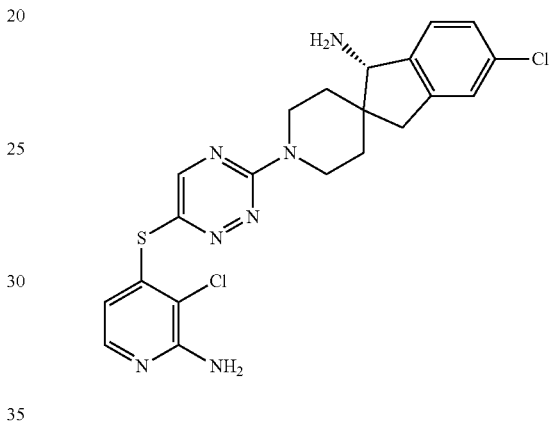

(S)-1'-(6-((2-amino-3-chloropyridin-4-yl)thio)-1,2,4-triazin-3-yl)-5-chloro-1,3-dihydrospiro[indene-2,4'-piperidin]-1-amine tert-Butyl (S)-1-(((R)-tert-butylsulfinyl)amino)-5-chloro-1,3-dihydrospiro[indene-2,4'-piperidine]-1'-carboxylate (0.100 g, 0.227 mmol) was dissolved in DCM (3 mL), and 4M HCl in dioxane (1 mL) was added to the solution. The mixture was stirred for 1 hour at room temperature, and Et$_2$O (10 mL) was added. The solid formed was filtered and dried. (S)-5-Chloro-1,3-dihydrospiro[indene-2,4'-piperidin]-1-amine dihydrochloride (30 mg, 0.097 mmol) was suspended in dioxane (3 mL), and triethylamine (29 mg, 0.29 mmol) was added to the mixture. The mixture was stirred at room temperature for 30 minutes then 3,6-dibromo-1,2,4-triazine (23 mg, 0.097 mmol) was added. The reaction was heated up to 50° C. and stirred for 1 hour. Sodium 2-amino-3-chloropyridine-4-thiolate (18 mg, 0.097 mmol) was added, and the reaction was heated up to 90° C. for 18 hours. The reaction was cooled to room temperature, quenched with water (10 mL), and the mixture was extracted with DCM/IPA mixture (3×10 mL). The combined organic layers were washed with brine (1×10 mL), dried and evaporated to give a residue. The residue was purified using 12 g silica gel column (MeOH/DCM mixture 2-20%) (S)-1'-(6-((2-amino-3-chloropyridin-4-yl)thio)-1,2,4-triazin-3-yl)-5-chloro-1,3-dihydrospiro[indene-2,4'-piperidin]-1-amine (15 mg, 0.032 mmol, 33% yield). m/z (esi/APCI) M+1=475.2. ¹H NMR (400 MHz, CDCl₃) δ 8.20 (s, 1H), 7.76 (s, 1H), 7.22 (s, 2H), 6.13 (s, 1H), 4.91 (s, 2H), 4.74 (s, 2H), 3.97 (s, 1H), 3.35 (d, J=12.1 Hz, 2H), 3.12 (d, J=16.2 Hz, 1H), 2.75 (d, J=16.1 Hz, 1H), 1.87 (d, J=12.4 Hz, 1H), 1.76 (d, J=11.5 Hz, 1H), 1.67 (d, J=13.0 Hz, 1H), 1.39 (d, J=12.5 Hz, 2H).

Example 18

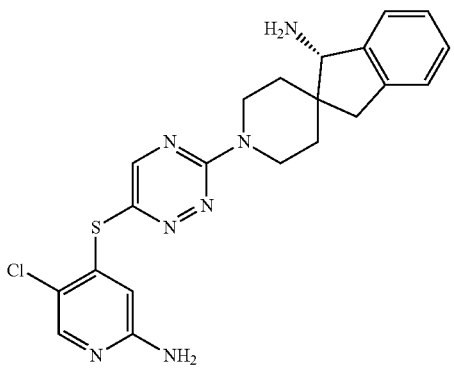 [SMILES: Nc1cc(Sc2cnc(N3CCC4(CC3)Cc3ccccc3[C@H]4N)nn2)c(Cl)cn1]

(S)-1'-(6-((2-amino-5-chloropyridin-4-yl)thio)-1,2,4-triazin-3-yl)-1,3-dihydrospiro[indene-2,4'-piperidin]-1-amine Step A: (R)-N-((S)-1'-(6-Chloro-1,2,4-triazin-3-yl)-1,3-dihydrospiro[indene-2,4'-piperidin]-1-yl)-2-methylpropane-2-sulfinamide (10 g, 0.24 mmol) and sodium 2-amino-5-chloropyridine-4-thiolate (0.088 g, 0.48 mmol) were constituted in N,N-dimethylacetamide (1.2 mL, 0.24 mmol). Triethylamine (0.13 mL, 0.96 mmol) was added, and the resulting solution was stirred at 100° C. for 96 hours. The crude material was loaded onto a 40 g silica gel column and isolated over a gradient of 0-10% MeOH:DCM+NH₄OH to afford (R)-N-((S)-1'-(6-((2-amino-5-chloropyridin-4-yl)thio)-1,2,4-triazin-3-yl)-1,3-dihydrospiro[indene-2,4'-piperidin]-1-yl)-2-methylpropane-2-sulfinamide (0.066 g, 0.12 mmol, 48%). m/z (esi/APCI) M+1=544.2.

Step B: (R)-N-((S)-1'-(6-((2-Amino-5-chloropyridin-4-yl)thio)-1,2,4-triazin-3-yl)-1,3-dihydrospiro[indene-2,4'-piperidin]-1-yl)-2-methylpropane-2-sulfinamide (0.028 g, 0.051 mmol) was constituted in dichloromethane (0.51 mL, 0.051 mmol). Hydrochloric acid solution (4.0M in 1,4-dioxane) (0.10 mL, 0.404 mmol) was added, and the resulting solution was stirred at room temperature for 30 minutes. The crude reaction was vacuum filtered to afford (S)-1'-(6-((2-amino-5-chloropyridin-4-yl)thio)-1,2,4-triazin-3-yl)-1,3-dihydrospiro[indene-2,4'-piperidin]-1-amine (0.015 g, 0.034 mmol, 68% yield) as a solid. ¹H NMR (400 MHz, (CD₃)₂SO) δ 8.52 (s, 1H), 7.86 (s, 1H), 7.31 (s, 1H), 7.19 (d, 2H, J=8.2 Hz), 6.15 (s, 2H), 5.86 (s, 1H), 5.76 (s, 1H), 4.64 (br, 3H), 3.88 (s, 1H), 3.14 (d, 1H, J=15.7 Hz), 2.68 (d, 1H, J=14.9), 1.76 (m, 4H), 1.20 (m, 3H); m/z (esi/APCI) M+1=440.2.

Example 19

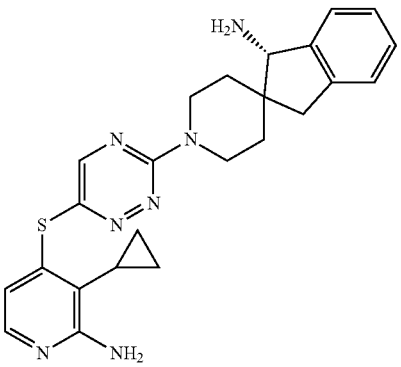 [SMILES: Nc1nccc(Sc2cnc(N3CCC4(CC3)Cc3ccccc3[C@H]4N)nn2)c1C1CC1]

(S)-1'-(6-((2-amino-3-cyclopropylpyridin-4-yl)thio)-1,2,4-triazin-3-yl)-1,3-dihydrospiro[indene-2,4'-piperidin]-1-amine Step A: 4-Bromo-3-cyclopropylpyridin-2-amine (0.013 g, 0.061 mmol), tris(dibenzylideneacetone)dipalladium (0) (0.0044 g, 0.0048 mmol), 4,5-bis(diphenylphosphino)-9,9-dimethylxanthene (0.0035 g, 0.0061 mmol), and tert-butyl (S)-(1'-(6-mercapto-1,2,4-triazin-3-yl)-1,3-dihydrospiro[indene-2,4'-piperidin]-1-yl)carbamate (0.025 g, 0.061 mmol) were dissolved in 1,4-dioxane (0.30 mL, 0.061 mmol). N-Ethyl-N-isopropylpropan-2-amine (0.022 mL, 0.12 mmol) was added, and the resulting solution was stirred at 100° C. for 4 hours. The crude material was loaded onto a 60 g C-18 column and isolated over a gradient of 5-95% MeCN:H₂O+0.1% TFA. Fractions were condensed, resuspended in DCM, washed with saturated NaHCO₃ and dried over Na₂SO₄. The solution was filtered and condensed to afford (R)-N-((S)-1'-(6-((2-amino-3-cyclopropyl pyridin-4-yl)thio)-1,2,4-triazin-3-yl)-1,3-dihydrospiro[indene-2,4'-piperidin]-1-yl)-2-methylpropane-2-sulfinamide (0.0089 g, 0.016 mmol, 27%) as a solid. m/z (esi/APCI) M+1=550.2.

Step B: (R)-N-((S)-1'-(6-((2-Amino-3-cyclopropylpyridin-4-yl)thio)-1,2,4-triazin-3-yl)-1,3-dihydrospiro[indene-2,4'-piperidin]-1-yl)-2-methylpropane-2-sulfinamide (0.0080 g, 0.015 mmol) was constituted in dichloromethane (0.10 mL, 0.015 mmol). Hydrochloric acid (4.0N in dioxane) (0.018 mL, 0.073 mmol) was added, and the solution was stirred at room temperature for 30 minutes. The crude reaction mixture was vacuum filtered. The precipitate was dissolved in MeOH and condensed, then resuspended in DCM. The solution was washed with saturated Na₂HCO₃ followed by water. The organics were dried over Na₂SO₄ and condensed to afford (S)-1'-(6-((2-amino-3-cyclopropylpyridin-4-yl)thio)-1,2,4-triazin-3-yl)-1,3-dihydrospiro[indene-2,4'-piperidin]-1-amine (0.0054 g, 0.011 mmol, 76% yield) as a solid. ¹H NMR (400 MHz, (CD₃)₂SO) δ 8.46 (s, 1H), 7.60 (s, 1H), 7.31 (d, 1H, J=6.3 Hz), 7.18 (m, 2H), 5.81 (s, 1H), 5.75 (d, 2H, J=2.2 Hz), 4.57 (br, 2H), 3.87 (s, 1H), 3.87 (m, 3H), 3.13 (m, 1H), 2.67 (m, 1H), 1.71 (m, 5H), 1.20 (m, 2H), 0.85 (m, 2H), 0.58 (m, 2H); m/z (esi/APCI) M+1=446.2.

Example 20

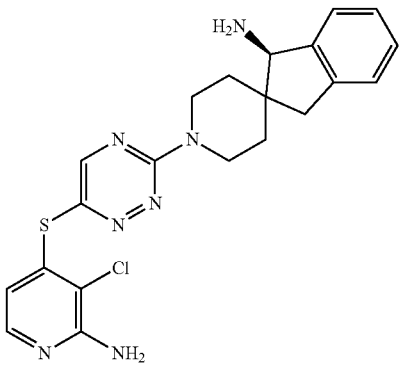

(R)-1'-(6-((2-amino-3-chloropyridin-4-yl)thio)-1,2,4-triazin-3-yl)-1,3-dihydrospiro[indene-2,4'-piperidin]-1-amine Step A: tert-Butyl (1R)-1-(3,3-dimethyl-1-oxido-1,2-thiaziridin-2-yl)-1,3-dihydrospiro[indene-2,4'-piperidine]-1'-carboxylate (1.2 g, 3.2 mmol) was dissolved in dichloromethane (8.0 mL, 3.2 mmol). Hydrochloric acid solution (4.0M in 1,4-dioxane, 7.9 mL, 32 mmol) was added, and the resulting solution was stirred at room temperature for 2 hours. The crude reaction was filtered, and the precipitate was washed with ether to afford (R)-1,3-dihydrospiro[indene-2,4'-piperidin]-1-amine (0.82 g, 3.0 mmol, 94%) as a solid. m/z (esi/APCI) M+1=203.2.

Step B: (R)-1,3-Dihydrospiro[indene-2,4'-piperidin]-1-amine (0.494 g, 2.44 mmol) and 3,6-dibromo-1,2,4-triazine (58 g, 2.4 mmol) were dissolved in 1,4-dioxane (9.8 mL, 2.4 mmol). Triethylamine (1.0 mL, 7.3 mmol) was added, and the resulting solution was stirred at 50° C. for 1.5 hours. The reaction was diluted with 3:1 DCM:IPA solution (25 mL) and washed with 2M NaCO₃ (15 mL). The organics were separated from the aqueous layer. The organic layers were combined and washed with water and saturated NaHCO₃. The crude material was dried over Na₂SO₄ and condensed to afford (R)-1'-(6-bromo-1,2,4-triazin-3-yl)-1,3-dihydrospiro[indene-2,4'-piperidin]-1-amine. m/z (esi/APCI) M+1=362.2.

Step C: (R)-1'-(6-Bromo-1,2,4-triazin-3-yl)-1,3-dihydrospiro[indene-2,4'-piperidin]-1-amine (0.88 g, 2.4 mmol) was constituted in N,N-dimethylacetamide (9.8 mL, 2.4 mmol). Sodium 2-amino-3-chloropyridine-4-thiolate (0.450 g, 2.4 mmol) was added, followed by triethylamine hydrochloride (0.34 g, 2.5 mmol). The resulting solution was stirred at 80° C. for 12 hours. The crude reaction was diluted with 3:1 IPA:DCM. The organics were washed with 2M Na₂CO₃ and saturated NaHCO₃. The organics were combined, dried over Na₂SO₄ and condensed. The crude material was loaded on a 80 g silica gel column and eluted with 0-10% MeOH:EtOAc to afford (R)-1'-(6-((2-amino-3-chloropyridin-4-yl)thio)-1,2,4-triazin-3-yl)-1,3-dihydrospiro[indene-2,4'-piperidin]-1-amine (0.14 g, 0.33 mmol, 13.5% yield) as a solid. ¹H NMR (400 MHz, (CD₃)₂SO) δ 8.48 (s, 1H), 7.70 (s, 1H), 7.31 (d, 1H, J=6.2 Hz), 7.18 (m, 2H), 6.42 (s, 1H), 5.93 (d, 1H, J=5.3 Hz), 4.54 (br, 2H), 3.88 (s, 1H), 3.39 (m, 1H), 3.13 (d, 1H, J=15.6 Hz), 2.67 (d, 1H, J=15.6), 1.85 (m, 5H), 1.59 (d, 1H, J=13.2 Hz), 1.20 (m, 3H); m/z (esi/APCI) M+1=440.1.

Example 21

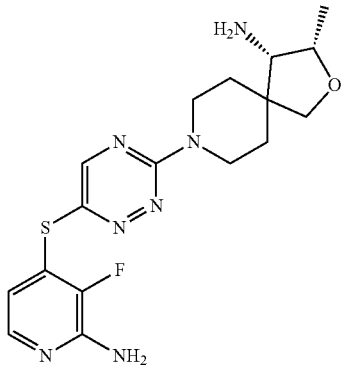 [SMILES: C[C@@H]1OCC2(CCN(c3ncc(Sc4ccnc(N)c4F)nn3)CC2)[C@@H]1N]

(3S,4S)-8-(6-((2-amino-3-fluoropyridin-4-yl)thio)-1,2,4-triazin-3-yl)-3-methyl-2-oxa-8-azaspiro[4.5]decan-4-amine (3S,4S)-8-(6-Chloro-1,2,4-triazin-3-yl)-3-methyl-2-oxa-8-azaspiro[4.5]decan-4-amine (0.026 g, 0.090 mmol) and methyl 3-((2-amino-3-fluoropyridin-4-yl)thio)propanoate (0.023 g, 0.099 mmol) was dissolved in N,N-dimethylacetamide (0.50 mL, 0.10 mmol). Potassium tert-butoxide (0.090 mL, 0.090 mmol) was added, and the resulting solution was stirred overnight at 80° C. The crude reaction was loaded onto a 40 g silica gel column and isolated over a gradient of 0-8% MeOH:DCM+NH₄OH to afford (3S,4S)-8-(6-((2-amino-3-fluoropyridin-4-yl)thio)-1,2,4-triazin-3-yl)-3-methyl-2-oxa-8-azaspiro[4.5]decan-4-amine (0.0092 g, 0.024 mmol, 26.0% yield) as a solid. ¹H NMR (400 MHz, (CD₃)₂SO) δ 8.23 (s, 1H), 7.92 (m, 1H), 7.57 (m, 1H), 6.67 (s, 2H), 5.73 (s, 2H), 3.99 (m, 1H), 3.64 (d, 3H, J=8.4 Hz), 2.88 (d, 2H, J=5.0 Hz), 1.96 (s, 2H), 1.54 (m, 4H), 1.15 (m, 1H), 1.05 (d, 2H, J=6.2 Hz); m/z (esi/APCI) M+1=393.2.

Example 22

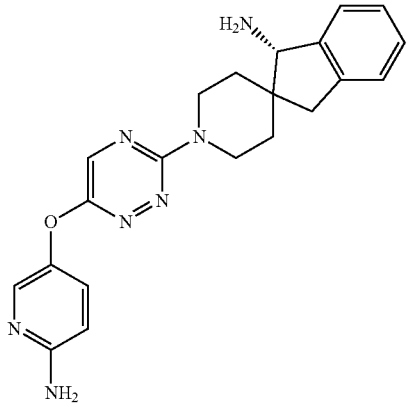 [SMILES: Nc1ccc(Oc2cnc(N3CCC4(CC3)Cc3ccccc3[C@H]4N)nn2)cn1]

(S)-1'-(6-((6-aminopyridin-3-yl)oxy)-1,2,4-triazin-3-yl)-1,3-dihydrospiro[indene-2,4'-piperidin]-1-amine Step A: (S)-N-((S)-1'-(6-Bromo-1,2,4-triazin-3-yl)-1,3-dihydrospiro[indene-2,4'-piperidin]-1-yl)-2-methylpropane- 2-sulfinamide (0.10 g, 0.22 mmol), 2-amino-5-hydroxypyridine HCl (0.033 g, 0.23 mmol), and cesium carbonate (0.22 g, 0.66 mmol) were dissolved in (methylsulfinyl)methane (2.0 mL, 0.22 mmol). The resulting solution was stirred at 100° C. overnight. The crude material was loaded onto a 40 g silica gel column and isolated over an isocratic method of 10% MeOH:EtOAc+NH$_4$OH to afford (R)-N-((S)-1'-(6-((6-aminopyridin-3-yl)oxy)-1,2,4-triazin-3-yl)-1,3-dihydrospiro[indene-2,4'-piperidin]-1-yl)-2-methylpropane-2-sulfinamide (0.015 g, 0.030 mmol, 14% yield). m/z (esi/APCI) M$^+$1=494.2.

Step B: (R)-N-((S)-1'-(6-((6-Aminopyridin-3-yl)oxy)-1,2,4-triazin-3-yl)-1,3-dihydrospiro[indene-2,4'-piperidin]-1-yl)-2-methylpropane-2-sulfinamide (0.015 g, 0.030 mmol) was dissolved in dichloromethane (0.10 mL, 0.030 mmol). Hydrochloric acid (4.0N in dioxane, 0.076 mL, 0.30 mmol) was added, and the reaction was stirred at room temperature for 1 hour. The crude reaction was vacuum filtered to afford a precipitate. The precipitate was washed into a separate filter flask with MeOH. The crude material was loaded onto a 4 g silica gel column and isolated over an isocratic gradient of 10% MeOH:EtOAc+NH$_4$OH to afford (S)-1'-(6-((6-aminopyridin-3-yl)oxy)-1,2,4-triazin-3-yl)-1,3-dihydrospiro[indene-2,4'-piperidin]-1-amine (0.0050 g, 0.013 mmol, 42% yield) as a solid. $^1$H NMR (400 MHz, (CD$_3$)$_2$SO) δ 8.37 (s, 1H), 7.80 (m, 1H), 7.30 (m, 2H), 7.17 (m, 2H), 6.46 (d, 1H, J=8.8 Hz), 5.87 (s, 2H), 4.33 (m, 1H), 3.87 (m, 1H), 3.20 (m, 1H), 3.08 (d, 2H, J=16.0 Hz), 2.65 (m, 1H), 1.96 (s, 2H), 1.73 (m, 1H), 1.62 (m, 1H), 1.47 (m, 1H), 1.21 (s, 1H), 1.15 (m, 2H); m/z (esi/APCI) M$^+$1=390.2.

Example 23

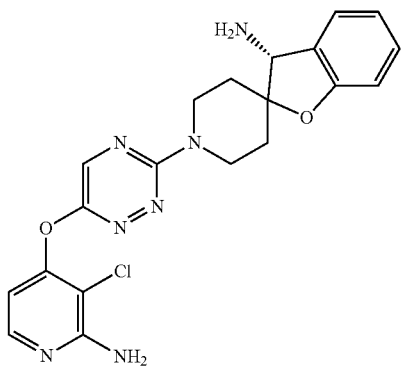 [SMILES: Nc1nccc(Oc2cnc(N3CCC4(CC3)Oc3ccccc3[C@H]4N)nn2)c1Cl]

(R)-1'-(6-((2-amino-3-chloropyridin-4-yl)thio)-1,2,4-triazin-3-yl)-3H-spiro[benzofuran-2,4'-piperidin]-3-amine Step A: (R)-N-((R)-1'-(6-Chloro-1,2,4-triazin-3-yl)-3H-spiro[benzofuran-2,4'-piperidin]-3-yl)-2-methylpropane-2-sulfinamide (0.037 g, 0.088 mmol) and sodium 2-amino-3-chloropyridine-4-thiolate (0.034 g, 0.18 mmol) were diluted in N,N-dimethylacetamide (0.44 mL, 0.088 mmol). Triethylamine (0.049 mL, 0.35 mmol) was added, and the resulting solution was stirred overnight at 100° C. The crude material was loaded onto a 40 g silica gel column and isolated over a gradient of 0-10% MeOH:EtOAc to afford (R)-N-((R)-1'-(6-((2-amino-3-chloropyridin-4-yl)thio)-1,2,4-triazin-3-yl)-3H-spiro[benzofuran-2,4'-piperidin]-3-yl)-2-methylpropane-2-sulfinamide. m/z (esi/APCI) M$^+$1=546.1.

Step B: (R)-N-((R)-1'-(6-((2-Amino-3-chloropyridin-4-yl)thio)-1,2,4-triazin-3-yl)-3H-spiro[benzofuran-2,4'-piperidin]-3-yl)-2-methylpropane-2-sulfinamide (0.039 g, 0.071 mmol) was constituted in 1,4-dioxane (0.71 mL, 0.071 mmol). Hydrochloric acid (4.0M in 1,4-dioxane, 0.14 mL, 0.57 mmol) was added, and the resulting solution was stirred at room temperature for 30 minutes. The reaction was quenched with saturated Na$_2$SO$_4$ (2.0 mL) until the solution was pH 9 and was extracted with EtOAc. The crude reaction was loaded onto a 24 g silica gel column and isolated over a gradient of 0-10% MeOH:EtOAc+NH$_4$OH to afford (R)-1'-(6-((2-amino-3-chloropyridin-4-yl)thio)-1,2,4-triazin-3-yl)-3H-spiro[benzofuran-2,4'-piperidin]-3-amine (0.0077 g, 0.017 mmol, 24% yield) as an oil. $^1$H NMR (400 MHz, CDCl$_3$) δ 8.22 (s, 1H), 7.71 (d, 1H, J=4.4 Hz), 7.34 (d, 1H, J=7.3 Hz), 7.23 (m, 1H), 6.94 (m, 1H), 6.84 (d, 1H, J=8.0 Hz), 6.14 (d, 1H, J=5.4 Hz), 4.80 (br, 2H), 4.14 (s, 1H), 3.01 (s, 1H), 2.49 (s, 1H), 2.00 (m, 4H), 1.81 (m, 1H), 1.26 (m, 3H); m/z (esi/APCI) M$^+$1=442.1.

Example 24

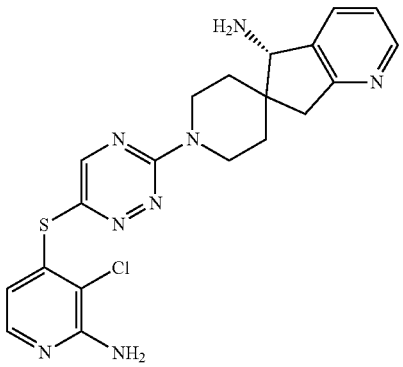

(S)-1'-(6-((2-amino-3-chloropyridin-4-yl)thio)-1,2,4-triazin-3-yl)-5,7-dihydrospiro[cyclopenta[b]pyridine-6,4'-piperidin]-5-amine Step A: tert-Butyl (S)-5-(((R)-tert-butylsulfinyl)amino)-5,7-dihydrospiro[cyclopenta[b]pyridine-6,4'-piperidine]-1'-carboxylate (0.20 g, 0.49 mmol) was constituted in dichloromethane (2.5 mL, 0.49 mmol). Trifluoroacetic acid (0.38 mL, 4.9 mmol) was added, and the resulting solution was stirred at room temperature for 1 hour. The reaction was condensed to afford (R)-N-((S)-5,7-dihydrospiro[cyclopenta[b]pyridine-6,4'-piperidin]-5-yl)-2-methylpropane-2-sulfinamide (0.15 g, 0.49 mmol, 99% yield) a glassy solid. m/z (esi/APCI) M$^+$1=308.2.

Step B: (R)-N-((S)-5,7-Dihydrospiro[cyclopenta[b]pyridine-6,4'-piperidin]-5-yl)-2-methylpropane-2-sulfinamide (0.15 g, 0.49 mmol) and 3,6-dichloro-1,2,4-triazine (0.084 g, 0.56 mmol) were dissolved in 1,4-dioxane (1.5 mL, 0.375 mmol). Triethylamine (0.21 mL, 1.47 mmol) was added, and the resulting solution was stirred at 100° C. overnight. The crude material was loaded onto a 40 g silica gel column and isolated over a gradient of 50-100% EtOAc/hexane to afford (R)-N-((S)-1'-(6-chloro-1,2,4-triazin-3-yl)-5,7-dihydrospiro[cyclopenta[b]pyridine-6,4'-piperidin]-5-yl)-2-methylpropane-2-sulfinamide (0.099 g, 0.23 mmol, 47% yield) as a solid. m/z (esi/APCI) M$^+$1=421.2.

Step C: (R)-N-((S)-1'-(6-chloro-1,2,4-triazin-3-yl)-5,7-dihydrospiro[cyclopenta[b]pyridine-6,4'-piperidin]-5-yl)-2-methylpropane-2-sulfinamide (0.099 g, 0.23 mmol) and sodium 2-amino-3-chloropyridine-4-thiolate (0.10 g, 0.56 mmol) were constituted in N,N-dimethylacetamide (1.2 mL, 0.23 mmol). Triethylamine (0.13 mL, 0.94 mmol) was added, and the resulting solution was stirred at 100° C. for 12 hours. The crude reaction was loaded onto a 40 g silica gel column and isolated over a gradient of 0-10% MeOH:EtOAc to afford (R)-N-((S)-1'-(6-((2-amino-3-chloropyridin-4-yl)thio)-1,2,4-triazin-3-yl)-5,7-dihydrospiro[cyclopenta[b]pyridine-6,4'-piperidin]-5-yl)-2-methylpropane-2-sulfinamide (0.027 g, 0.050 mmol, 21% yield) as a solid. m/z (esi/APCI) M$^+$1=545.1.

Step D: (R)-N-((S)-1'-(6-((2-Amino-3-chloropyridin-4-yl)thio)-1,2,4-triazin-3-yl)-5,7-dihydrospiro[cyclopenta[b]pyridine-6,4'-piperidin]-5-yl)-2-methylpropane-2-sulfinamide (0.027 g, 0.05 mmol) was constituted in 1,4-dioxane (0.50 mL, 0.05 mmol). Hydrochloric acid solution (4.0M in 1,4-dioxane, 0.099 mL, 0.40 mmol) was added, and the resulting solution was stirred at room temperature for 15 minutes. The reaction was quenched with saturated Na$_2$HCO$_3$, and the desired product was extracted with EtOAc. The organics were dried over Na$_2$SO$_4$, condensed and loaded onto a 24 g silica gel column and isolated over a gradient of 0-20% MeOH:EtOAc+NH$_4$OH to afford (S)-1'-(6-((2-amino-3-chloropyridin-4-yl)thio)-1,2,4-triazin-3-yl)-5,7-dihydrospiro[cyclopenta[b]pyridine-6,4'-piperidin]-5-amine (0.0073 g, 0.017 mmol, 33% yield). $^1$H NMR (400 MHz, (CD$_3$)$_2$SO) δ 8.45 (s, 1H), 8.20 (s, 1H), 7.77 (d, 1H, J=5.2 Hz), 7.65 (d, 1H, J=7.5 Hz), 7.15 (m, 1H), 6.15 (d, 1H, J=5.3 Hz), 4.91 (s, 3H), 4.79 (br, 2H), 4.06 (s, 1H), 3.35 (m, 2H), 3.26 (d, 1H, J=16.3), 2.93 (d, 1H, J=16.3 Hz), 1.86 (m, 2H), 1.70 (m, 1H), 1.43 (d, 1H, J=13.2 Hz), 1.25 (s, 1H); m/z (esi/APCI) M$^+$1=441.2.

Example 25

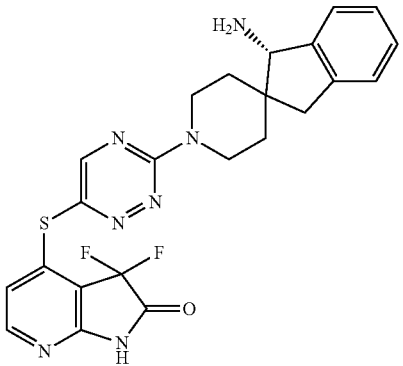 [SMILES: N[C@@H]1c2ccccc2CC12CCN(c1ncc(Sc3ccnc4c3C(F)(F)C(=O)N4)nn1)CC2]

(S)-4-((3-(1-amino-1,3-dihydrospiro[indene-2,4'-piperidin]-1'-yl)-1,2,4-triazin-6-yl)thio)-3,3-difluoro-1,3-dihydro-2H-pyrrolo[2,3-b]pyridin-2-one Step A: DIEA (0.030 mL, 0.17 mmol) was added to a mixture of 3,3-difluoro-4-iodo-1,3-dihydro-2H-pyrrolo[2,3-b]pyridin-2-one (0.028 g, 0.093 mmol), tert-butyl (S)-(1'-(6-mercapto-1,2,4-triazin-3-yl)-1,3-dihydrospiro[indene-2,4'-piperidin]-1-yl)carbamate (0.035 g, 0.085 mmol), tris(dibenzylideneacetone)dipalladium (0) (0.0039 g, 0.0042 mmol) and 4,5-bis(diphenylphosphino)-9,9-dimethylxanthene (0.0049 g, 0.0085 mmol) in 1,4-dioxane (0.85 mL, 0.085 mmol) at room temperature while stirring. The mixture was degassed with argon for 5 minutes before it was heated to 100° C. for 1 hour. The reaction was concentrated in vacuo and then purified using flash chromatography, eluting with a 0 to 20% MeOH in EtOAc gradient and a 2% NH$_4$OH additive, to yield tert-butyl (S)-(1'-(6-((3,3-difluoro-2-oxo-2,3-dihydro-1H-pyrrolo[2,3-b]pyridin-4-yl)thio)-1,2,4-triazin-3-yl)-1,3-dihydrospiro[indene-2,4'-piperidin]-1-yl)carbamate (assumed quantitative yield). m/z (esi/APCI) M$^+$1=582.2.

Step B: tert-Butyl (S)-(1'-(6-((3,3-difluoro-2-oxo-2,3-dihydro-1H-pyrrolo[2,3-b]pyridin-4-yl)thio)-1,2,4-triazin-3-yl)-1,3-dihydrospiro[indene-2,4'-piperidin]-1-yl)carbamate was suspended in 5 mL DCM and subjected to TFA (5 mL) while stirring at room temperature for 15 minutes. The mixture was concentrated in vacuo and resuspended in 25 mL of a mixture of 3:1 DCM:IPA. Saturated NaHCO$_3$ (25 mL) was added and let stir for 5 minutes. Separated the layers and then extracted more organics from the aqueous layer with DCM:IPA (2×15 mL). The organic layers were pooled and washed with brine (25 mL), dried over Na$_2$SO$_4$, filtered and concentrated in vacuo to yield (S)-4-((3-(1-amino-1,3-dihydrospiro[indene-2,4'-piperidin]-1'-yl)-1,2,4-triazin-6-yl)thio)-3,3-difluoro-1,3-dihydro-2H-pyrrolo[2,3-b]pyridin-2-one (0.023 g, 0.048 mmol, 57% yield) as a solid. $^1$H NMR (400 MHz, (CD$_3$)$_2$SO) δ 8.54 (s, 1H), 8.09 (d, J=5.7 Hz, 1H), 7.33 (m, 1H), 7.24 7.16 (m, 4H), 6.56 (d, J=5.9 Hz, 1H), 4.55 (br, 2H), 3.94 (s, 1H), 3.41 (br, 2H), 3.14 (d, J=15.5 Hz, 1H), 2.72 (d, J=15.85 Hz, 1H), 1.86 1.66 (m, 2H), 1.60 (d, J=13.5 Hz, 1H), 1.24 (m, 2H). m/z (esi/APCI) M$^+$1=482.1.

Example 26

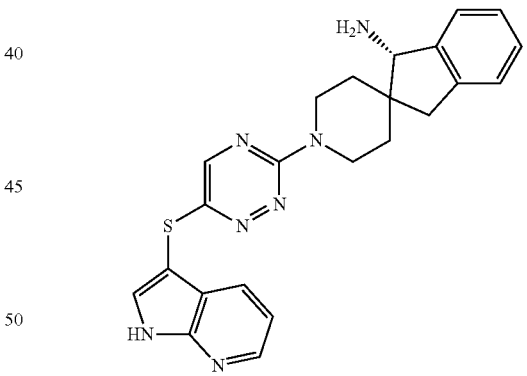

(S)-1'-(6-((1H-pyrrolo[2,3-b]pyridin-3-yl)thio)-1,2,4-triazin-3-yl)-1,3-dihydrospiro[indene-2,4'-piperidin]-1-amine A mixture of 3-iodo-1H-pyrrolo[2,3-b]pyridine (0.015 g, 0.061 mmol), tert-butyl (S)-(1'-(6-mercapto-1,2,4-triazin-3-yl)-1,3-dihydrospiro[indene-2,4'-piperidin]-1-yl)carbamate (0.025 g, 0.061 mmol), potassium carbonate (0.015 g, 0.091 mmol) and copper(I) iodide (0.0031 mL, 0.091 mmol) in DMF (0.61 mL, 0.061 mmol) was heated to 75° C. for 1 hour. The reaction was cooled to room temperature and then quenched with EtOAc (25 mL) and water (25 mL). This biphasic mixture was filtered over GF/F paper, and then the layers were separated. The organic phase was washed with brine (25 mL), dried over Na₂SO₄, filtered and then concentrated in vacuo. The resultant residue was resuspended in DCM (5 mL) and subjected to TFA (5 mL) while stirring at room temperature for 15 minutes. The mixture was concentrated in vacuo and resuspended in DCM:IPA (3:1) (25 mL). Saturated NaHCO₃ (25 mL) was added and was stirred at room temperature for 5 minutes. The biphasic mixture was separated, and the remaining organics from the aqueous layer were extracted with DCM:IPA (2×15 mL). The resulting organic layers were pooled and washed with brine (25 mL), dried over Na₂SO₄, filtered and concentrated in vacuo. The crude material was purified using flash chromatography, eluting with a 0 to 20% MeOH in EtOAc gradient with a 2% NH₄OH additive to yield (S)-1'-(6-((1H-pyrrolo[2,3-b]pyridin-3-yl)thio)-1,2,4-triazin-3-yl)-1,3-dihydrospiro[indene-2,4'-piperidin]-1-amine (0.011 g, 0.025 mmol, 41% yield) as a solid. ¹H NMR (400 MHz, (CD₃)₂SO) δ 12.28 (s, 1H), 8.30 (dd, J=4.7, 1.6 Hz, 1H), 8.18 (br, 2H), 8.10 (s, 1H), 7.94 (d, J=2.7 Hz, 1H), 7.90 (dd, J=8.2, 1.6 Hz, 1H), 7.46 (d, J=7.2 Hz, 1H), 7.36-7.24 (m, 4H), 7.15 (dd, J=7.8, 4.7 Hz, 1H), 4.45-4.31 (m, 3H), 3.24 (t, J=12.9 Hz, 2H), 3.15 (d, J=16.0 Hz, 1H), 2.97 (d, J=16.2 Hz, 1H), 1.71-1.56 (m, 2H), 1.47 (d, J=13.3 Hz, 2H). m/z (esi/APCI) M⁺1=430.2.

5 minutes. The biphasic mixture was separated, and the remaining organics from the aqueous layer were extracted with DCM:IPA (2×15 mL). The resulting organic layers were pooled and washed with brine (25 mL), dried over Na₂SO₄, filtered and concentrated in vacuo. The crude material was purified using preparatory HPLC, eluting with a 5 to 95% ACN in water gradient with a 0.1% TFA modifier. Product fractions were freebased using saturated NaHCO₃ (25 mL). The resulting biphasic mixture was separated, and the remaining organics from the aqueous layer were extracted with DCM:IPA (2×15 mL). The resulting organic layers were pooled and washed with brine (25 mL), dried over Na₂SO₄, filtered and concentrated in vacuo to yield (S)-1'-(6-((1H-pyrazolo[3,4-b]pyridin-3-yl)thio)-1,2,4-triazin-3-yl)-1,3-dihydrospiro[indene-2,4'-piperidin]-1-amine (0.011 g, 0.025 mmol, 41% yield) as a solid. ¹H NMR (400 MHz, (CD₃)₂SO) δ 8.59 (dd, J=4.5, 1.6 Hz, 1H), 8.36 (s, 1H), 8.12 (dd, J=8.0, 1.6 Hz, 1H), 7.30 (d, J=6.3 Hz, 1H), 7.27 (dd, J=8.2, 4.5 Hz, 1H), 7.21-7.14 (m, 3H), 4.42 (t, J=14.3 Hz, 2H), 3.87 (s, 1H), 3.24 (m, 2H), 3.08 (d, J=15.8 Hz, 1H), 2.65 (d, J=15.8 Hz, 1H), 1.73 (td, J=12.3, 4.5 Hz, 1H), 1.62 (td, J=12.7, 4.3 Hz, 1H), 1.51 (d, J=13.3 Hz, 1H), 1.13 (d, J=13.7 Hz, 1H). m/z (esi/APCI) M⁺1=431.2.

Example 27

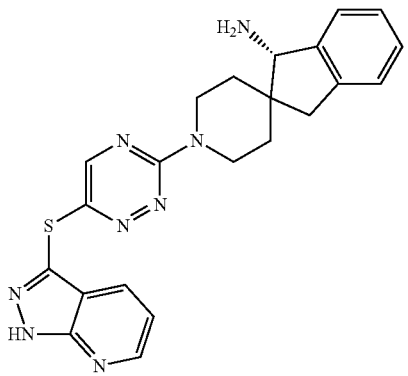 [SMILES: N[C@@H]1c2ccccc2CC12CCN(c1ncc(Sc3n[nH]c4ncccc34)nn1)CC2]

(S)-1'-(6-((1H-pyrazolo[3,4-b]pyridin-3-yl)thio)-1,2,4-triazin-3-yl)-1,3-dihydrospiro[indene-2,4'-piperidin]-1-amine A mixture of 1-boc-3-iodo-1H-pyrazolo[3,4-b]pyridine (0.027 g, 0.079 mmol), (R)-N-((S)-1'-(6-mercapto-1,2,4-triazin-3-yl)-1,3-dihydrospiro[indene-2,4'-piperidin]-1-yl)-2-methylpropane-2-sulfinamide (0.030 g, 0.072 mmol), potassium carbonate (0.015 g, 0.11 mmol) and copper(I) iodide (0.0037 mL, 0.11 mmol) in DMF (0.72 mL, 0.072 mmol) was heated to 100° C. for 16 hours. The reaction was cooled to room temperature and quenched with EtOAc (25 mL) and water (25 mL). This biphasic mixture was filtered over GF/F paper, and the layers were separated. The organic phase was washed with brine (25 mL), dried over Na₂SO₄, filtered and concentrated in vacuo. The resultant residue was resuspended in 1,4-dioxane (5 mL) and subjected to 4N HCl in dioxane (5 mL) while stirring at room temperature for 15 minutes. This was concentrated in vacuo and resuspended in DCM:IPA (3:1) (25 mL). Saturated NaHCO₃ (25 mL) was added, and this mixture was stirred at room temperature for Example 28

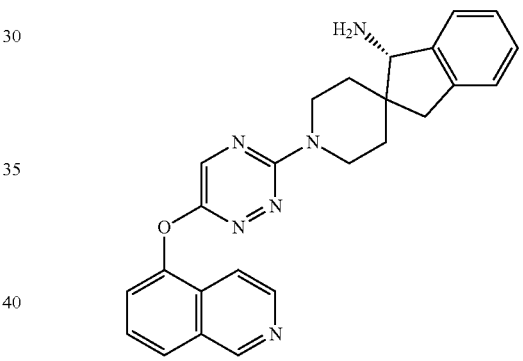

(S)-1'-(6-(isoquinolin-5-yloxy)-1,2,4-triazin-3-yl)-1,3-dihydrospiro[indene-2,4'-piperidin]-1-amine Step A: A solution of 5-hydroxyisoquinoline (0.031 g, 0.22 mmol), (R)-N-((S)-1'-(6-bromo-1,2,4-triazin-3-yl)-1,3-dihydrospiro[indene-2,4'-piperidin]-1-yl)-2-methylpropane-2-sulfinamide (0.050 g, 0.11 mmol) and cesium carbonate (0.11 g, 0.32 mmol) in DMSO (1.1 mL, 0.11 mmol) was heated to 100° C. for 72 hours. The reaction mixture was cooled to and added to water (25 mL) and EtOAc (25 mL). The two phases were separated, and the water phase was extracted with EtOAc (2×25 mL). The organics were combined, washed with brine (50 mL), dried over Na₂SO₄, filtered and concentrated in vacuo. This was resuspended in DCM (2 mL) and purified using flash chromatography, eluting with a 20 to 100% EtOAc in hexanes gradient, to obtain (R)-N-((S)-1'-(6-(iso quinolin-5-yloxy)-1,2,4-triazin-3-yl)-1,3-dihydrospiro[indene-2,4'-piperidin]-1-yl)-2-methylpropane-2-sulfinamide (assumed quantitative yield). m/z (esi/APCI) M⁺1=529.2.

Step B: (R)-N-((S)-1'-(6-(Isoquinolin-5-yloxy)-1,2,4-triazin-3-yl)-1,3-dihydrospiro[indene-2,4'-piperidin]-1-yl)-2-methylpropane-2-sulfinamide was suspended in 1,4-dioxane (5 mL), and 4N HCl in 1,4-dioxane (1 mL) was added while stirring at room temperature for 30 minutes. The reaction was concentrated in vacuo and then resuspended in DCM (15 mL). The crude product was freebased with saturated NaHCO₃ (15 mL) and left to stir for 10 minutes at room temperature. The resultant biphasic mixture was separated, and the remaining organics were extracted with DCM (2×15 mL). The organic layers were pooled, washed with brine (10 mL), dried over Na₂SO₄, filtered and concentrated in vacuo. The crude material was purified using preparatory HPLC, eluting with a 5 to 95% ACN in water gradient with a 0.1% TFA modifier. Product fractions were freebased using saturated NaHCO₃ (25 mL), and then DCM (25 mL) was added. The resulting biphasic mixture was separated, and the remaining organics from the aqueous layer were extracted with DCM (2×15 mL). The resulting organic layers were pooled and washed with brine (25 mL), dried over Na₂SO₄, filtered and concentrated in vacuo to yield (S)-1'-(6-(isoquinolin-5-yloxy)-1,2,4-triazin-3-yl)-1,3-dihydrospiro[indene-2,4'-piperidin]-1-amine (0.0013 g, 0.0031 mmol, 3% yield over two steps) as a solid. ¹H NMR (400 MHz, (CD₃)₂SO) δ 9.22 (s, 1H), 9.16 (s, 1H), 8.45 (d, J=5.9 Hz, 1H), 8.24 (d, J=5.9 Hz, 1H), 8.12 (d, J=9.0 Hz, 1H), 7.64 (d, J=8.8 Hz, 1H), 7.39 (t, J=4.3 Hz, 1H), 7.29-7.21 (m, 4H), 4.69 (m, 2H), 4.04 (s, 1H), 3.46 (m, 2H), 3.22 (d, J=15.6 Hz, 1H), 2.91 (d, J=15.5 Hz, 1H), 1.93-1.78 (m, 2H), 1.66 (d, J=13.1 Hz, 1H), 1.52 (d, J=13.9 Hz, 1H). m/z (esi/APCI) M⁺1=425.2.

Example 29

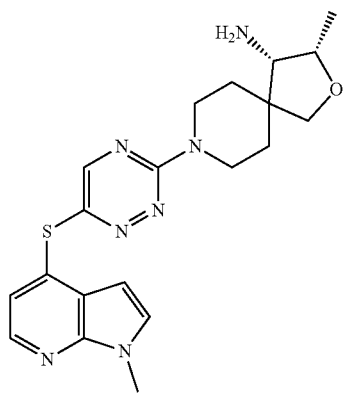 [SMILES: C[C@@H]1OCC2(CCN(c3ncc(Sc4ccnc5c4ccn5C)nn3)CC2)[C@@H]1N]

(3S,4S)-3-methyl-8-(6-((1-methyl-1H-pyrrolo[2,3-b]pyridin-4-yl)thio)-1,2,4-triazin-3-yl)-2-oxa-8-azaspiro[4.5]decan-4-amine Step A: DIEA (0.77 mL, 4.32 mmol) was added to a solution of 3,6-dichloro-1,2,4-triazine (0.19 g, 1.23 mmol) and (3S,4S)-3-methyl-2-oxa-8-azaspiro[4.5]decan-4-amine dihydrochloride (0.30 g, 1.23 mmol) in 1,4-dioxane (6.2 mL, 1.23 mmol) at room temperature. This mixture was heated to 50° C. and stirred for 4 hours. The reaction was allowed to cool and was diluted with 3:1 DCM:IPA (25 mL) and 1M sodium carbonate (25 mL). The layers were separated, and additional organics in the aqueous layer were extracted with DCM:IPA (3×15 mL). The organic layers were combined, dried over Na₂SO₄, filtered and concentrated in vacuo. The resulting residue was purified by flash chromatography, eluting with a 0 to 15% MeOH in DCM gradient with a 1% NH₄OH modifier to yield (3S,4S)-8-(6-chloro-1,2,4-triazin-3-yl)-3-methyl-2-oxa-8-azaspiro[4.5]decan-4-amine (0.25 g, 0.88 mmol, 71% yield) as a solid. m/z (esi/APCI) M⁺1=284.1.

Step B: 1-Methyl-1H-pyrrolo[2,3-b]pyridine-4-thiol, sodium salt (0.035 g, 0.19 mmol), (3S,4S)-8-(6-chloro-1,2,4-triazin-3-yl)-3-methyl-2-oxa-8-azaspiro[4.5]decan-4-amine (0.035 g, 0.12 mmol) and DIEA (0.065 mL, 0.37 mmol) were placed in DMA (1.23 mL, 0.12 mmol), and the mixture was heated to 100° C. for 16 hours. The mixture was cooled and purified by flash chromatography using a 0 to 20% MeOH in DCM gradient with a 2% NH₄OH additive. Product fractions were concentrated in vacuo and further purified using preparatory HPLC, eluting with a 5 to 95% ACN in water gradient with a 0.1% TFA modifier. Product fractions were freebased using saturated NaHCO₃ (25 mL), and then 3:1 DCM:IPA (25 mL) was added. The resulting biphasic mixture was separated, and the remaining organics from the aqueous layer were extracted with DCM:IPA (2×15 mL). The resulting organic layers were pooled and washed with brine (25 mL), dried over Na₂SO₄, filtered and concentrated in vacuo to yield (3S,4S)-3-methyl-8464(1-methyl-1H-pyrrolo[2,3-b]pyridin-4-yl)thio)-1,2,4-triazin-3-yl)-2-oxa-8-azaspiro[4.5]decan-4-amine (0.013 g, 0.032 mmol, 26% yield) as a solid. ¹H NMR (400 MHz, CDCl₃) δ 8.42 (s, 1H), 8.11 (d, J=5.1 Hz, 1H), 7.55 (d, J=3.5 Hz, 1H), 6.75 (d, J=5.1 Hz, 1H), 6.35 (d, J=3.3 Hz, 1H), 4.06 (m, 3H), 3.80 (s, 3H), 3.68 (d, J=8.4 Hz, 1H), 3.60 (m, 2H), 3.48 (d, J=8.4 Hz, 1H), 2.92 (d, J=5.3 Hz, 1H), 1.76 (m, 1H), 1.66 (m, 1H), 1.58-1.45 (m, 2H), 1.07 (d, J=6.5 Hz, 3H). m/z (esi/APCI) M⁺1=412.2.

Example 30

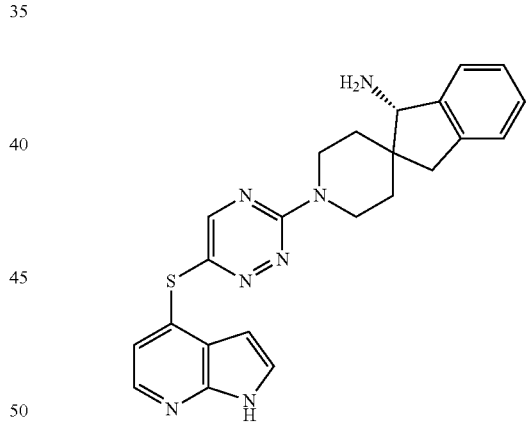

(S)-1'-(6-((1H-pyrrolo[2,3-b]pyridin-4-yl)thio)-1,2,4-triazin-3-yl)-1,3-dihydrospiro[indene-2,4'-piperidin]-1-amine Step A: 1H-Pyrrolo[2,3-b]pyridine-4-thiol (0.043 g, 0.29 mmol), Hunig's base (0.17 mL, 0.95 mmol), and N-((S)-1'-(6-chloro-1,2,4-triazin-3-yl)-1,3-dihydrospiro[indene-2,4'-piperidin]-1-yl)-2-methylpropane-2-sulfinamide (0.080 g, 0.19 mmol) were placed in DMA (1.90 mL, 0.19 mmol), and the mixture was heated to 70° C. for 16 hours. The reaction mixture was cooled and purified directly by flash chromatography, eluting with a 0 to 20% MeOH in DCM gradient with 2% NH₄OH as an additive to yield (S)-N-((S)-1'-(6-((1H-pyrrolo[2,3-b]pyridin-4-yl)thio)-1,2,4-triazin-3-yl)-1, 3-dihydrospiro[indene-2,4'-piperidin]-1-yl)-2-methyl propane-2-sulfinamide. Assumed quantitative yield. m/z (esi/APCI) M+1=534.2.

Step B: (S)-N-((S)-1'-(6-((1H-Pyrrolo[2,3-b]pyridin-4-yl)thio)-1,2,4-triazin-3-yl)-1,3-dihydrospiro[indene-2,4'-piperidin]-1-yl)-2-methylpropane-2-sulfinamide was suspended in 1,4-dioxane (5 mL), and 4N HCl in 1,4-dioxane (5 mL) was added while stirring at room temperature for 30 minutes. This was concentrated in vacuo and resuspended in 3:1 DCM:IPA (25 mL). The crude product was freebased with saturated NaHCO₃ (15 mL) and left to stir for 10 minutes at room temperature. The resultant biphasic mixture was separated, and the remaining organics were extracted with more DCM:IPA (2×15 mL). The organic layers were pooled and were washed with brine (10 mL), dried over Na₂SO₄, filtered and concentrated in vacuo. The crude material was purified using preparatory HPLC, eluting with a 5 to 95% ACN in water gradient with a 0.1% TFA modifier. Product fractions were freebased using saturated NaHCO₃ (25 mL), and DCM:IPA (25 mL) was added. The resulting biphasic mixture was separated and, the remaining organics from the aqueous layer were extracted with DCM:IPA (2×15 mL). The resulting organic layers were pooled and washed with brine (25 mL), dried over Na₂SO₄, filtered and concentrated in vacuo to yield (S)-1'-(6-((1H-pyrrolo[2,3-b]pyridin-4-yl)thio)-1,2,4-triazin-3-yl)-1,3-dihydrospiro[indene-2,4'-piperidin]-1-amine (0.015 g, 0.035 mmol, 19% yield) as a solid. $^1$H NMR (400 MHz, CDCl₃) δ 11.87 (s, 1H), 8.45 (s, 1H), 8.09 (d, J=5.1 Hz, 1H), 7.51 (t, J=2.9 Hz, 1H), 7.31 (d, J=6.1 Hz, 1H), 7.22-7.14 (m, 3H), 6.73 (d, J=8.7 Hz, 1H), 6.36 (dd, J=3.3, 1.4 Hz, 1H), 4.64-4.42 (br, 2H), 3.87 (s, 1H), 3.34 (m, 2H), 3.12 (d, J=15.5 Hz, 1H), 2.66 (d, J=15.8 Hz, 1H), 1.80 (td, J=12.5, 3.7 Hz, 1H), 1.69 (td, J=12.3, 4.1 Hz, 1H), 1.58 (d, J=13.1 Hz, 1H), 1.17 (d, J=13.1 Hz, 1H). m/z (esi/APCI) M+1=430.2.

Example 31

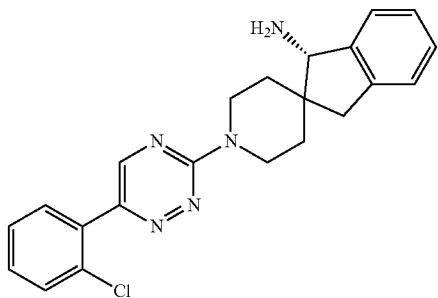 [SMILES: N[C@@H]1c2ccccc2CC12CCN(c1ncc(-c3ccccc3Cl)nn1)CC2]

(S)-1'-(6-(2-chlorophenyl)-1,2,4-triazin-3-yl)-1,3-dihydrospiro[indene-2,4'-piperidin]-1-amine Step A: N-((S)-1'-(6-Bromo-1,2,4-triazin-3-yl)-1,3-dihydrospiro[indene-2,4'-piperidin]-1-yl)-2-methylpropane-2-sulfinamide (50 mg, 0.11 mmol), (2-chlorophenyl)boronic acid (20 mg, 0.13 mmol) and Tetrakis (12 mg, 0.011 mmol) were dissolved in dioxane (1 mL), followed by the addition of Na₂CO₃ (135 µL, 0.27 mmol). The reaction was purged with argon, sealed and heated to 90° C. After stirring for 12 hours, the reaction was cooled and diluted with ethyl acetate and water. The layers were separated. The ethyl acetate was dried over MgSO₄, filtered and concentrated. The residue was purified on silica gel eluting with 20-70% ethyl acetate/hexanes to afford N-((S)-1'-(6-(2-chlorophenyl)-1,2,4-triazin-3-yl)-1,3-dihydrospiro[indene-2,4'-piperidin]-1-yl)-2-methylpropane-2-sulfinamide (20 mg, 0.040 mmol, 37% yield). m/z (esi/APCI) M+1=496.2.

Step B: N-((S)-1'-(6-(2-chlorophenyl)-1,2,4-triazin-3-yl)-1,3-dihydrospiro[indene-2,4'-piperidin]-1-yl)-2-methylpropane-2-sulfinamide (20 mg, 0.040 mmol) was diluted with DCM (50 µL) and HCl (101 µL of 4M solution, 0.4 mmol). After stirring for 1 hour, the reaction was concentrated. The residue was diluted with ethyl acetate and saturated sodium bicarbonate. The mixture was stirred for 10 minutes and placed into a separatory funnel. The layers were separated. The ethyl acetate was dried over MgSO₄, filtered and concentrated. The material was purified on silica gel eluting with 10% methanol/ethyl acetate to afford (S)-1'-(6-(2-chlorophenyl)-1,2,4-triazin-3-yl)-1,3-dihydrospiro[indene-2,4'-piperidin]-1-amine (9.5 mg, 0.024 mmol, 60% yield). $^1$H NMR (400 MHz, CDCl₃) δ 8.55 (s, 1H), 7.75 (dd, J=7.04, 2.3 Hz, 1H), 7.48 (dd, J=7.82, 1.57 Hz, 1H), 7.38 (m, 3H), 7.23 (m, 3H), 4.74 (s, 2H), 4.03 (s, 1H), 3.38 (m, 2H), 3.15 (d, J=15.65 Hz, 1H), 2.79 (d, J=15.65 Hz, 1H), 1.84 (m, 4H), 1.66 (m, 1H), 1.42 (m, 1H). m/z (esi/APCI) M+1=392.1.

Example 32

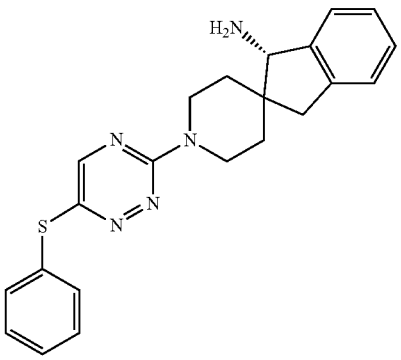 [SMILES: N[C@@H]1c2ccccc2CC12CCN(c1ncc(Sc3ccccc3)nn1)CC2]

(S)-1'-(6-(phenylthio)-1,2,4-triazin-3-yl)-1,3-dihydrospiro[indene-2,4'-piperidin]-1-amine Step A: N-((S)-1'-(6-bromo-1,2,4-triazin-3-yl)-1,3-dihydrospiro[indene-2,4'-piperidin]-1-yl)-2-methylpropane-2-sulfinamide (50 mg, 0.11 mmol) was diluted with DMSO (300 µL), followed by the addition of benzenethiol (24 mg, 0.22 mmol) and Cs₂CO₃ (88 mg, 0.27 mmol). The reaction was placed under nitrogen and heated to 100° C. After stirring for 1 hour, the reaction was cooled, diluted with ethyl acetate and water. The layers were separated. The ethyl acetate was dried over MgSO₄, filtered and concentrated. The material was purified on silica gel eluting with 30% ethyl acetate/hexanes to afford 2-methyl-N-((S)-1'-(6-(phenylthio)-1,2,4-triazin-3-yl)-1,3-dihydrospiro[indene-2,4'-piperidin]-1-yl) propane-2-sulfinamide (25 mg, 0.051 mmol, 47% yield). m/z (esi/APCI) M+1=494.1.

Step B: 2-Methyl-N-((S)-1'-(6-(phenylthio)-1,2,4-triazin-3-yl)-1,3-dihydrospiro[indene-2,4'-piperidin]-1-yl) propane-2-sulfinamide (25 mg, 0.051 mmol) was diluted with DCM (500 µL) and HCl (127 µL of 4M solution, 0.51 mmol). After stirring for 1 hour, the reaction was concentrated. The residue was diluted with ethyl acetate and saturated sodium bicarbonate. The mixture was stirred for 10 minutes and placed into a separatory funnel. The layers were separated. The ethyl acetate was dried over MgSO$_4$, filtered and concentrated. The material was purified on silica gel eluting with 10% methanol/ethyl acetate to afford (S)-1'-(6-(phenylthio)-1,2,4-triazin-3-yl)-1,3-dihydrospiro[indene-2,4'-piperidin]-1-amine (11 mg, 0.028 mmol, 56% yield). $^1$H NMR (400 MHz, CDCl$_3$) δ 8.05 (s, 1H), 7.47 (m, 2H), 7.32 (m, 4H), 7.22 (m, 3H), 4.62 (s, 2H), 3.98 (s, 1H), 3.30 (m, 2H), 3.11 (d, J=15.65 Hz, 1H), 2.75 (d, J=15.65 Hz, 1H), 1.35-1.85 (m, 6H), m/z (esi/APCI) M$^+$1=390.2.

Example 33

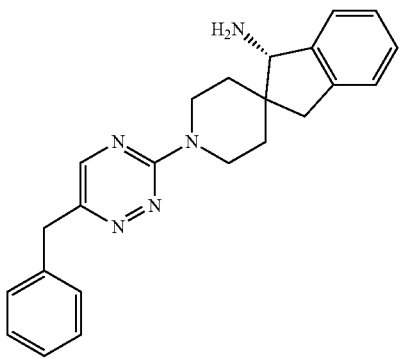 [SMILES: N[C@@H]1c2ccccc2CC12CCN(c1ncc(Cc3ccccc3)nn1)CC2]

(S)-1'-(6-benzyl-1,2,4-triazin-3-yl)-1,3-dihydrospiro[indene-2,4'-piperidin]-1-amine Step A: N-((S)-1'-(6-Bromo-1,2,4-triazin-3-yl)-1,3-dihydrospiro[indene-2,4'-piperidin]-1-yl)-2-methylpropane-2-sulfinamide (20 mg, 0.043 mmol) and Tetrakis (5.0 mg, 0.0043 mmol) were diluted with benzyl zinc (II) bromide (129 μL, 0.065 mmol). The reaction was purged with argon, sealed and heated to 70° C. and stirred for 12 hours. The reaction was cooled, diluted with ethyl acetate and saturated sodium bicarbonate. The layers were separated, and the ethyl acetate was dried over MgSO$_4$, filtered and concentrated. The material was purified on silica gel eluting with 30% ethyl acetate/hexanes to afford N-((S)-1'-(6-benzyl-1,2,4-triazin-3-yl)-1,3-dihydrospiro[indene-2,4'-piperidin]-1-yl)-2-methylpropane-2-sulfinamide (5 mg, 0.011 mmol, 24% yield). m/z (esi/APCI) M$^+$1=476.2.

Step B: N-((S)-1'-(6-Benzyl-1,2,4-triazin-3-yl)-1,3-dihydrospiro[indene-2,4'-piperidin]-1-yl)-2-methylpropane-2-sulfinamide (8 mg, 0.017 mmol) was diluted with DCM (100 μL) and HCl (42 μL, 0.17 mmol). After stirring for 1 hour, the reaction was concentrated. The residue was diluted with ethyl acetate and saturated sodium bicarbonate. The mixture was stirred for 10 minutes and placed into a separatory funnel. The layers were separated, and the ethyl acetate was dried over MgSO$_4$, filtered and concentrated. The material was purified on silica gel eluting with 10% methanol/ethyl acetate to afford (S)-1'-(6-benzyl-1,2,4-triazin-3-yl)-1,3-dihydrospiro[indene-2,4'-piperidin]-1-amine (5 mg, 0.013 mmol, 80% yield). $^1$H NMR (400 MHz, CDCl$_3$) δ 7.97 (s, 1H), 7.20-7.35 (m, 9H), 4.61 (s, 2H), 4.15 (s, 2H), 3.98 (s, 1H), 3.28 (m, 2H), 3.11 (d, J=15.65 Hz, 1H), 2.75 (d, J=15.65 Hz, 1H), 1.50-1.85 (m, 5H), 1.34 (m, 1H). m/z (esi/APCI) M$^+$1=372.2.

Example 34

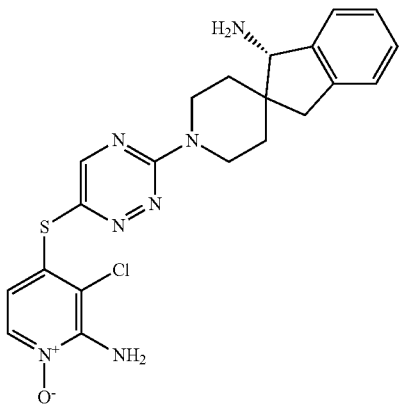 [SMILES: Nc1c(Cl)c(Sc2cnc(N3CCC4(CC3)Cc3ccccc3[C@H]4N)nn2)cc[n+]1[O-]]

(S)-2-amino-4-((3-(1-amino-1,3-dihydrospiro[indene-2,4'-piperidin]-1'-yl)-1,2,4-triazin-6-yl)thio)-3-chloropyridine 1-oxide (S)-1'-(6-((2-Amino-3-chloropyridin-4-yl)thio)-1,2,4-triazin-3-yl)-1,3-dihydrospiro[indene-2,4'-piperidin]-1-amine (100 mg, 0.23 mmol) was placed in MeOH (36.4 mL, 0.23 mmol), and meta-chloroperoxybenzoic acid ("m-CPBA") (84.0 mg, 0.34 mmol) was added and stirred at room temperature for 18 hours. The reaction was concentrated down to about 10 mL, and saturated bicarbonate was added and extracted with DCM. The extracts were combined and concentrated. The resulting residue was purified by reverse phase chromatography (5-70% ACN:water with 0.1% TFA). The material was brought up in 10% MeOH in DCM. Saturated bicarbonate was added, and the layers were separated. The organic layer was dried, filtered and concentrated to provide (S)-2-amino-4-((3-(1-amino-1,3-dihydrospiro[indene-2,4'-piperidin]-1'-yl)-1,2,4-triazin-6-yl)thio)-3-chloropyridine 1-oxide (3.6 mg, 0.0079 mmol, 3% yield). $^1$H NMR (400 MHz, (CD$_3$)$_2$SO) δ 8.47 (s, 1H), 7.99 (d, 1H, J=7.3 Hz), 7.31 (d, 1H, J=5.5 Hz), 7.26-7.11 (m, 5H), 6.21 (d, 1H, J=7.3 Hz), 4.54 (br, 2H), 4.09 (m, 2H), 3.87 (s, 1H), 3.12 (d, 1H, J=14.6 Hz), 2.68 (s, 1H), 1.86-1.54 (m, 3H), 1.19 (m, 1H); m/z (esi/APCI) M$^+$1=456.1.

Example 35

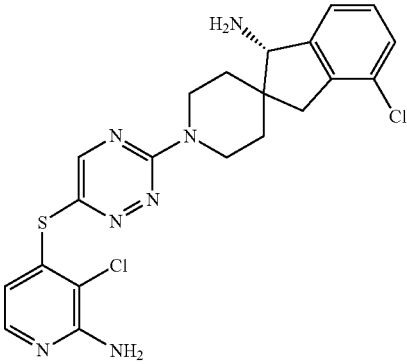 [SMILES: Nc1nccc(Sc2cnc(N3CCC4(CC3)Cc3c(Cl)cccc3[C@H]4N)nn2)c1Cl]

(S)-1'-(6-((2-amino-3-chloropyridin-4-yl)thio)-1,2,4-triazin-3-yl)-4-chloro-1,3-dihydrospiro[indene-2,4'-piperidin]-1-amine Step A: tert-Butyl (S)-1-(((R)-tert-butylsulfinyl)amino)-4-chloro-1,3-dihydrospiro[indene-2,4'-piperidine]-1'-carboxylate (100 mg, 0.227 mmol) was dissolved in CH$_2$Cl$_2$ (0.1 mL), and then 4N HCl in dioxane (0.5 mL) was added and stirred at room temperature for 30 minutes. The solids were further precipitated by the addition of Et$_2$O (3 mL) and filtered. The tacky solid was dried in a vacuum oven and used without further characterization.

Step B: (S)-4-Chloro-1,3-dihydrospiro[indene-2,4'-piperidin]-1-amine dihydrochloride (35 mg, 0.113 mmol) was suspended in dioxane (1 mL). 3,6-Dibromo-1,2,4-triazine (27.0 mg, 0.113 mmol) was added to the suspension, followed by triethylamine (78.8 µL, 0.565 mmol). The reaction was heated to 50° C. for 30 minutes. The reaction was purged with nitrogen. Sodium 3-amino-2-chlorobenzenethiolate (20.5 mg, 0.113 mmol) was added, and the reaction was heated to 90° C. for 2 hours. The reaction was concentrated and purified over silica gel (0-10% MeOH in EtOAc with 1% NH$_4$OH) to afford (S)-1'-(6-((2-amino-3-chloropyridin-4-yl)thio)-1,2,4-triazin-3-yl)-4-chloro-1,3-dihydrospiro[indene-2,4'-piperidin]-1-amine (25.1 mg, 0.053 mmol, 47% yield) as a solid. $^1$H (400 MHz, CD Cl$_3$) δ 8.22 (s, 1H), 7.73 (d, J=5.5 Hz, 1H), 7.26-7.18 (m, 3H), 6.13 (d, J=5.5 Hz, 1H), 4.75 (br s, 2H), 4.04 (s, 1H0, 3.45-3.34 (m, 2H), 3.20 (d, J=16.2 Hz, 1H), 2.81 (d, J=16.2 Hz, 1H), 2.10-2.00 (m, 2H), 1.93-1.84 (m, 1H), 1.83-1.74 (m, 1H), 1.73-1.66 (m, 1H), 1.47-1.41 (m, 1H). m/z (esi/APCI) M$^+$1=474.1.

Example 36

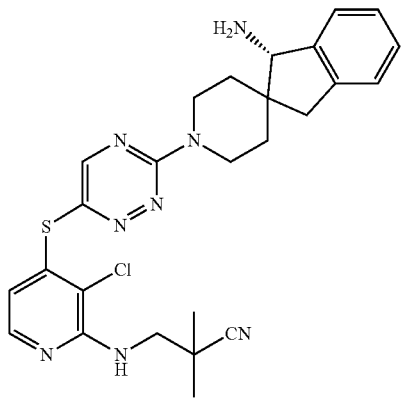 [SMILES: CC(C)(C#N)CNc1nccc(Sc2cnc(N3CCC4(CC3)Cc3ccccc3[C@H]4N)nn2)c1Cl]

(S)-3-((4-((3-(1-amino-1,3-dihydrospiro[indene-2,4'-piperidin]-1'-yl)-1,2,4-triazin-6-yl)thio)-3-chloro-pyridin-2-yl)amino)-2,2-dimethylpropanenitrile Step A: 3-Amino-2,2-dimethylpropanenitrile (115 mg, 1.16 mmol) was added to a stirred solution of 3-chloro-2-fluoro-4-iodopyridine (250 mg, 0.97 mmol) in DMSO (2.5 mL) and stirred at 120° C. for 16 hours. The reaction mixture was diluted with water and extracted with EtOAc. The organic part was dried, concentrated the resulting residue was purified by silica gel column chromatography (30% EtOAc-hexane) to afford 3-((3-chloro-4-iodopyridin-2-yl)amino)-2,2-dimethylpropanenitrile (250 mg, 77% yield) as a solid. m/z (esi) M$^+$1=335.7.

Step B: DIEA (0.26 mL, 1.49 mmol) was added to a stirred solution of 3-((3-chloro-4-iodopyridin-2-yl)amino)-2,2-dimethylpropanenitrile (250 mg, 0.74 mmol) and methyl 3-mercaptopropanoate (0.09 mL, 0.82 mmol) in dioxane (5 mL) and degassed with argon for 10 minutes. Xantphos (22 mg, 0.03 mmol) and Pd(OAc)$_2$ (10 mg, 0.04 mmol) were added and degassed for another 10 minutes. The reaction mixture was stirred in preheated oil bath at 100° C. for 4 hours. The reaction mixture was filtered through Celite® pad and washed with EtOAc. The solvent was evaporated, and the crude material was purified through silica gel column chromatography (50% EtOAc-hexane) to afford methyl 3-((3-chloro-2-((2-cyano-2-methylpropyl)amino)pyridin-4-yl)thio)propanoate (230 mg, 94% yield) as a solid. m/z (esi) M$^+$1=327.9.

Step C: NaOEt (21% weight in EtOH) (0.25 mL, 0.77 mmol) was added to a stirred solution of 3-((3-chloro-2-((2-cyano-2-methylpropyl)amino)pyridin-4-yl)thio)propanoate (210 mg, 0.64 mmol) in THF (5 mL) at 0° C. and stirred for 30 minutes at 0° C. The reaction was concentrated at 25° C., and diethyl ether (10 mL) was added. The resulting solid was filtered to afford sodium 3-chloro-2-((2-cyano-2-methylpropyl)amino)pyridine-4-thiolate (130 mg, 90% yield) as a solid. m/z (esi) M$^+$1=242.1.

Step D: Sodium 3-chloro-2-((2-cyano-2-methylpropyl)amino)pyridine-4-thiolate (132.34 mg, 0.5 mmol) was added to a stirred solution of (S)-1'-(6-bromo-1,2,4-triazin-3-yl)-1,3-dihydrospiro[indene-2,4'-piperidin]-1-amine (60.0 mg, 0.1 mmol) in n-butanol (1.5 mL) and stirred at 120° C. for 16 hours in a sealed tube. The reaction was concentrated, and the crude material was purified by reverse phase preparative HPLC (30-95% ACN:water (0.1% NH$_3$)) to get (S)-3-((4-((3-(1-amino-1,3-dihydrospiro[indene-2,4'-piperidin]-1'-yl)-1,2,4-triazin-6-yl)thio)-3-chloropyridin-2-yl)amino)-2,2-dimethylpropanenitrile (8 mg, 0.017 mmol, 9% yield) as a solid. $^1$H NMR (400 MHz, Methanol-d4) δ 8.37 (s, 1H), 7.76 (d, J=5.5 Hz, 1H), 7.40-7.33 (m, 1H), 7.25-7.16 (m, 3H), 6.05 (d, J=5.5 Hz, 1H), 4.69 (s, 2H), 3.98 (s, 1H), 1.40-1.22 (m, 7H), 3.72 (s, 2H), 3.51-3.35 (m, 2H), 3.20 (d, J=15.7 Hz, 1H), 2.84 (d, J=15.8 Hz, 1H), 1.97-1.70 (m, 2H), 1.65 (d, J=13.3 Hz, 1H), 1.46 (d, J=13.4 Hz, 1H), 1.36 (s, 6H); m/z (esi) M$^+$1=521.5.

Example 37

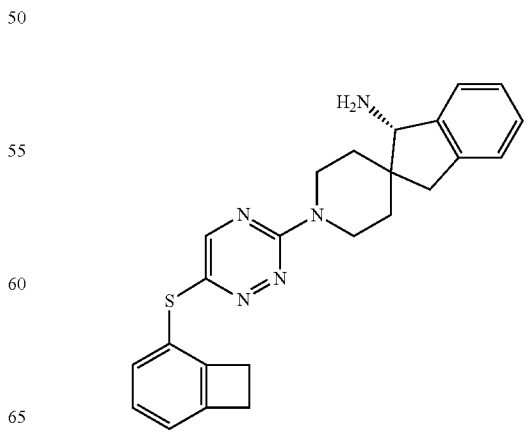

(S)-1'-(6-(bicyclo[4.2.0]octa-1(6),2,4-trien-2-ylthio)-1,2,4-triazin-3-yl)-1,3-dihydrospiro[indene-2,4'-piperidin]-1-amine Step A: t-BuLi (56 mL, 96 mmol, 1.7 M in pentane) was added dropwise to a stirring solution of 1-fluoro-2-(2-iodoethyl)benzene (6.0 g, 24.0 mmol) in pentane (60 mL) and Et$_2$O (20 mL) at −78° C. under argon. The reaction mixture was stirred at −78° C. for an additional 30 minutes, and anhydrous THF (12.0 mL) was added into it. The cooling bath was removed, and the reaction mixture was stirred for an additional 15 minutes. 12 (7.31 g, 28.8 mmol) was added by dissolving in E$_t$2O (60 mL). Prior to addition, the ether solution of 12 was degassed for 5 minutes with argon. The reaction mixture was quenched with NH$_4$Cl and extracted with Et$_2$O. The combined organic layer was dried (Na$_2$SO$_4$) and evaporated to afford 2-iodobicyclo[4.2.0]octa-1,3,5-triene (6.6 g, crude), which was used for the next step. m/z (gc-ms) M=230.

Step B: DIEA (4.24 mL, 24.35 mmol) was added to a stirred solution of 2-iodobicyclo[4.2.0]octa-1,3,5-triene (6.6 g, crude) and methyl 3-mercaptopropanoate (1.48 mL, 13.39 mmol) in dioxane (25 mL) and degassed with argon for 10 minutes. Xantphos (352 mg, 0.61 mmol) and Pd(OAc)$_2$ (164 mg, 0.73 mmol) were added and degassed for another 10 minutes. The reaction mixture was stirred in preheated oil bath in sealed tube at 100° C. for 4 hours. The reaction mixture was filtered through Celite® pad and washed with ethyl acetate. Solvent was evaporated, and crude was purified by silica gel column chromatography (5% MeOH/DCM) to afford methyl 3-(bicyclo[4.2.0]octa-1,3,5-trien-2-ylthio)propanoate (2.5 g, 46% yield, 2 steps) as a solid. m/z (esi) M+1=223.

Step C: NaOEt (1.7 mL, 5.40 mmol, 21% weight in EtOH) was added to a stirred solution of methyl 3-(bicyclo[4.2.0]octa-1,3,5-trien-2-ylthio)propanoate (1 g, 4.50 mmol) in THF (15 mL) at −78° C. and stirred for 30 minutes at same temperature. The reaction mixture was concentrated, and crude was triturated with ether. The solids were filtered to afford sodium bicyclo[4.2.0]octa-1,3,5-triene-2-thiolate (520 mg, 73% yield) as a solid. m/z (esi) M-Na=134.9.

Step D: Sodium bicyclo[4.2.0]octa-1,3,5-triene-2-thiolate (88 mg, 0.56 mmol) was added to a stirred solution of (S)-1'-(6-bromo-1,2,4-triazin-3-yl)-1,3-dihydrospiro[indene-2,4'-piperidin]-1-amine (100 mg, 0.28 mmol) in butanol (5 mL) and stirred at 100° C. for 4 hours. The reaction mixture was concentrated and purified by reverse phase preparative HPLC (50-90% ACN:0.1% NH$_4$OH in H$_2$O) to afford (S)-1'-(6-(bicyclo[4.2.0]octa-1(6),2,4-trien-2-ylthio)-1,2,4-triazin-3-yl)-1,3-dihydrospiro[indene-2,4'-piperidin]-1-amine (30 mg, 26% yield) as a solid. $^1$H NMR (400 MHz, (CD$_3$)$_2$SO) δ 8.36 (s, 1H), 7.30 (d, J=6.5 Hz, 1H), 7.23-7.09 (m, 5H), 7.00 (d, J=7.1 Hz, 1H), 4.49 (s, 2H), 3.86 (s, 1H), 3.40-3.34 (m, 1H), 3.29-3.21 (m, 1H), 3.16-3.03 (m, 3H), 2.82 (t, J=4.2 Hz, 2H), 2.66 (d, J=15.3 Hz, 1H), 2.16-1.83 (m, 2H), 1.77 (t, J=11.6 Hz, 1H), 1.66 (t, J=11.6 Hz, 1H), 1.55 (d, J=13.0 Hz, 1H), 1.14 (d, J=13.1 Hz, 1H). m/z (esi) M$^+$1=416.2.

Example 38

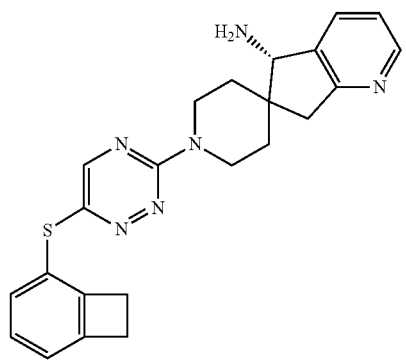 [SMILES: N[C@@H]1c2cccnc2CC12CCN(c1ncc(Sc3cccc4c3CC4)nn1)CC2]

(S)-1'-(6-(bicyclo[4.2.0]octa-1(6),2,4-trien-2-ylthio)-1,2,4-triazin-3-yl)-5,7-dihydrospiro[cyclopenta[b]pyridine-6,4'-piperidin]-5-amine Step A: Triethylamine (0.30 mL, 2.12 mmol) was added to a stirring solution of dihydrochloride salt of (S)-5,7-dihydrospiro[cyclopenta[b]pyridine-6,4'-piperidin]-5-amine (117 mg, 0.42 mmol) in 1,4 dioxane (2.8 mL) at room temperature and stirred for 20 minutes. 3,6-Dibromo-1,2,4-triazine (100 mg, 0.42 mmol) was added, stirred for 2 hours at room temperature and heated at 50° C. for 1 hour. The solvent was evaporated and purified by silica gel chromatography (3% MeOH-DCM) to afford (S)-1'-(6-bromo-1,2,4-triazin-3-yl)-5,7-dihydrospiro[cyclopenta[b]pyridine-6,4'-piperidin]-5-amine (75 mg, 49% yield) as a solid. m/z (esi) M$^+$1=360.8.

Step B: Sodium bicyclo[4.2.0]octa-1,3,5-triene-2-thiolate (63.2 mg, 0.4 mmol) was added to a stirring solution of (S)-1'-(6-bromo-1,2,4-triazin-3-yl)-5,7-dihydrospiro[cyclopenta[b]pyridine-6,4'-piperidin]-5-amine (72 mg, 0.2 mmol) in n-butanol (4 mL) and stirred at 100° C. for 4 hours. The reaction mixture was evaporated, and the crude reaction mixture was dissolved in DMSO and purified by reverse phase preparative HPLC (30-70% ACN: water (0.1% NH$_3$)) to obtain (S)-1'-(6-(bicyclo[4.2.0]octa-1(6),2,4-trien-2-ylthio)-1,2,4-triazin-3-yl)-5,7-dihydrospiro[cyclopenta[b]pyridine-6,4'-piperidin]-5-amine (19.3 mg, 24% yield) as a solid. $^1$H NMR (400 MHz, (CD$_3$)$_2$SO) δ 8.37 (s, 1H), 8.32 (d, J=5.0 Hz, 1H), 7.65 (d, J=7.5 Hz, 1H), 7.23-7.09 (m, 3H), 7.01 (d, J=7.1 Hz, 1H), 4.50 (s, 2H), 3.91 (s, 1H), 3.44-3.36

(m, 1H), 3.30-3.23 (m, 1H), 3.20-3.02 (m, 3H), 2.86-2.73 (m, 3H), 2.18-2.13 (m, 2H), 1.85-1.62 (m, 2H), 1.58 (d, J=13.3 Hz, 1H), 1.17 (d, J=13.6 Hz, 1H). m/z (esi) M$^+$1=417.2.

Example 39

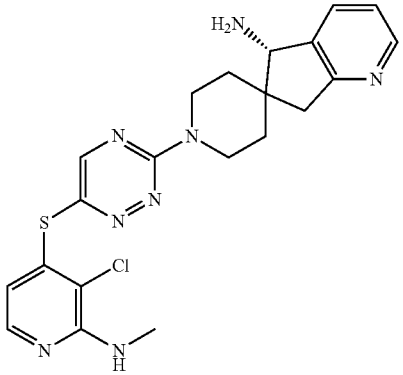 [SMILES: CNc1nccc(Sc2cnc(N3CCC4(CC3)Cc3ncccc3[C@H]4N)nn2)c1Cl]

(S)-1'-(6-((3-chloro-2-(methylamino)pyridin-4-yl)thio)-1,2,4-triazin-3-yl)-5,7-dihydrospiro[cyclopenta[b]pyridine-6,4'-piperidin]-5-amine Step A: TEA (0.15 mL, 1.06 mmol) was added to a stirred solution of (S)-5,7-dihydrospiro[cyclopenta[b]pyridine-6,4'-piperidin]-5-amine hydrochloride (58.47 mg, 0.21 mmol) in 1,4-dioxane (1.4 mL) at room temperature and stirred for 20 minutes. 3,6-Dibromo-1,2,4-triazine (50 mg, 0.21 mmol) was added and stirred for 2 hours at room temperature and then heated at 50° C. for 1 hour. The solvent was evaporated and purified with silica gel column chromatography (7-14% MeOH/DCM) to get (S)-1'-(6-bromo-1,2,4-triazin-3-yl)-5,7-dihydrospiro[cyclopenta[b]pyridine-6,4'-piperidin]-5-amine (70 mg, 91% yield) as a solid. m/z (esi) M$^+$1=362.9.

Step B: 3-Chloro-2-(methylamino)pyridine-4-thiol (72.5 mg, 0.42 mmol) was added to a stirred solution of (S)-1'-(6-bromo-1,2,4-triazin-3-yl)-5,7-dihydrospiro[cyclopenta[b]pyridine-6,4'-piperidin]-5-amine (50 mg, 0.14 mmol) in n-BuOH (5 mL) and heated to 90° C. for 16 hours. The reaction was purified with reverse phase preparative HPLC (20-50% ACN:water (0.1% NH$_3$)) to get (S)-1'-(6-((3-chloro-2-(methylamino)pyridin-4-yl)thio)-1,2,4-triazin-3-yl)-5,7-dihydrospiro[cyclopenta[b]pyridine-6,4'-piperidin]-5-amine (13 mg, 21% yield) as a sticky solid. $^1$H NMR (400 MHz, Methanol-d4) δ 8.38 (s, 2H), 7.85 (d, J=7.6 Hz, 1H), 7.74 (d, J=5.6 Hz, 1H), 7.30 (t, J=6.3 Hz, 1H), 5.98 (d, J=5.4 Hz, 1H), 4.79-4.67 (m, 2H), 4.15 (s, 1H), 3.47-3.42 (m, 2H), 3.02 (d, J=16.7 Hz, 1H), 2.94 (s, 3H), 1.98-1.76 (m, 2H), 1.69 (d, J=13.6 Hz, 1H), 1.52 (d, J=13.4 Hz, 1H). m/z (esi) M$^+$1=455.4.

Example 40

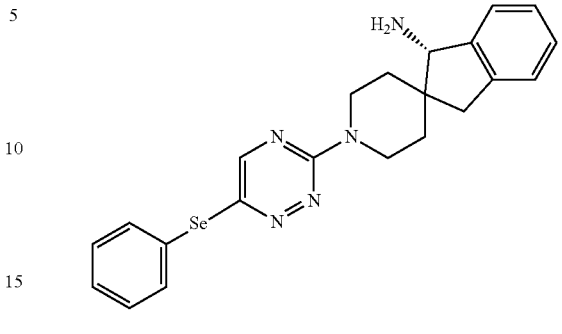

(S)-1'-(6-(phenylselanyl)-1,2,4-triazin-3-yl)-1,3-dihydrospiro[indene-2,4'-piperidin]-1-amine Step A: NaBH$_4$ (163 mg, 4.3 mmol) was added to a stirred solution of diphenyldiselenium (161 mg, 0.5 mmol) in PEG-400 (5 mL), and the reaction mixture was heated at 70° C. for 1 hour. The reaction was cooled to room temperature, and N-((S)-1'-(6-bromo-1,2,4-triazin-3-yl)-1,3-dihydrospiro[indene-2,4'-piperidin]-1-yl)-2-methylpropane-2-sulfinamide (200 mg, 0.43 mmol) was added. The reaction was again heated at 70° C. for 16 hours under nitrogen atmosphere. The reaction was cooled to room temperature, poured onto water, extracted with ethyl acetate (3×150 mL), dried over anhydrous Na$_2$SO$_4$, and concentrated under reduced pressure. The resulting residue was purified by column chromatography over silica gel using 70% ethyl acetate in hexane to afford 2-methyl-N-((S)-1'-(6-(phenylselanyl)-1,2,4-triazin-3-yl)-1,3-dihydrospiro[indene-2,4'-piperidin]-1-yl)propane-2-sulfinamide (100 mg, 43%) as a solid. MS (m/z)=542.2 (M$^+$H).

Step B: 4N HCl in dioxane (1 mL) was added to a stirred solution of 2-methyl-N-((S)-1'-(6-(phenylselanyl)-1,2,4-triazin-3-yl)-1,3-dihydrospiro[indene-2,4'-piperidin]-1-yl)propane-2-sulfinamide (50 mg, 0.09 mmol) in MeOH (1 mL), and the reaction mixture was stirred for 30 minutes at room temperature. The reaction mixture was concentrated under reduced pressure, and the crude was washed with diethyl ether, dried under reduced pressure and purified by preparative HPLC (Xbridge C18 (50×19 mm, 5μ) operating at ambient temperature and flow rate of 20 mL/minute. Mobile phase: A=20 mM ammonium bicarbonate in water, B=acetonitrile; Gradient Profile: Mobile phase initial composition of 80% A and 20% B, then to 20% A and 80% B in 12 minutes, then to 5% A and 95% B in 13 minutes, held this composition up to 15 minutes) to afford (S)-1'-(6-(phenylselanyl)-1,2,4-triazin-3-yl)-1,3-dihydrospiro[indene-2,4'-piperidin]-1-amine (15 mg, 37%) as a solid. $^1$H NMR (400 MHz, (CD$_3$)$_2$SO) δ 8.36 (s, 1H), 7.52 (dd, J=3.1, 6.5 Hz, 2H), 7.39-7.26 (m, 4H), 7.23-7.10 (m, 3H), 4.46 (t, J=13.9 Hz, 2H), 3.84 (s, 1H), 3.42-3.33 (m, 1H), 3.24 (d, J=12.8 Hz, 1H), 3.10 (d, J=15.6 Hz, 1H), 2.64 (d, J=15.7 Hz, 1H), 1.82-1.70 (m, 2H), 1.69-1.58 (m, 2H), 1.54 (d, J=13.4 Hz, 1H), 1.13 (d, J=14.2 Hz, 1H); MS (m/z)=438.4 (M$^+$H).

Example 41

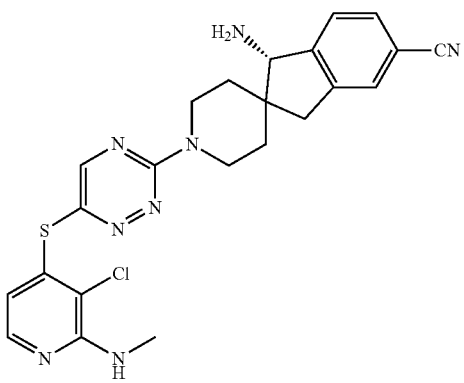 [SMILES: CNc1nccc(Sc2cnc(N3CCC4(CC3)Cc3cc(C#N)ccc3[C@H]4N)nn2)c1Cl]

(S)-1-amino-1'-(6-((3-chloro-2-(methylamino)pyridin-4-yl)thio)-1,2,4-triazin-3-yl)-1,3-dihydrospiro[indene-2,4'-piperidine]-5-carbonitrile Step A: Triethylamine (0.26 mL, 1.88 mmol) was added to a stirred solution of 3,6-dibromo-1,2,4-triazine (180 mg, 0.75 mmol) in dioxane (5 mL) at 0° C. and stirred for 5 minutes. 1-Amino-1,3-dihydrospiro[indene-2,4'-piperidine]-5-carbonitrile hydrochloride (224 mg, 0.75 mmol) in dioxane (1 mL) was added dropwise at 0° C. and stirred for 1 hour. The reaction mixture was diluted with water and extracted with EtOAc. The organic part was dried over anhydrous $Na_2SO_4$, filtered, concentrated under reduced pressure and purified by silica gel column chromatography (10% MeOH/DCM) to afford (S)-1-amino-1'-(6-bromo-1,2,4-triazin-3-yl)-1,3-dihydrospiro[indene-2,4'-piperidine]-5-carbonitrile (200 mg, 69% yield) as a solid. m/z (esi) $M^+1=385.2$.

Step B: Sodium 3-chloro-2-(methylamino)pyridine-4-thiolate (92 mg, 0.46 mmol) was added to a stirred solution of (S)-1-amino-1'-(6-bromo-1,2,4-triazin-3-yl)-1,3-dihydrospiro[indene-2,4'-piperidine]-5-carbonitrile (90 mg, 0.23 mmol) in n-butanol (5 mL) and stirred in microwave at 120° C. for 1 hour. The reaction mixture was concentrated, and the resulting residue was purified by reverse phase preparative HPLC (40-75% ACN:water (0.1% $NH_3$)) to afford racemic product, which was subjected to chiral separation (chiralpak OJ-H (250×20 mm) 5µ, Flow: 25 g/minute, Mobile Phase: 60% $CO_2$+40% (0.5% Isopropylamine in methanol), ABPR: 120 bar, temperature: 35° C.). Collecting the first eluting peak provided (S)-1-amino-1'-(6-((3-chloro-2-(methylamino)pyridin-4-yl)thio)-1,2,4-triazin-3-yl)-1,3-dihydrospiro[indene-2,4'-piperidine]-5-carbonitrile (10 mg, 9% yield). $^1$H NMR (400 MHz, $(CD_3)_2SO$) δ 8.48 (s, 1H), 7.80 (d, J=5.3 Hz, 1H), 7.67 (d, J=6.9 Hz, 2H), 7.50 (d, J=7.7 Hz, 1H), 6.66 (d, J=4.8 Hz, 1H), 5.93 (d, J=5.3 Hz, 1H), 4.57 (s, 2H), 3.93 (s, 1H), 3.20 (d, J=15.9 Hz, 1H), 2.85 (d, J=4.5 Hz, 3H), 2.72 (d, J=16.0 Hz, 1H), 2.15 1.90 (m, 2H), 1.90 1.76 (m, 2H), 1.64 (t, J=14.3 Hz, 2H), 1.11 (d, J=13.8 Hz, 1H), m/z (esi) $M^+1=479.1$.

Example 42

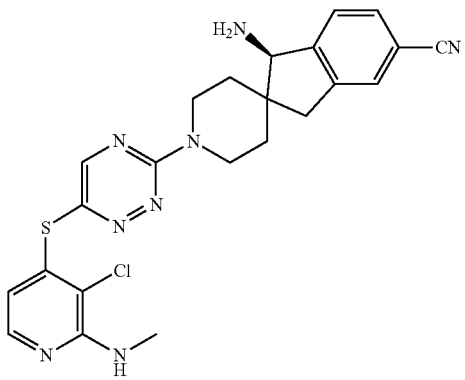 [SMILES: CNc1nccc(Sc2cnc(N3CCC4(CC3)Cc3cc(C#N)ccc3[C@@H]4N)nn2)c1Cl]

(R)-1-amino-1'-(6-((3-chloro-2-(methylamino)pyridin-4-yl)thio)-1,2,4-triazin-3-yl)-1,3-dihydrospiro[indene-2,4'-piperidine]-5-carbonitrile (R)-1-Amino-1'-(6-((3-chloro-2-(methylamino)pyridin-4-yl)thio)-1,2,4-triazin-3-yl)-1,3-dihydrospiro[indene-2,4'-piperidine]-5-carbonitrile (10 mg, 9% yield) was prepared according to Example 41, collecting the second eluting peak in Step B. $^1$H NMR (400 MHz, Methanol-d4) δ 8.38 (s, 1H), 7.76 (d, J=5.6 Hz, 1H), 7.61 (d, J=6.3 Hz, 2H), 7.55 (d, J=8.0 Hz, 1H), 6.00 (d, J=5.6 Hz, 1H), 3.49-3.34 (m, 3H), 3.31-3.17 (m, 2H), 2.97 (s, 3H), 2.88 (d, J=16.1 Hz, 1H), 2.02-1.88 (m, 1H), 1.86-1.73 (m, 1H), 1.69 (d, J=13.3 Hz, 1H), 1.38 (d, J=14.0 Hz, 1H), 1.30 (s, 2H), 0.91 (d, J=7.2 Hz, 1H), m/z (esi) $M^+1=479.1$.

Example 43

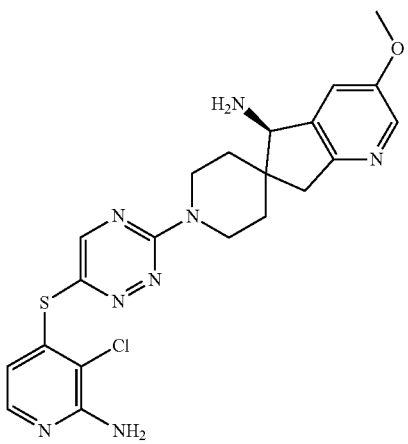 [SMILES: COc1cnc2c(c1)[C@H](N)C1(CCN(c3ncc(Sc4ccnc(N)c4Cl)nn3)CC1)C2]

(R)-1'-(6-((2-amino-3-chloropyridin-4-yl)thio)-1,2,4-triazin-3-yl)-3-methoxy-5,7-dihydrospiro[cyclopenta[b]pyridine-6,4'-piperidin]-5-amine Step A: Triethylamine (0.74 mL, 5.0 mmol) was added to a stirred solution of 3-methoxy-5,7-dihydrospiro[cyclopenta[b]pyridine-6,4'-piperidin]-5-amine hydrochloride (418 mg, 1.37 mmol) in dioxane (10 mL) and stirred at room temperature for 20 minutes. 3,6-Dibromo-1,2,4-triazine (249 mg, 1.05 mmol) was added and stirred at room temperature for 2 hours. The reaction was heated at 50° C. for 1 hour. The solvent was concentrated to dryness and washed with Et$_2$O to afford 1'-(6-bromo-1,2,4-triazin-3-yl)-3-methoxy-5,7-dihydrospiro[cyclopenta[b]pyridine-6,4'-piperidin]-5-amine (410 mg, crude) as a solid. The crude mass was used in the next step without purification. m/z (esi) M$^+$1=391.1.

Step B: Sodium 2-amino-3-chloropyridine-4-thiolate (93 mg, 0.511 mmol) was added to a stirred solution of 1'-(6-bromo-1,2,4-triazin-3-yl)-3-methoxy-5,7-dihydrospiro[cyclopenta[b]pyridine-6,4'-piperidin]-5-amine (100 mg, 0.256 mmol) in n-butanol (2.0 mL) and stirred at 120° C. for 3 hours. The reaction mixture was cooled to room temperature, and sodium 2-amino-3-chloropyridine-4-thiolate (93 mg, 0.51 mmol) was added and stirred at 120° C. for 16 hours. The reaction was concentrated under reduced pressure and washed with Et$_2$O. The crude was mixed with another batch (S)-1'-(6-bromo-1,2,4-triazin-3-yl)-3-methoxy-5,7-dihydrospiro[cyclopenta[b]pyridine-6,4'-piperidin]-5-amine (100 mg) and was purified by chiral HPLC (Chiralpak IG (21.0×250 mm), 5μ, DCM/EtOH/Isopropylamine 40/60/0.1, 9.0 mL/minute). Collection of the first eluting peak provided (S)-1'-(6-((2-amino-3-chloropyridin-4-yl)thio)-1,2,4-triazin-3-yl)-3-methoxy-5,7-dihydrospiro[cyclopenta[b]pyridine-6,4'-piperidin]-5-amine (12 mg, 5% three step yield) as a solid. $^1$H NMR (400 MHz, Methanol-d4) δ 8.42 (s, 1H), 8.24 (d, J=2.8 Hz, 1H), 7.66 (d, J=5.5 Hz, 1H), 7.53 (s, 1H), 6.04 (d, J=5.5 Hz, 1H), 4.77-4.66 (m, 2H), 4.46 (s, 1H), 3.91 (s, 3H), 3.50-3.39 (m, 2H), 3.28-3.12 (m, 2H), 1.95-1.60 (m, 4H).

Example 44

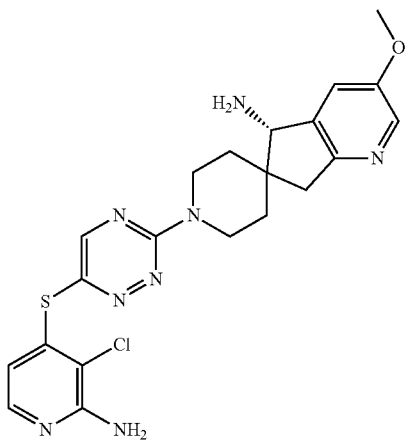 [SMILES: COc1cnc2c(c1)[C@@H](N)C1(CCN(c3ncc(Sc4ccnc(N)c4Cl)nn3)CC1)C2]

(S)-1'-(6-((2-amino-3-chloropyridin-4-yl)thio)-1,2,4-triazin-3-yl)-3-methoxy-5,7-dihydrospiro[cyclopenta[b]pyridine-6,4'-piperidin]-5-amine (S)-1'-(6-((2-Amino-3-chloropyridin-4-yl)thio)-1,2,4-triazin-3-yl)-3-methoxy-5,7-dihydrospiro[cyclopenta[b]pyridine-6,4'-piperidin]-5-amine (5 mg, 5% two step yield) was prepared according to Example 43, collecting the second eluting peak as a solid. $^1$H NMR (400 MHz, Methanol-d4) δ 8.40 (s, 1H), 8.16 (s, 1H), 7.66 (d, J=5.4 Hz, 1H), 7.50 (s, 1H), 6.04 (d, J=5.5 Hz, 1H), 4.84-4.64 (m, 2H), 4.30 (s, 1H), 3.89 (s, 3H), 3.44 (t, J=12.7 Hz, 2H), 3.26-3.17 (m, 1H), 3.06 (d, J=16.5 Hz, 1H), 1.94-1.75 (m, 2H), 1.76-1.58 (m, 2H); m/z (esi) M$^+$1=471.1.

The following compounds in Table 4 were prepared according to the above procedures using appropriate starting materials and intermediates.

TABLE 4

| Ex. # | Structure | Name | Prep | MS |
|---|---|---|---|---|
| 45 | 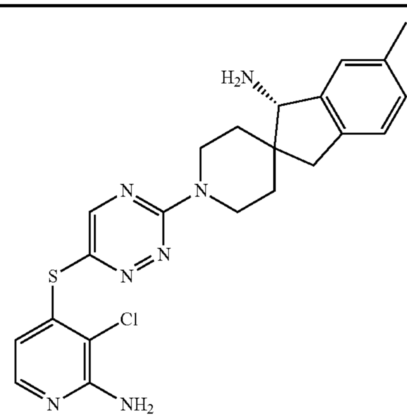 | (S)-1'-(6-((2-amino-3-chloropyridin-4-yl)thio)-1,2,4-triazin-3-yl)-6-methyl-1,3-dihydrospiro[indene-2,4'-piperidin]-1-amine | Ex. 17 | 454.1 |

TABLE 4-continued

| Ex. # | Structure | Name | Prep | MS |
|---|---|---|---|---|
| 46 | 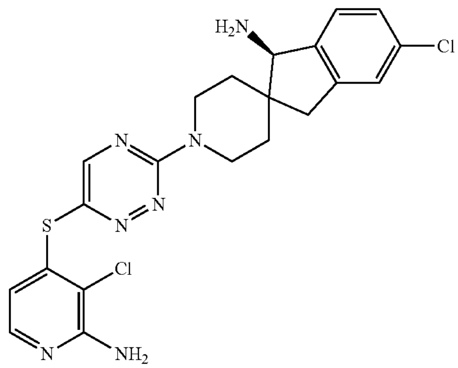 [SMILES: Nc1nccc(Sc2cnc(N3CCC4(CC3)Cc3cc(Cl)ccc3[C@@H]4N)nn2)c1Cl] | (R)-1'-(6-((2-amino-3-chloropyridin-4-yl)thio)-1,2,4-triazin-3-yl)-5-chloro-1,3-dihydrospiro[indene-2,4'-piperidin]-1-amine | Ex. 17 | 474.1 |
| 47 | 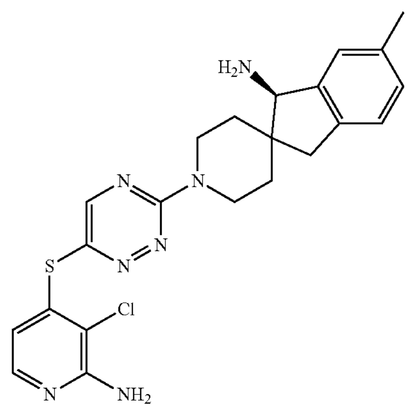 [SMILES: Cc1ccc2c(c1)[C@H](N)C1(CCN(c3ncc(Sc4ccnc(N)c4Cl)nn3)CC1)C2] | (R)-1'-(6-((2-amino-3-chloropyridin-4-yl)thio)-1,2,4-triazin-3-yl)-6-methyl-1,3-dihydrospiro[indene-2,4'-piperidin]-1-amine | Ex. 17 | 454.1 |
| 48 | 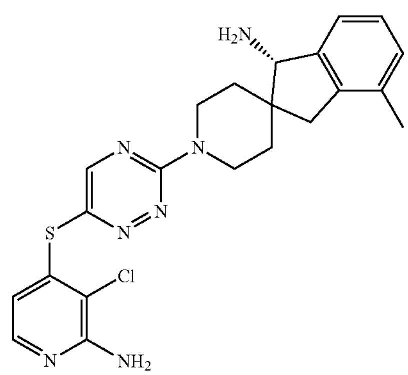 [SMILES: Cc1cccc2c1CC1(CCN(c3ncc(Sc4ccnc(N)c4Cl)nn3)CC1)[C@@H]2N] | (S)-1'-(6-((2-amino-3-chloropyridin-4-yl)thio)-1,2,4-triazin-3-yl)-4-methyl-1,3-dihydrospiro[indene-2,4'-piperidin]-1-amine | Ex. 17 | 454.1 |
| 49 | 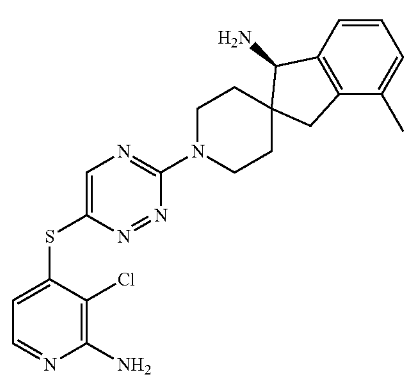 [SMILES: Cc1cccc2c1CC1(CCN(c3ncc(Sc4ccnc(N)c4Cl)nn3)CC1)[C@H]2N] | (R)-1'-(6-((2-amino-3-chloropyridin-4-yl)thio)-1,2,4-triazin-3-yl)-4-methyl-1,3-dihydrospiro[indene-2,4'-piperidin]-1-amine | Ex. 17 | 454.1 |

TABLE 4-continued

| Ex. # | Structure | Name | Prep | MS |
|---|---|---|---|---|
| 50 | 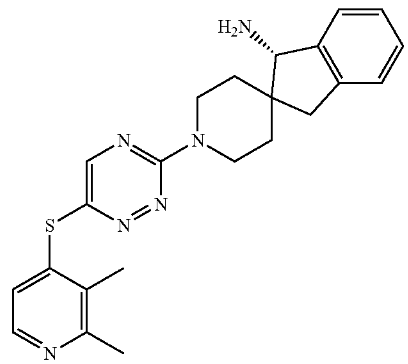 [SMILES: Cc1nccc(Sc2cnc(N3CCC4(CC3)Cc3ccccc3[C@H]4N)nn2)c1C] | (S)-1'-(6-((2,3-dimethylpyridin-4-yl)thio)-1,2,4-triazin-3-yl)-1,3-dihydrospiro[indene-2,4'-piperidin]-1-amine | Ex. 18 | 419.2 |
| 51 | 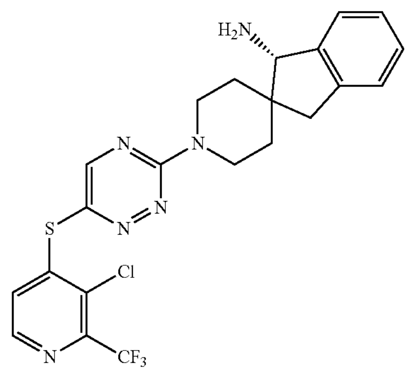 [SMILES: N[C@@H]1c2ccccc2CC12CCN(c1ncc(Sc3ccnc(C(F)(F)F)c3Cl)nn1)CC2] | (S)-1'-(6-((3-chloro-2-(trifluoromethyl)pyridin-4-yl)thio)-1,2,4-triazin-3-yl)-1,3-dihydrospiro[indene-2,4'-piperidin]-1-amine | Ex. 18 | 493.1 |
| 52 | 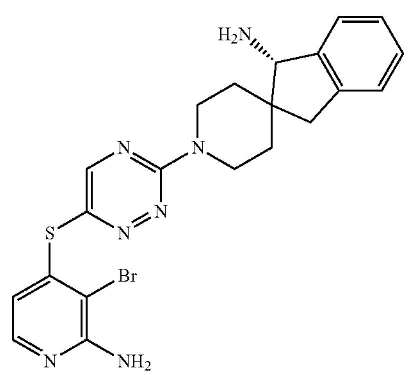 | (S)-1'-(6-((2-amino-3-bromopyridin-4-yl)thio)-1,2,4-triazin-3-yl)-1,3-dihydrospiro[indene-2,4'-piperidin]-1-amine | Ex. 18 | 486.1 |
| 53 | 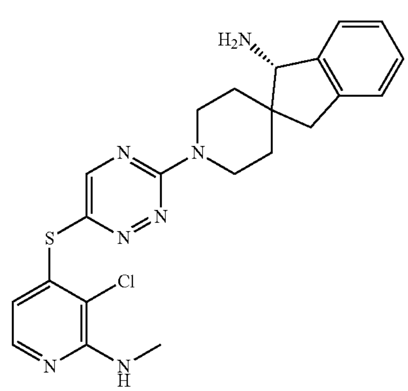 [SMILES: CNc1nccc(Sc2cnc(N3CCC4(CC3)Cc3ccccc3[C@H]4N)nn2)c1Cl] | (S)-1'-(6-((3-chloro-2-(methylamino)pyridin-4-yl)thio)-1,2,4-triazin-3-yl)-1,3-dihydrospiro[indene-2,4'-piperidin]-1-amine | Ex. 18 | 454.2 |

| Ex. # | Structure | Name | Prep | MS |
|---|---|---|---|---|
| 54 | 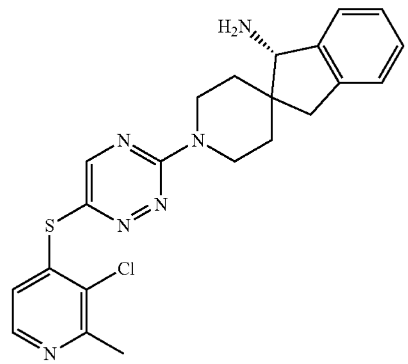 [SMILES: Cc1nccc(Sc2cnc(N3CCC4(CC3)Cc3ccccc3[C@H]4N)nn2)c1Cl] | (S)-1'-(6-((3-chloro-2-methylpyridin-4-yl)thio)-1,2,4-triazin-3-yl)-1,3-dihydrospiro[indene-2,4'-piperidin]-1-amine | Ex. 18 | 439.1 |
| 55 | 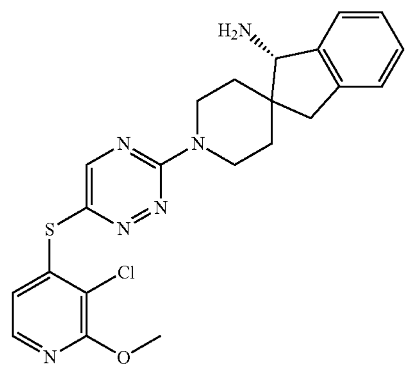 [SMILES: COc1nccc(Sc2cnc(N3CCC4(CC3)Cc3ccccc3[C@H]4N)nn2)c1Cl] | (S)-1'-(6-((3-chloro-2-methoxypyridin-4-yl)thio)-1,2,4-triazin-3-yl)-1,3-dihydrospiro[indene-2,4'-piperidin]-1-amine | Ex. 18 | 455.2 |
| 56 | 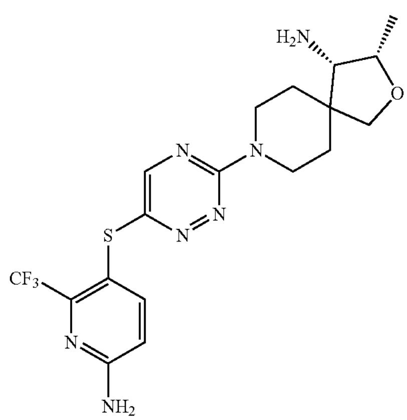 [SMILES: C[C@@H]1OCC2(CCN(c3ncc(Sc4ccc(N)nc4C(F)(F)F)nn3)CC2)[C@@H]1N] | (3S,4S)-8-(6-((6-amino-2-(trifluoromethyl)pyridin-3-yl)thio)-1,2,4-triazin-3-yl)-3-methyl-2-oxa-8-azaspiro[4.5]decan-4-amine | Ex. 21 | 442.2 |
| 57 | 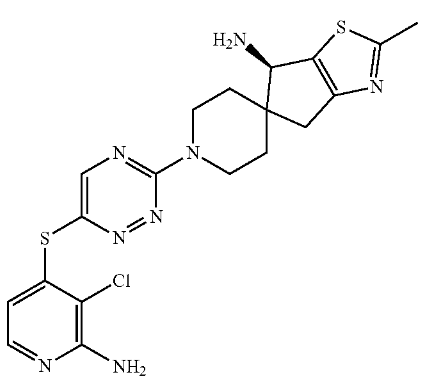 [SMILES: Cc1nc2c(s1)[C@H](N)C1(CCN(c3ncc(Sc4ccnc(N)c4Cl)nn3)CC1)C2] | (R)-1'-(6-((2-amino-3-chloropyridin-4-yl)thio)-1,2,4-triazin-3-yl)-2-methyl-4,6-dihydrospiro[cyclopenta[d]thiazole-5,4'-piperidin]-6-amine | Ex. 24 | 461.1 |

TABLE 4-continued

| Ex. # | Structure | Name | Prep | MS |
|---|---|---|---|---|
| 58 | 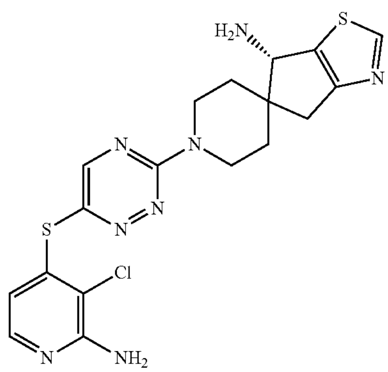 [SMILES: Nc1nccc(Sc2cnc(N3CCC4(CC3)Cc3ncsc3[C@H]4N)nn2)c1Cl] | (S)-1'-(6-((2-amino-3-chloropyridin-4-yl)thio)-1,2,4-triazin-3-yl)-4,6-dihydrospiro[cyclopenta[d]thiazole-5,4'-piperidin]-6-amine | Ex. 24 | 447.1 |
| 59 | 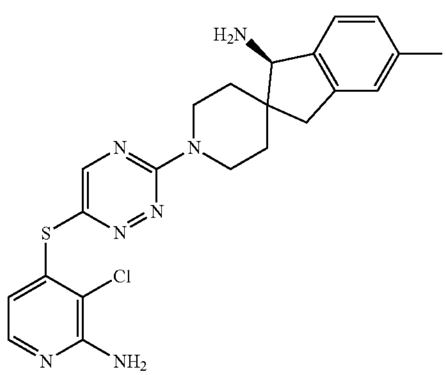 [SMILES: Cc1ccc2c(c1)CC1(CCN(c3ncc(Sc4ccnc(N)c4Cl)nn3)CC1)[C@H]2N] | (R)-1'-(6-((2-amino-3-chloropyridin-4-yl)thio)-1,2,4-triazin-3-yl)-5-methyl-1,3-dihydrospiro[indene-2,4'-piperidin]-1-amine | Ex. 24 | 454.1 |
| 60 | 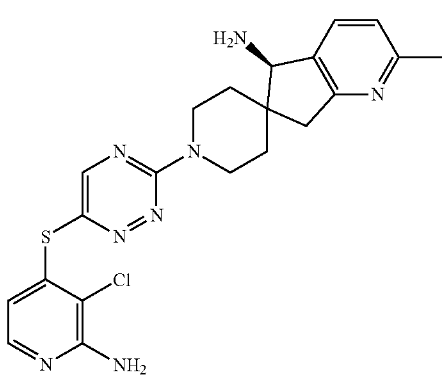 [SMILES: Cc1ccc2c(n1)CC1(CCN(c3ncc(Sc4ccnc(N)c4Cl)nn3)CC1)[C@H]2N] | (R)-1'-(6-((2-amino-3-chloropyridin-4-yl)thio)-1,2,4-triazin-3-yl)-2-methyl-5,7-dihydrospiro[cyclopenta[b]pyridine-6,4'-piperidin]-5-amine | Ex. 24 | 455.2 |
| 61 | 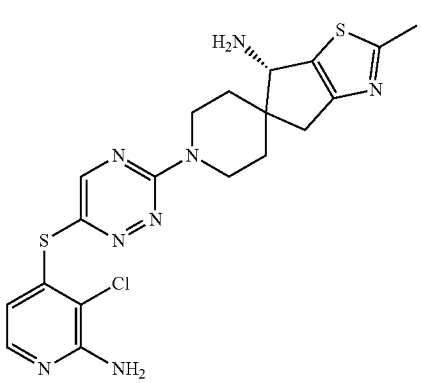 [SMILES: Cc1nc2c(s1)[C@@H](N)C1(CCN(c3ncc(Sc4ccnc(N)c4Cl)nn3)CC1)C2] | (S)-1'-(6-((2-amino-3-chloropyridin-4-yl)thio)-1,2,4-triazin-3-yl)-2-methyl-4,6-dihydrospiro[cyclopenta[d]thiazole-5,4'-piperidin]-6-amine | Ex. 24 | 461.1 |

TABLE 4-continued

| Ex. # | Structure | Name | Prep | MS |
|---|---|---|---|---|
| 62 | 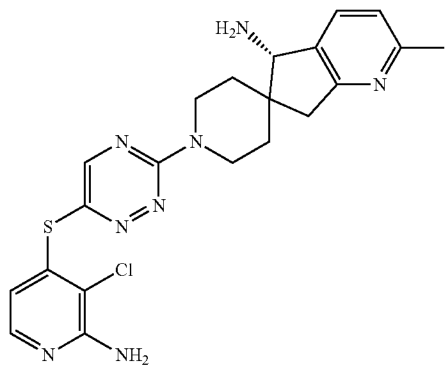 [SMILES: Cc1ccc2c(n1)CC1(CCN(c3ncc(Sc4ccnc(N)c4Cl)nn3)CC1)[C@@H]2N] | (S)-1'-(6-((2-amino-3-chloropyridin-4-yl)thio)-1,2,4-triazin-3-yl)-5-methyl-1,3-dihydrospiro[indene-2,4'-piperidin]-1-amine | Ex. 24 | 455.1 |
| 63 | 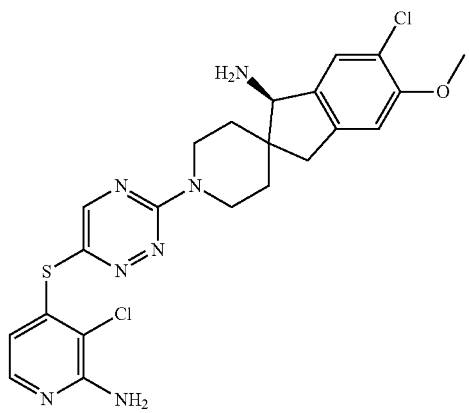 [SMILES: COc1cc2c(cc1Cl)[C@H](N)C1(CCN(c3ncc(Sc4ccnc(N)c4Cl)nn3)CC1)C2] | (R)-1'-(6-((2-amino-3-chloropyridin-4-yl)thio)-1,2,4-triazin-3-yl)-6-chloro-5-methoxy-1,3-dihydrospiro[indene-2,4'-piperidin]-1-amine | Ex. 24 | 504.1 |
| 64 | 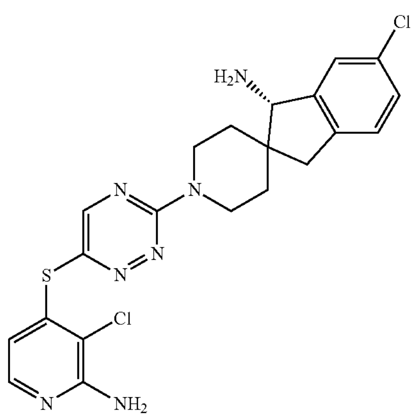 [SMILES: Nc1nccc(Sc2cnc(N3CCC4(CC3)Cc3ccc(Cl)cc3[C@H]4N)nn2)c1Cl] | (S)-1'-(6-((2-amino-3-chloropyridin-4-yl)thio)-1,2,4-triazin-3-yl)-6-chloro-1,3-dihydrospiro[indene-2,4'-piperidin]-1-amine | Ex. 24 | 474.1 |
| 65 | 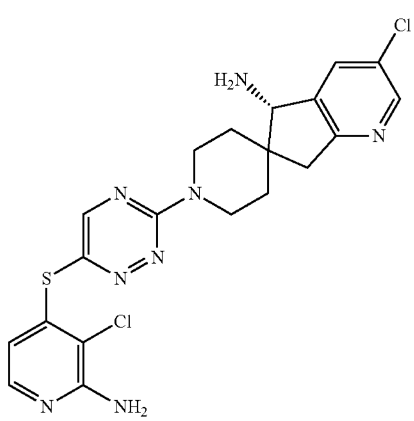 [SMILES: Nc1nccc(Sc2cnc(N3CCC4(CC3)Cc3ncc(Cl)cc3[C@H]4N)nn2)c1Cl] | (S)-1'-(6-((2-amino-3-chloropyridin-4-yl)thio)-1,2,4-triazin-3-yl)-3-chloro-5,7-dihydrospiro[cyclopenta[b]pyridine-6,4'-piperidin]-5-amine | Ex. 24 | 475.1 |

TABLE 4-continued

| Ex. # | Structure | Name | Prep | MS |
|---|---|---|---|---|
| 66 | 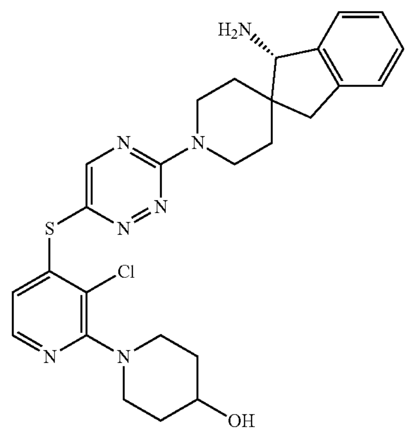 [SMILES: N[C@@H]1c2ccccc2CC12CCN(c1ncc(Sc3ccnc(N4CCC(O)CC4)c3Cl)nn1)CC2] | (S)-1-(4-((3-(5-amino-5,7-dihydrospiro[cyclopenta[b]pyridine-6,4'-piperidin]-1'-yl)-1,2,4-triazin-6-yl)thio)-3-chloropyridin-2-yl)piperidin-4-ol | Ex. 17 | 524.3 |
| 67 | 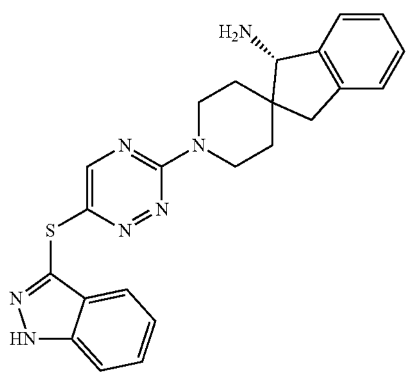 [SMILES: N[C@@H]1c2ccccc2CC12CCN(c1ncc(Sc3n[nH]c4ccccc34)nn1)CC2] | (S)-1'-(6-(1H-indazol-3-yl)thio)-1,2,4-triazin-3-yl)-1,3-dihydrospiro[indene-2,4'-piperidin]-1-amine | Ex. 25 | 430.2 |
| 68 | 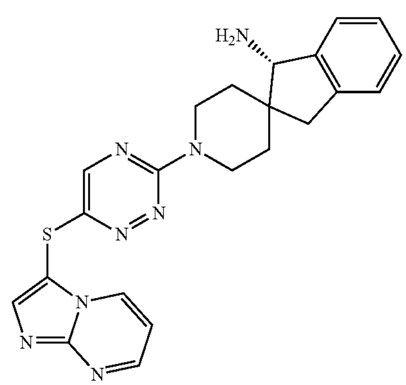 [SMILES: N[C@@H]1c2ccccc2CC12CCN(c1ncc(Sc3cnc4ncccn34)nn1)CC2] | (S)-1'-(6-(imidazo[1,2-a]pyrimidin-3-ylthio)-1,2,4-triazin-3-yl)-1,3-dihydrospiro[indene-2,4'-piperidin]-1-amine | Ex. 26 | 431.2 |
| 69 | 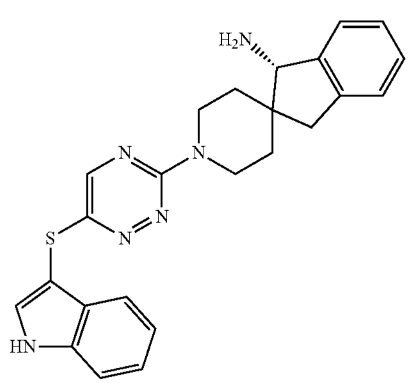 [SMILES: N[C@@H]1c2ccccc2CC12CCN(c1ncc(Sc3c[nH]c4ccccc34)nn1)CC2] | (S)-1'-(6-((1H-indol-3-yl)thio)-1,2,4-triazin-3-yl)-1,3-dihydrospiro[indene-2,4'-piperidin]-1-amine | Ex. 26 | 429.2 |

TABLE 4-continued

| Ex. # | Structure | Name | Prep | MS |
|---|---|---|---|---|
| 70 | 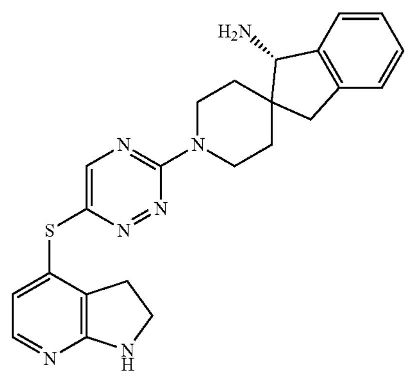 [SMILES: N[C@@H]1c2ccccc2CC12CCN(c1ncc(Sc3ccnc4c3CCN4)nn1)CC2] | (S)-1'-(6-((2,3-dihydro-1H-pyrrolo[2,3-b]pyridin-4-yl)thio)-1,2,4-triazin-3-yl)-1,3-dihydrospiro[indene-2,4'-piperidin]-1-amine | Ex. 27 | 432.2 |
| 71 | 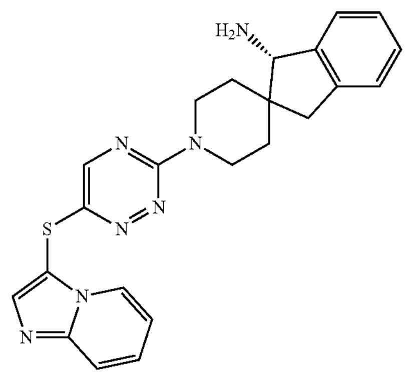 [SMILES: N[C@@H]1c2ccccc2CC12CCN(c1ncc(Sc3cnc4ccccn34)nn1)CC2] | (S)-1'-(6-(imidazo[1,2-a]pyridin-3-ylthio)-1,2,4-triazin-3-yl)-1,3-dihydrospiro[indene-2,4'-piperidin]-1-amine | Ex. 27 | 430.2 |
| 72 | 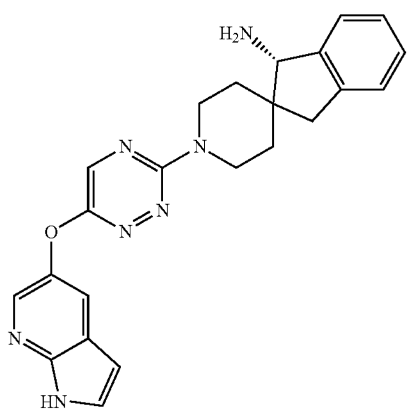 [SMILES: N[C@@H]1c2ccccc2CC12CCN(c1ncc(Oc3cnc4[nH]ccc4c3)nn1)CC2] | (S)-1'-(6-((1H-pyrrolo[2,3-b]pyridin-5-yl)oxy)-1,2,4-triazin-3-yl)-1,3-dihydrospiro[indene-2,4'-piperidin]-1-amine | Ex. 28 | 414.2 |
| 73 | 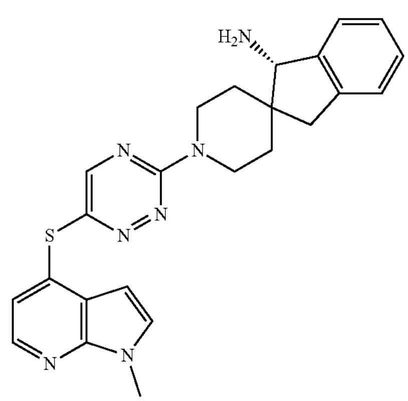 [SMILES: Cn1ccc2c(Sc3cnc(N4CCC5(CC4)Cc4ccccc4[C@H]5N)nn3)ccnc21] | (S)-1'-(6-((1-methyl-1H-pyrrolo[2,3-b]pyridin-4-yl)thio)-1,2,4-triazin-3-yl)-1,3-dihydrospiro[indene-2,4'-piperidin]-1-amine | Ex. 30 | 444.2 |

TABLE 4-continued

| Ex. # | Structure | Name | Prep | MS |
|---|---|---|---|---|
| 74 | 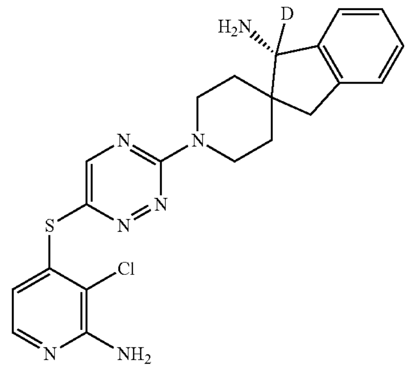 [SMILES: [2H][C@@]1(N)c2ccccc2CC12CCN(c1ncc(Sc3ccnc(N)c3Cl)nn1)CC2] | (S)-1'-(6-((2-amino-3-chloropyridin-4-yl)thio)-1,2,4-triazin-3-yl)-1,3-dihydrospiro[indene-2,4'-piperidin]-1-d-1-amine | Ex. 17 | 442.1 |
| 75 | 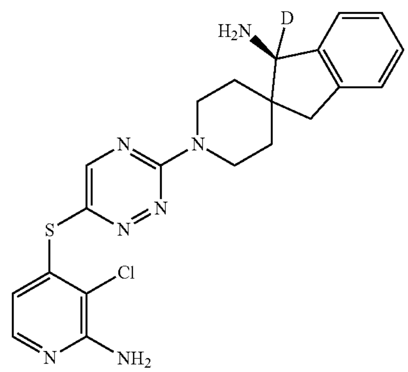 [SMILES: [2H][C@]1(N)c2ccccc2CC12CCN(c1ncc(Sc3ccnc(N)c3Cl)nn1)CC2] | (R)-1'-(6-((2-amino-3-chloropyridin-4-yl)thio)-1,2,4-triazin-3-yl)-1,3-dihydrospiro[indene-2,4'-piperidin]-1-d-1-amine | Ex. 17 | 442.1 |
| 76 | 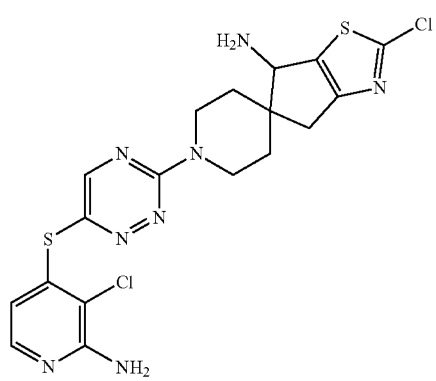 [SMILES: Nc1nccc(Sc2cnc(N3CCC4(CC3)Cc3nc(Cl)sc3C4N)nn2)c1Cl] | 1'-(6-((2-amino-3-chloropyridin-4-yl)thio)-1,2,4-triazin-3-yl)-2-chloro-4,6-dihydrospiro[cyclopenta[d]thiazole-5,4'-piperidin]-6-amine | Ex. 17 | 483.0 |
| 77 | 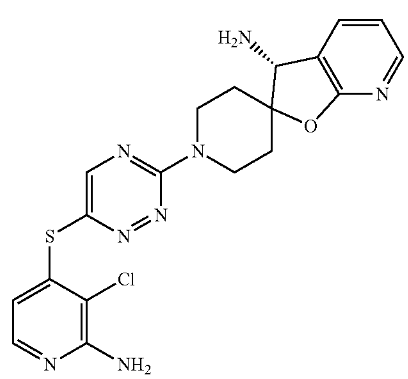 [SMILES: Nc1nccc(Sc2cnc(N3CCC4(CC3)Oc3ncccc3[C@H]4N)nn2)c1Cl] | (S)-1'-(6-(4-fluorophenoxy)pyrido[2,3-b]pyrazin-2-yl)-1,3-dihydrospiro[indene-2,4'-piperidin]-1-amine | Ex. 17 | 443.1 |

TABLE 4-continued

| Ex. # | Structure | Name | Prep | MS |
|---|---|---|---|---|
| 78 | 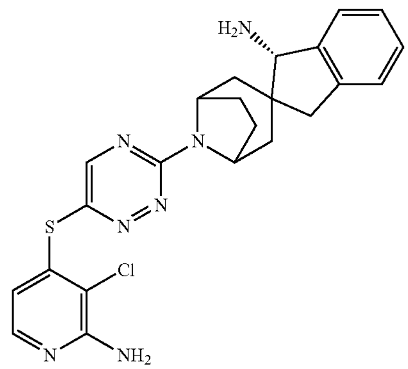 [SMILES: Nc1nccc(Sc2cnc(N3C4CCC3CC3(Cc5ccccc5[C@H]3N)C4)nn2)c1Cl] | (1'S)-8-(6-((2-amino-3-chloropyridin-4-yl)thio)-1,2,4-triazin-3-yl)-1',3'-dihydro-8-azaspiro[bicyclo[3.2.1]octane-3,2'-inden]-1'-amine | Ex. 17 | 466.1 |
| 79 | 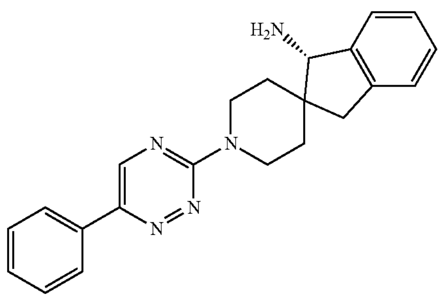 [SMILES: N[C@@H]1c2ccccc2CC12CCN(c1ncc(-c3ccccc3)nn1)CC2] | (S)-1'-(6-phenyl-1,2,4-triazin-3-yl)-1,3-dihydrospiro[indene-2,4'-piperidin]-1-amine | Ex. 31 | 358.2 |
| 80 | 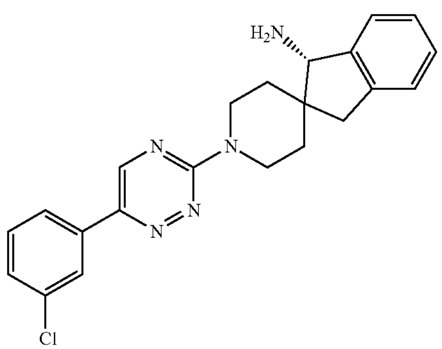 [SMILES: N[C@@H]1c2ccccc2CC12CCN(c1ncc(-c3cccc(Cl)c3)nn1)CC2] | (S)-1'-(6-(3-chlorophenyl)-1,2,4-triazin-3-yl)-1,3-dihydrospiro[indene-2,4'-piperidin]-1-amine | Ex. 31 | 392.1 |
| 81 | 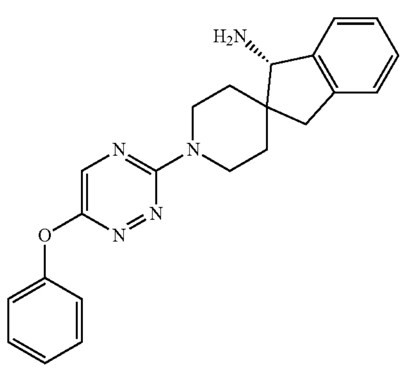 [SMILES: N[C@@H]1c2ccccc2CC12CCN(c1ncc(Oc3ccccc3)nn1)CC2] | (S)-1'-(6-phenoxy-1,2,4-triazol-3-yl)-1,3-dihydrospiro[indene-2,4'-piperidin]-1-amine | Ex. 32 | 374.2 |

TABLE 4-continued

| Ex. # | Structure | Name | Prep | MS |
|---|---|---|---|---|
| 82 | 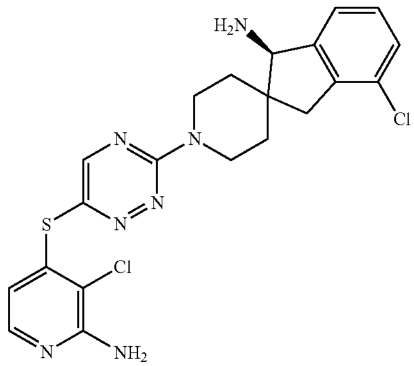 [SMILES: Nc1nccc(Sc2cnc(N3CCC4(CC3)Cc3c(Cl)cccc3[C@@H]4N)nn2)c1Cl] | (R)-1'-(6-((2-amino-3-chloropyridin-4-yl)thio)-1,2,4-triazin-3-yl)-4-chloro-1,3-dihydrospiro[indene-2,4'-piperidin]-1-amine | Ex. 35 | 474.1 |
| 83 | 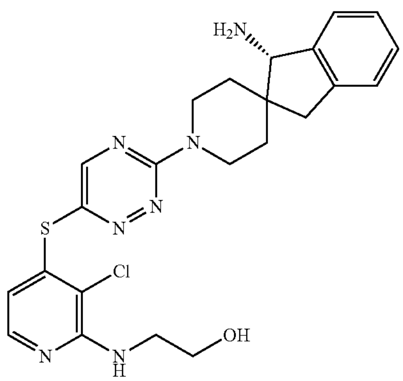 [SMILES: N[C@@H]1c2ccccc2CC12CCN(c1ncc(Sc3ccnc(NCCO)c3Cl)nn1)CC2] | (S)-2-((4-((3-(1-amino-1,3-dihydrospiro[indene-2,4'-piperidin]-1'-yl)-1,2,4-triazin-6-yl)thio)-3-chloropyridin-2-yl)amino)ethan-1-ol | Ex. 17 | 484.5 |
| 84 | 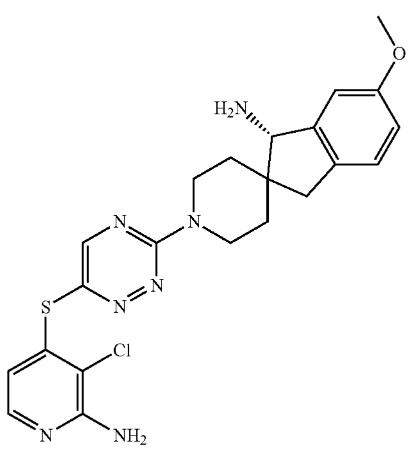 [SMILES: COc1ccc2c(c1)[C@@H](N)C1(CCN(c3ncc(Sc4ccnc(N)c4Cl)nn3)CC1)C2] | (S)-1'-(6-((2-amino-3-chloropyridin-4-yl)thio)-1,2,4-triazin-3-yl)-6-methoxy-1,3-dihydrospiro[indene-2,4'-piperidin]-1-amine | Ex. 6 | 470.2 |

It will be understood that the enumerated embodiments are not intended to limit the invention to those embodiments. On the contrary, the invention is intended to cover all alternatives, modifications and equivalents, which may be included within the scope of the present invention as defined by the claims. Thus, the foregoing description is considered as illustrative only of the principles of the invention.

What is claimed is:
1. A compound selected from Formula I:

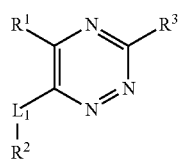

I or a stereoisomer, tautomer, or pharmaceutically acceptable salt thereof, wherein:
$L_1$ is O;
$R_1$ is selected from hydrogen and methyl;
$R_2$ is selected from (a) phenyl, (b) a 5 to 6 membered heteroaryl wherein the heteroaryl contains one to four heteroatoms selected from the group consisting of nitrogen, oxygen and sulfur, wherein one nitrogen heteroatom may be substituted with oxygen to form an oxide, (c) an 8-10 membered bicyclic cycloalkyl, (d) a 10 membered bicyclic aryl, (e) a 9-10 membered bicyclic heterocycle wherein the heterocycle contains one to three heteroatoms selected from the group consisting of nitrogen, oxygen and sulfur, and (f) a 9-10 membered bicyclic heteroaryl wherein the bicyclic heteroaryl contains one to three heteroatoms selected from the group consisting of nitrogen, oxygen and sulfur, wherein the phenyl, heteroaryl, bicyclic cycloalkyl, bicyclic aryl, bicyclic heterocycle and bicyclic heteroaryl are optionally substituted with one or more groups selected from the group consisting of halogen, cyano, oxo, $C_1$-$C_3$ alkyl optionally substituted with 1 to 3 groups selected from halogen, cyano and OH, $C_3$-$C_6$ cycloalkyl, $C_1$-$C_3$ alkoxy optionally substituted with 1 to 3 groups selected from halogen, cyano and OH, NHR$^a$, and a 3 to 6 membered heterocycle optionally substituted with 1 to 3 groups selected from halogen, cyano and OH, wherein the heterocycle contains one or two heteroatoms selected from nitrogen, oxygen and sulfur;
$R^3$ is selected from the group consisting of:

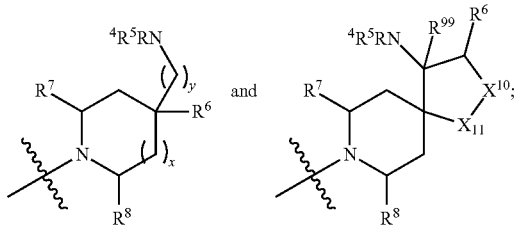

$X^{10}$ is $CR^9$ or O,
$X^{11}$ is $CH_2$ or O, wherein only one of $X^{10}$ and $X^{11}$ may be O;

$R^4$ and $R^5$ are independently selected from hydrogen and $C_1$-$C_3$ alkyl;
$R^6$ is selected from the group consisting of hydrogen, OH and $C_1$-$C_3$ alkyl optionally substituted with an OH group, or
$R^6$ and $R^9$ together with the atoms to which they are attached form a 6 membered aryl or a 5 to 6 membered heteroaryl, wherein the heteroaryl contains 1 or 2 heteroatoms selected from nitrogen, oxygen and sulfur, wherein the aryl and heteroaryl are optionally substituted with 1 or 2 groups selected from the group consisting of halogen, cyano, $C_1$-$C_3$ alkyl and $C_1$-$C_3$ alkoxy;
$R^7$ and $R^8$ are hydrogen, or
$R^7$ and $R^8$ together with the atoms to which they are attached form an ethyl bridge such that $R^3$ is an azabicyclic ring;
$R^{99}$ is hydrogen or deuterium;
x is 1 or 2;
y is 0 or 1; and
$R^a$ is hydrogen or $C_1$-$C_4$ alkyl optionally substituted with 1 to 3 groups selected from OH, methoxy, halogen and cyano.

2. The compound of claim 1, wherein:
$R^2$ is selected from (a) phenyl optionally substituted with one or two halogen groups; (b) a 5 to 6 membered heteroaryl wherein the heteroaryl contains one to four heteroatoms selected from the group consisting of nitrogen, oxygen and sulfur, wherein the heteroaryl is optionally substituted with one or two substituents selected from halogen, $C_1$-$C_3$ alkyl optionally substituted with 1 to 3 halogen groups, $C_3$-$C_6$ cycloalkyl, $C_1$-$C_3$ alkoxy, NHR$^a$, and a 3 to 6 membered heterocycle optionally substituted with an OH group, wherein the heterocycle contains one or two heteroatoms selected from nitrogen and oxygen; (c) an 8-10 membered bicyclic partially unsaturated cycloalkyl; (d) a 9-10 membered bicyclic partially unsaturated heterocycle, wherein the heterocycle contains one to three heteroatoms selected from nitrogen, oxygen and sulfur, wherein the heterocycle is optionally substituted with one to three groups selected from halogen and oxo; (e) a 9-10 membered bicyclic heteroaryl wherein the bicyclic heteroaryl contains one to three heteroatoms selected from the group consisting of nitrogen, oxygen and sulfur, wherein the bicyclic heteroaryl is optionally substituted with 1 to 3 groups selected from halogen and $C_1$-$C_3$ alkyl,
or a stereoisomer, tautomer, or pharmaceutically acceptable salt thereof.

3. The compound of claim 1, or a stereoisomer, tautomer, or pharmaceutically acceptable salt thereof, wherein $R^1$ is hydrogen.

4. The compound of claim 1, or a stereoisomer, tautomer, or pharmaceutically acceptable salt thereof, wherein $R^2$ is selected from the group consisting of phenyl, 2-chlorophenyl, 3-chlorophenyl, 2,3-dichlorophenyl, 2-amino-3-chloropyridin-4-yl, 2,3-dichloropyridin-4-yl, 3-chloro-2-methylpyridin-4-yl, 3-chloro-2-(4-hydroxypiperidin-1-yl)pyridin-4-yl, 3-chloro-2-(methylamino)pyridin-4-yl, 2,3-dimethylpyridin-4-yl, 2-amino-3-cyclopropylpyridin-4-yl, 2-amino-5-chloropyridin-4-yl, 3-chloro-2-methoxypyridin-4-yl, 3-chloro-2-(trifluoromethyl)pyridin-4-yl, 6-amino-2-(trifluoromethyl)pyridin-3-yl, 2-amino-3-bromopyridin-4-yl, 6-aminopyridin-3-yl, 2-amino-3-fluoropyridin-4-yl, 3-chloro-2-((2-cyano-2-methylpropyl)amino)pyridin-4-yl, 2-amino-3-chloro-1-oxidopyridin-4-yl, 3-chloro-2-((2-hydroxyethyl)amino)pyridin-4-yl, bicyclo[4.2.0]octa-(6),2,4-trien-2-yl, 2,3-dihydro-1H-pyrrolo[3,2-c]pyridin-1-yl, 3,3-difluoro-2-oxo-2,3-dihydro-1H-pyrrolo[2,3-b]pyridin-4-yl, 2,3-dihydro-1H-pyrrolo[2,3-b]pyridin-4-yl, 1H-pyrrolo[2,3-b]pyridin-4-yl, 5-chloro-1H-pyrrolo[2,3-b]pyridin-4-yl, 1-methyl-1H-pyrrolo[2,3-b]pyridin-4-yl, 1H-pyrrolo[2,3-b]pyridin-3-yl, 1H-pyrazolo[3,4-b]pyridin-3-yl, 1H-indazol-3-yl, 1H-pyrrolo[2,3-b]pyridin-5-yl, isoquinolin-5-yl and 1H-indol-3-yl.

5. The compound of claim 1, or a stereoisomer, tautomer, or pharmaceutically acceptable salt thereof, wherein R³ is selected from the group consisting of:

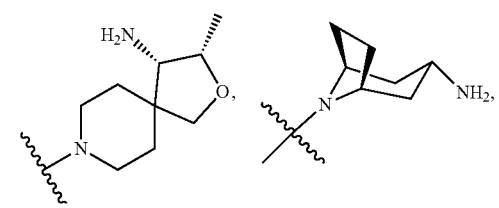

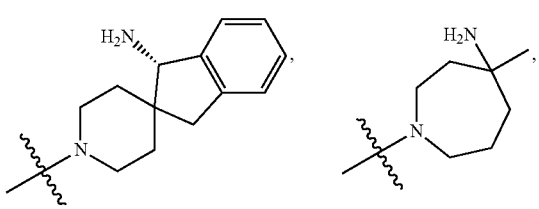

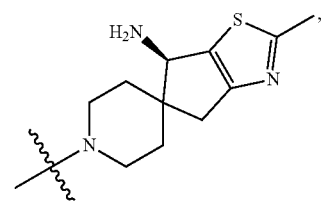

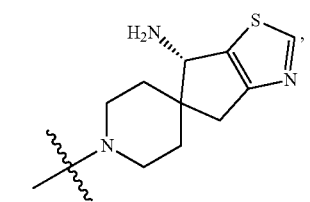

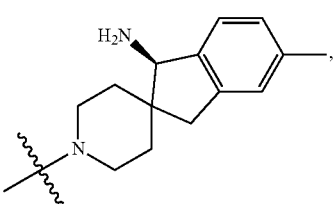

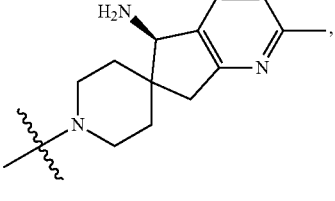

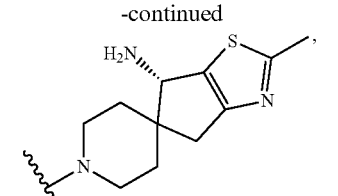

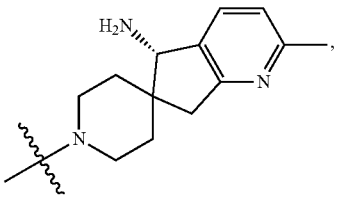

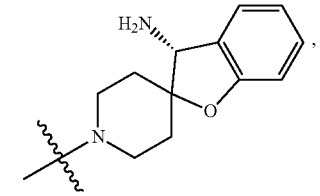

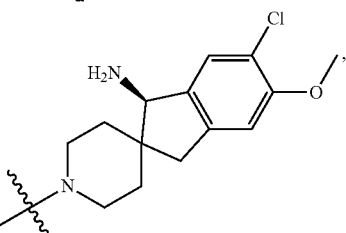

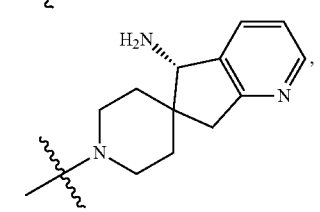

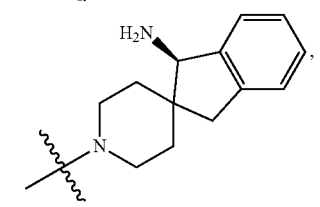

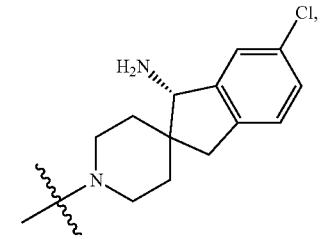

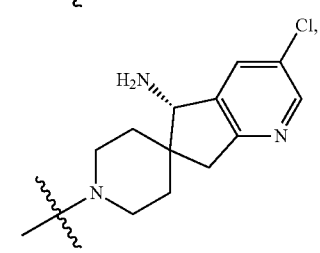

151
-continued
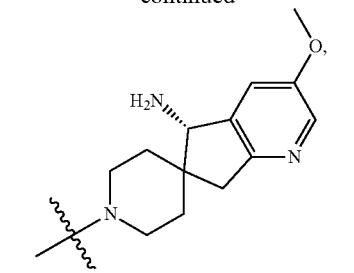
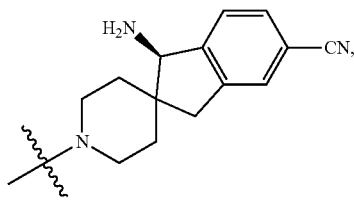
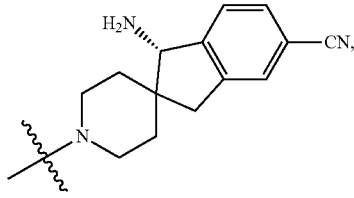
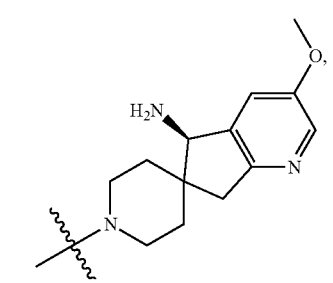
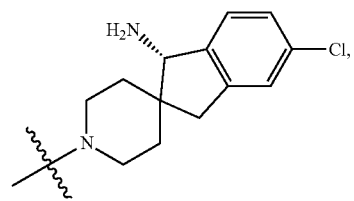
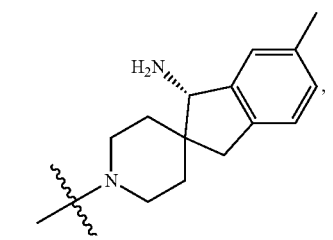
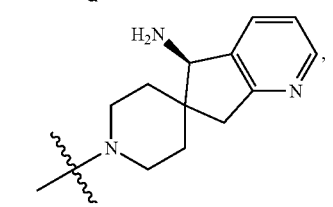
152
-continued
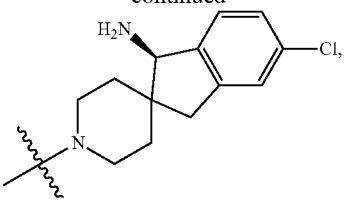
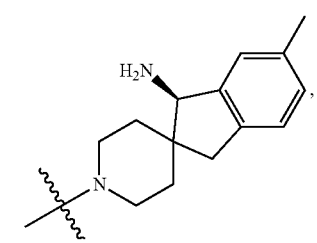
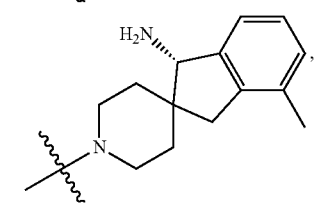
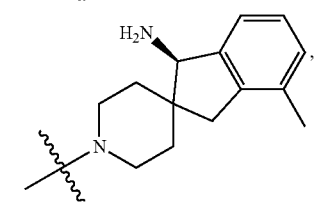
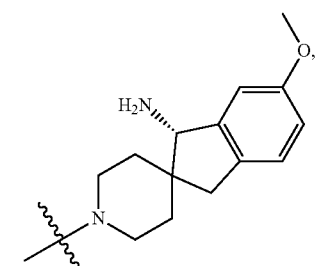
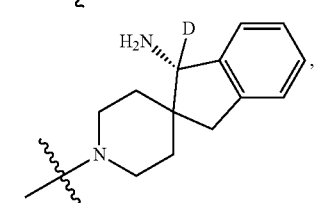
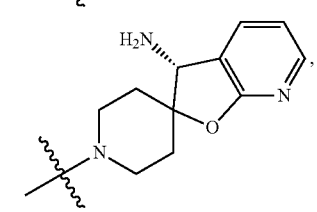
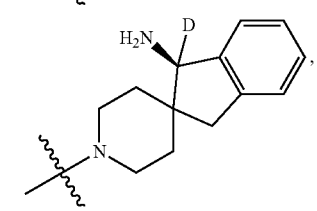

-continued

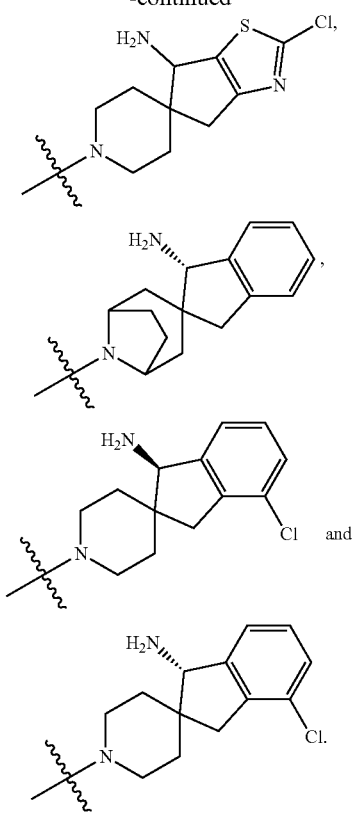

6. The compound of claim 1, selected from the group consisting of:

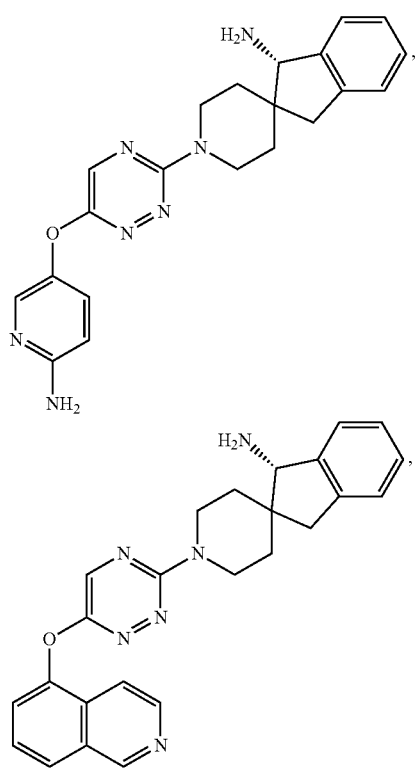

-continued

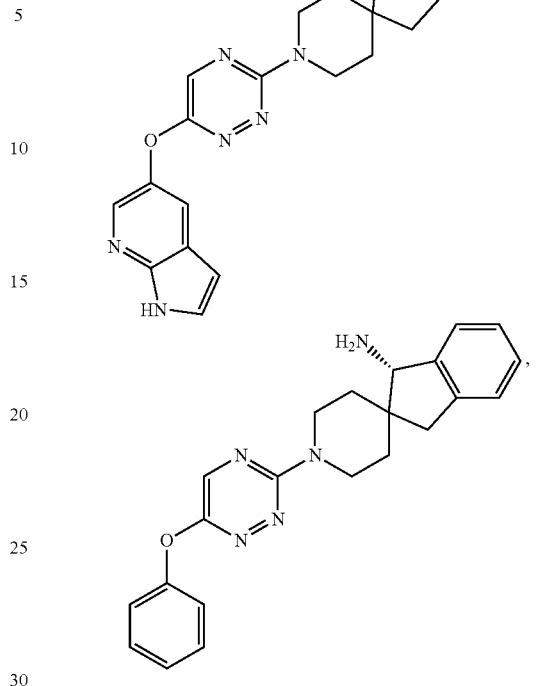

or a stereoisomer, tautomer, or pharmaceutically acceptable salt thereof.

7. A pharmaceutical composition comprising a compound of claim 1, or a stereoisomer, tautomer, or pharmaceutically acceptable salt thereof.

8. A pharmaceutical composition comprising a compound of claim 6, or a stereoisomer, tautomer, or pharmaceutically acceptable salt thereof, and at least one pharmaceutically acceptable carrier, excipient or diluent.

9. A method of inhibiting SHP2 protein tyrosine phosphatase activity in a cell comprising treating the cell with a compound of claim 1, or a stereoisomer, tautomer, or pharmaceutically acceptable salt thereof.

10. A method of inhibiting SHP2 protein tyrosine phosphatase activity in a patient in need thereof comprising the step of administering to the patient a compound according to claim 1, or a stereoisomer, tautomer, or pharmaceutically acceptable salt thereof.

11. A method of treating or ameliorating the severity of a hyperproliferative disorder in a patient in need thereof comprising administering to the patient a compound according to claim 1, or a stereoisomer, tautomer, or pharmaceutically acceptable salt thereof.

12. The method of claim 11, wherein the hyperproliferative disease is selected from the group consisting of melanoma, juvenile myelomoncytic leukemias, neuroblastoma, Philadelphia chromosome positive chronic myeloid, Philadelphia chromosome positive acute lymphoblastic leukemias, acute myeloid leukemias, myeloproliferative neoplasms (such as Polycythemia Vera, Essential Thrombocythemia and Primary Myelofibrosis), breast cancer, lung cancer, liver cancer, colorectal cancer, esophageal cancer, gastric cancer, squamous-cell carcinoma of the head and neck, glioblastoma, anaplastic large-cell lymphoma, thyroid carcinoma, and spitzoid neoplasms.

13. The method of claim 11, wherein the hyperproliferative disease is selected from the group consisting of Neurofibromatosis and Noonan Syndrome.

14. The method of claim 9, wherein the compound of claim 1, or a stereoisomer, tautomer, or pharmaceutically acceptable salt thereof, is co-administered with at least one other chemotherapeutic agent used to treat or ameliorate a hyperproliferative disorder.

15. The method of claim 14, wherein the other chemotherapeutic agent is selected from the group consisting of trametinib, binimetinib, selumetinib, cobimetinib, encorafenib, vemurafenib, dabrafenib, lorlatinib, crizotinib, ceritinib, alectinib and brigatinib.

16. A method of inhibiting SHP2 protein tyrosine phosphatase activity in a cell comprising treating the cell with a compound of claim 6.

* * * * *